US008652469B2

(12) United States Patent
Kavanaugh et al.

(10) Patent No.: US 8,652,469 B2
(45) Date of Patent: Feb. 18, 2014

(54) M-CSF-SPECIFIC MONOCLONAL ANTIBODY AND USES THEREOF

(75) Inventors: William M. Kavanaugh, Orinda, CA (US); Lea Aukerman, Moraga, CA (US); Victoria Sung, San Francisco, CA (US)

(73) Assignees: Novartis AG, Basel (CH); Xoma Technology Ltd., Berkeley, CA (US)

( * ) Notice: Subject to any disclaimer, the term of this patent is extended or adjusted under 35 U.S.C. 154(b) by 999 days.

(21) Appl. No.: 11/996,905

(22) PCT Filed: Jul. 27, 2006

(86) PCT No.: PCT/US2006/029279
§ 371 (c)(1),
(2), (4) Date: Nov. 18, 2009

(87) PCT Pub. No.: WO2007/016285
PCT Pub. Date: Feb. 8, 2007

(65) Prior Publication Data
US 2010/0092464 A1    Apr. 15, 2010

Related U.S. Application Data

(60) Provisional application No. 60/703,218, filed on Jul. 28, 2005, provisional application No. 60/703,314, filed on Jul. 28, 2005.

(51) Int. Cl.
*A61K 39/00*    (2006.01)
(52) U.S. Cl.
USPC ............... 424/133.1; 424/130.1; 530/387.1
(58) Field of Classification Search
None
See application file for complete search history.

(56) References Cited

U.S. PATENT DOCUMENTS

| | | | |
|---|---|---|---|
| 30,985 A | 12/1860 | Pye |
| 3,773,919 A | 11/1973 | Boswell et al. |
| 4,179,337 A | 12/1979 | Davis et al. |
| 4,301,144 A | 11/1981 | Iwashita et al. |
| 4,419,446 A | 12/1983 | Howley et al. |
| 4,485,045 A | 11/1984 | Regen |
| 4,495,285 A | 1/1985 | Shimizu et al. |
| 4,496,689 A | 1/1985 | Mitra |
| 4,544,545 A | 10/1985 | Ryan et al. |
| 4,560,655 A | 12/1985 | Baker |
| 4,601,978 A | 7/1986 | Karin |
| 4,609,546 A | 9/1986 | Hiratani et al. |
| 4,640,835 A | 2/1987 | Shimizu et al. |
| 4,657,866 A | 4/1987 | Kumar |
| 4,670,417 A | 6/1987 | Iwasaki et al. |
| 4,675,187 A | 6/1987 | Konishi et al. |
| 4,676,980 A | 6/1987 | Segal et al. |
| 4,766,106 A | 8/1988 | Katre et al. |
| 4,767,704 A | 8/1988 | Cleveland et al. |
| 4,791,192 A | 12/1988 | Nakagawa et al. |
| 4,816,567 A | 3/1989 | Cabilly et al. |
| 4,837,028 A | 6/1989 | Allen et al. |
| 4,892,538 A | 1/1990 | Aebischer et al. |
| 4,927,762 A | 5/1990 | Darfler |
| 4,929,700 A | 5/1990 | Halenbeck et al. |
| 4,965,199 A | 10/1990 | Capon et al. |
| 4,975,278 A | 12/1990 | Senter et al. |
| 5,013,556 A | 5/1991 | Woodle et al. |
| 5,019,369 A | 5/1991 | Presant et al. |
| 5,057,313 A | 10/1991 | Shih et al. |
| 5,122,469 A | 6/1992 | Mather et al. |
| 5,229,275 A | 7/1993 | Goroff |
| 5,283,187 A | 2/1994 | Aebischer et al. |
| 5,443,953 A | 8/1995 | Hansen et al. |
| 5,491,065 A | 2/1996 | Halenbeck et al. |
| 5,530,101 A | 6/1996 | Queen et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,585,089 A | 12/1996 | Queen et al. |
| 5,589,369 A | 12/1996 | Seidman et al. |
| 5,591,669 A | 1/1997 | Krimpenfort et al. |
| 5,624,821 A | 4/1997 | Winter et al. |
| 5,693,762 A | 12/1997 | Queen et al. |
| 5,766,866 A | 6/1998 | Center et al. |
| 5,766,886 A | 6/1998 | Studnicka et al. |
| 5,877,293 A | 3/1999 | Adair et al. |

(Continued)

FOREIGN PATENT DOCUMENTS

| | | |
|---|---|---|
| EP | 0073657 | 3/1983 |
| EP | 0120694 | 10/1984 |
| EP | 0125023 | 11/1984 |
| EP | 0171496 | 2/1986 |
| EP | 0173494 | 3/1986 |
| EP | 0194276 | 9/1986 |
| EP | 0315456 | 5/1989 |
| EP | 0404097 | 12/1990 |
| WO | WO-81/01145 | 4/1981 |
| WO | WO-86/01533 | 3/1986 |

(Continued)

OTHER PUBLICATIONS

Bendig (1995) Methods: a companion methods in enzymology 8: 83-93.*
Paul (1993) Fundamental Immunology, 3rd edition, pp. 292-295.*
Mac Callum et al. (1996) J. Mol. Biol. 262: 732-745.*
Opposition against European patent EP 1 572 106, Feb. 4, 2011.
Aharinejad, et al., "Colony-stimulating Factor-1 Antisense Treatment Suppresses Growth of Human Tumor Xenografts in Mice," Cancer Research, 62, 5317-5324 (Sep. 15, 2002).

(Continued)

*Primary Examiner* — Michael Pak
(74) *Attorney, Agent, or Firm* — Marshall, Gerstein & Borun LLP

(57) ABSTRACT

M-CSF-specific RX1-based or RX-I derived antibodies are provided, along with pharmaceutical compositions containing such antibody, kits containing a pharmaceutical composition, and methods of preventing and treating bone loss in or remodeling in a subject afflicted with an osteoblastic or osteolytic disease.

13 Claims, 45 Drawing Sheets

(56) References Cited

U.S. PATENT DOCUMENTS

| | | | |
|---|---|---|---|
| 6,054,287 | A | 4/2000 | Gao et al. |
| 6,194,551 | B1 | 2/2001 | Idusogie et al. |
| 6,255,458 | B1 | 7/2001 | Lonberg et al. |
| 6,306,393 | B1 | 10/2001 | Goldenberg |
| 6,737,056 | B1 | 5/2004 | Presta |
| 2002/0004215 | A1 | 1/2002 | Osbourne et al. |
| 2002/0091240 | A1 | 7/2002 | Vasquez et al. |
| 2002/0199213 | A1 | 12/2002 | Tomizuka et al. |
| 2003/0028071 | A1 | 2/2003 | Handy et al. |
| 2003/0031667 | A1 | 2/2003 | Deo et al. |
| 2003/0032995 | A1 | 2/2003 | Handy et al. |
| 2003/0044772 | A1 | 3/2003 | Watkins et al. |
| 2003/0092125 | A1 | 5/2003 | Davis et al. |
| 2003/0190317 | A1 | 10/2003 | Baca et al. |
| 2003/0194404 | A1 | 10/2003 | Greenfeder et al. |
| 2004/0132101 | A1 | 7/2004 | Lazar et al. |
| 2005/0059113 | A1 | 3/2005 | Bedian et al. |

FOREIGN PATENT DOCUMENTS

| | | |
|---|---|---|
| WO | WO-87/00195 | 1/1987 |
| WO | WO-88/07378 | 10/1988 |
| WO | WO-90/07861 | 7/1990 |
| WO | WO-90/13646 | 11/1990 |
| WO | WO-91/09967 | 7/1991 |
| WO | WO-91/17271 | 11/1991 |
| WO | WO-92/01047 | 1/1992 |
| WO | WO-92/11018 | 7/1992 |
| WO | WO-93/11161 | 6/1993 |
| WO | WO-93/11794 | 6/1993 |
| WO | WO-93/25673 | 12/1993 |
| WO | WO-94/02602 | 2/1994 |
| WO | WO-94/11026 | 5/1994 |
| WO | WO-96/27011 | 9/1996 |
| WO | WO-96/30498 | 10/1996 |
| WO | WO-96/32478 | 10/1996 |
| WO | WO-96/33735 | 10/1996 |
| WO | WO-96/34096 | 10/1996 |
| WO | WO-97/34631 | 9/1997 |
| WO | WO-98/24893 | 6/1998 |
| WO | WO-98/37177 | 8/1998 |
| WO | WO-99/58572 | 11/1999 |
| WO | WO-01/30381 A2 | 5/2001 |
| WO | WO-2004/045532 | 6/2004 |

OTHER PUBLICATIONS

Cenci, et al., "M-CSF neutralization and Egr-1 deficiency prevent ovariectomy-induced bone loss," The Journal of Clinical Investigation, vol. 105, No. 9, 1279-1287 (May 2000).

Fan, et al., "Macrophage Colony Stimulating Factor Down-Regulates MCSF-Receptor Expression and Entry of Progenitors into the Osteoclast Lineage," J. of Bone and Mineral Research, vol. 12, No. 9, pp. 1387-1395 (1997).

Itoh, et al., "Importance of Membrane- or Matrix-Associated Forms of M-CSF and RANKL/ODF in Osteoclastogenesis Supported by SaOS-4/3 Cells Expressing Recombinant PTH/PTHrP Receptors," Journal of Bone and Mineral Research, vol. 15, No. 9, 1766-1775 (2000).

Lin, et al., "The Macrophage Growth Factor CSF-1 in Mammary Gland Development and Tumor Progression," Journal of Mammary Gland Biology and Neoplasia, vol. 7, No. 2, 147-162 (2002).

Lokeshwar, et al., "Development and Characterization of Monoclonal Antibodies to Murine Macrophage Colony-Stimulating Factor," The J. of Immun. vol. 141, No. 2, pp. 483-488 (1988).

Mancino, M.D., et al., "Breast Cancer Increases Osteoclastogenesis by Secreting M-CSF and Upregulating RANKL in Stromal Cells," Journal of Surgical Research, 100, 18-24 (2001).

Neale, et al., "Macrophage Colony-Stimulating Factor and Interleukin-6 Release by Periprosthetic Cells Stimulates Osteoclast Formation and Bone Resorption," Journal of Orthopaedic Research, 17:686-694 (1999).

Romas, et al., "Cytokines in the Pathogenesis of Osteoporosis," Osteoporos Int., Suppl. 3:47-53 (1997).

Roux, et al., "Human Cord Blood Monocytes Undergo Terminal Osteoclast Differentiation in Vitro in the Presence of Culture Medium Conditioned by Giant Cell Tumor of Bone," J. of Cell. Phy. 168:489-498 (1996).

Tanaka, et al., "Macrophage Colony-stimulating Factor is Indispensable for both Proliferation and Differentiation of Osteoclast Progenitors," J. Clin. Invest. vol. 91, 257-263 (Jan. 1993).

Weir, et al., "Colony Stimulating Factor-1 Plays a Role in Osteoclast Formation and Function in Bone Resorption Induced by Parathyroid Hormone and Parathyroid Hormone-Related Protein," Journal of Bone and Mineral Research, vol. 11, No. 10, 1474-1481 (1996).

Yao, et al., "A Role for Cell-Surface CSF-1 in Osteoblast-mediated Osteoclastogenesis," Calcif Tissue Int. 70:339-346 (2002).

Yoneda, et al., "Actions of Bisphosphonate on Bone Metastasis in Animal Models of Breas Carcinoma," Cancer Supplement, vol. 88, No. 12, 2979-2988 (2000).

Internet page print out of www.lgcstandards-atcc.org (3 pages), Jan. 28, 2011.

Internet page print out of www.lgcstandards-atcc.org (2 pages), Jan. 28, 2011.

Anderson, Human gene therapy. *Nature*. 392: Suppl. 6679 25-30 (1998).

Angal et al., A single amino acid substitution abolishes the heterogeneity of chimeric mouse/human (IgG4) antibody. *Mol. Immunol*. 30: 105-8 (1993).

Aplin et al., Preparation, properties, and applications of carbohydrate conjugates of proteins and lipids. *CRC Crit. Rev. Biochem*. 10: 259-306 (1981).

Arguello et al., A murine model of experimental metastasis to bone and bone marrow. *Cancer Res*. 48: 6876-81 (1988).

Armour et al., Differential binding to human FcgammaRIIa and FcgammaRIIb receptors by human IgG wildtype and mutant antibodies. *Mol Immunol*. 40: 585-93 (2003).

Ash et al., Osteoclasts derived from haematopoietic stem cells. *Nature*. 283: 669-70 (1980).

Athanasou et al., Immunocytochemical analysis of the human osteoclast: phenotypic relationship to other marrow-derived cells. *Bone Miner Res*. 3: 317-33 (1988).

Ballas et al., Liposomes baring a quaternary ammonium detergent as an efficient vehicle for functional transfer of TMV-RNA into plant protoplasts. *Biochim. Biophys. Acta*. 939: 8-18 (1988).

Barnes et al., Methods for growth of cultured cells in serum-free medium. *Anal. Biochem*. 102: 255-70 (1980).

Batra et al., Recombinant anti-erbB2 immunotoxins containing Pseudomonas exotoxin. *Proc. Natl. Acad. Sci. USA*. 89: 5867-71 (1992).

Bayer et al., The avidin-biotin complex in affinity cytochemistry. *Meth. Enzyme* 62: 308 (1979).

Becker et al., An antibody-interleukin 2 fusion protein overcomes tumor heterogeneity by induction of a cellular immune response. *Proc. Natl. Acad. Sci. USA*. 93: 7826-31 (1996).

Behr et al., DNA strongly binds to micelles and vesicles containing lipopolyamines or lipointercalants. *Tetrahedron Lett*. 27: 5861-4 (1986).

Behr et al., Efficient gene transfer into mammalian primary endocrine cells with lipopolyamine-coated DNA. *Proc. Natl. Acad. Sci. USA*. 86: 6982-6 (1989).

Behr et al., Gene transfer with synthetic cationic amphiphiles: prospects for gene therapy. *Bioconjugate Chem*. 5: 382-9 (1994).

Better et al., *Escherichia coli* secretion of an active chimeric antibody fragment. *Science* 240: 1041-3 (1988).

Better et al., Potent anti-CD5 ricin A chain immunoconjugates from bacterially produced Fab' and F(ab')2. *Proc. Natl. Acad. Sci. USA*. 90: 457-61 (1993).

Blair et al., Isolated osteoclasts resorb the organic and inorganic components of bone. *J. Cell Biol*. 102: 1164-72 (1986).

Boleti et al., Construction, expression and characterisation of a single chain anti-tumour antibody (scFv)-IL-2 fusion protein. *Ann. Oncol*. 6: 945-7 (1995).

Boulianne et al., Production of functional chimaeric mouse/human antibody. *Nature*. 312: 643-6 (1984).

(56) References Cited

OTHER PUBLICATIONS

Brennan et al., Preparation of biospecific antibodies by chemical recombination of monoclonal immunoglobulin G1 fragments. *Science*. 229: 81-3 (1985).
Brinkmann et al., B3(Fv)-PE38KDEL, a single-chain immunotoxin that causes complete regression of a human carcinoma in mice. *Proc. Natl. Acad. Sci. USA*. 88: 8616-20 (1991).
Brodeur et al., Monoclonal Antibody Production Techniques and Applications. Marcel Dekker, Inc., N.Y.: 51-63 (1987).
Bruggermann et al., Designer mice: the production of human antibody repertoires in transgenic animals. *Year in Immuno*. 7: 33 (1993).
Burton et al., Human antibodies from combinatorial libraries. *Adv. Immunol*. 57: 191-280 (1994).
Caron et al., Engineered humanized dimeric forms of IgG are more effective antibodies. *J. Exp Med*. 176: 1191-5 (1992).
Carter et al., High level *Escherichia coli* expression and production of a bivalent humanized antibody fragment. *Bio/Technology* 10: 163-7 (1992).
Caton et al., Influenza virus hemagglutinin-specific antibodies isolated from a combinatorial expression library are closely related to the immune response of the donor. *Proc. Natl. Acad. Sci. USA*. 87: 6450-4 (1990).
Cenci et al., M-CSF neutralization and egr-1 deficiency prevent ovariectomy-induced bone loss. *J Clin. Invest*. 1055: 1279-87 (2000).
Cerretti et al., Human macrophage-colony stimulating factor: alternative RNA and protein processing from a single gene. *Molec. Immunol*. 25: 761-70 (1988).
Champe et al., Monoclonal antibodies that block the activity of leukocytes function-associated antigen 1 recognize three discrete epitopes in the inserted domain of CD11a. *J. Biol. Chem*. 270: 1388-94 (1995).
Chappel et al., Identification of the $Fc_\gamma$ receptor class I binding site in human IgG through the use of recombinant IgG1/IgG2 hybrid and point mutated antibodies. *Proc Natl Acad U S A*. 88: 9036-40 (1991).
Chaudhary et al., A recombinant immunotoxin consisting of two antibody variable domains fused to Pseudomonas exotoxin. *Nature*. 339: 394-7 (1989).
Chothia et al., Canonical structures for the hypervariable regions of immunoglobulins. *J. Mol. Biol*. 196: 901-17 (1987).
Clackson et al., In vitro selection from protein and peptide libraries. *Trends Biotechnol*. 12: 173-84 (1994).
Clackson et al., Making antibody fragments using phage display libraries. *Nature*. 352: 624-8 (1991).
Clohisy et al., Osteoclasts are required for bone tumors to grow and destroy bone. *Orthop Res*. 16: 660-6 (1998).
Co, et al., A humanized antibody specific for platelet integrin gpIIb/IIIa. *J. Immunol*. 152: 2968-76 (1994).
Culp et al., Plasticity of CD44s expression during progression and metastasis of fibrosarcoma in an animal model system. *Front Biosci*. 3: D672-83 (1998).
Cunningham et al., High-resolution epitope mapping the hGH-receptor interactions by alanine-scanning mutagenesis. *Science*. 244: 1081-5 (1989).
Davies et al., The osteoclast functional antigen, implicated in the regulation of bone resorption, is biochemically related to the vitronectin receptor. *J Cell Biol*. 109: 1817-26 (1989).
Dohlsten et al., Monoclonal antibody-superantigen fusion proteins: tumor-specific agents for T-cell-based tumor therapy. *Proc. Natl. Acad. Sci. USA*. 91: 8945-9 (1994).
Edge et al., Deglycosylation of glycoproteins by trifluoromethanesulfonic acid. *Anal Biochem*. 118: 131-7 (1981).
Eppstein et al., Biological activity of liposome-encapsulated murine interferon γ is mediated by a cell membrane receptor. *Proc. Natl. Acad. Sci. USA* 82: 3688-92 (1985).
Evan et al., Isolation of monoclonal antibodies specific for humen c-myc proto-oncogene product. *Mol. Cell. Biol*. 5: 3610-6 (1985).
Felgner et al., Lipofection: a highly efficient, lipid-mediated DNA-transfection procedure. *Proc. Natl. Acad. Sci USA*. 84: 7413-7 (1987).

Field et al., Purification of a RAS-responsive andenylyl cyclase complex from *Saccharomyces cerevisiae* by use of an epitope addition method. *Mol. Cell. Biol*. 8: 2159-65 (1988).
Filderman et al., Macrophage colony-stimulating factor (CSF-1) enhances invasiveness in CSF-1 receptor-positive carcinoma cell lines. *Cancer Res*. 52: 3661-6 (1992).
Fixe et al., M-CSF: haematopoietic growth factor or inflammatory cytokine? *Cytokine*. 10: 32-7 (1998).
Fleer et al., Stable multicopy vectors for high-level secretion of recombinant human serum albumin by Kluyveromyces yeasts. *Bio/Technology*. 9: 968-75 (1991).
Fominaya et al., Target cell-specific DNA transfer mediated by a chimeric multidomain protein. Novel non-viral gene delivery system. *J. Biol. Chem*. 271: 10560 (1996).
Friedmann et al., Antitumor activity of the single-chain immunotoxin BR96 sFv-PE40 against established breast and lung tumor xenografts. *J. Immunol*. 150: 3054-61 (1993).
Friedmann, Progress toward human gene therapy. *Science*. 244: 1275-81 (1989).
Gabizon et al., Pharmacokinetics and tissue distribution of doxorubicin encapsulated in stable liposomes with long circulation times. *J. Natl Cancer Inst*. 8: 1484-8 (1989).
Galasko, Mechanisms of lytic and blastic metastatic disease of bone. *Clin. Orthop. Relat Res*. 169: 20-7 (1982).
Gerhardt et al., Functional characteristics of heterologously expressed 5-HT receptors. *Eur. J. Pharmacology*. 334: 1-23 (1997).
Goding et al., Conjugation of antibodies with fluorochromes: Modification to the standard method. *J. Immunol. Meth*. 13: 215-26 (1976).
Goldenberg, New developments in monoclonal antibodies for cancer detection and therapy. *Cancer J. Clin*. 44: 43-63 (1994).
Graham et al., Characteristics of a human cell line transformed by DNA from human adenovirus type 5. *J. Gen Virol.*. 36: 59-74 (1977).
Gruber et al., Efficient tumor cell lysis mediated by a bispecific single chain antibody expressed in *Escherichia coli*. *J. Immunol*. 152: 5368-74 (1994).
Guss et al., Structure of the IgG-binding regions of streptococcal protein G. *EMBO J*. 5: 1567-75 (1986).
Hagenaars et al., Osteoclast formation from cloned pluripotent hemopoietic stem cells. *Bone Miner*. 6: 179-89 (1989).
Ham et al., Media and growth requirements. *Methods Enzymol*. 58: 44-93 (1979).
Hamilton et al., CSF-1 signal transduction. *J. Leikoc Biol*. 62: 145-55 (1997).
Hamilton et al., CSF-I signal transduction: what is of functional significance? *Immuno Today*. 18: 313-7 (1997).
Hank et al., Activation of human effector cells by a tumor reactive recombinant anti-ganglioside GD2 interleukin-2 fusion protein (ch14.18-IL2). *Clin. Cancer. Res*. 2: 1951-9 (1996).
Hollinger et al., "Diabodies": Small bivalent and bispecific antibody fragments. *Proc. Natl. Acad. Sci. USA*, 90: 6444-8 (1993).
Hoogenboom et al., By-passing immunisation. Human antibodies from synthetic repertoires of germline VH gene segments rearranged in vitro. *J. Mol. Biol*. 227: 381-8 (1991).
Hu et al., A chimeric Lym-1/interleukin 2 fusion protein for increasing tumor vascular permeability and enhancing antibody uptake. *Cancer Res*. 56: 4998-5004 (1996).
Hwang et al., Hepatic uptake and degradation of unilamellar sphingomyelin/cholesterol liposomes: A kinetic study. *Proc. Natl. Acad. Sci. USA*. 77: 4030-4 (1980).
Ingall, A model for the study of experimental bone metastases. *Proc. Soc. Exp. Biol. Med*. 117: 819-22 (1964).
Isaacs et al., Therapy with monoclonal antibodies. II. The contribution of Fc gamma receptor binding and the influence of C(H)1 and C(H)3 domains on in vivo effector function. *J. Immunol*. 161: 3862-9 (1998).
Ito et al., Synthetic cationic amphiphiles for liposome-mediated DNA transfection. *Biochim. Inter*. 22: 235-41 (1990).
Jakobovits et al., Analysis of homozygous mutant chimeric mice: Deletion of the immunoglobulin heavy-chain joining region blocks B-cell development and antibody production. *Proc. Natl. Acad. Sci. USA*. 90: 2551-5 (1993).
Jakobovits et al., Germ-line transmission and expression of a human-derived yeast artificial chromosome. *Nature*. 362: 255-8 (1993).

(56) References Cited

OTHER PUBLICATIONS

Jayawickreme et al., Gene expression systems in the development of high-throughput screens. *Curr Opin Biotechnol.* 8: 629-634 (1997).
Jespers et al., Guiding the selection of human antibodies from phage display repertoires to a single epitope of an antigen. *Bio/Technology.* 12: 899-903 (1994).
Jones et al., Replacing the complementarity-determining regions in a human antibody with those from a mouse. *Nature.* 312: 522-5 (1986).
Kabat, Origins of antibody complementarity and specificity—hypervariable regions and the minigene hypothosis. *J. Immunol.* 125: 961-9 (1980).
Kacinski, CSF-1 and its receptor in ovarian, endometrial and breast cancer. *Ann. Med.* 27: 79-85 (1995).
Kahn et al., Investigation of cell lineage in bone using a chimaera of chick and quial embryonic tissue. *Nature.* 258: 325-7 (1975).
Kawasaki et al., Molecular cloning of a complementary DNA encoding human macrophage-specific colony-stimulating factor (CSF-1). *Science.* 230: 291-6 (1985).
Kerby et al., Derivation of osteoclasts from hematopoietic colony-forming cells in culture. *J. Bone Miner Res.* 7: 353-62 (1992).
Kettleborough et al., Humanization of a mouse monoclonal antibody by CDR-grafting: the importance of framework residues on loop conformation. *Protein Eng.* 4: 773-83 (1991).
Kohler et al., Continuous cultures of fused cells secreting antibody of predefined specificity. *Nature.* 256: 495-7 (1975).
Kostelny et al., Formation of a bispecific antibody by the use of leucine zippers. *J. Immunol.* 148: 1547-53 (1992).
Kozbor, A human hybrid myeloma for production of human monoclonal antibodies. *J. Immunol.*, 133: 3001-5 (1984).
Kuan et al., Recombinant immunotoxin containing a disulfide-stabilized Fv directed at erbB2 that does not require proteolytic activation. *Biochemistry.* 35: 2872-7 (1996).
Lacey et al., Osteoprotegerin ligand is a cytokine that regulates osteoclast differentiation and activation. *Cell.* 93: 165-76 (1998).
Ladner et al., Human CSF-1: gene structure and alternative splicing of mRNA precursors. *EMBO J.* 6: 2693-8 (1987).
Letsinger, Cholesteryl-conjugated oligonucleotides: Synthesis, properties, and activity as inhibitors of replication of human Immunodeficiency virus in cell culture. *Proc Natl Acad Sci USA.* 86: 6553-6 (1989).
Leung et al., Engineering a unique glycosylation site for site-specific conjugation of haptens to antibody fragments. *J. Immunol.* 154: 5919-26 (1995).
Leventis et al., Interactions of mammalian cells with lipid dispersions containing novel metabolizable cationic amphiphiles. *Biochem. Biophys. Acta.* 1023: 124-32 (1990).
Lin et al., Colony-stimulating factor 1 promotes progression of mammary tumors to malignancy. *J. Exp. Med.* 193: 727-40 (2001).
Lindmark et al., Binding of immunoglobulins to protein A and immunoglobulin levels in mammalian sera. *J. Immunol. Meth.* 62: 1-13 (1983).
Malone et al., Cationic liposome-mediated RNA transfection. *Proc. Natl. Acad. Sci. USA.* 86: 6077-81 (1989).
Mancino et al., Breast cancer increases osteoclastogenesis by secreting M-CSF and upregulating RANKL in stromal cells. *J. Surg. Res.* 100: 18-24 (2001).
Marks et al., By-passing immunization. Human antibodies from V-gene libraries displayed on phage. *J. Mol. Biol.* 222: 581-97 (1991).
Martin et al., Hormonal regulation of osteoclast function. *Trends Endocrinol. Metab.* 9: 6-12 (1998).
Martin et al., Interleukins in the control of osteoclast differentiation. *Crit. Rev. Eukaryot Gene Expr.* 8: 107-23 (1998).
Martin et al., Irreversible coupling of immunoglobulin fragments to preformed vesicles. *J. Biol. Chem.* 257: 286-8 (1982).
Massey, Catalytic antibodies catching on. *Nature.* 328: 457-8 (1987).
Mather et al., Culture of testicular cells in hormone-supplemented serum-free medium. *Ann. N.Y. Acad. Sci.* 383: 44-68 (1982).
Miller, Human gene therapy comes of age. *Nature.* 357: 455-60 (1992).
Monoclonal Anti-human M-CSF antibody, Cat. No. MAB216, Clone 26730, R&D Systems XP002414616, Feb. 15, 2007.
Morimoto et al., Single-step purification of F(ab')2 fragments of mouse monoclonal antibodies (immunoglobulins G1) by hydrophobic interaction high performance liquid chromatography using TSKgel Phenyl-5PW. *J. Biochem. Biophys. Methods.* 24: 107-17 (1992).
Morrison et al., Chimeric human antibody molecules; Mouse antigen binding domains with human constant region domains, *Proc. Natl. Acad. Sci. USA.* 81: 6851-55 (1984).
Morrison et al., Genetically engineered antibody molecules. *Adv. Immunol.* 44: 65-92 (1989).
Mouse anti-Human M-CSF Monoclonal Antibody [116] Datasheet, Catalogue No. MO-C40048A, Clone No. 116, Anogen. XP002414614, Feb. 15, 2007.
Mouse anti-Human M-CSF Monoclonal Antibody [692] Datasheet, Catalogue No. MO-C40048B, Clone No. 692, Anogen. XP002414615, Feb. 15, 2007.
Mouse anti-Human M-CSF Monoclonal Antibody [21] Datasheet, Catalogue No. MO-C40048D, Clone No. 21, Anogen. XP002414616, Feb. 15, 2007.
Munson et al., Ligand: a versatile computerized approach for characterization of ligand-binding systems. *Anal. Biochem.* 107: 220-39 (1980).
Neuberger et al., Recombinant antibodies possessing novel effector functions. *Nature.* 312: 604-8 (1984).
Nicholls et al., Characterization of single-chain antibody (sFv)-toxin fusion proteins produced in vitro in rabbit reticulocyte lysate. *J. Biol. Chem.* 268: 5302-8 (1993).
Nicolet et al., Expression of a tumor-reactive antibody-interleukin 2 fusion protein after in vivo particle-mediated gene delivery. *Cancer Gene Ther.* 2: 161-70 (1995).
Oettinger et al., RAG-1 and RAG-2, adjacent genes that synergistically activate V(D)J recombination. *Science.* 248: 1517-23 (1990).
Ohmori et al., The enhancing effect of anionic alpha-helical peptide on cationic peptide-mediating transfection systems. *Biochem Biophys Res Commun.* 235: 726-9 (1997).
Paborsky et al., Mammalian cell transient expression of tissue factor for the production of antigen. *Protein Eng.* 3: 547-53 (1990).
Padlan, A possible procedure for reducing the immunogenicity of antibody variable domains while preserving their ligand-binding properties. *Molec. Immun.* 28: 489-98 (1991).
Padlan, Anatomy of the antibody molecule. *Molec. Immun.* 31: 169-217 (1994).
Pandit et al., Three-dimensional structure of dimeric human recombinant macrophage colony-stimulating factor. *Science.* 258: 1358-62 (1992).
Pastan et al., Immunotoxins. *Cell.* 47: 641-8 (1986).
Pinnaduwage et al., Use of a quaternary ammonium detergent in liposome mediated DNA transfection of mouse L-cells. *Biochim. Biophys. Acta.* 985: 33-7 (1989).
Pluckthun, The Pharmacology of Monoclonal Antibodies, Springer-Verlag, N.Y. 1-13: 269-315 (1994).
Pollard et al., Polyethylenimine by not cationic lipids promotes transgene delivery to the nucleus in mammalian cells. *J. Biol. Chem.* 273: 7507-11 (1998).
Powles et al., The inhibition by aspirin and indomethacin of osteolytic tumour deposits and hypercalcaemia in rats with walker tumous, and its possible application to human breast cancer. *Br. J. Cancer.* 28: 316-21 (1972).
Presta et al., Engineering therapeutic antibodies for improved function. *Biochem. Soc. Trans.* 30: 487-90 (2001).
Price, Production and characterization of synthetic peptide-derived antibodies. Monoclonal Antibodies: Production, Engineering and Clinical Application. Cambridge University Press. 60-84 (1995).
Reyes et al., Expression of human beta-interferon cDNA under the control of a thymidine kinase promoter from herpes simplex virus. *Nature* 297: 598-601 (1982).
Riechmann et al., Reshaping human antibodies for therapy. *Nature.* 332: 323-7 (1988).

(56) References Cited

OTHER PUBLICATIONS

Rose et al., A new cationic liposome reagent mediating nearly quantitative transfection of animal cells. *Biotechnique*. 10: 520-5 (1991).
Roth et al., VDJ recombination: a transposase goes to work. *Cell*. 94: 411-4 (1998).
Sarmay et al., Mapping and comparison of the interaction sites on the Fc region of IgG responsible for triggering antibody dependent cellular cytotoxicity (ADCC) through different types of human Fc gamma receptor. *Molec. Immunol*. 29: 633-9 (1992).
Sasaki et al., Angiogenesis inhibitor TNP-470 inhibits human breast cancer osteolytic bone metastasis in nude mice through the reduction of bone resorption. *Cancer Res*. 58: 462-7 (1998).
Sasaki et al., Bisphosphonate risedronate reduces metastatic human breast cancer burden in bone in nude mice. *Cancer Res*. 55: 3551-7 (1995).
Scatchard et al., The attractions of proteins for small molecules and ions. *Ann. NY Acad Sci. USA*. 51: 660 (1949).
Schmidt et al., A bivalent single-chain antibody-toxin specific for ErbB-2 and the EGF receptor. *Int. J. Cancer*. 65: 538-46 (1996).
Schuurman et al., The inter-heavy chain disulfide bonds of IgG4 are in equilibrium with intra-chain disulfide bonds. *Mol. Immunol*. 38: 1-8 (2001).
Shalaby et al., Development of humanized bispecific antibodies reactive with cytotoxic lymphocytes and tumor calls overexpressing the HER2 protooncogene. *J. Exp. Med*. 175: 217-25 (1992).
Shields et al., High resolution mapping of the binding site on human IgG1 for Fc gamma RI, Fc gamma RII, Fc gamma RIII, and FcRn and design of IgG1 variants with improved binding to the Fc gamma R. *J. Biol. Chem*. 276: 6591-04 (2001).
Shih et al., A fluorouridine-anti-CEA immunoconjugate is therapeutically effective in a human colonic cancer xenograft model. *Int. J. Cancer*. 46: 1101-6 (1990).
Shih et al., Site-specific linkage of methotrexate to monoclonal antibodies using an intermediate carrier. *Int J. Cancer*. 41: 832-9 (1988).
Shopes et al., A genetically engineered human IgG mutant with enhanced cytolytic activity. *J. Immunol*. 148: 2918-22 (1992).
Skerra et al., Assembly of a functional immunoglobulin Fv fragment in *Escherichia coli*. *Science* 240: 1038-41 (1988).
Smith et al., The role of colony-stimulating factor 1 and its receptor in the etiopathogenesis of endometrial adenocarcinoma. *Clin. Cancer Res*. 1: 313-25 (1995).
Sojar et al., A chemical method for the deglycosylation of proteins. *Arch. Biochem. Biophys*. 259: 52-7 (1987).
Steplewski et al., Biological activity of human-mouse IgG1, IgG2, IgG3, and IgG4 chimeric monoclonal antibodies with antitumor specificity. *Proc. Natl. Acad. Sci. USA*. 85: 4852-6 (1988).
Sternberger, et al., The unlabeled antibody enzyme method of immunohistochemistry: preparation and properties of soluble antigen-antibody complex (horseradish peroxidase-antihorseradish peroxidase) and its use in identification of spirochetes. *J. Histochem. Cytochem*. 18: 315-33 (1970).
Stevenson et al., A chimeric antibody with dual Fc regions (bisFabFc) prepared by manipulations at the IgG hinge. *Anticancer Drug Des*. 3: 219-30 (1989).
Stinchcomb et al., Isolation and characterisation of a yeast chromosomal replicator. *Nature*. 282: 39-43 (1979).
Studnicka et al., Human-engineered monoclonal antibodies retain full specific binding activity by preserving non-CDR complementarity-modulating residues. *Protein Eng*. 7: 805-14 (1994).
Suda et al., Modulation of osteoclast differentiation. *Endocr. Rev*. 13: 66-80 (1992).
Thotakura et al., Enzymatic deglycosylation of glycoproteins. *Meth. Enzymol*. 138: 350-9 (1987).
Tutt et al., Trispecific F(ab')3 derivatives that use cooperative signaling via the TCR/CD3 complex and CD2 to activate and redirect resting cytotoxic T cells. *J. Immunol*. 147: 60-9 (1991).
Vallera et al., Anti-graft-versus-host disease effect of DT390-anti-CD3sFv, a single-chain Fv fusion immunotoxin specifically targeting the CD3 epsilon moiety of the T-cell receptor. *Blood*. 88: 2342-53 (1996).
Van den Berg, Kluyveromyces as a host for heterologous gene expression: expression and secretion of prochymosin. *Bio/Technology*. 8: 135-9 (1991).
Verhoeyen et al., Reshaping human antibodies: grafting an antilysozyme activity. *Science*. 239: 1534-6 (1988).
Verma, Gene therapy. *Sci. Am*. 263: 68-84 (1990).
Vitetta et al., Redesigning nature's poisons to create anti-tumor reagents. *Science* 238: 1098-104 (1987).
Walker, Bone resorption restored in osteopetrotic mice by transplants of normal bone marrow and spleen cells. *Science*. 190: 784-5 (1975).
Walker, Osteopetrosis cured by temporary parabiosis. *Science*. 180: 875 (1973).
Walker, Spleen cells transmit osteopetrosis in mice. *Science*. 190: 785-7 (1975).
Watkins, Screening of phage-expressed antibody libraries by capture lift. *Methods in Molecular Biology, Antibody Phage Display: Methods and Protocols*. 178: 187-193, 2002.
Wels et al., EGF receptor and p185erbB-2-specific single-chain antibody toxins differ in their cell-killing activity on tumor cells expressing both receptor proteins. *Int. J. Cancer*. 60: 137-44 (1995).
Wiktor-Jedrzejczak et al., Total absence of colony-stimulating factor 1 in the macrophage-deficient osteopetrotic (op/op) mouse. *Proc. Natl. Acad. Sci. USA*. 87: 4828-32 (1990).
Wilman, Prodrugs in cancer chemotherapy. *Biochem. Soc. Trans*. 14: 375-82 615th Meeting Belfast (1986).
Winter et al., Making antibodies by phage display technology. *Annu. Rev. Immunol*. 12: 433-55 (1994).
Wolff et al., Monoclonal antibody homodimers: enhanced antitumor activity in nude mice. *Cancer Res*. 53: 2560-5 (1993).
Wong et al., TRANCE (tumor necrosis factor [TNF]-related activation-induced cytokine), a new TNF family member predominantly expressed in T cells, is a dendritic cell-specific survival factor. *J. Exp. Med*. 186: 2075-80 (1997).
Wong et al., TRANCE is a novel ligand of the tumor necrosis factor receptor family that activates c-Jun N-terminal kinase in T cells. *J. Biol. Chem*. 272: 25190-4 (1997).
Xu et al., Residue at position 331 in the IgG1 and IgG4 CH2 domains contributes to their differential ability to bind and activate complement. *J. Biol. Chem*. 269: 3469-74 (1994).
Yang et al., A genetically engineered fusion protein M4/TNF with increased bifunctional activity refolded in the presence of protein disulfide isomerase. *Hum. Antibodies Hybridomas*. 6: 129-36 (1995).
Yaniv et al., Enhancing elements for activation of eukaryotic promoters. *Nature*. 297: 17-8 (1982).
Yasuda et al., Identity of osteoclastogenesis inhibitory factor (OCIF) and osteoprotegerin (OPG): a mechanism by which OPG/OCIF inhibits osteoclastogenesis in vitro. *Endocrinology*. 139: 1329-37 (1998).
Yasuda et al., Osteoclast differentiation factor is a ligand for osteoprotegerin/osteoclastogenesis-inhibitory factor and is identical to TRANCE/RANKL. *Proc. Natl. Acad. Sci. USA*. 95: 3597-602 (1998).
Yi et al., Tumor-derived platelet-derived growth factor-BB plays a critical role in osteosclerotic bone metastasis in an animal model of human breast cancer. *Cancer Res*. 62: 917-23 (2002).
Yin et al., TGF-beta signaling blockade inhibits PTHrP secretion by breast cancer cells and bone metastases development. *J. Clin. Invest*. 103: 197-206 (1999).
Yoneda et al., Inhibition of osteolytic bone metastasis of breast cancer by combined treatment with the bisphosphonate ibandronate and tissue inhibitor of the matrix metalloproteinase-2. *J. Clin. Invest*. 99: 2509-17 (1997).
Yoshida et al., The murine mutation osteopetrosis is in the coding region of the macrophage colony stimulating factor gene. *Nature*. 345: 442-4 (1990).

(56) References Cited

OTHER PUBLICATIONS

Yu et al., Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells. *Int. J. Cancer*. 56: 244-8 (1994).
Zapata et al., Engineering linear F(ab')2 fragments for efficient production in *Escherichia coli* and enhanced antiproliferative activity. *Protein Eng*. 8: 1057-62 (1995).

Zhou et al., Lipophilic polylysines mediate efficient DNA transduction in mammalian cells. *Biochim. Biophys. Acta*. 939: 8-18 (1991).

International Search Report and Written Opinion, PCT/US2006/029279, Feb. 15, 2007.

International Preliminary Report on Patentability, PCT/US2006/029279, Feb. 15, 2007.

* cited by examiner

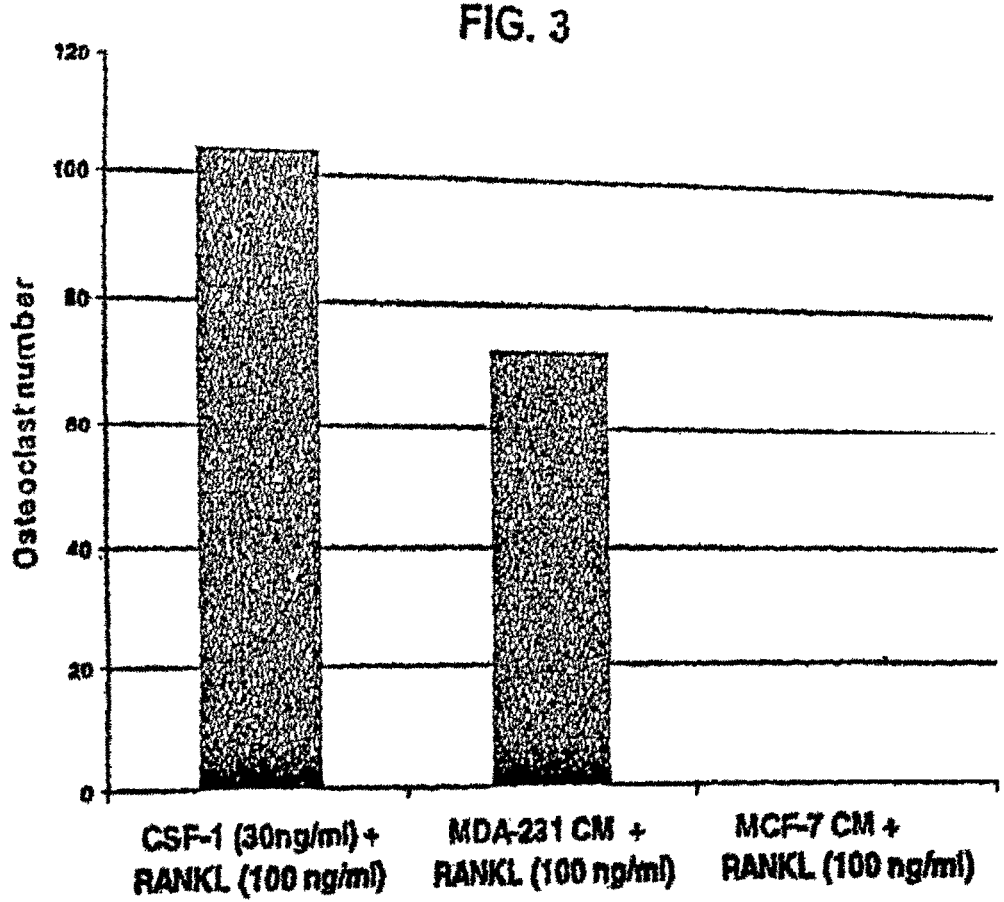

Fig. 4A

RX1 Light chain amino acid sequence:

1                                            2
DILLTQSPAILSVSPGERVSFSCRASQSIGTSIHWYQQRTNGSPRLILIKYASESISGIPSRFSGSGSGTDFTLSINSVESEDIADYCCQQINSWPTTFGGGTKLEIKRADAAPTVSIFPPSSE
                                                                                           3
QLTSGGASVVCFLNNFYPKDINVKWKIDGSERQNGVLNSWTDQDSKDSTYSMSSTLTLTKDEYERHNSYTCEATHKTSTSPIVKSFNRNEC

RX1 Heavy Chain amino acid sequence:
                                                                                                 6
DVQLQESGPGLVKPSQSLSLTCTVTDYSITSDYAWNWIRQFPGNKLEWMGYISYSGSTSYNPSLKSRISITRDTSKNQFFLQLNSVTTEDTATYYCASFDYAHAMDYWGQGTSVTVSSAKTTA
                              4                             5
PSVYPLAPVCGDTTGSSVTLGCLVKGYFPEPVTLTWNSGSLSSGVHTFPAVLQSDLYTLSSSVTVTSSTWPSQSITCNVAHPASSTKVDKKIEPRGPTIKPCPPCKCPAPNLLGGPSVFIFPP
KIKDVLMISLSPIVTCVVVDVSEDDPDVQISWFVNNVEVHTAQTQTHREDYNSTLRVVSALPIQHQDWMSGKEFKCKVNNKDLPAPIERTISKPKGSVRAPQVYVLPPPEEEMTKKQVTLTCM
VTDFMPEDIYVEWTNNGKTELNYKNTEPVLDSDGSYFMYSKLRVEKKNWVERNSYSCSVVHEGLHNHhttKSFSRTPG RX1 heavy chain nucleotide sequence:

atggtggtcctgtatcatcctattcctggccactgccacaggtgtgcactccgacgtgcagcttcaggagtcaggacctggcctgtgaaacctcagatgtctgtcctcacctgt
actgtcactgactactccatcaccagtgattacgctgaactggataggcaattcccaggagttcaggtacatagctacagtggtagcacttcctacaatcatct
ctcaaaagtcgatcgatccaatcactctgagacacagttcttccgcaaaacaacagcccatgtctgactgtcatcttcgactgactctagatgc
atgattactgggtatttcctgagccaggactccctgagccagcagtcagtccctcacctcactgacctcgtcgttgtcgtacacccctcagagctcagtg
ctgtcaaggtgtatttccctgagcagcaccctaacctctggtgtgaccagtcctatcctgggtgccaaagatccaagatgtactcctcatagcacactgtgtgtggatgtgagc
actgtaacctgcccagcaccactcctgggtgaccatcgtttcatctcctcccaaagatgtactcactgaggatgtactcatctcgggtgaggtgcaacatgtggtggtccctcat
cagcaccaagactgtgatgagtgagaggatcagctgttgtcaaagaccctcccagctccatccaaaccatctcgaagaaccatctcaaaaccccaaaaggtcagttgaccttgtcagtcgtaaacagagctaaac
tacagaaccactgaaccagtctggcgactgaaccaactgactgactggtgaaagaaatagctactctgttcagtgtccagaggt
ctgcacaatcaccacgactaagagcttctcccgactccggta aa RX1 light chain nucleotide sequence:

atggtatccacacctcagttcctgtattttgtttgcttggacactcgcagcctcagagaggtgacatctgctgactcagtctccagcctccctggtctgtgagtcccaggagaaagagtcagttgtc
tcctgcagggccagtcagagcattggcacagcatactgttcctccaaggctgtcagtatcgtgagtctatctgtgagtctaaagtatgctctgactccttccagttt
agtcagtggatcaggacagttctactcttgcatcaactgtgagctgaaatgcagattactggtatgagcagtttaaatcatcggagcagttacatctggaggtgcctcagtgtgtgctcttgaacactctaccccaaaaagaatc
ttggaaataaacgggctgatgctgcacaatctgatcctcccaactgtcccagtgagcagttaacatctggaggtgcctcagtgtgtgcttctgcagacagaggacactagcaagcatagcagcacctcagcaagcaacattctacccaaaagacatc
aatgtcaagtggaagattgatggcagtgaacgacaaattggacttggactgatcaagacagcaaagacacctacagtagcatgagctgctacagtgaaaaggctcagtcatagcatctgctacccaccctcacctttgaccaggacacagccaaggac
tgaacgactataacagctatacctgtgaggccactcacgagcacttccccattgtcaagagcttcaacaggaatgagtgt

FIG. 4B

CHIR-R1X Light Chain Risk Assignments

| V-Region | Amino Acids 1-52 |
|---|---|
| Risk | LHLHLHLMLHLHLMLLMHHHHHHHHHMHLMLLMHHHHHHH |
| Mouse | DILLTQSPAILSVSPGERVSFSCRASQSIGTSIH----WYQQRTNGSPRLLIKYAS |

| V-Region | Amino Acids 53-109 |
|---|---|
| Risk | HLMMLHMLMHLHLHLHLLHLLHLHHHHHHHHHHHHHHHHHHHHHHLHLLHLLLLL |
| Mouse | ESISGIPSRFSGSGSGTDFTLSINSVESEDIADYYCQQINSWPT------TFGGGTKLEI-KRA |

FIG. 4C

CHIR-RX1 Heavy Chain Risk Assignments

| V-Region | | |
|---|---|---|
| Risk | MHLHLHLHLHMLLMLLLHLHLHLHMHHHHHHHHMHLMLLMHHHHHHHHHHHHH | Amino Acids 1-57 |
| Mouse | DVQLQESGPGLVKPSQSLSLTCTVTDYSITSDYAWN-WIRQFPGNKLEWMGYIS---YSGST | |

| V-Region | | |
|---|---|---|
| Risk | HMHMHMHMLMHLHLHLHLMLLMLLHLHLLHLHLLHLHLMHHHHHHHHHHHHHHHHHHLHLHLLL | Amino Acids 58-113 |
| Mouse | SYNPSLKSRISITRDTSKNQFFLQLNSVTTEDTATYYCASFDYAHAM--------DYWGQGTSVTVSS | |

FIG. 5B
MC1 Neutralizes human MCSF activity
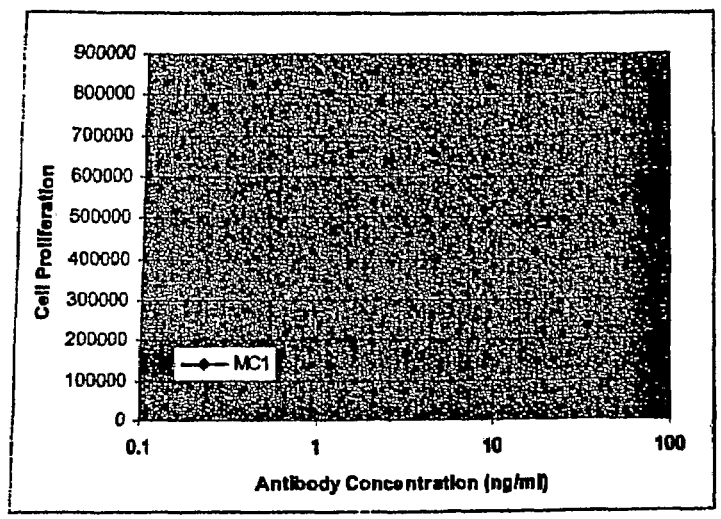
MC3 Neutralizes human MCSF activity
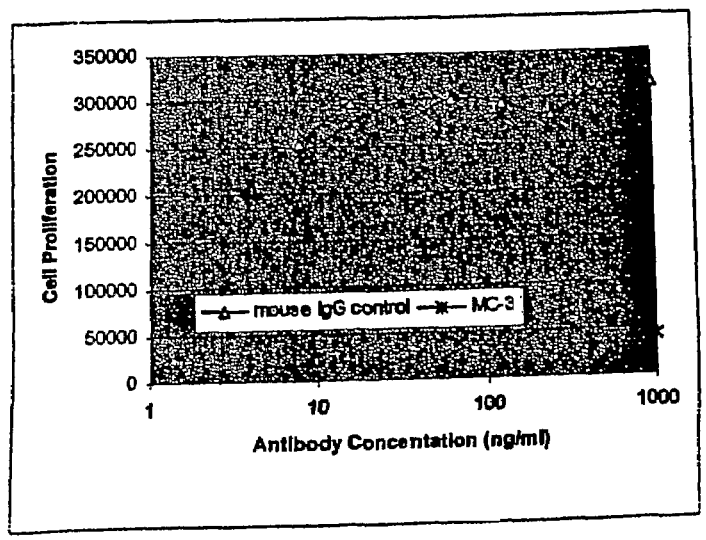

Binding of MCSF-specific antibody to breast cancer cell line MDA231

Red: no antibody control
Black: M-CSF antibody 1 ug/ml
Green: M-CSF antibody 10 ug/ml
Blue: M-CSF antibody 50 ug/ml Binding of MCSF-specific antibody to multiple myeloma cancer cell line ARH77

Red: no antibody control
Green: M-CSF antibody 5 ug/ml
Blue: control IgG2a 5 ug/ml

FIG. 9

| Cancer Type | Cancer Status | Score 0 | Score 1 | Score 2 | Score 3 | Score 4 | % with scores 3 or higher |
|---|---|---|---|---|---|---|---|
| adrenal | normal | 10 | 5 | 5 | 0 | 0 | 0 |
| basal cell | cancer | 5 | 0 | 0 | 0 | 0 | 0 |
| bladder | normal | 6 | 1 | 2 | 1 | 0 | 10 |
| brain | normal | 17 | 1 | 2 | 0 | 0 | 0 |
| breast | cancer | 6 | 5 | 13 | 62 | 0 | 72 |
| breast | normal | 7 | 5 | 7 | 6 | 0 | 24 |
| carcinoids | cancer | 9 | 2 | 2 | 0 | 0 | 0 |
| carcinoids (muscle) | cancer | 1 | 0 | 1 | 0 | 0 | 0 |
| choriocarcinoma | cancer | 1 | 0 | 0 | 0 | 0 | 0 |
| colon | normal | 4 | 0 | 2 | 0 | 0 | 0 |
| colon | cancer | 9 | 0 | 1 | 4 | 0 | 27 |
| fibrosarcoma | cancer | 3 | 1 | 0 | 0 | 0 | 0 |
| gallbladder | normal | 2 | 1 | 0 | 1 | 0 | 25 |
| germ cell | cancer | 1 | 0 | 0 | 0 | 0 | 0 |
| heart | normal | 7 | 3 | 2 | 4 | 0 | 25 |
| kidney | normal | 5 | 10 | 1 | 4 | 0 | 20 |
| kidney | cancer | 8 | 1 | 0 | 3 | 0 | 25 |
| leiomyosarcoma | cancer | 5 | 0 | 0 | 0 | 0 | 0 |
| liver | normal | 11 | 3 | 4 | 1 | 0 | 5 |
| liver | cancer | 5 | 3 | 0 | 3 | 0 | 27 |
| lung | normal | 19 | 0 | 1 | 0 | 0 | 0 |
| lung | cancer | 3 | 1 | 0 | 3 | 0 | 43 |
| lymphoma | cancer | 13 | 0 | 3 | 2 | 0 | 12 |
| melanoma | cancer | 7 | 0 | 2 | 5 | 0 | 36 |
| melanoma (inflammation) | cancer | 0 | 0 | 0 | 1 | 0 | 100 |
| mesothelioma | cancer | 6 | 0 | 0 | 0 | 0 | 0 |
| neuroblastoma | cancer | 1 | 0 | 0 | 0 | 0 | 0 |
| ovary | normal | 6 | 0 | 2 | 0 | 0 | 0 |
| ovary | cancer | 8 | 2 | 0 | 4 | 0 | 29 |
| pancreas | normal | 9 | 2 | 5 | 4 | 0 | 20 |
| pancreas | cancer | 8 | 1 | 0 | 3 | 0 | 25 |
| prostate | normal | 0 | 3 | 8 | 3 | 0 | 21 |
| prostate | cancer | 9 | 1 | 1 | 4 | 0 | 27 |
| sarcoma all | cancer | 6 | 0 | 2 | 2 | 0 | 20 |
| sarcoma | cancer | 3 | 0 | 2 | 1 | 0 | 17 |
| sarcoma (kidney) | cancer | 3 | 0 | 2 | 1 | 0 | 17 |
| sarcoma mm | cancer | 2 | 0 | 0 | 0 | 0 | 0 |
| seminoma | cancer | 3 | 0 | 0 | 0 | 0 | 0 |
| small intestine | normal | 2 | 1 | 0 | 1 | 0 | 25 |
| spleen | normal | 14 | 2 | 3 | 0 | 0 | 0 |
| squamous cell | cancer | 3 | 0 | 0 | 0 | 0 | 0 |
| stomach | normal | 3 | 2 | 2 | 1 | 0 | 13 |
| stomach | cancer | 7 | 1 | 1 | 1 | 0 | 10 |
| teratoma | cancer | 1 | 0 | 0 | 0 | 0 | 0 |
| testis | normal | 5 | 1 | 3 | 3 | 0 | 25 |
| thyroid | normal | 15 | 0 | 0 | 0 | 0 | 0 |
| thyroid | cancer | 6 | 2 | 1 | 2 | 0 | 18 |
| undiff all | cancer | 6 | 0 | 2 | 1 | 0 | 11 |
| undif | cancer | 5 | 0 | 2 | 0 | 0 | 0 |

Fig. 10

Met Thr Ala Pro Gly Ala Ala Gly Arg Cys Pro Pro Thr Thr Trp Leu
1              5                    10              15

Gly Ser Leu Leu Leu Leu Val Cys Leu Leu Ala Ser Arg Ser Ile Thr
            20              25              30

Glu Glu Val Ser Glu Tyr Cys Ser His Met Ile Gly Ser Gly His Leu
        35              40              45

Gln Ser Leu Gln Arg Leu Ile Asp Ser Gln Met Glu Thr Ser Cys Gln
    50              55              60

Ile Thr Phe Glu Phe Val Asp Gln Glu Gln Leu Lys Asp Pro Val Cys
65              70              75              80

Tyr Leu Lys Lys Ala Phe Leu Leu Val Gln Asp Ile Met Glu Asp Thr
            85              90              95

Met Arg Phe Arg Asp Asn Thr Pro Asn Ala Ile Ala Ile Val Gln Leu
            100             105             110

Gln Glu Leu Ser Leu Arg Leu Lys Ser Cys Phe Thr Lys Asp Tyr Glu
        115             120             125

Glu His Asp Lys Ala Cys Val Arg Thr Phe Tyr Glu Thr Pro Leu Gln
    130             135             140

Leu Leu Glu Lys Val Lys Asn Val Phe Asn Glu Thr Lys Asn Leu Leu
145             150             155             160

Asp Lys Asp Trp Asn Ile Phe Ser Lys Asn Cys Asn Asn Ser Phe Ala
            165             170             175

Glu Cys Ser Ser Gln Gly His Glu Arg Gln Ser Glu Gly Ser Ser Ser
            180             185             190

Pro Gln Leu Gln Glu Ser Val Phe His Leu Leu Val Pro Ser Val Ile
        195             200             205

Leu Val Leu Leu Ala Val Gly Gly Leu Leu Phe Tyr Arg Trp Arg Arg
        210             215             220

Arg Ser His Gln Glu Pro Gln Arg Ala Asp Ser Pro Leu Glu Gln Pro
225             230             235             240

Glu Gly Ser Pro Leu Thr Gln Asp Asp Arg Gln Val Glu Leu Pro Val
            245             250             255

Fig. 11

```
Met Thr Ala Pro Gly Ala Ala Gly Arg Cys Pro Pro Thr Thr Trp Leu
1               5               10              15
Gly Ser Leu Leu Leu Leu Val Cys Leu Leu Ala Ser Arg Ser Ile Thr
            20              25              30
Glu Glu Val Ser Glu Tyr Cys Ser His Met Ile Gly Ser Gly His Leu
            35              40              45
Gln Ser Leu Gln Arg Leu Ile Asp Ser Gln Met Glu Thr Ser Cys Gln
        50              55              60
Ile Thr Phe Glu Phe Val Asp Gln Glu Gln Leu Lys Asp Pro Val Cys
65              70              75              80
Tyr Leu Lys Lys Ala Phe Leu Leu Val Gln Asp Ile Met Glu Asp Thr
                85              90              95
Met Arg Phe Arg Asp Asn Thr Pro Asn Ala Ile Ala Ile Val Gln Leu
            100             105             110
Gln Glu Leu Ser Leu Arg Leu Lys Ser Cys Phe Thr Lys Asp Tyr Glu
        115             120             125
Glu His Asp Lys Ala Cys Val Arg Thr Phe Tyr Glu Thr Pro Leu Gln
        130             135             140
Leu Leu Glu Lys Val Lys Asn Val Phe Asn Glu Thr Lys Asn Leu Leu
145             150             155             160
Asp Lys Asp Trp Asn Ile Phe Ser Lys Asn Cys Asn Asn Ser Phe Ala
                165             170             175
Glu Cys Ser Ser Gln Asp Val Val Thr Lys Pro Asp Cys Asn Cys Leu
            180             185             190
Tyr Pro Lys Ala Ile Pro Ser Ser Asp Pro Ala Ser Val Ser Pro His
        195             200             205
Gln Pro Leu Ala Pro Ser Met Ala Pro Val Ala Gly Leu Thr Trp Glu
    210             215             220
Asp Ser Glu Gly Thr Glu Gly Ser Ser Leu Leu Pro Gly Glu Gln Pro
225             230             235             240
Leu His Thr Val Asp Pro Gly Ser Ala Lys Gln Arg Pro Pro Arg Ser
            245             250             255
Thr Cys Gln Ser Phe Glu Pro Pro Glu Thr Pro Val Val Lys Asp Ser
        260             265             270
Thr Ile Gly Gly Ser Pro Gln Pro Arg Pro Ser Val Gly Ala Phe Asn
    275             280             285
Pro Gly Met Glu Asp Ile Leu Asp Ser Ala Met Gly Thr Asn Trp Val
290             295             300
Pro Glu Glu Ala Ser Gly Glu Ala Ser Glu Ile Pro Val Pro Gln Gly
305             310             315             320
Thr Glu Leu Ser Pro Ser Arg Pro Gly Gly Gly Ser Met Gln Thr Glu
            325             330             335
Pro Ala Arg Pro Ser Asn Phe Leu Ser Ala Ser Ser Pro Leu Pro Ala
            340             345             350
Ser Ala Lys Gly Gln Gln Pro Ala Asp Val Thr Gly Thr Ala Leu Pro
            355             360             365
Arg Val Gly Pro Val Arg Pro Thr Gly Gln Asp Trp Asn His Thr Pro
370             375             380
Gln Lys Thr Asp His Pro Ser Ala Leu Leu Arg Asp Pro Pro Glu Pro
385             390             395             400
Gly Ser Pro Arg Ile Ser Ser Leu Arg Pro Gln Gly Leu Ser Asn Pro
            405             410             415
Ser Thr Leu Ser Ala Gln Pro Gln Leu Ser Arg Ser His Ser Ser Gly
            420             425             430
Ser Val Leu Pro Leu Gly Glu Leu Glu Gly Arg Arg Ser Thr Arg Asp
            435             440             445
Arg Arg Ser Pro Ala Glu Pro Glu Gly Gly Pro Ala Ser Glu Gly Ala
450             455             460
Ala Arg Pro Leu Pro Arg Phe Asn Ser Val Pro Leu Thr Asp Thr Gly
465             470             475             480
His Glu Arg Gln Ser Glu Gly Ser Ser Ser Pro Gln Leu Gln Glu Ser
            485             490             495
Val Phe His Leu Leu Val Pro Ser Val Ile Leu Val Leu Leu Ala Val
            500             505             510
Gly Gly Leu Leu Phe Tyr Arg Trp Arg Arg Ser His Gln Glu Pro
            515             520             525
Gln Arg Ala Asp Ser Pro Leu Glu Gln Pro Glu Gly Ser Pro Leu Thr
530             535             540
Gln Asp Asp Arg Gln Val Glu Leu Pro Val
```

Fig. 12

```
Met Thr Ala Pro Gly Ala Ala Gly Arg Cys Pro Pro Thr Thr Trp Leu
1             5                   10                  15
Gly Ser Leu Leu Leu Leu Val Cys Leu Leu Ala Ser Arg Ser Ile Thr
            20                  25                  30
Glu Glu Val Ser Glu Tyr Cys Ser His Met Ile Gly Ser Gly His Leu
        35                  40                  45
Gln Ser Leu Gln Arg Leu Ile Asp Ser Gln Met Glu Thr Ser Cys Gln
    50                  55                  60
Ile Thr Phe Glu Phe Val Asp Gln Glu Gln Leu Lys Asp Pro Val Cys
65                  70                  75                  80
Tyr Leu Lys Lys Ala Phe Leu Leu Val Gln Asp Ile Met Glu Asp Thr
            85                  90                  95
Met Arg Phe Arg Asp Asn Thr Pro Asn Ala Ile Ala Ile Val Gln Leu
            100                 105                 110
Gln Glu Leu Ser Leu Arg Leu Lys Ser Cys Phe Thr Lys Asp Tyr Glu
        115                 120                 125
Glu His Asp Lys Ala Cys Val Arg Thr Phe Tyr Glu Thr Pro Leu Gln
    130                 135                 140
Leu Leu Glu Lys Val Lys Asn Val Phe Asn Glu Thr Lys Asn Leu Leu
145                 150                 155                 160
Asp Lys Asp Trp Asn Ile Phe Ser Lys Asn Cys Asn Asn Ser Phe Ala
            165                 170                 175
Glu Cys Ser Ser Gln Asp Val Val Thr Lys Pro Asp Cys Asn Cys Leu
            180                 185                 190
Tyr Pro Lys Ala Ile Pro Ser Ser Asp Pro Ala Ser Val Ser Pro His
        195                 200                 205
Gln Pro Leu Ala Pro Ser Met Ala Pro Val Ala Gly Leu Thr Trp Glu
    210                 215                 220
Asp Ser Glu Gly Thr Glu Gly Ser Ser Leu Leu Pro Gly Glu Gln Pro
225                 230                 235                 240
Leu His Thr Val Asp Pro Gly Ser Ala Lys Gln Arg Pro Pro Arg Ser
            245                 250                 255
Thr Cys Gln Ser Phe Glu Pro Pro Glu Thr Pro Val Val Lys Asp Ser
            260                 265                 270
Thr Ile Gly Gly Ser Pro Gln Pro Arg Pro Ser Val Gly Ala Phe Asn
        275                 280                 285
Pro Gly Met Glu Asp Ile Leu Asp Ser Ala Met Gly Thr Asn Trp Val
    290                 295                 300
Pro Glu Glu Ala Ser Gly Glu Ala Ser Glu Ile Pro Val Pro Gln Gly
305                 310                 315                 320
Thr Glu Leu Ser Pro Ser Arg Pro Gly Gly Gly Ser Met Gln Thr Glu
            325                 330                 335
Pro Ala Arg Pro Ser Asn Phe Leu Ser Ala Ser Ser Pro Leu Pro Ala
            340                 345                 350
Ser Ala Lys Gly Gln Gln Pro Ala Asp Val Thr Gly His Glu Arg Gln
        355                 360                 365
Ser Glu Gly Ser Ser Ser Pro Gln Leu Gln Glu Ser Val Phe His Leu
    370                 375                 380
Leu Val Pro Ser Val Ile Leu Val Leu Leu Ala Val Gly Gly Leu Leu
385                 390                 395                 400
Phe Tyr Arg Trp Arg Arg Arg Ser His Gln Glu Pro Gln Arg Ala Asp
            405                 410                 415
Ser Pro Leu Glu Gln Pro Glu Gly Ser Pro Leu Thr Gln Asp Asp Arg
            420                 425                 430
Gln Val Glu Leu Pro Val
```

FIG. 13

5H4 heavy chain protein sequence:

```
  1   EIQLQQSGPE  LVKTGTSVKI  SCKASGYSFT  GYFMHWVKQS  HGKSLEWIGY
 51   ISCYNGDTNY  NQNFKGKATF  TVDTSSSTAY  MQFNSLTSED  SAVYYCAREG
101   GNYPAYWGQG  TLVTVSAAKT  TPPSVYPLAP  GSAAQTNSMV  TLGCLVKGYF
151   PEPVTVTWNS  GSLSSGVHTF  PAVLQSDLYT  LSSSVTVPSS  TWPSETVTCN
201   VAHPASSTKV  DKKIVPRDCG  CKPCICTVPE  VSSVFIFPPK  PKDVLTITLT
251   PKVTCVVVDI  SKDDPEVQFS  WFVDDVEVHT  AQTQPREEQF  NSTFRSVSEL
301   PIMHQDWLNG  KEFKCRVNSA  AFPAPIEKTI  SKTKGRPKAP  QVYTIPPPKE
351   QMAKDKVSLT  CMITDFFPED  ITVEWQWNGQ  PAENYKNTQP  IMDTDGSYFV
401   YSKLNVQKSN  WEAGNTFTCS  VLHEGLHNHH  TEKSLSHSPG  K
```

5H4 light chain protein sequence:

```
  1   DIVMTQSHKF  MSTSVGDRVT  ITCKASQNVG  TAVTWYQQKP  GQSPKLLIYW
 51   TSTRHAGVPD  RFTGSGSGTD  FTLTISDVQS  EDLADYFCQQ  YSSYPLTFGA
101   GTKLELKRAD  AAPTVSIFPP  SSEQLTSGGA  SVVCFLNNFY  PKDINVKWKI
151   DGSERQNGVL  NSWTDQDSKD  STYSMSSTLT  LTKDEYERHN  SYTCEATHKT
201   STSPIVKSFN  RNEC
```

FIG. 14

MC-1 heavy chain protein sequence:

```
  1  EVKLVESGGG LVQPGGSLKL SCATSGFTFS DYYMYWVRQT PEKRLEWVAY
 51  ISNGGGSTYY PDTVKGRFTI SRDNAKNTLY LQMSRLKSED TAMYYCARQG
101  SYGYPFAYWG QGTLVTVSAA KTTAPSVYPL APVCGDTTGS SVTLGCLVKG
151  YFPEPVTLTW NSGSLSSGVH TFPAVLQSDL YTLSSSVTVT SSTWPSQSIT
201  CNVAHPASST KVDKKIEPRG PTIKPCPPCK CPAPNLLGGP SVFIFPPKIK
251  DVLMISLSPI VTCVVVDVSE DDPDVQISWF VNNVEVHTAQ TQTHREDYNS
301  TLRVVSALPI QHQDWMSGKE FKCKVNNKDL PAPIERTISK PKGSVRAPQV
351  YVLPPPEEEM TKKQVTLTCM VTDFMPEDIY VEWTNNGKTE LNYKNTEPVL
401  DSDGSYFMYS KLRVEKKNWV ERNSYSCSVV HEGLHNHHTT KSFSRTPGK
```

MC-1 light chain protein sequence:

```
  1  AIQMTQTTSS LSASLGDRVT ISCSASQGIS NYLNWYQQKP DGTVKLLIYY
 51  TSSLHSGVPS RFSGSGSGTD YSLTISNLEP EDIATYYCQQ YSKLPWTFGG
101  GTKLEIKRAD AAPTVSIFPP SSEQLTSGGA SVVCFLNNFY PKDINVKWKI
151  DGSERQNGVL NSWTDQDSKD STYSMSSTLT LTKDEYERHN SYTCEATHKT
201  STSPIVKSFN RNEC
```

FIG. 15

MC-3 heavy chain protein sequence:

```
  1   DVQLQESGPG LVKPSQSLSL TCTVTGYSIT SDYAWNWIRQ FPGNKLEWMG
 51   YISYSGSTSY NPSLKSRISI TRDTSKNQFF LQLNSVTTED TATYYCARLE
101   TWLFDYWGQG TTLTVSSAKT TPPSVYPLAP GCGDTTGSSV TLGCLVKGYF
151   PESVTVTWNS GSLSSSVHTF PALLQSGLYT MSSSVTVPSS TWPSQTVTCS
201   VAHPASSTTV DKKLEPSGPI STINPCPPCK ECHKCPAPNL EGGPSVFIFP
251   PNIKDVLMIS LTPKVTCVVV DVSEDDPDVQ ISWFVNNVEV HTAQTQTHRE
301   DYNSTIRVVS TLPIQHQDWM SGKEFKCKVN NKDLPSPIER TISKIKGLVR
351   APQVYILPPP AEQLSRKDVS LTCLVVGFNP GDISVEWTSN GHTEENYKDT
401   APVLDSDGSY FIYSKLNMKT SKWEKTDSFS CNVRHEGLKN YYLKKTISRS
451   PGLDLDDICA EAKDGELDGL WTTITIFISL FLLSVCYSAS VTLFKVKWIF
501   SSVVELKQKI SPDYRNMIGQ GA
```

MC-3 light chain protein sequence:

```
  1   DILLTQSPAI LSVSPGERVS FSCRASQSIG TSIHWYQQRT NGSPRLLIKY
 51   ASESISGIPS RFSGSGSGTD FTLSINSVES EDIADYYCQQ SNSWPTTFGG
101   GTKLEIKWAD AAPTVSIFPP SSEQLTSGGA SVVCFLNNFY PKDINVKWKI
151   DGSERQNGVL NSWTDQDSKD STYSMSSTLT LTKDEYERHN SYTCEATHKT
201   STSPIVKSFN RNEC
```

FIG. 16A

For heavy chain CDR1:

```
                          1
    H_CDR1_5H4      (1)  -G YFMH
    H_CDR1_MC-1     (1)  -  YMY
 H_CDR1_CHIR-RX1    (1)
    H_CDR1_MC-3     (1)
       Consensus    (1)  SDYAWN
```

For heavy chain CDR2:

```
                          1               17
    H_CDR2_5H4      (1)  YISC NGDINY QNF G
    H_CDR2_MC-1     (1)  Y SNGGG TY PD  G
 H_CDR2_CHIR-RX1    (1)  YIS- GSTSYNPS K
    H_CDR2_MC-3     (1)  YIS- GSTSYNPS K
       Consensus    (1)  YIS YSGSTSYNPSLKS
```

For heavy chain CDR3:

```
                          1
    H_CDR3_5H4      (1)  -- G NYPA
    H_CDR3_MC-1     (1)  QGS   P A
 H_CDR3_CHIR-RX1    (1)  -F   HAM
    H_CDR3_MC-3     (1)  --LET L
       Consensus    (1)    DYGW FDY
```

FIG. 16B

For light chain CDR1:

```
                           1         11
  L_CDR1_5H4    (1)  RASQN___T
  L_CDR1_MC-1   (1)  SASQG_SNY_N
  L_CDR1_CHIR-RX1 (1) RASQ_____
  L_CDR1_MC-3   (1)  RASQ_____
  Consensus     (1)  RASQSIGTSIH
```

For light chain CDR2:

```
                    1
  L_CDR2_5H4    (1)  _STRH_
  L_CDR2_MC-1   (1)  __SLH_
  L_CDR2_CHIR-RX1 (1) _AS_S_
  L_CDR2_MC-3   (1)  _AS_S_
  Consensus     (1)  YTSESIS
```

For light chain CDR3:

```
                    1
  L_CDR3_5H4    (1)  QQ___L_
  L_CDR3_MC-1   (1)  QQ_KL_W_
  L_CDR3_CHIR-RX1 (1) QQIN_W__
  L_CDR3_MC-3   (1)  QQSN_P__
  Consensus     (1)  QQYSSWPTT
```

Neutralization Activities of Intact mAbs vs. Fabs

MCSF Structure with RX1 Epitopes Highlighted

FIG. 19 A

Heavy Chain

| V-Region | No. of Changes | Amino Acids 1-57 |
|---|---|---|
| Risk | | MHLHLHLHMLLMLLLHLHLHLMHHHHMHLMLLMHMHHHHHHHHHHH |
| Mouse | | DVQLQESGPGLVKPSQSLSLTCTVTDYSITSDYAWN-WIRQFPGNKLEWMGYIS---YSGST |
| Human | | qvqLqesGpgLvkPsqTLsLTCxvsGxsxSsxxxxWiRQpPgkgLEWigxiyyraxxgxt |
| Low Risk | 2 | DVQLQESGPGLVKPSQTLSLTCTVTDYSITSDYAWN-WIRQFPGKKLEWMGYIS---YSGST |
| Low+Mod | 5 | QVQLQESGPGLVKPSQTLSLTCTVSDYSITSDYAWN-WIRQFPGKGLEWMGYIS---YSGST |

| V-Region | No. of Changes | Amino Acids 58-113 |
|---|---|---|
| Risk | | HMHMMMHLHLHLMLLMLHLHLLHLLLLMHHHHHHHHHHHHHHHHHHLHHLHLHLL |
| Mouse | | SYNPSLKSRISITRDTSKNQFFLQLNSVTTEDTATYYCASFDYAHAM-------DYWGQGTSVTVSS |
| Human | | xynpSlksRvTisvDTSKNQfsLxLxsvtaaDTAvYyCArxxxxxxxxxxxxfdxWgGtxVTVSS |
| Low Risk | 6 | SYNPSLKSRITISRDTSKNQFSLQLNSVTAADTATYYCASFDYAHAM-------DYWGQGTTVTVSS |
| Low+Mod | 7 | SYNPSLKSRITISRDTSKNQFSLQLNSVTAADTAVYYCASFDYAHAM-------DYWGQGTTVTVSS |

FIG. 19B

Low Risk Heavy Chain Vs. Kabat Vh2 Consensus:

Protein Seq:

DVQLQESGPGLVKPSQTLSLTCTVTDYSITSDYAWNWIRQFPGKKLEWMGYISYSGSTSYNPSLKSRITISRDTSKNQFSLQLNSVTAADTATYYCASFDYAHAMD
YWGQGTTVTVSS

DNA Seq:

GACGTACAACTTCAAGAATCTGGCCCAGGTCTCGTTCAAACTCTCACTTGTGACTGACTACTCTATTACATCCGACTACGCTT
GGAACTGGATCCGACAATTTCCTGGTAAAAAACTGAATGGGTTATATTCTTACTCTGGCTCCACTTCTTACAATCCTTCTCTGAAATCACGATCAC
AATTTCCCGCGATACCTCTAAAAATCAATTTCACTCAACTCTGTTACCGCGATACTCGTACTGTGCCTCTTTGACTACGGTCACG
CCATGGATTATTGGGGACAGGGTACCGTTACGGTAAGCTCA

Low Risk + Moderate Risk Heavy Chain Vs. Kabat Vh2 Consensus:

Protein Seq:

QVQLQESGPGLVKPSQTLSLTCTVSDYSITSDYAWNWIRQFPGKGLEWMGYISYSGSTSYNPSLKSRITISRDTSKNQFSLQLNSVTAADTAVYYCASFDYAHAMD
YWGQGTTVTVSS

DNA Seq:

CAAGTTCAACTTCAAGAATCAGGCCCCGGACTCGTTAAACCCTCTCAAACTCTCTCTTACTTGCACTGTATCCGATTACTCTATTACTTCAGACTACGCTTG
GAACTGGATCAGACACAATTTCCCGAAAAGGAACTGAATGGATGGGATATATCTTACTCTGGCTCAACCCTCTTCTCAAATCTCGAATAAC
AATCTCACGCGATACTTCTAAAAATCAATTCTCACTTCAACTTAACCCTTACAACCCCTCTCAAACTCTCTCTCTTACTTGCTTGTCTTCCTTCGATTACGCCACG
CTATGGATTATTGGGGACAAGGAACTACCGTCACTGTCAGCTCA

FIG. 20 A

Light Chain

| V-Region | No. of Changes | Amino Acids 1-52 |
|---|---|---|
| Risk | | LHLHLHLHLMLLMLHLMLLLHLHLHLMHHHHHHHHHHHHHHHHHHMHLLMLLMHMHHHHHH |
| Mouse | | DILLTQSPAILSVSPGERVSFSCRASQSIGTSIH----WYQQRTNGSPRLLIKYAS |
| Human | | EIVLTQSPgTLSlSPGERaTLSCRASQSvsssyL---AWYQQkPGQAPRLLIYgAS |
| Low Risk | 8 | EIVLTQSPGTLSVSPGERVTFSCRASQSIGTSIH----WYQQKTGQSPRLLIKYAS |
| Low+Mod | 9 | EIVLTQSPGTLSVSPGERVTFSCRASQSIGTSIH----WYQQKTGQAPRLLIKYAS |

| V-Region | No. of Changes | Amino Acids 53-109 |
|---|---|---|
| Risk | | HLMMLHMLMHLHLHLHLHLLHLLHLLHLHHHHHHHHHHHHHHHHLHHLHLLLLLL |
| Mouse | | ESISGIPSRFSGSGSGTDFTLSINSVESEDIADYYCQQINSWPT------TFGGGTKLEI-KRA |
| Human | | sRATGIPdRFSGSGSGTDFTLTISrLepEDFAVYYCQQygsspp-----xTFGqGTKvEI-KRT |
| Low Risk | 8 | ERISGIPDRFSGSGSGTDFTLTISRVESEDFADYYCQQINSWPT------TFGQGTKLEI-KRT |
| Low+Mod | 10 | ERATGIPDRFSGSGSGTDFTLTISRVESEDFADYYCQQINSWPT------TFGQGTKLEI-KRT |

FIG. 20B

Low Risk Light Chain Vs. Kabat Vk3 Consensus:

Protein Seq:

EIVLTQSPGTLSVSPGERVTFSCRASQSIGTSIHWYQQKTGQSPRLLIKYASERISGIPDRFSGSGSGTDFTLTISRVESEDFADYYCQQINSWPTTFGQGTKLEIKRT

Nucleotide Seq:

GAAATAGTCCTTACCCAATCTCCCGGAACCCTCTCAGTATCTCCCGGGAACGAGTAACCTTTCATGTAGAGCATCCAATCCATGGCACTTCAATTCACT
GGTATCAGCAGAAACAGGTCAATCCCACGGCTTCTTATAAAATATCAGGCATTCCAGACAGATTCTCAGGTTCAGGC
ACAGATTCACACTTCACAATTTCCCGGCGTCGAATCCGAAGACTTCGGTCGACTATTACTGCCAACAATCAACTCATGGCCTACTACTTTCGGTCAAGGCACC
AAACTCGAAATTAAACGTACG

Low Risk + Moderate Risk Light Chain Vs. Kabat Vk3 Consensus:

Protein Seq:

EIVLTQSPGTLSVSPGERVTFSCRASQSIGTSIHWYQQKTGQAPRLLIKYASERATGIPDRFSGSGSGTDFTLTISRVESEDFADYYCQQINSWPTTFGQGTKLEIKRT

Nucleotide Seq:

GAAATAGTTCTTACTCAATCCCCGGTACACTCTCAGTTCCCAGGGCGAACGCGTCACTTTCTTGCAGAGCATCACAATCAATCGGCACTTCAATTCATT
GGTATCAACAAAAACAGGACAGGCCCAGACTTCTTATTAAATATGCAGAGCCACAGCAGATTTCAGGTTCAGGATCAGGC
GGTATCCAGACAGATTTCAGGTTCAGGATCAGGC
ACCGATTTCACACTTCACAATATCCAGAGTCGAATCAGAAGATTTGTCAACAAATAAACAGCTGGCCCACTACATTCGGACAAGGCACA
AACTCGAAATTAAACGTACG

FIG. 21 A

Light Chain – Changes back to Murine

| V-Region | No. of Changes | Amino Acids 1-52 |
|---|---|---|
| Risk | | LHLHLHLMLLHLMLLHLHLHLMHHHHHHHHHHMHLMLLMHMHHHHHH |
| Mouse | | DILLTQSPAILSVSPGERVSFSCRASQSIGTSIH----WYQQRTNGSPRLLIKYAS |
| Human | | EIVLTQSPgTLSlSPGERaTLSCRASQsvsssyL---AWYQQkPGQAPRLLIYgAS |
| Low Risk | 8 | EIVLTQSPGTLSVSPGERVTFSCRASQSIGTSIH----WYQQKTGQSPRLLIKYAS |
| Low+Mod | 9 | EIVLTQSPGTLSVSPGERVTFSCRASQSIGTSIH----WYQQKTGQAPRLLIKYAS |

| V-Region | No. of Changes | Amino Acids 53-109 |
|---|---|---|
| Risk | | HLMMLHMLMHLHLHLLHLHLLHLLHHHHHHHHHHHHHHHHHHHLHHLHLLLLL |
| Mouse | | ESISGIPSRFSGSGSGTDFTLSINSVESEDIADYYCQQINSWPT------TFGGGTKLEI-KRA |
| Human | | sRATGIPdRFSGSGSGTDFTLTISrLepEDFAVYYCQQygsspp----xTFGqGTKvEI-KRT |
| Low Risk | 8 | ERISGIPDRFSGSGSGTDFTLTISRVESEDFADYYCQQINSWPT------TFGQGTKLEI-KRT |
| Low+Mod | 10 | ERATGIPDRFSGSGSGTDFTLTISRVESEDFADYYCQQINSWPT------TFGQGTKLEI-KRT |
| Low+Mod Alternate | 7 | ESISGIPDRFSGSGSGTDFTLTISRVESEDFADYYCQQINSWPT------TFGQGTKLEI-KRT |

FIG. 21B

Low Risk Light Chain Vs. Kabat Vk3 Consensus; AA54 changed back to murine:

Protein Seq:

EIVLTQSPGTLSVSPGERVTFSCRASQSIGTSIHWYQQKTGQSPRLLIKYASESISGIPDRFSGSGSGTDFTLTISRVESEDFADYYCQQINSWPTTFGQGTKLEIKRT

Nucleotide Seq:

GAAATAGTTCCTTACCCAATCTCCCGGAACCCTCTCAGTATCTCCGGGGAACGAGTAACCTTTCATGTAGAGCATCCAATCCATGGCACTTCAATTCACT
GGTATCAGCAGAAAACAGGTCAATCCCCACGGCTCTTATAAAATATGCATCCCAGACAGATTCTGGCATCCAGAATCAATTTCTGGCATCCAGAGATTTCAGGTTCAGGATCAGGCA
CCGATTTCACACTTCACAATATCCAGAGTCGAATCAGAGAAGATTTGCAGATTACTATTGTCAACAAATAAACAGCTGGCCACTACATTCGGACAAGGCACAA
AACTCGAAATTAAACGTACG

Low Risk + Moderate Risk Light Chain Vs. Kabat Vk3 Consensus; AA54, 55, 56 changed back to murine:

Protein Seq:

EIVLTQSPGTLSVSPGERVTFSCRASQSIGTSIHWYQQKTGQAPRLLIKYASESISGIPDRFSGSGSGTDFTLTISRVESEDFADYYCQQINSWPTTFGQGTKLEIKRT

Nucleotide Seq:

GAAATAGTTCTTACTCAATCCCCCGGTACACTCTCAGTTTCCCAGGCGAACGCGTCACTTTTCTTGCAGAGCATCACAATCAATGGCACTTCAATTCATT
GGTATCAACAAAAAACAGGACAGGCCCCACGACTTCTTATTAAATATGCATCAGAATCAATTTCTGGCATCCAGACAGATTTCAGGTTTCAGGATCAGGCA
CCGATTTCACACTTCACAATATCCAGAGTCGAATCAGAGAAGATTTGCAGATTACTATTGTCAACAAATAAACAGCTGGCCCACTACTACATTCGGACAAGGCACAA
AACTCGAAATTAAACGTACG

FIG. 22 A

Light Chain – Changes based on HK6 2-1-1(A14)

| V-Region | No. of Changes | Amino Acids 1-52 |
|---|---|---|
| Risk | | LHLHLHLHLMLLMLHLMLLLHLHLHLMHHHHHHHHHHHHMHLMLLMHMHHHHHH |
| Mouse | | DILLTQSPAILSVSPGERVSFSCRASQSIGTSIH----WYQQRTNGSPRLLIKYAS |
| Human | | DVVMTQSPAFLSVTPGEKVTITCQASEGIGNYLY----WYQQKPDQAPKLLIKYAS |
| Low Risk | 10 | DIVLTQSPAFLSVTPGEKVTFTCQASQSIGTSIH----WYQQKTDQSPRLLIKYAS |
| Low+Mod | 12 | DIVLTQSPAFLSVTPGEKVTFTCQASQSIGTSIH----WYQQKTDQAPKLLIKYAS |

| V-Region | No. of Changes | Amino Acids 53-109 |
|---|---|---|
| Risk | | HLMLHMLHLHLHLHLLHLHLLHLHHHHHHHHHHHHHHHHHHHLHLHLLLLL |
| Mouse | | ESISGIPSRFSGSGSGTDFTLSINSVESEDIADYYCQQINSWPT-----TFGGGTKLEI-KRA |
| Human | | QSISGVPSRFSGSGSGTDFTFTISSLEAEDAATYYCQQGNKHP-----LTFGGGTKVEI-KRT |
| Low Risk | 5 | ESISGIPSRFSGSGSGTDFTLTISSVEAEDAADYYCQQINSWPT-----TFGGGTKLEI-KRT |
| Low+Mod | 5 | ESISGIPSRFSGSGSGTDFTLTISSVEAEDAADYYCQQINSWPT-----TFGGGTKLEI-KRT |

FIG. 22B

Low Risk Light Chain vs. VK6 Subgroup 2-1-(1) A14:

Protein Seq:

DIVLTQSPAFLSVTPGEKVTFTCQASQSIGTSIHWYQQKTDQSPRLLIKYASESISGIPSRFSGSGSGTDFTLTISSVEAEDAADYYCQQINSWPTTFGGGTKLEIKRT

Nucleotide Seq: Not synthesized

Low Risk + Moderate Risk Light Chain vs. VK6 Subgroup 2-1-(1) A14:

DIVLTQSPAFLSVTPGEKVTFTCQASQSIGTSIHWYQQKTDQAPKLLIKYASESISGIPSRFSGSGSGTDFTLTISSVEAEDAADYYCQQI
NSWPTTFGGGTKLEIKRT

Nucleotide Seq:

GACATAGTTCTCACACAATCACCAGCATTCCTCTCAGTTACACCCGGGGAAAAAGTAACCTTTACCTGTCAGGCTTCTCAATCTATCGGCACTTCTATTCACT
GGTATCAACAAAAAACCGATCAAGCTCCTAAACTCCTCATAAAATACGAATCCATCCGTATCCCCTCCAGATTTTCAGGCTCCGGCTCCGGCA
CAGATTTCACCCTTACCATTAGCTCAGTTGAAGCCGAAGACGCAGCTGATTACTACTGTCAACAAATAAACTCGAAATAAACTCGAAATAAACGTACG
AACTCGAAATAAACGTACG

FIG. 23A

Murine RX-1 Light Chain:
DILLTQSPAILSVSPGERVSFSCRASQSIGTSIHWYQQRTNGSPRLLLIKYASESISGIPSRFSGSGSGTDFTLSINSVESEDIADYYCQQINSWPTTFGGGTK
LEIKRA

```
            RX1 KV   (1) DILLTQSPAILSVSPGERVSFSCRASQSIG.....TSIHWYQQRTNGSPRLLLIKYASESI..................SGIPSRFSGSGSGTDFTLSINSVESEDIADYYCQQINSWPTTFG
Consensus Germline LC
    hVK I Consensus  (1) DIQMTQSPSSLSASVGDRVTITCRASQSISS.......Y.....LNWYQQKPGKAPKLLIYAASSLQSGVPSR.................FSGSGSGTDFTLTISSLQPEDFATYYCQQSYSTP-----
    hVK II Consensus (1) DIVMTQTPLSLPVTPGEPASISCRSSQSLLDSDDGNTYLDWYLQKPGQSPQLLIYTLSRASGVPD..................RFSGSGSGTDFTLKISRVEAEDVGVYYCMQRIE.P-----
    hVK III Consensus(1) EIVLTQSPGTLSLSPGERATLSCRASQS...........VSSSYLAWYQQKPGQAPRLLIYGASSRAT.....................GIPDRFSGSGSGTDFTLTISRLEPEDFAVYYCQQYGSSP-----
    hVK IV Consensus (1) DIVMTQSPDSLAVSLGERATINCKSSQSVLYSSNNKNYLAWYQQKPGQPPKLLIYWAS........TRES................GVPDRFSGSGSGTDFTLTISSLQAEDVAVYYCQQYYSTP-----
    hVK V Consensus  (1) ETTLTQSPAFMSATPGDKVNISCKASQDID....D....D.....MNWYQQKPGEAAIFIIQEATYPR.................VPD.RFTGS.GYGTDFTLTINNIESEAAYYCLQHDNLP-----
    hVK VI Consensus (1) EIVLTQSPDFQSVTPKEKVTITCRASQSIGS....S......SLHWYQQKPDQSPKLLIKYASQSFS....................GVPSRFSGSGSGTDFTLTINSLEAEDAATYYCHQSSLP-----
```

LIGHT CHAIN amino half

RX-1   DILLTQSPAILSVSPGERVSFSCRASQSI--GTSIH----WYQQRTNGSPRLLLIKYAS pos...     10         20      abcdef  30          40        50

Kabat:

HK1...DIQMTQSPSSLSASVGDRVTITCRASQS------ISSYLNWYQQKPGKAPKLLIYAAS
HK2...DIVMTQSPLSLPVTPGEPASISCRSSQSLLDSDDGNTYLDWYLQKPGQSPQLLIYXXS
HK3...EIVLTQSPGTLSLSPGERATLSCRASQS----VSSSYLAWYQQKPGQAPRLLIYGAS
HK4...DIVMTQSPDSLAVSLGERATINCKSSQSVLYSSNNKNYLAWYQQKPGQPPKKLLIYWAS

Germline Consensus (with JK4):

hVK1   DIQMTQSPSSLSASVGDRVTITCRASQS------ISSYLNWYQQKPGKAPKLLIYAAS
hVK2   DIVMTQTPLSLPVTPGEPASISCRSSQSLLDSDDGNTYLDWYLQKPGQSPQLLIYTLS
hVK3   EIVLTQSPGTLSLSPGERATLSCRASQS----VSSSYLAWYQQKPGQAPRLLIYGAS
hVK4   DIVMTQSPDSLAVSLGERATINCKSSQSVLYSSNNKNYLAWYQQKPGQPPKKLLIYWAS
hVK5   ETTLTQSPAFMSATPGDKVNISCKASQDIDD------DMNWYQQKPGEAAIFIIQEAT
hVK6   EIVLTQSPDFQSVTPKEKVTITCRASQSIG------SSLHWYQQKPDQSPKLLIKYAS

FIG. 23B

LIGHT CHAIN carboxy half

```
RX-1   ESISGIPSRFSGSGSGTDFTLSINSVESEDIADYYCQQINSWPT------TFGGGTKLEI-KRA pos...     60         70         80         90  abcdef 100       a
Kabat:

HK1...XLXSGVPSRFSGSGSGTDFTLTISSLQPEDFATYYCQQXXXXPE-----XTFGQGTKVEI-KRT
HK2...NRXSGVPDRFSGSGSGTDFTLKISRVEAEDVGVYYCMQAXQXPR-----XTFGQGTKVEI-KRT
HK3...SRATGIPDRFSGSGSGTDFTLTISRLEPEDFAVYYCQQYGSSPP-----XTFGQGTKVEI-KRT
HK4...TRESGVPDRFSGSGSGTDFTLTISSLQAEDVAVYYCQQYYSTP------XTFGQGTKVEI-KRT

Germline Consensus (with JK4):

hVK1   SLQSGVPSRFSGSGSGTDFTLTISSLQPEDFATYYCQQSYSTP------LTFGGGTKVEI-KRT
hVK2   YRASGVPDRFSGSGSGTDFTLKISRVEAEDVGVYYCMQRIEFP------LTFGGGTKVEI-KRT
hVK3   SRATGIPDRFSGSGSGTDFTLTISRLEPEDFAVYYCQQYGSSP------LTFGGGTKVEI-KRT
hVK4   TRESGVPDRFSGSGSGTDFTLTISSLQAEDVAVYYCQQYYSTP------LTFGGGTKVEI-KRT
hVK5   TLVPGIPPRFSGSGYGTDFTLTINNIESEDAAYYFCLQHDNFP------LTFGGGTKVEI-KRT
hVK6   QSFSGVPSRFSGSGSGTDFTLTINSLEAEDAATYYCHQSSSLP------LTFGGGTKVEI-KRT
```

FIG. 24A

Murine RX-1 Heavy Chain:
DVQLQESGPGLVKPSQSLSLTCTVTDYSITSDYAWNWIRQFPGNKLEMMGYISYSGSTSYNPSLKSRISITRDTSKNQFFLQLNSVTTEDTATYYC
ASFDYAHAMDYWGQGTSVTVSS

```
RX1 VH              (1) D VQLQESGPGLVKPSQSLS LTCTVTDYSITS-DYAWNWIRQFPGNKLEWMGYISYSGSTS ---NPSLKSRISITRDTSKNQFFLQLNSVTTEDTATYYCASFDY
Consensus Germline
hVH I Consensus     (1) QVQLVQSGAEVKKPGASVKVSCKASGYTFTG---YYMHWVRQAPGQGLEWMGWINP--NSGGTNVAQKFQGRVTMTRDTSISTAYMELSRLRSDDTAVYYCAR---
hVH II Consensus    (1) QITLKESGPTLVKPTQTLTLTCTFSGFSLSTSGVGVGWIRQPPGKALEWLALIYWNDDKR---YSPSLKSRLTITKDTSKNQVVLTMNNDPVDTATYYCAHR---
hVH III Consensus   (1) EVQLVESGGGLVQPGGSLRLSCAASGFTFSS---YWMSWVRQAPGKGLEWVANIKQ--DGSEKYYVDSVKGRFTISRDNAKNSLYLQMNSLRAEDTAVYYCAR---
hVH IV Consensus    (1) QVQLQESGPGLVKPSGTLSLTCAVSGGSISSS---NWWSWVRQPPGKGLEWIGHSGSTN---YNPSLKSRVTISVDKSKNQFSLKLSSVTAADTAVYYCAR---
hVH V Consensus     (1) EVQLVQSGAEVKKPGESLKISCKGSGYSFTS---YWIGWVRQMPGKGLEWMGIIYP--GDSDTRYSPQGQVTISADKSISHAYLQWSLKASDTAMYYCAR---
hVH VI Consensus    (1) QVQLQQSGPGLVKPSQTLSLTCAISGDSVSSNW---SAAWNWIRQSPSGHELEWIGRTYYRSKWYN-DTAVSVKSRLTINPDTSKNQFSLQLNSVTPEDTAVYYCAR---
hVH VII Consensus   (1) QVQLVQSGSELKKPGASVKVSCKASGYTFTS---YAMNWVRQAPGQGLEWMGWINT--NTGNPTAQGFTGRFVFSLDTSVSTAYLQICSLRAEDTAVYYCAR---
```

HEAVY CHAIN amino half

```
           DVQLQESGPGLVKPSQSLSLTCTVTDYSITSDYAWN-WIRQFPGNKLEMMGYIS---YSGST pos ...    10         20         30      ab    40           50   abc
Kabat:

HH1 ...XVQLVQSGAEVKKPGXSVKVSCKASGYTFXSYXIX---WVRQAPGQGLEWMGXIXPY-XXGXT
HH2 ...QVQLQESGPGLVKPSQTLSLTCXVSGXSXSXSXXXXXWIRQPPGKGLEWIGXIYYRAXXGXT
HH3 ...EVQLVESGGGLVQPGGSLRLSCAASGFTFSXYXXMX---WVRQAPGKGLEWVXXIXXKXXGXXT
```

Germline Consensus (with JH4):

```
hVHI    QVQLVQSGAEVKKPGASVKVSCKASGYTFTGYYMH--WVRQAPGQGLEWMGWINP--NSGGT
hVHII   QITLKESGPTLVKPTQTLTLTCTFSGFSLSTSGVGWIRQPPGKALEWLALIY---WNDDK
hVHIII  EVQLVESGGGLVQPGGSLRLSCAASGFTFSSYWMS--WVRQAPGKGLEWVANIK--QDGSEK
hVHIV   QVQLQESGPGLVKPSGTLSLTCAVSGGSISSNWW-SWVRQPPGKGLEWIGELY---HSGST
hVHV    EVQLVQSGAEVKKPGESLKISCKGSGYSFTSYWIG--WVRQMPGKGLEWMGIIYP--GDSDT
hVHVI   QVQLQQSGPGLVKPSQTLSLTCAISGDSVSSNSAAWNWIRQSPSRGLEWLGRTYY-RSKWYN
hVHVII  QVQLVQSGSELKKPGASVKVSCKASGYTFTSYAMN--WVRQAPGQGLEWMGWINT--NTGNP
```

FIG. 24B

HEAVY CHAIN carboxy half

```
                                                                            SYNPSLKSRISITTRDTSKNQFFLQLNSVTTEDTATYYCASFDYAHAM---------DYWGQGTSVTVSS
pos ...  60         70         80  abc        90              100 abcdefghijk          110
Kabat:

HH1    ...NYAQKFQGRVTITXDXSTSTAYMELSSLRSXDTAVYYCARXXXXXXXXXXXXXXXXDXXFDXWGQGTLVTVSS
HH2    ...XYNPSLKSRVTISVDTSKNQFSLXLXSVTAADTAVYYCARXXXXXXXXXXXXXXXXXXFDXWGQGTXVTVSS
HH3    ...YYADSVKGRFTISRDNSKNTLYLQMNSLRAEDTAVYYCAXXXXXXXXXXXXXXXXYYXXFDXWGQGTLVTVSS

Germline Consensus (with JH4):

hVHI   NYAQKFQGRVTMTRDTSISTAYMELSRLRSDDTAVYYCARXXXXXXXXXXXXXXXXXXXXYFDYWGQGTLVTVSS
hVHII  RYSPSLKSRLTITKDTSKNQVVLTMTNMDPVDTATYYCAHRXXXXXXXXXXXXXXXXXXXYFDYWGQGTLVTVSS
hVHIII YYVDSVKGRFTISRDNAKNSLYLQMNSLRAEDTAVYYCARXXXXXXXXXXXXXXXXXXXXYFDYWGQGTLVTVSS
hVHIV  NYNPSLKSRVTISVDKSKNQFSLKLSSVTAADTAVYYCARXXXXXXXXXXXXXXXXXXXXYFDYWGQGTLVTVSS
hVHV   RYSPSFQGQVTISADKSISTAYLQWSSLKASDTAMYYCARXXXXXXXXXXXXXXXXXXXXYFDYWGQGTLVTVSS
hVHVI  DYAVSVKSRITINPDTSKNQFSLQLNSVTPEDTAVYYCARXXXXXXXXXXXXXXXXXXXXYFDYWGQGTLVTVSS
hVHVII TYAQGFTGRFVFSLDTSVSTAYLQICSLKAEDTAVYYCARXXXXXXXXXXXXXXXXXXXXYFDYWGQGTLVTVSS
```

Figure 24C:

Kabat numbering of 5H4:

5H4 heavy chain protein sequence:

```
1-30:      EIQLQQSGPE LVKTGTSVKI SCKASGYSFT
31-35:     GYFMH
36-49:     WVKQSHGKSLEWIG
50-65:     YIS C (52A) YNGDTNY NQNFKG
66-94:     KATF TVDTSSSTAY MQF N (82A) S(82B) L(82C) TSED SAVYYCAR
95-102:    EGGNYPAY
103-437:   WGQG TLVTVSAAKT TPPSVYPLAP GSAAQTNSMV
TLGCLVKGYFPEPVTVTWNS GSLSSGVHTF PAVLQSDLYT LSSSVTVPSS TWPSETVTCN
VAHPASSTKV DKKIVPRDCG CKPCICTVPE VSSVFIFPPK PKDVLTITLT PKVTCVVVDI
SKDDPEVQFS WFVDDVEVHT AQTQPREEQF NSTFRSVSEL PIMHQDWLNG KEFKCRVNSA
AFPAPIEKTI SKTKGRPKAP QVYTIPPPKE QMAKDKVSLT CMITDFFPED ITVEWQWNGQ
PAENYKNTQP IMDTDGSYFV YSKLNVQKSN WEAGNTFTCS VLHEGLHNHH TEKSLSHSPG K
```

5H4 light chain protein sequence:

```
1-23:      DIVMTQSHKF MSTSVGDRVT ITC
24-34:     KASQNVG TAVT
35-49:     WYQQKPGQSPKLLIY
50-56:     WTSTRHA
57-88:     GVPD RFTGSGSGTD FTLTISDVQS EDLADYFC
89-97:     QQYSSYPLT
98-214:    FGAGTKLELKRAD AAPTVSIFPP SSEQLTSGGA SVVCFLNNFY PKDINVKWKI
     DGSERQNGVL NSWTDQDSKD STYSMSSTLT LTKDEYERHN SYTCEATHKT
     STSPIVKSFN RNEC
```

Figure 24D:

Kabat numbering of MC1

MC-1 heavy chain protein sequence:

| | |
|---|---|
| 1-30: | EVKLVESGGG LVQPGGSLKL SCATSGFTFS |
| 31-35: | DYYMY |
| 36-49: | WVRQTPEKRLEWVA |
| 50-65: | YIS N (52A) GGGSTYY PDTVKG |
| 66-94: | RFTI SRDNAKNTLY LQM S (82A) R (82B) L (82C) KSED TAMYYCAR |
| 95-102: | QGSYGYPFAY |
| 103-449: | WG QGTLVTVSAA KTTAPSVYPL APVCGDTTGS SVTLGCLVKG YFPEPVTLTW |

NSGSLSSGVH TFPAVLQSDL YTLSSSVTVT SSTWPSQSIT CNVAHPASST KVDKKIEPRG
PTIKPCPPCK CPAPNLLGGP SVFIFPPKIK DVLMISLSPI VTCVVVDVSE DDPDVQISWF
VNNVEVHTAQ TQTHREDYNS TLRVVSALPI QHQDWMSGKE FKCKVNNKDL PAPIERTISK
PKGSVRAPQV YVLPPPEEEM TKKQVTLTCM VTDFMPEDIY VEWTNNGKTE LNYKNTEPVL
DSDGSYFMYS KLRVEKKNWV ERNSYSCSVV HEGLHNHHTT KSFSRTPGK

MC-1 light chain protein sequence:

| | |
|---|---|
| 1-23: | AIQMTQTTSS LSASLGDRVT ISC |
| 24-34: | SASQGIS NYLN |
| 35-49: | WYQQKP DGTVKLLIY |
| 50-56: | YTSSLHS |
| 57-88: | GVPS RFSGSGSGTD YSLTISNLEP EDIATYYC |
| 89-97: | QQ YSKLPWT |
| 98-214: | FGGGTKLEIKRAD AAPTVSIFPP SSEQLTSGGA SVVCFLNNFY PKDINVKWKI |

DGSERQNGVL NSWTDQDSKD STYSMSSTLT LTKDEYERHN SYTCEATHKT STSPIVKSFN
RNEC

Figure 24E

Kabat numbering of MC3

MC-3 heavy chain protein sequence:

```
1-30:    DVQLQESGPG LVKPSQSLSL TCTVTGYSIT
31-35:   SDYAW N (35A)
36-49:   WIRQ FPGNKLEWMG
50-65:   YISYSGSTSY NPSLKS
66-94:   RISIT RDTSKNQFFL QL N (82A) S (82B) V (82C) TTEDT ATYYCAR
95-102:  LETWLFDY 103-522: WGQG TTLTVSSAKT TPPSVYPLAP GCGDTTGSSV TLGCLVKGYF PESVTVTWNS
         GSLSSSVHTF PALLQSGLYT MSSSVTVPSS TWPSQTVTCS VAHPASSTTV
         DKKLEPSGPI STINPCPPCK ECHKCPAPNL EGGPSVFIFP PNIKDVLMIS
         LTPKVTCVVV DVSEDDPDVQ ISWFVNNVEV HTAQTQTHRE DYNSTIRVVS
         TLPIQHQDWM SGKEFKCKVN NKDLPSPIER TISKIKGLVR APQVYILPPP
         AEQLSRKDVS LTCLVVGFNP GDISVEWTSN GHTEENYKDT APVLDSDGSY
         FIYSKLNMKT SKWEKTDSFS CNVRHEGLKN YYLKKTISRS PGLDLDDICA
         EAKDGELDGL WTTITIFISL FLLSVCYSAS VTLFKVKWIF SSVVELKQKI
         SPDYRNMIGQ GA
```

MC-3 light chain protein sequence:

```
1-23:    DILLTQSPAI LSVSPGERVS FSC
24-34:   RASQSIG TSIH
35-49:   WYQQRT NGSPRLLIK
50-56:   YASESIS
57-88:   GIPS RFSGSGSGTD FTLSINSVES EDIADYYC
89-97:   QQ SNSWPTT
98-214:  FGG GTKLEIKWAD AAPTVSIFPP SSEQLTSGGA SVVCFLNNFY PKDINVKWKI
         DGSERQNGVL NSWTDQDSKD STYSMSSTLT LTKDEYERHN SYTCEATHKT
         STSPIVKSFN RNEC
```

Measurement of Neutralizing Activity of heRX1 With Different IgG Subclass Constant Regions Against recombinant human MCSF Activity of heRX1-1 With Different IgG Subclasses Against Other Forms of MCSF Similar results observed against Cyno MCSF in serum and recombinant Cyno MCSF Activity of heRX1-1 With Different IgG Subclasses Against Other Forms of MCSF Similar results observed against Cyno MCSF in serum and recombinant Cyno MCSF

Fig. 29A

HeRX-1 Low Risk Heavy Chain Gamma-1

Amino Acids

MGWSCIILFLVATATGVHS

DVQLQESGPGLVKPSQTLSLTCTVTDYSITSDYAWNWIRQFPGKKLEWMGYISYSGSTSYNPSLKSRITISRDTSKNQFSL
QLNSVTAADTATYYCASFDYAHAMDYWGQGTTVTVSS

ASTKGPSVFPLAPSSKSTSGGTAALGCLVKDYFPEPVTVSWNSGALTSGVHTFPAVLQSSGLYSLSSVVTVPSSSLGTQTY
ICNVNHKPSNTKVDKRVEPKSCDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRWQQGNVFSCSVMHEALHNH
YTQKSLSLSPGK•

Nucleotides

ATGGGATGGAGTTGCATTATACTTTTCCTCGTTGCCACCGCCACTGGAGTTCACTCTGACGTACAACTTCAAGAATC
TGGCCCAGGTCTCGTCAAACCTTCTCAAACTCTCTCACTCACCTGCACTGTTACTGACTACTCTATTACATCCGACTA
CGCTTGGAACTGGATCCGACAATTTCCTGGTAAAAAACTCGAATGGATGGGTTATATTTCTTACTCTGGCTCCACCT
CCTACAATCCTTCTCTGAAATCACGCATCACAATTTCCCGCGATACCTCTAAAAATCAATTTTCACTCCAACTCAATT
CTGTTACCGCCGCCGATACTGCCACCTACTACTGTGCCTCTTTTGACTACGCTCACGCCATGGATTATTGGGGACAG
GGTACTACCGTTACCGTAAGCTCAGCCAGCACAAAGGGCCCATCGGTCTTCCCCCTGGCACCCTCCTCCAAGAGCA
CCTCTGGGGGCACAGCGGCCCTGGGCTGCCTGGTCAAGGACTACTTCCCCGAACCGGTGACGGTGTCGTGGAACTC
AGGCGCCCTGACCAGCGGCGTGCACACCTTCCCGGCTGTCCTACAGTCCTCAGGACTCTACTCCCTCAGCAGCGTGG
TGACCGTGCCCTCCAGCAGCTTGGGCACCCAGACCTACATCTGCAACGTGAATCACAAGCCCAGCAACACCAAGGT
GGACAAGAGAGTTGAGCCCAAATCTTGTGACAAAACTCACACATGTCCACCGTGCCCAGCACCTGAACTCCTGGGG
GGACCGTCAGTCTTCCTCTTCCCCCCAAAACCCAAGGACACCCTCATGATCTCCCGGACCCCTGAGGTCACATGCGT
GGTGGTGGACGTGAGCCACGAAGACCCTGAGGTCAAGTTCAACTGGTACGTGGACGGCGTGGAGGTGCATAATGC
CAAGACAAAGCCGCGGGAGGAGCAGTACAACAGCACGTACCGTGTGGTCAGCGTCCTCACCGTCCTGCACCAGGA
CTGGCTGAATGGCAAGGAGTACAAGTGCAAGGTCTCCAACAAAGCCCTCCCAGCCCCCATCGAGAAAACCATCTCC
AAAGCCAAAGGGCAGCCCCGAGAACCACAGGTGTACACCCTGCCCCCATCCCGGGAGGAGATGACCAAGAACCAG
GTCAGCCTGACCTGCCTGGTCAAAGGCTTCTATCCCAGCGACATCGCCGTGGAGTGGGAGAGCAATGGGCAGCCGG
AGAACAACTACAAGACCACGCCTCCCGTGCTGGACTCCGACGGCTCCTTCTTCCTCTATAGCAAGCTCACCGTGGAC
AAGAGCAGGTGGCAGCAGGGGAACGTCTTCTCATGCTCCGTGATGCATGAGGCTCTGCACAACCACTACACGCAGA
AGAGCCTCTCCCTGTCCCCGGGTAAATGA

Fig. 29B

HeRX-1 Low + Moderate Risk Heavy Chain Gamma-1

Amino Acids

MGWSCIILFLVATATGVHS

QVQLQESGPGLVKPSQTLSLTCTVSDYSITSDYAWNWIRQFPGKGLEWMGYISYSGSTSYNPSLKSRITISRDTSKNQFSL
QLNSVTAADTAVYYCASFDYAHAMDYWGQGTTVTVSS

ASTKGPSVFPLAPSSKSTSGGTAALGCLVKDYFPEPVTVSWNSGALTSGVHTFPAVLQSSGLYSLSSVVTVPSSSLGTQTY
ICNVNHKPSNTKVDKRVEPKSCDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRWQQGNVFSCSVMHEALHNH
YTQKSLSLSPGK•

Nucleotides

ATGGGTTGGTCTTGCATCATTCTCTTTCTCGTCGCTACCGCAACTGGTGTACACTCCCAAGTTCAACTTCAAGAATCA
GGCCCCGGACTCGTTAAACCCTCTCAAACTCTCTCTCTTACTTGCACTGTATCCGATTACTCTATTACTTCAGACTAC
GCTTGGAACTGGATCAGACAATTTCCCGGAAAAGGACTCGAATGGATGGGATATATCTCTTACTCTGGCTCAACCT
CTTACAACCCCTCTCTCAAATCTCGAATAACAATCTCACGCGATACTTCTAAAAATCAATTCTCACTTCAACTTAAC
TCCGTTACTGCCGCCGACACTGCCGTTTACTACTGTGCTTCCTTCGATTACGCCCACGCTATGGATTATTGGGGACA
AGGAACTACCGTCACTGTCAGCTCAGCCAGCACAAAGGGCCCATCGGTCTTCCCCCTGGCACCCTCCTCCAAGAGC
ACCTCTGGGGGCACAGCGGCCCTGGGCTGCCTGGTCAAGGACTACTTCCCCGAACCGGTGACGGTGTCGTGGAACT
CAGGCGCCCTGACCAGCGGCGTGCACACCTTCCCGGCTGTCCTACAGTCCTCAGGACTCTACTCCCTCAGCAGCGTG
GTGACCGTGCCCTCCAGCAGCTTGGGCACCCAGACCTACATCTGCAACGTGAATCACAAGCCCAGCAACACCAAGG
TGGACAAGAGAGTTGAGCCCAAATCTTGTGACAAAACTCACACATGTCCACCGTGCCCAGCACCTGAACTCCTGGG
GGGACCGTCAGTCTTCCTCTTCCCCCCAAAACCCAAGGACACCCTCATGATCTCCCGGACCCCTGAGGTCACATGCG
TGGTGGTGGACGTGAGCCACGAAGACCCTGAGGTCAAGTTCAACTGGTACGTGGACGGCGTGGAGGTGCATAATG
CCAAGACAAAGCCGCGGGAGGAGCAGTACAACAGCACGTACCGTGTGGTCAGCGTCCTCACCGTCCTGCACCAGG
ACTGGCTGAATGGCAAGGAGTACAAGTGCAAGGTCTCCAACAAAGCCCTCCCAGCCCCCATCGAGAAAACCATCTC
CAAAGCCAAAGGGCAGCCCCGAGAACCACAGGTGTACACCCTGCCCCCATCCCGGGAGGAGATGACCAAGAACCA
GGTCAGCCTGACCTGCCTGGTCAAAGGCTTCTATCCCAGCGACATCGCCGTGGAGTGGGAGAGCAATGGGCAGCCG
GAGAACAACTACAAGACCACGCCTCCCGTGCTGGACTCCGACGGCTCCTTCTTCCTCTATAGCAAGCTCACCGTGG
ACAAGAGCAGGTGGCAGCAGGGGAACGTCTTCTCATGCTCCGTGATGCATGAGGCTCTGCACAACCACTACACGCA
GAAGAGCCTCTCCCTGTCCCCGGGTAAATGA

Fig. 30

HeRX-1 Low Risk Heavy Chain Gamma-4

Amino Acids

MGWSCIILFLVATATGVHSDVQLQESGPGLVKPSQTLSLTCTVTDYSITSDYAWNWIRQFPGKKLEWMGYISYSGSTSYN
PSLKSRITISRDTSKNQFSLQLNSVTAADTATYYCASFDYAHAMDYWGQGTTVTVSSASTKGPSVFPLAPCSRSTSESTA
ALGCLVKDYFPEPVTVSWNSGALTSGVHTFPAVLQSSGLYSLSSVVTVPSSSLGTKTYTCNVDHKPSNTKVDKRVESKY
GPPCPSCPAPEFLGGPSVFLFPPKPKDTLMISRTPEVTCVVVDVSQEDPEVQFNWYVDGVEVHNAKTKPREEQFNSTYRV
VSVLTVLHQDWLNGKEYKCKVSNKGLPSSIEKTISKAKGQPREPQVYTLPPSQEEMTKNQVSLTCLVKGFYPSDIAVEW
ESNGQPENNYKTTPPVLDSDGSFFLYSRLTVDKSRWQEGNVFSCSVMHEALHNHYTQKSLSLSLGK

Nucleotides cDNA

ATGGGATGGAGTTGCATTATACTTTTCCTCGTTGCCACCGCCACTGGAGTTCACTCTGACGTACAACTTCAAGAATC
TGGCCCAGGTCTCGTCAAACCTTCTCAAACTCTCTCACTCACCTGCACTGTTACTGACTACTCTATTACATCCGACTA
CGCTTGGAACTGGATCCGACAATTTCCTGGTAAAAAACTCGAATGGATGGGTTATATTTCTTACTCTGGCTCCACCT
CCTACAATCCTTCTCTGAAATCACGCATCACAATTTCCCGCGATACCTCTAAAAATCAATTTTCACTCCAACTCAATT
CTGTTACCGCCGCCGATACTGCCACCTACTACTGTGCCTCTTTTGACTACGCTCACGCCATGGATTATTGGGGACAG
GGTACTACCGTTACCGTAAGCTCAGCCAGCACAAAGGGCCCATCCGTCTTCCCCCTGGCGCCCTGCTCCAGGAGCA
CCTCCGAGAGCACAGCCGCCCTGGGCTGCCTGGTCAAGGACTACTTCCCCGAACCGGTGACGGTGTCGTGGAACTC
AGGCGCCCTGACCAGCGGCGTGCACACCTTCCCGGCTGTCCTACAGTCCTCAGGACTCTACTCCCTCAGCAGCGTGG
TGACCGTGCCCTCCAGCAGCTTGGGCACGAAGACCTACACCTGCAACGTAGATCACAAGCCCAGCAACACCAAGGT
GGACAAGAGAGTTGAGTCCAAATATGGTCCCCCATGCCCATCATGCCCAGCACCTGAGTTCCTGGGGGGACCATCA
GTCTTCCTGTTCCCCCCAAAACCCAAGGACACTCTCATGATCTCCCGGACCCCTGAGGTCACGTGCGTGGTGGTGGA
CGTGAGCCAGGAAGACCCCGAGGTCCAGTTCAACTGGTACGTGGATGGCGTGGAGGTGCATAATGCCAAGACAAA
GCCGCGGGAGGAGCAGTTCAACAGCACGTACCGTGTGGTCAGCGTCCTCACCGTCCTGCACCAGGACTGGCTGAAC
GGCAAGGAGTACAAGTGCAAGGTCTCCAACAAAGGCCTCCCGTCCTCCATCGAGAAAACCATCTCCAAAGCCAAA
GGGCAGCCCCGAGAGCCACAGGTGTACACCCTGCCCCCATCCCAGGAGGAGATGACCAAGAACCAGGTCAGCCTG
ACCTGCCTGGTCAAAGGCTTCTACCCCAGCGACATCGCCGTGGAGTGGGAGAGCAATGGGCAGCCGGAGAACAAC
TACAAGACCACGCCTCCCGTGCTGGACTCCGACGGCTCCTTCTTCCTCTACAGCAGGCTAACCGTGGACAAGAGCA
GGTGGCAGGAGGGGAATGTCTTCTCATGCTCCGTGATGCATGAGGCTCTGCACAACCACTACACACAGAAGAGCCT
CTCCCTGTCTCTGGGTAAATGA

Genomic

ATGGGATGGAGTTGCATTATACTTTTCCTCGTTGCCACCGCCACTGGAGTTCACTCTGACGTACAACTTCAAGAATC
TGGCCCAGGTCTCGTCAAACCTTCTCAAACTCTCTCACTCACCTGCACTGTTACTGACTACTCTATTACATCCGACTA
CGCTTGGAACTGGATCCGACAATTTCCTGGTAAAAAACTCGAATGGATGGGTTATATTTCTTACTCTGGCTCCACCT
CCTACAATCCTTCTCTGAAATCACGCATCACAATTTCCCGCGATACCTCTAAAAATCAATTTTCACTCCAACTCAATT
CTGTTACCGCCGCCGATACTGCCACCTACTACTGTGCCTCTTTTGACTACGCTCACGCCATGGATTATTGGGGACAG
GGTACTACCGTTACCGTAAGCTCAGCCAGCACAAAGGGCCCATCCGTCTTCCCCCTGGCGCCCTGCTCCAGGAGCA
CCTCCGAGAGCACAGCCGCCCTGGGCTGCCTGGTCAAGGACTACTTCCCCGAACCGGTGACGGTGTCGTGGAACTC
AGGCGCCCTGACCAGCGGCGTGCACACCTTCCCGGCTGTCCTACAGTCCTCAGGACTCTACTCCCTCAGCAGCGTGG
TGACCGTGCCCTCCAGCAGCTTGGGCACGAAGACCTACACCTGCAACGTAGATCACAAGCCCAGCAACACCAAGGT
GGACAAGAGAGTTGGTGAGAGGCCAGCACAGGGAGGGAGGGTGTCTGCTGGAAGCCAGGCTCAGCCCTCCTGCCT
GGACGCACCCCGGCTGTGCAGCCCCAGCCCAGGGCAGCAAGGCATGCCCCATCTGTCTCCTCACCCGGAGGCCTCT
GACCACCCCACTCATGCTCAGGGAGAGGGTCTTCTGGATTTTTCCACCAGGCTCCGGGCAGCCACAGGCTGGATGC
CCCTACCCCAGGCCCTGCGCATACAGGGGCAGGTGCTGCGCTCAGACCTGCCAAGAGCCATATCCGGGAGGACCCT
GCCCCTGACCTAAGCCCCACCCCAAAGGCCAAACTTCCACTCCCTCAGCTCAGACACCTTCTCTCCTCCCAGATCTG
AGTAACTCCCAATCTTCTCTCTGCAGAGTCCAAATATGGTCCCCATGCCCATCATGCCCAGGTAAGCCAACCCAGG
CCTCGCCCTCCAGCTCAAGGCGGGACAGGTGCCCTAGAGTAGCCTGCATCCAGGGACAGGCCCCAGCCGGGTGCTG
ACGCATCCACCTCCATCTCTTCCTCAGCACCTGAGTTCCTGGGGGGACCATCAGTCTTCCTGTTCCCCCCAAAACCC
AAGGACACTCTCATGATCTCCCGGACCCCTGAGGTCACGTGCGTGGTGGTGGACGTGAGCCAGGAAGACCCCGAGG
TCCAGTTCAACTGGTACGTGGATGGCGTGGAGGTGCATAATGCCAAGACAAAGCCGCGGGAGGAGCAGTTCAACA
GCACGTACCGTGTGGTCAGCGTCCTCACCGTCCTGCACCAGGACTGGCTGAACGGCAAGGAGTACAAGTGCAAGGT
CTCCAACAAAGGCCTCCCGTCCTCCATCGAGAAAACCATCTCCAAAGCCAAAGGTGGGACCCACGGGGTGCGAGG
GCCACATGGACAGAGGTCAGCTCGGCCCACCCTCTGCCCTGGGAGTGACCGCTGTGCCAACCTCTGTCCCTACAGG
GCAGCCCCGAGAGCCACAGGTGTACACCCTGCCCCCATCCCAGGAGGAGATGACCAAGAACCAGGTCAGCCTGAC
CTGCCTGGTCAAAGGCTTCTACCCCAGCGACATCGCCGTGGAGTGGGAGAGCAATGGGCAGCCGGAGAACAACTA
CAAGACCACGCCTCCCGTGCTGGACTCCGACGGCTCCTTCTTCCTCTACAGCAGGCTAACCGTGGACAAGAGCAGG
TGGCAGGAGGGGAATGTCTTCTCATGCTCCGTGATGCATGAGGCTCTGCACAACCACTACACACAGAAGAGCCTCT
CCCTGTCTCTGGGTAAATGA

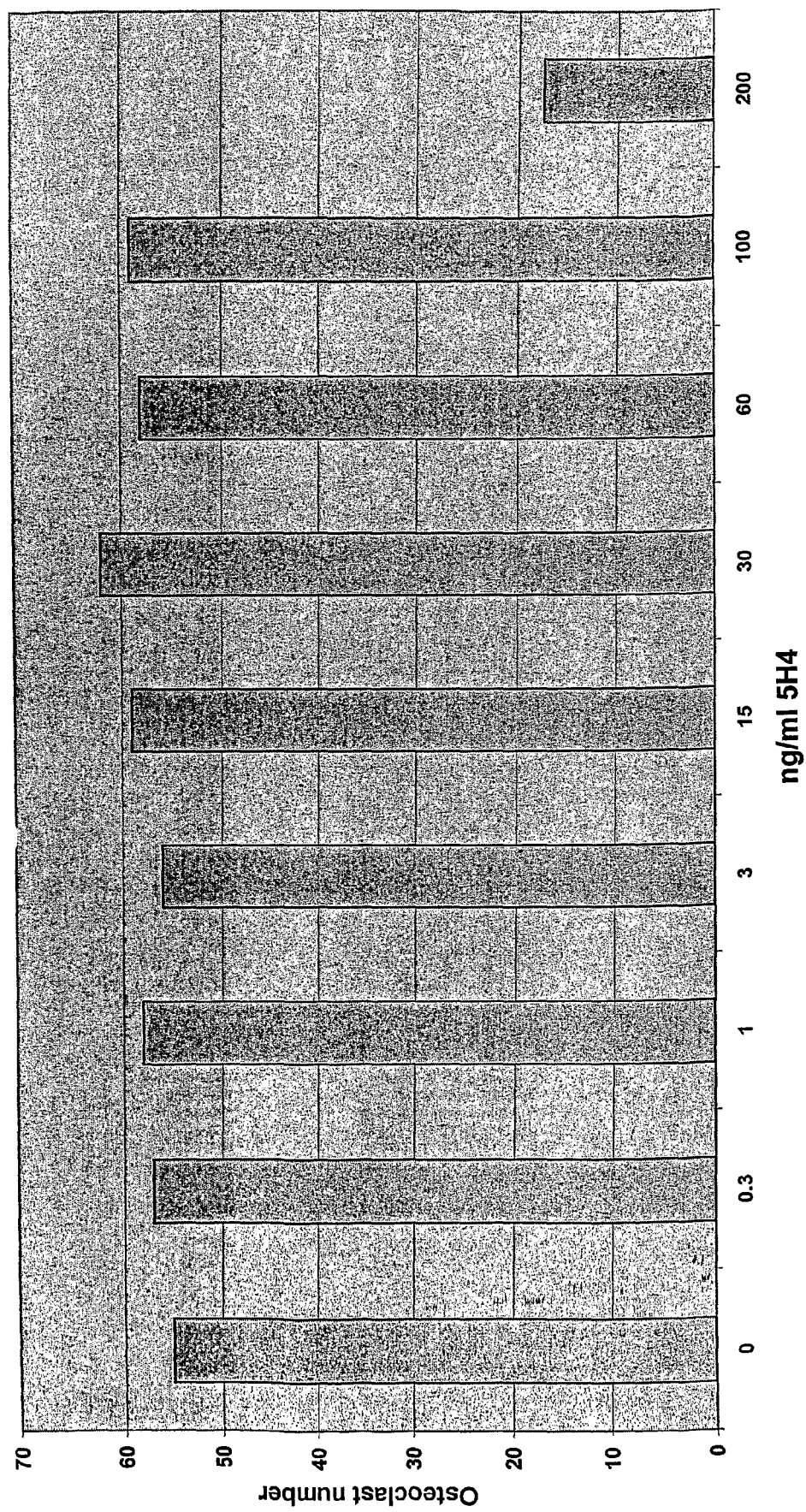

M-CSF-SPECIFIC MONOCLONAL ANTIBODY AND USES THEREOF

TECHNICAL FIELD

This invention relates to methods for preventing and treating, osteolysis, cancer metastasis and bone loss or remodeling associated with cancer metastasis by administering an M-CSF-specific antibody to a subject.

BACKGROUND OF THE INVENTION

Cancer metastasis is the primary cause of post-operation or post-therapy recurrence in cancer patients. Despite intensive efforts to develop treatments, cancer metastasis remains substantially refractory to therapy. Bone is one of the most common sites of metastasis of various types of human cancers (e.g., breast, lung, prostate and thyroid cancers). The occurrence of osteolytic bone metastases causes serious morbidity due to intractable pain, high susceptibility to fracture, nerve compression and hypercalcemia. Despite the importance of these clinical problems, there are few available treatments for cancer metastasis or bone remodeling associated with cancer metastasis.

The balance between the activities of osteoblasts (bone-forming cells) and osteoclasts (bone-lysing cells) in general determines the phenotype of metastatic bone lesions, and both osteoblasts and osteoclasts have been implicated—directly or indirectly—in bone metastasis. Bone metastases with a relative bone-forming (osteoblastic) phenotype are the result of comparative stimulation of osteoblasts or inhibition of osteoclasts (or both) by the cancer cells, whereas metastases with a relative bone-lysing (osteolytic) phenotype reflect comparative inhibition of osteoblasts or stimulation of osteoclast function (or both) by the cancer cells. Metastases from prostate cancer, most of which are adenocarcinomas, nearly always form lesions in bone that are more osteoblastic than osteolytic; by contrast, bone metastases from kidney, lung or breast cancers more often are osteolytic. However, metastases from the relatively uncommon neuroendocrine tumours of the prostate also produce osteolytic lesions. Additionally, patients can exhibit a mixed form of disease with osteoblastic and lytic lesions present.

Osteoclasts mediate bone readsorption osteoclasts are multinucleated cells differentiated from haemopoietic cells. It is generally accepted that osteoclasts are formed by the fusion of mononuclear precursors derived from haemopoietic stem cells in the bone marrow, rather than incomplete cell divisions (Chambers, Bone and Mineral Research, 6: 1-25, 1989; Göthling et al., Clin Orthop Relat R. 120: 201-228, 1976; Kahn et al., Nature 258: 325-327, 1975, Suda et al., Endocr Rev 13: 66-80, 1992; Walker, Science 180: 875, 1973; Walker, Science 190: 785-787, 1975; Walker, Science 190: 784-785, 1975). They share a common stem cell with monocyte-macrophage lineage cells (Ash et al., Nature 283: 669-670, 1980, Kerby et al., J. Bone Miner Res 7: 353-62, 1992). The differentiation of osteoclast precursors into mature multinucleated osteoclasts requires different factors including hormonal and local stimuli (Athanasou et al., Bone Miner 3: 317-333, 1988; Feldman et al., Endocrinology 107: 1137-1143, 1980; Walker, Science 190: 784-785, 1975; Zheng et al., Histochem J 23: 180-188, 1991) and living bone and bone cells have been shown to play a critical role in osteoclast development (Hagenaars et al., Bone Miner 6: 179-189, 1989). Osteoblastic or bone marrow stromal cells are also required for osteoclast differentiation. One of the factors produced by these cells that supports osteoclast formation is macrophage-colony stimulating factor, M-CSF (Wiktor-Jedrzejczak et al., Proc Natl Acad Sci USA 87: 4828-4832, 1990; Yoshida et al., Nature 345: 442-444, 1990). Receptor activator for NF-κB ligand (RANKL, also known as TRANCE, ODF and OPGL) is another signal (Suda et al., Endocr Rev 13: 66-80, 1992) through which osteoblastic/stromal cells stimulate osteoclast formation and resorption via a receptor, RANK (TRANCER), located on osteoclasts and osteoclast precursors (Lacey et al., Cell 93: 165-176, 1998; Tsuda et al., Biochem Biophys Res Co 234: 137-142, 1997; Wong et al., J Exp Med 186: 2075-2080, 1997; Wong et al., J Biol. Chem 272: 25190-25194, 1997; Yasuda et al., Endocrinology 139: 1329-1337, 1998; Yasuda et al., Proc Natl Acad Sci US 95: 3597-3602, 1998). Osteoblasts also secrete a protein that strongly inhibits osteoclast formation called osteoprotegerin (OPG, also known as OCIF), which acts as a decoy receptor for the RANKL thus inhibiting the positive signal between osteoclasts and osteoblasts via RANK and RANKL.

Osteoclasts are responsible for dissolving both the mineral and organic bone matrix (Blair et al., J Cell Biol 102: 1164-1172, 1986). Osteoclasts represent terminally differentiated cells expressing a unique polarized morphology with specialized membrane areas and several membrane and cytoplasmic markers, such as tartrate resistant acid phosphatase (TRAP) (Anderson et al. 1979), carbonic anhydrase II (Väänänen et al., Histochemistry 78: 481-485, 1983), calcitonin receptor (Warshafsky et al., Bone 6: 179-185, 1985) and vitronectin receptor (Davies et al., J Cell Biol 109: 1817-1826, 1989). Multinucleated osteoclasts usually contain less than 10 nuclei, but they may contain up to 100 nuclei being between 10 and 100 μm in diameter (Göthling et al., Clin Orthop Relat R 120: 201-228, 1976). This makes them relatively easy to identify by light microscopy. They are highly vacuolated when in the active state, and also contain many mitochondria, indicative of a high metabolic rate (Mundy, in Primer on the metabolic bone diseases and disorders of mineral metabolism, pages 18-22, 1990). Since osteoclasts play a major role in osteolytic bone metastases, as well as other osteolytic diseases such as osteoporosis, for example, there is a need in the art for new agents and methods for preventing osteoclast stimulation and function.

Thus, there remains a need in the art to identify new agents and methods for preventing or treating osteolysis or cancer metastasis, including mixed osteoblastic and osteolytic bone metastases and bone diseases associated with increased osteoclast activity.

SUMMARY OF THE INVENTION

The materials and methods of the present invention fulfill the aforementioned and other related needs in the art. In one embodiment of the invention, a non-murine monoclonal antibody is provided, including functional fragment, that specifically binds to the same epitope of M-CSF as any one of murine monoclonal antibody RX1, MC1, or MC3 having the amino acid sequences set forth in FIGS. 4, 14, and 15, respectively. In a related embodiment, an aformentioned antibody is provided wherein the antibody is selected from the group consisting of a polyclonal antibody; a monoclonal antibody including a Human Engineered™ antibody; a humanized antibody; a human antibody; a chimeric antibody; Fab, F(ab')2; Fv; Sc Fv or SCA antibody fragment; a diabody; linear antibody; or a mutein of any one of these antibodies, that preferably retain binding affinity of at least $10^{-7}$, $10^{-8}$ or $10^{-9}$ or higher. A non-murine monoclonal antibody, including functional fragment, that competes with monoclonal antibody RX1, MC1, and/or MC3 having the amino acid sequence set forth in FIG. 4 for binding to M-CSF by more than 75%, is also contemplated.

In another embodiment, a non-murine monoclonal antibody, including functional fragment, wherein said non-murine monoclonal antibody or functional fragment thereof binds an epitope of M-CSF that includes at least 4, 5, 6, 7 or 8 contiguous residues of amino acids 98-105 of FIG. 12 is provided.

In another embodiment, the invention provides a non-murine monoclonal antibody, including functional fragment, wherein said non-murine monoclonal antibody or functional fragment thereof binds an epitope of M-CSF that includes at least 4, 5, 6, 7 or 8 contiguous residues of amino acids 65-73 or 138-144 of FIG. 12 (corresponding to M-CSF epitopes recognized by 5H4 or MC3).

In yet another embodiment, the aforementioned antibody or fragment that binds an epitope of M-CSF that includes amino acids 98-105 of FIG. 12 is provided. In a related embodiment, the aforementioned antibody is provided comprising CDR3 of FIG. 4A. In another embodiment, the antibody is provided comprising at least 1, 2, 3, 4, 5, or 6 CDRs of murine antibody RX1 set forth in FIG. 4A. Such an antibody that comprises at least 1, 2, 3, 4, or 5 CDRs of murine antibody RX1 may also comprise at least 1, 2, 3, 4, or 5 CDRs of any of the 6 CDRs of antibody 5H4 set forth in FIG. 16A-B. Alternatively, the antibody that comprises at least 1, 2, 3, 4, or 5 CDRs of murine antibody RX1 may also comprise at least 1, 2, 3, 4, or 5 CDRs of any of the 6 CDRs of antibody MC1 set forth in FIG. 16A-B. In yet another alternative, the aforementioned antibody may also comprise at least 1, 2, 3, 4, or 5 CDRs of any of the 6 CDRs of antibody MC3 set forth in FIG. 16A-B. In a related embodiment, the antibody that comprises at least 1, 2, 3, 4, or 5 CDRs of murine antibody RX1 may comprise at least 1, 2, 3, 4 or 5 CDRs of the consensus CDRs set forth in FIG. 16A-B is provided. In still another related embodiment, in the aforementioned antibody one or more residues of the consensus CDR(s) is substituted by the corresponding residue of any of the CDRs of antibody murine RX1, 5H4, MC1 or MC3. The desired binding affinity may be retained even though one or more of the amino acids in the antibody have been mutated, e.g. by conservative substitutions in the CDRs, and/or conservative or non-conservative changes in the low and moderate risk residues.

In another embodiment of the invention, variants of the aforementioned antibody are provided, comprising a variable heavy chain amino acid sequence which is at least 60, 65, 70, 75, 80, 85, 90, 91, 92, 93, 94, 95, 96, 97, 98, or 99% homologous to the amino acid sequence set forth in FIG. 4A, 13, 14, or 15. In a related embodiment, the antibody comprises a variable light chain amino acid sequence which is at least 60, 65, 70, 75, 80, 85, 90, 91, 92, 93, 94, 95, 96, 97, 98, or 99% homologous to the amino acid sequence set forth in FIG. 4A, 13, 14, or 15.

In yet another embodiment, the antibody comprises a constant region and one or more heavy and light chain variable framework regions of a human antibody sequence. In a related embodiment, the antibody comprises a modified or unmodified constant region of a human IgG1, IgG2, IgG3 or IgG4. In a preferred embodiment, the constant region is human IgG1 or IgG4, which may optionally be modified to enhance or decrease certain properties. In the case of IgG1, modifications to the constant region, particularly the hinge or CH2 region, may increase or decrease effector function, including ADCC and/or CDC activity. In other embodiments, an IgG2 constant region is modified to decrease antibody-antigen aggregate formation. In the case of IgG4, modifications to the constant region, particularly the hinge region, may reduce the formation of half-antibodies.

In yet another embodiment of the invention, the aforementioned antibody is derived from, based on, or contains part of a human consensus sequence, human germline sequence, human consensus germline sequence, or any one of the human antibody sequences in Kabat, NCBI Ig Blast, http://www.ncbi.nlm.nih.gov/igblast/showGermline.cgi, Kabat Database http://www.bioinf.org.uk/abs/seqtest.html, FTP site for Kabat Release 5.0 (1992) ftp://ftp.ncbi.nih.gov/repository/kabat/Rel5.0/, ImMunoGeneTics database (Montpellier France) http://imgt.cnusc.fr:8104/, V-Base http://www.mrc-cpe.cam.ac.uk/LIST.php?menu=901, Zurich University http://www.unizh.ch/antibody/Sequences/index.html, The Therapeutic Antibody Human Homology Project (TAHHP) http://www.path.cam.ac.uk/~mrc7/humanisation/TAHHP.html, Protein Sequence and Structure Analysis of Antibody Domains http://how.to/AnalyseAntibodies/, Humanization by design http://people.cryst.bbk.ac.uk/~ubcg07s/, Antibody Resources http://www.antibodyresource.com/educational.html, Antibody Engineering (by T T Wu), Humana Press.

In a preferred aspect of the invention, the aforementioned antibody is a Human Engineered™ antibody. For example, the Human Engineered™ antibody sequence is any one of the sequences set forth in FIGS. 23-24. Other Human Engineered™ antibodies or variants thereof are contemplated.

For example, in one embodiment, the aforementioned RX1-based antibody is provided, wherein the heavy chain variable region comprises the amino acid sequence $X_1VX_2LX_3EX_4GX_5X_6X_7X_8X_9X_{10}X_{11}X_{12}X_{13}LX_{14}LX_{15}C$-$X_{16}VX_{17}$DYSITSDYAWNWIX$_{18}$QX$_{19}$X$_{20}$X$_{21}$X$_{22}$X$_{23}$LX$_{24}$-WMGYISYSGSTSX$_{25}$NX$_{26}$X$_{27}$LX$_{28}$X$_{29}$X$_{30}$IX$_{31}$IX$_{32}$R-$X_{33}X_{34}X_{35}X_{36}X_{37}X_{38}$FX$_{39}$LX$_{40}$LX$_{41}$X$_{42}$VX$_{43}$X$_{44}$X$_{45}$D-$X_{46}$AX$_{47}$YYCASFDYAHAMDYWGX$_{48}$GTX$_{49}$VX$_{50}$VX$_{51}$-$X_{52}$ (SEQ ID NO: 124), wherein X is any amino acid. In a related embodiment, the antibody is provided wherein the heavy chain variable region comprises the amino acid sequence DVX$_1$LX$_2$EX$_3$GPX$_4$X$_5$VX$_6$PX$_7$X$_8$X$_9$LX$_{10}$LX$_{11}$-CX$_{12}$VTDYSITSDYAWNWIRQX$_{13}$PX$_{14}$X$_{15}$KLEWMGY-ISYSGSTSYNPSLKX$_{16}$RIX$_{17}$IX$_{18}$RX$_{19}$TX$_{20}$X$_{21}$NX$_{22}$F-$X_{23}$LX$_{24}$LX$_{25}$X$_{26}$VX$_{27}$X$_{28}$X$_{29}$DX$_{30}$ATYYCASFDYAHA-MDYWGX$_{31}$GTX$_{32}$VX$_{33}$VX$_{34}$X$_{35}$ (SEQ ID NO: 125), wherein X is any amino acid.

In still another embodiment of the invention, the aforementioned antibody is provided, wherein the heavy chain variable region comprises the amino acid sequence $X_1$VQLQESG-PGLVKPSQX$_2$LSLTCTVX$_3$DYSITSDYAWNWIRQFPG-X$_4$X$_5$LEWMGYISYSGSTSYNPSLKSRIX$_6$IX$_7$RDTSKN-QFX$_8$LQLNSVTX$_9$X$_{10}$DTAX$_{11}$YYCASFDYAHAMDYW-GQGTX$_{12}$VTVSS (SEQ ID NO: 126), wherein X is any amino acid. In a related embodiment, the antibody is provided, wherein the heavy chain variable region comprises the amino acid sequence DVQLQESGPGLVKPSQX$_1$LSLTCT-VTDYSITSDYAWNWIRQFPGX$_2$KLEWMGYISYSGSTS-YNPSLKSRIX$_3$IX$_4$RDTSKNQFX$_5$LQLNSVTX$_6$X$_7$DTAT-YYCASFDYAHAMDYWGQGTX$_8$VTVSS (SEQ ID NO: 127), wherein X is any amino acid. In yet another embodiment, the antibody is provided wherein the heavy chain variable region comprises the amino acid sequence DVQLQES-GPGLVKPSQTLSLTCTVTDYSITSDYAWNWIRQFPGK-KLEWMGYISYSGSTSYNPSLKSRITISRDTSKNQFSL-QLNSVTAADTATYYCASFDYAHAMDYWGQGTTVT-VSS (SEQ ID NO: 41). In still another embodiment, the antibody is provided wherein the heavy chain variable region comprises the amino acid sequence (SEQ ID NO: 43)
QVQLQESGPGLVKPSQTLSLTCTVSDYSITSDYAWNWIRQFPGKGLEWMG

YISYSGSTSYNPSLKSRITISRDTSKNQFSLQLNSVTAADTAVYYCASFD

YAHAMDYWGQGTTVTVSS.

In another embodiment of the invention, the aforementioned antibody is provided wherein the light chain variable region comprises the amino acid sequence $X_1IX_2LX_3Q$-$X_4X_5X_6X_7X_8X_9VX_{10}X_{11}X_{12}X_{13}X_{14}VX_{15}FX_{16}CX_{17}AX_{18}$-QSIGTSIHWYX$_{19}$QX$_{20}$X$_{21}$X$_{22}$X$_{23}$X$_{24}$PX$_{25}$LLIKYASE-$X_{26}X_{27}X_{28}X_{29}IX_{30}X_{31}X_{32}FX_{33}GX_{34}GX_{35}GX_{36}X_{37}FX_{38}$-$LX_{39}LX_{40}X_{41}VX_{42}X_{43}X_{44}DX_{45}$ADYYCQQINSWPTTFG-$X_{46}GTX_{47}LX_{48}X_{49}X_{50}X_{51}X_{52}$ (SEQ ID NO: 128), wherein X is any amino acid. In a related embodiment, the antibody is provided wherein the light chain variable region comprises the amino acid sequence $X_1IX_2LX_3QX_4PX_5X_6LX_7VX_8$-$PX_9X_{10}X_{11}VX_{12}FX_{13}CX_{14}$ASQSIGTSIHWYQQX$_{15}$TX$_{16}$-$X_{17}$SPRLLIKYASEX$_{18}$ISX$_{19}$IPX$_{20}$RFX$_{21}$GX$_{22}$GX$_{23}$GX$_{24}$-$X_{25}FX_{26}LX_{27}IX_{28}X_{29}VX_{30}X_{31}X_{32}DX_{33}$ADYYCQQINS-WPTTFGX$_{34}$GTX$_{35}$LX$_{36}$X$_{37}$X$_{38}$X$_{39}$X$_{40}$ (SEQ ID NO: 129), wherein X is any amino acid. In yet another embodiment, the antibody is provided wherein the light chain variable region comprises the amino acid sequence $X_1IX_2$LT-QSPX$_3$X$_4$LSVSPGERVX$_5$FSCRASQSIGTSIHWYQQX$_6$T-$X_7X_8X_9$PRLLIKYASEX$_{10}X_{11}X_{12}$GIPX$_{13}$RFSGSGSGTD-FTLX$_{14}$IX$_{15}$X$_{16}$VESEDX$_{17}$ADYYCQQINSWPTTFGX$_{18}$-GTKLEIKRX$_{19}$ (SEQ ID NO: 130), wherein X is any amino acid.

In another embodiment of the invention, the aforementioned antibody is provided wherein the light chain variable region comprises the amino acid sequence $X_1IX_2$LT-QSPX$_3$X$_4$LSVSPGERVX$_5$FSCRASQSIGTSIHWYQQX$_6$T-$X_7X_8$SPRLLIKYASEX$_9$ISGIPX$_{10}$RFSGSGSGTDFTLX$_{11}$-IX$_{12}$X$_{13}$VESEDX$_{14}$ADYYCQQINSWPTTFGX$_{15}$GTKLEI-KRX$_{16}$ (SEQ ID NO: 131), wherein X is any amino acid. In a related embodiment, the antibody is provided wherein the light chain variable region comprises the amino acid sequence $X_1IX_2$LTQSPX$_3$X$_4$LSVSPGERVX$_5$FSCRASQSI-GTSIHWYQQX$_6$TX$_7$X$_8$X$_9$PRLLIKYASESISGIPX$_{10}$RFS-GSGSGTDFTLX$_{11}$IX$_{12}$X$_{13}$VESEDX$_{14}$ADYYCQQINSW-PTTFGX$_{15}$GTKLEIKRX$_{16}$ (SEQ ID NO: 132), wherein X is any amino acid. In yet another embodiment, the antibody is provided wherein the light chain variable region comprises the amino acid sequence (SEQ ID NO: 45)
EIVLTQSPGTLSVSPGERVTFSCRASQSIGTSIHWYQQKTGQAPRLLIKY

ASESISGIPDRFSGSGSGTDFTLTISRVESEDFADYYCQQINSWPTTFGQ

GTKLEIKRT.

In still another embodiment of the invention, the aforementioned antibody is provided wherein the light chain variable region comprises the amino acid sequence EIVLTQSPG-TLSVSPGERVTFSCRASQSIGTSIHWYQQKTGQAPRL-LIKYASERATGIPDRFSGSGSGTDFTLTISRVESEDFA-DYYCQQINSWPTTFGQGTKLEIKRT (SEQ ID NO: 47). In another embodiment, the antibody is provided, wherein the light chain variable region comprises the amino acid sequence (SEQ ID NO: 48)
EIVLTQSPGTLSVSPGERVTFSCRASQSIGTSIHWYQQKTGQSPRLLIKY

ASERISGIPDRFSGSGSGTDFTLTISRVESEDFADYYCQQINSWPTTFGQ

GTKLEIKRT.

In another embodiment of the invention, the aforementioned antibody wherein at least one X is a corresponding amino acid within the amino acid sequence set forth in FIG. 4A is provided. In a related embodiment, the antibody is provided wherein at least one X is a conservative substitution (according to Table 1) of a corresponding amino acid within the amino acid sequence set forth in FIG. 4A. In yet another related embodiment, the antibody is provided wherein at least one X is a non-conservative substitution (according to Table 1) of a corresponding amino acid within the amino acid sequence set forth in FIG. 4A. In still another embodiment of the invention, the antibody is provided wherein at least one X is a corresponding amino acid within a human antibody sequence.

The aforementioned Human Engineered™ antibody is derived from, based on, or contains part of the human antibody consensus sequence, human germline sequence, human consensus germline sequence, or any one of the human antibody sequences in Kabat, NCBI Ig Blast, http://www.ncbi.nlm.nih.gov/igblast/showGermline.cgi, Kabat Database http://wwvv.bioinforg.uldabs/seqtest.html, FTP site for Kabat Release 5.0 (1992) ftp://ftp.ncbi.nih.gov/repository/kabat/Rel5.0/, ImMunoGeneTics database (Montpellier France) http://imgt.cnusc.fr:8104//, V-Base http://wvvw.mrc-cpe.cam.ac.uk/LIST.php?menu=901, Zurich University http://www.unizh.ch/~antibody/Sequences/index.html, The Therapeutic Antibody Human Homology Project (TAHHP) http://www.path.cam.ac.uk/~mrc7/humanisation/TAHHP.html, Protein Sequence and Structure Analysis of Antibody Domains http://how.to/AnalyseAntibodies/, Humanization by design http://people.cryst.bbk.ac.uk/~ubcg07s/, Antibody Resources http://www.antibodyresource.com/educational.html, Antibody Engineering (by TT Wu), Humana Press.

In another embodiment of the invention, the aforementioned antibody wherein the Human Engineered™ antibody sequence is one of the sequences set forth in FIG. 23-24 or 29-30 is provided. In another embodiment, the antibody comprises a variable heavy chain amino acid sequence which is at least 60, 65, 70, 75, 80, 85, 90, 91, 92, 93, 94, 95, 96, 97, 98, or 99% identical to one of the heavy chain amino acid sequences set forth in FIG. 19B. In yet another embodiment, the antibody comprises a variable light chain amino acid sequence which is at least 60, 65, 70, 75, 80, 85, 90, 91, 92, 93, 94, 95, 96, 97, 98, or 99% identical to one of the light chain amino acid sequences set forth in any of FIGS. 20B-22B.

In yet another embodiment, the aforementioned antibody such as 5H4, MC1 or MC3 antibody with the sequences set forth in one of FIGS. 24C-24E is Human Engineered™ according to the methods set forth in Studnicka et al., U.S. Pat. No. 5,766,886 and Example 5 herein, using the Kabat numbering set forth in FIGS. 24C-24E to identify low, moderate and high risk residues. In a related embodiment, the aforementioned antibody is provided wherein all of the low risk residues of either the heavy or light chain or both are modified, where necessary, to be the same residues as a human reference immunoglobulin sequence. Similarly, another embodiment of the invention provides the aforementioned antibody wherein all of the low+moderate risk residues of either the heavy or light chain or both are modified, where necessary, to be the same residues as a human reference immunoglobulin sequence. A heavy chain wherein all of the low risk residues have been modified may be combined with a light chain wherein all of the low and moderate risk residues have been modified, and vice versa. Similarly, an aforementioned Human Engineered™ light or heavy chain May be combined with a light or heavy chain of a humanized or chimeric antibody.

In still another embodiment, the antibody comprises a variable heavy chain amino acid sequence which is at least 60, 65, 70, 75, 80, 85, 90, 91, 92, 93, 94, 95, 96, 97, 98, or 99% identical to one of the heavy chain amino acid sequences described immediately above Human Engineered™ according to the Studnicka method. In yet another embodiment, the antibody comprises a variable light chain amino acid sequence which is at least 60, 65, 70, 75, 80, 85, 90, 91, 92, 93, 94, 95, 96, 97, 98, or 99% identical to one of the light chain amino acid sequences described immediately above Human Engineered™ according to the Studnicka method.

In still another embodiment, an antibody is provided comprising a heavy chain as set forth above and a light chain as set forth above.

In yet another embodiment of the invention, the aforementioned antibody has an affinity Kd of at least 10[−7]. In a related embodiment, the antibody has an affinity Kd of at least 10[9−9].

In another embodiment of the invention, the aforementioned antibody is provided which is a polyclonal antibody; a monoclonal antibody including a Human Engineered™ antibody; a humanized antibody; a human antibody; a chimeric antibody; Fab, F(ab')2, Fv, ScFv or SCA antibody fragment; a diabody; a linear antibody; or a mutein of any one of these antibodies. In a related embodiment, the monoclonal antibody is an isolated antibody.

In still another embodiment of the invention, an isolated nucleic acid is provided comprising a nucleic acid sequence encoding a light chain of the aforementioned antibody. In a related embodiment, the isolated nucleic acid comprises a heavy chain nucleic acid sequence which is at least 60, 65, 70, 75, 80, 85, 90, 91, 92, 93, 94, 95, 96, 97, 98, or 99% identical to the heavy chain nucleotide sequence set forth in FIG. 4A, 13, 14, or 15. In yet another related embodiment, the isolated nucleic acid comprises a light chain nucleic acid sequence which is at least 60, 65, 70, 75, 80, 85, 90, 91, 92, 93, 94, 95, 96, 97, 98, or 99% identical to the light chain nucleotide sequence set forth in FIG. 4A, 13, 14, or 15.

In another embodiment, a vector comprising the aforementioned isolated nucleic acid is provided. In a related embodiment, the aforementioned vector is provided wherein the isolated nucleic acid is operably linked to a regulatory control sequence. In still another embodiment, a host cell is provided comprising the aforementioned vector.

Numerous methods are contemplated in the present invention. For example, a method of producing an aforementioned antibody is provided comprising culturing the aforementioend host cell such that the isolated nucleic acid is expressed to produce the antibody. In a related embodiment, the method further comprises the step of recovering the antibody from the host cell culture. In a related embodiment, an isolated antibody produced by the aforementioned method is provided.

A hybridoma that secretes an aforementioned antibody is also provided by the present invention. Additionally, an aforementioned antibody that is conjugated to a toxin is provided.

In another embodiment of the invention, a pharmaceutical composition is provided comprising any one of the aforementioned antibodies and a pharmaceutically suitable carrier, excipient or diluent. In a related embodiment, the pharmaceutical composition further comprises a second therapeutic agent. In yet another related embodiment, the pharmaceutical composition is provided wherein the second therapeutic agent is a cancer chemotherapeutic agent. In still another related embodiment, the pharmaceutical composition is provided wherein the second therapeutic agent is a bisphosphonate. In another embodiment the second therapeutic agent is another antibody.

Antibodies of the present invention are contemplated to have numerous desirable characteristics for the treatment of diseases and disorders. In one embodiment of the invention, the any one of aforementioned antibodies that bind to M-CSF for preventing a subject afflicted with a disease that causes or contributes to or results from-osteolysis, wherein the antibody effectively reduces the severity of bone loss or remodeling associated with the disease, is provided. Similarly, any one of aforementioned antibodies that bind to M-CSF is provided for treating a subject afflicted with a disease that causes or contributes to or results from osteolysis, wherein said antibody effectively reduces the severity of bone loss or remodeling associated with the disease.

Numerous diseases and disorders are contemplated to be amenable to antibody-based treatment in the present invention. In one embodiment of the invention, the aforementioned antibody is provided wherein said disease is selected from the group consisting of osteolytic diseases associated with relatively increased osteoclast activity or the osteoclastic/osteoblastic process required for bone remodeling (associated with both increased osteoclastic activity and increased osteoblastic activity), including metabolic bone diseases, endocrinopathies (hypercortisolism, hypogonadism, primary or secondary hyperparathyroidism, hyperthyroidism), hypercalcemia, deficiency states (rickets/osteomalacia, scurvy, malnutrition), chronic diseases (malabsorption syndromes, chronic renal failure (renal osteodystrophy), chronic liver disease (hepatic osteodystrophy)), drugs (glucocorticoids (glucocorticoid-induced osteoporosis), heparin, alcohol), and hereditary diseases (osteogenesis imperfecta, homocystinuria), cancer, osteoporosis, periprosthetic bone loss (for example, due to a foreign implant in bone or joint replacement with a prosthesis, including total hip arthroplasty), -inflammation of bone associated with arthritis and rheumatoid arthritis, periodontal disease, fibrous dysplasia, and/or Paget's disease.

In a related embodiment, the aforementioned antibody that binds to M-CSF is provided for preventing or treating metastatic cancer to bone, wherein the metastatic cancer is breast, lung, renal, multiple myeloma, thyroid, prostate, adenocarcinoma, blood cell malignancies, including leukemia and lymphoma; head and neck cancers; gastrointestinal cancers, including esophageal cancer, stomach cancer, colon cancer, intestinal cancer, colorectal cancer, rectal cancer, pancreatic cancer, liver cancer, cancer of the bile duct or gall bladder; malignancies of the female genital tract, including ovarian carcinoma, uterine endometrial cancers, vaginal cancer, and cervical cancer; bladder cancer; brain cancer, including neuroblastoma; sarcoma, osteosarcoma; and skin cancer, including malignant melanoma or squamous cell cancer.

In another embodiment of the invention, a method of screening for an M-CSF-specific antibody is provided comprising the steps of contacting metastatic tumor cell medium, osteoclasts and a candidate antibody; detecting osteoclast formation, proliferation and/or differentiation; and identifying said candidate antibody as a M-CSF-specific antibody if a decrease in osteoclast formation, proliferation and/or differentiation is detected. Similarly, the aforementioned method is provided wherein said metastatic tumor cell medium includes tumor cells.

In a related embodiment, the aforementioned method is provided further comprising the step of determining if the candidate antibody binds to M-CSF. Similarly, another embodiment of the invention provides the aforementioned method further comprising the step of determining if said candidate antibody inhibits interaction between M-CSF and its receptor M-CSFR.

In another embodiment of the invention, a method of identifying an M-CSF-specific antibody that can prevent or treat metastatic cancer to bone is provided, comprising the steps of: (a) detecting binding of a candidate antibody to an epitope of M-CSF that includes at least 4 contiguous residues of amino acids 98-105 of FIG. 12; and (b) assaying the ability of said candidate antibody to prevent or treat metastatic cancer to bone in vitro or in vivo.

In another embodiment of the invention, a method of identifying an M-CSF-specific antibody that can prevent or treat metastatic cancer to bone is provided, comprising the steps of: (a) detecting binding of a candidate antibody to an epitope of M-CSF that includes at least 4 contiguous residues of amino acids 65-73 or 138-144 of FIG. 12 (corresponding to M-CSF epitopes recognized by 5H4 or MC3); and (b) assaying the ability of said candidate antibody to prevent or treat metastatic cancer to bone in vitro or in vivo.

In yet another embodiment of the invention, a method of altering a CDR of an antibody that binds an epitope of M-CSF that includes amino acids 98-105 of FIG. 12 is provided comprising altering an amino acid within a CDR of the amino acid sequence set forth in FIG. 4A and selecting for an antibody that binds M-CSF with an affinity Ka of at least 10[−7]. In another embodiment, a method of systematically altering up to 60% of the heavy chain amino acid sequence set forth in FIG. 4A is provided comprising altering any of X1-X52 in the amino acid sequence $X_1VX_2LX_3EX_4GX_5X_6X_7X_8X_9X_{10}$-$X_{11}X_{12}X_{13}LX_{14}LX_{15}CX_{16}VX_{17}DYSITSDYAWNWIX_{18}Q$-$X_{19}X_{20}X_{21}X_{22}X_{23}LX_{24}WMGYISYSGSTSX_{25}NX_{26}X_{27}L$-$X_{28}X_{29}X_{30}IX_{31}IX_{32}RX_{33}X_{34}X_{35}X_{36}X_{37}X_{38}FX_{39}LX_{40}L$-$X_{41}X_{42}VX_{43}X_{44}X_{45}DX_{46}AX_{47}YYCASFDYAHAMDYW$-$GX_{48}GTX_{49}VX_{50}VX_{51}X_{52}$ (SEQ ID NO: 133), and testing an antibody comprising the altered amino acid sequence for binding to an epitope of M-CSF that includes amino acids 98-105 of FIG. 12.

In a related embodiment, a method of systematically altering up to 60% of the light chain amino acid sequence set forth in FIG. 4A is provided comprising altering any of X1-X52 in the amino acid sequence $X_1IX_2LX_3QX_4X_5X_6X_7X_8X_9VX_{10}$-$X_{11}X_{12}X_{13}X_{14}VX_{15}FX_{16}CX_{17}AX_{18}QSIGTSIHWYX_{19}Q$-$X_{20}X_{21}X_{22}X_{23}X_{24}PX_{25}LLIKYASEX_{26}X_{27}X_{28}X_{29}IX_{30}X_{31}$-$X_{32}FX_{33}GX_{34}GX_{35}GX_{36}X_{37}X_{38}LX_{39}IX_{40}X_{41}VX_{42}X_{43}$-$X_{44}DX_{45}ADYYCQQINSWMFGX_{46}GTX_{47}LX_{48}X_{49}X_{50}$-$X_{51}X_{52}$ (SEQ ID NO: 134), and testing an antibody comprising the altered amino acid sequence for binding to an epitope of M-CSF that includes amino acids 98-105 of FIG. 12.

In yet another embodiment of the invention, a method of altering a CDR of an antibody that binds an epitope of M-CSF that includes amino acids 65-73 or 138-144 of FIG. 12 (corresponding to M-CSF epitopes recognized by 5H4 or MC3) is provided comprising altering an amino acid within a CDR of the amino acid sequence set forth in one of FIGS. 13, 14, and 15, and selecting for an antibody that binds M-CSF with an affinity Ka of at least 10[−7]. In another embodiment, a method of systematically altering up to 60% of the heavy chain amino acid sequence set forth in one of FIGS. 13, 14, and 15, is provided comprising altering the aforementioned sequences according to the methods set forth in Studnicka et al., U.S. Pat. No. 5,766,886 and Example 5 herein, and according to the Kabat numbering set forth in FIGS. 24C-24E, and testing an antibody comprising the altered amino acid sequence for binding to an epitope of M-CSF that includes amino acids 65-73 or 138-144 of FIG. 12 (corresponding to M-CSF epitopes recognized by 5H4 or MC3). In a related embodiment, all of the low risk residues are modified. Similarly, in another embodiment of the invention all of the low and moderate risk residues are modified. In yet another embodiment, all of the low and moderate risk residues excluding prolines are modified.

In another embodiment of the invention, a method of expressing an antibody having CDRs designed by the aforementioned process is provided. In another embodiment, a pharmaceutical composition comprising an antibody that binds MCSF wherein said antibody is made using the aforementioned method is provided.

In still another embodiment of the invention, a method of preventing or reducing bone loss or remodeling is provided comprising administering to a subject afflicted with a disease that causes or contributes to or results from osteolysis a therapeutically effective amount of any one of the aforementioned antibodies, thereby preventing or reducing bone loss or remodeling associated with the disease. In a related embodiment, a method of treating a subject afflicted with a disease that causes or contributes to or results from osteolysis is provided comprising administering to said subject a therapeutically effective amount of the antibody of any one of the aforementioned antibodies, thereby reducing the severity of bone loss or remodeling associated with the disease.

In a related embodiment, the aforementioned method is provided wherein said disease is selected from the group consisting of metabolic bone or osteolytic diseases associated with relatively increased osteoclast activity or the osteoclastic/osteoblastic process required for bone remodeling, including metabolic bone diseases, endocrinopathies (hypercortisolism, hypogonadism, primary or secondary hyperparathyroidism, hyperthyroidism), hypercalcemia, deficiency states (rickets/osteomalacia, scurvy, malnutrition), chronic diseases (malabsorption syndromes, chronic renal failure (renal osteodystrophy), chronic liver disease (hepatic osteodystrophy)), drugs (glucocorticoids (glucocorticoid-induced osteoporosis), heparin, alcohol), and hereditary diseases (osteogenesis imperfecta, homocystinuria), cancer, osteoporosis, -periprosthetic bone loss (for example, due to a foreign implant in bone or joint replacement with a prosthesis, including total hip arthroplasty), inflammation of bone associated with arthritis and rheumatoid arthritis, periodontal disease, fibrous dysplasia, and/or Paget's disease.

In still another embodiment, a method of preventing or treating metastatic cancer to bone is provided comprising administering to a subject afflicted with metastatic cancer a therapeutically effective amount of any one of the aforementioned antibodies. In a related embodiment, the method is provided wherein the metastatic cancer is breast, lung, renal, multiple myeloma, thyroid, prostate, adenocarcinoma, blood cell malignancies, including leukemia and lymphoma; head and neck cancers; gastrointestinal cancers, including esophageal cancer, stomach cancer, colon cancer, intestinal cancer, colorectal cancer, rectal cancer, pancreatic cancer, liver cancer, cancer of the bile duct or gall bladder; malignancies of the female genital tract, including ovarian carcinoma, uterine endometrial cancers, vaginal cancer, and cervical cancer; bladder cancer; brain cancer, including neuroblastoma; sarcoma, osteosarcoma; and skin cancer, including malignant melanoma or squamous cell cancer.

In yet another embodiment of the invention, a method of preventing bone loss or tumor growth is provided comprising administering to a subject in need thereof therapeutically effective amounts of any one of the aforementioned antibodies.

Any one of the therapeutic methods described herein may include administering a second therapeutic agent. In still another related embodiment, the method is provided wherein the second therapeutic agent is a cancer chemotherapeutic agent or a bisphosphonate. In yet another related embodiment, the method is provided wherein the bisphonate is zeledronate, pamidronate, clodronate, etidronate, tilundronate, alendronate, or ibandronate. In yet another related embodiment, the aforementioned methods are provided wherein the therapeutic agent is a cytotoxic chemotherapeutic agent. In another embodiment, the aforementioned method is provided wherein the subject is precluded from receiving bisphosphonate treatment.

In still another related embodiment, the aforementioned method is provided wherein the antibody is effective to reduce the dosage of second therapeutic agent required to achieve a therapeutic effect. In another embodiment, the second therapeutic agent is a non-M-CSF colony stimulating factor, for example G-CSF, or anti-RANKL antibody, or soluble RANKL receptor.

In another embodiment of the invention, the aforementioned methods are provided wherein the subject is a mammal. In a related embodiment, the mammal is human.

In another embodiment, the aforementioned methods are provided wherein the antibody inhibits the interaction between M-CSF and its receptor (M-CSFR). In another related embodiment, the antibody inhibits osteoclast proliferation and/or differentiation induced by tumor cells. In yet another embodiment, the aforementioned methods are provided wherein the antibody is administered at a dose between about 1.0 µg/kg to about 100 mg/kg, 2 µg/kg to 30 mg/kg, 0.1 mg/kg to 30 mg/kg or 0.1 mg/kg to 10 mg/kg body weight.

In another embodiment of the invention, the use of an antibody of the invention is contemplated in the manufacture of a medicament for preventing or reducing bone loss or remodeling in a patient exhibiting symptoms of osteolysis or osteoclastic disease, and in the manufacture of a medicament for treating a patient afflicted with a disease that causes or contributes to or results from osteolysis or osteoclastic disease. The aforementioned use is further contemplated wherein the disease is selected from the group consisting of osteolytic diseases associated with relatively increased osteoclast activity or the osteoclastic/osteoblastic process required for bone remodeling, including metabolic bone diseases, endocrinopathies (including hypercortisolism, hypogonadism, primary or secondary hyperparathyroidism, hyperthyroidism), hypercalcemia, deficiency states (including rickets/osteomalacia, scurvy, malnutrition), chronic diseases (including malabsorption syndromes, chronic renal failure (including renal osteodystrophy), chronic liver disease (including hepatic osteodystrophy)), drugs (including glucocorticoids (glucocorticoid-induced osteoporosis), heparin, alcohol), and hereditary diseases (including osteogenesis imperfecta, homocystinuria), cancer, osteoporosis, periprosthetic bone loss (for example, due to a foreign implant in bone or joint replacement with a prosthesis, including total hip arthroplasty), inflammation of bone associated with arthritis and rheumatoid arthritis, periodontal disease, fibrous dysplasia, and/or Paget's disease.

In another embodiment use of an antibody of the invention is contemplated in the manufacture of a medicament for preventing or treating metastatic cancer to bone in a patient suffering from metastatic cancer. In a related embodiment, the metastatic cancer is breast, lung, renal, multiple myeloma, thyroid, prostate, adenocarcinoma, blood cell malignancies, including leukemia or lymphoma; head or neck cancers; gastrointestinal cancers, including esophageal cancer, stomach cancer, colon cancer, intestinal cancer, colorectal cancer, rectal cancer, pancreatic cancer, liver cancer, cancer of the bile duct or gall bladder; malignancies of the female genital tract, including ovarian carcinoma, uterine endometrial cancers, vaginal cancer, or cervical cancer; bladder cancer; brain cancer, including neuroblastoma; sarcoma, osteosarcoma; or skin cancer, including malignant melanoma or squamous cell cancer.

In still another embodiment, use of an antibody of the invention is contemplated in the manufacture of a medicament for treating a patient having cancer.

In any of the aforementioned uses, the medicament is coordinated with treatment using a second therapeutic agent. In a related embodiment, the second therapeutic agent is a cancer chemotherapeutic agent. In related embodiments, the second therapeutic agent is a non-M-CSF colony stimulating factor, or anti-RANKL antibody, or soluble RANKL receptor, or a bisphosphonate. In a related embodiment, the bisphonate is zeledronate, pamidronate, clodronate, etidronate, tilundronate, alendronate, or ibandronate.

In yet another embodiment of the invention, any of the aforementioned uses is contemplated wherein the patient is precluded from receiving bisphosphonate treatment, and/or wherein the patient has been pre-treated with the second therapeutic agent. In a related embodiment, the second therapeutic agent is a cancer chemotherapeutic agent, a non-M-CSF colony stimulating factor, or anti-RANKL antibody, or soluble RANKL receptor, or a bisphosphonate. In yet another related embodiment, the bisphonate is zeledronate, pamidronate, clodronate, etidronate, tilundronate, alendronate, or ibandronate. In still another related embodiment, the patient is precluded from receiving bisphosphonate treatment.

In another embodiment of the invention, the use of a synergistic combination of an antibody of the invention for preparation of a medicament for treating a patient exhibiting symptoms of osteolysis wherein the medicament is coordinated with treatment using a second therapeutic agent is contemplated. In a related embodiment, the second therapeutic agent is a cancer chemotherapeutic agent, a non-M-CSF colony stimulating factor, or anti-RANKL antibody, or soluble RANKL receptor, or a bisphosphonate. In a related embodiment, the bisphonate is zeledronate, pamidronate, clodronate, etidronate, tilundronate, alendronate, or ibandronate. In still another embodiment, the patient is precluded from receiving bisphosphonate treatment.

Embodiments of any of the aforementioned uses are contemplated wherein the amount of antibody in the medicament is at a dose effective to reduce the dosage of second therapeutic agent required to achieve a therapeutic effect. In any of the aforementioned embodiments relating to bone loss or remodeling associated with cancer, the amount of antibody in the medicament is preferably effective to inhibit osteoclast proliferation and/or differentiation induced by tumor cells.

The amount of antibody in any of the aforementioned medicaments may be at a dose between about 1.0 µg/kg to about 100 mg/kg or 2 µg/kg to 30 mg/kg body weight. In a related embodiment, the amount of antibody in the medicament is at a dose between about 0.1 mg/kg to 30 mg/kg body weight. In still another embodiment, the amount of antibody in the medicament is at a dose between about 0.1 mg/kg to 10 mg/kg body weight.

Kits are also contemplated by the present invention. In one embodiment, a kit comprising a therapeutically effective amount of an antibody of the invention, packaged in a container, such as a vial or bottle or prefilled syringe, and further comprising a label attached to or packaged with the container, the label describing the contents of the container and providing indications and/or instructions regarding use of the contents of the container to prevent or reduce bone loss is provided. In another embodiment, a kit comprising a therapeutically effective amount of an antibody of the invention, packaged in a container, such as a vial or bottle, and further comprising a label attached to or packaged with the container, the label describing the contents of the container and providing indications and/or instructions The container optionally further comprises a container with a second therapeutic agent and/or a container with suitable solution for reconstituting lyophilized antibody. The label may provide instructions, for example, regarding use of the contents of the container to a patient afflicted with a disease that causes or contributes to osteolysis or to prevent or reduce bone remodeling, to prevent or treat is provided. In a related embodiment, the kit is provided wherein said disease is selected from the group consisting of, or osteolytic diseases associated with relatively increased osteoclast activity or the osteoclastic/osteoblastic process required for bone remodeling, including metabolic bone diseases, endocrinopathies (including hypercortisolism, hypogonadism, primary or secondary hyperparathyroidism, hyperthyroidism), hypercalcemia, deficiency states (including rickets/osteomalacia, scurvy, malnutrition), chronic diseases (including malabsorption syndromes, chronic renal failure (including renal osteodystrophy), chronic liver disease (including hepatic osteodystrophy)), drugs (including glucocorticoids (glucocorticoid-induced osteoporosis), heparin, alcohol), and hereditary diseases (including osteogenesis imperfecta, homocystinuria), cancer, osteoporosis, periprosthetic bone loss (for example, due to a foreign implant in bone or joint replacement with a prosthesis, including total hip arthroplasty), inflammation of bone associated with arthritis and rheumatoid arthritis, periodontal disease, fibrous dysplasia, and/or Paget's disease. Such osteolytic disease associated with metastatic cancer to bone can result from breast, lung, renal, multiple myeloma, thyroid, prostate, adenocarcinoma, blood cell malignancies, including leukemia or lymphoma; head or neck cancers; gastrointestinal cancers, including esophageal cancer, stomach cancer, colon cancer, intestinal cancer, colorectal cancer, rectal cancer, pancreatic cancer, liver cancer, cancer of the bile duct or gall bladder; malignancies of the female genital tract, including ovarian carcinoma, uterine endometrial cancers, vaginal cancer, or cervical cancer; bladder cancer; brain cancer, including neuroblastoma; sarcoma, osteosarcoma; or skin cancer, including malignant melanoma or squamous cell cancer.

In yet another embodiment, a kit is provided comprising a therapeutically effective amount of an antibody of the invention, packaged in a container, such as a vial or bottle or prefilled syringe, and further comprising a label attached to or packaged with the container, the label describing the contents of the container and providing indications and/or instructions regarding use of the contents of the container to treat bone loss cancer.

In another embodiment, the kit further comprises a second therapeutic agent. In a related embodiment, the second therapeutic agent is a cancer chemotherapeutic agent, a non-M-CSF colony stimulating factor, or anti-RANKL antibody, or soluble RANKL receptor, or a bisphosphonate. In a related embodiment, the bisphonate is zeledronate, pamidronate, clodronate, etidronate, tilundronate, alendronate, or ibandronate. In yet another embodiment, the kit inludes instructions to treat a patient precluded from receiving bisphosphonate treatment.

In another embodiment, the aforementioned kit is provided comprising a dose of anti-M-CSF antibody effective to reduce the dosage of second therapeutic agent required to achieve a therapeutic effect. In another embodiment, the kit comprises a dose of anti-M-CSF antibody that is synergistic with the second therapeutic agent. In yet another embodiment, the kit comprises a dose of antibody effective to inhibit osteoclast proliferation and/or differentiation, induced by tumor cells.

In still another embodiment of the invention, the aforementioned kit comprises a dose of antibody between about 1.0 µg/kg to about 100 mg/kg or 2 µg/kg to 30 mg/kg body weight. In another embodiment, the kit comprises a dose of antibody between about 0.1 mg/kg to 30 mg/kg body weight. In still another embodiment, the kit comprises a dose of antibody between about 0.1 mg/kg to 10 mg/kg body weight.

In still another embodiment of the invention, a method of preventing bone loss package, vial, prefilled syringe or container is provided comprising a medicament comprising one or more of the aforementioned antibodies and instructions that the medicament should be used in combination with surgery or radiation therapy. In another embodiment, a method of preventing or treating metastatic cancer to bone comprising the steps of administering any one of the aforementioned antibodies to a subject and treating the subject with surgery or radiation therapy is provided. In another embodiment, a method of targeting a tumor cell expressing membrane-bound M-CSF on its surface is provided comprising the step of administering any one of the aforementioned antibodies, wherein the antibody is conjugated to a radionuclide or other toxin. In yet another embodiment, a method of treating a subject suffering from a cancer is provided comprising administering a therapeutically effective amount of the any one of the aforementioned antibodies.

In still another embodiment of the invention, a method of preventing bone remodeling is provided comprising administering to a subject afflicted with a disease that causes or contributes to osteolysis an amount of any one of the aforementioned antibodies in an amount effective to neutralize M-CSF produced by the subject's cells, the amount being larger than the amount effective to neutralize M-CSF produced by the cancer cells. In a related embodiment, a method of treating a subject afflicted with a disease that causes or contributes to osteolysis is provided comprising administering to said subject an amount of any one of the aforementioned antibodies in an amount effective to neutralize M-CSF produced by the subject's cells, the amount being larger than the amount effective to neutralize M-CSF produced by the cancer cells.

In one embodiment of the invention, a pharmaceutical composition is provided comprising antibody RX1, 5H4, MC1 and/or MC3, or a non-murine RX1, 5H4, MC1 and/or MC3 derived antibody or an RX1, 5H4, MC1 and/or MC3 competing antibody, and a cancer therapeutic agent. In another embodiment of the invention, a package, vial or container is provided comprising a medicament comprising antibody RX1, 5H4, MC1 and/or MC3, or a non-murine RX1, 5H4, MC1 and/or MC3 derived antibody or an RX1, 5H4, MC1 and/or MC3 competing antibody, and instructions that the medicament should be used in combination with surgery or radiation therapy.

In still another embodiment of the invention, a method of treating a subject suffering from a cancer is provided, wherein the cells comprising the cancer do not secrete M-CSF, comprising the step of administering any one of the aforementioned antibodies.

BRIEF DESCRIPTION OF THE DRAWINGS

FIG. 3 is a comparison of osteoclast inducing activity between purified M-CSF and conditioned medium (CM) from MDA 231 cells and MCF7 cells.

FIG. 4A shows the amino acid sequence of M-CSF-specific murine antibody RX1 (SEQ ID NOs: 2 and 4) (encoded by the cDNA insert of the plasmid deposited with the American Type Culture Collection, Manassas, Va., USA, under ATCC deposit number PTA-6113) and a corresponding nucleic acid sequence (SEQ ID NOs: 1 and 3). The CDR regions are numbered and shown in bold.

FIGS. 4B and 4C show the amino acid sequences of M-CSF specific murine antibody RX1 light (SEQ ID NO: 5) and heavy chains (SEQ ID NO: 6), respectively, with high risk (bold), moderate risk (underline), and low risk residues identified according to Studnicka et al., WO93/11794.

FIG. 5B shows the M-CSF neutralization activity of antibodies MC1 and MC3.

FIG. 9 shows that M-CSF is prevalent on a number of cancer cell surfaces.

FIG. 10 is the amino acid sequence of M-CSFα (SEQ ID NO: 7).

FIG. 11 is the amino acid sequence of M-CSFβ (SEQ ID NO: 8).

FIG. 12 is the amino acid sequence of M-CSFγ (SEQ ID NO: 9). A number of polymorphisms in the DNA sequence may result in amino acid differences. For example, a common polymorphism provides an Ala rather than Pro at position 104.

FIGS. 13, 14, and 15 show the amino acid sequences of MCSF-specific murine antibodies 5H4 (SEQ ID NOs: 10 and 11), MC1 (SEQ ID NOs: 12 and 13) (produced by the hybridoma deposited under ATCC deposit number PTA-6263) and MC3 (SEQ ID NOs: 14 and 15) (produced by the hybridoma deposited under ATCC deposit number PTA-6264), respectively.

FIGS. 16A and B are an alignment of CDR regions of the heavy and light chain amino acid sequences of human M-CSF specific murine antibodies RX1; 5H4; MC1; and MC3 (SEQ ID NOs: 16-38).

FIG. 19A shows (a) the risk line for the murine RX1 heavy chain (H=high risk, M=moderate risk, L=low risk), (b) the RX1 heavy chain amino acid sequence (SEQ ID NO: 6), (c) the amino acid sequence of the closest human consensus sequence, Kabat Vh2 consensus, aligned to RX1 (SEQ ID NO: 39) and (d) changes that were made to produce two exemplary Human Engineered™ sequences (SEQ ID NOs: 41 and 43). FIG. 19B shows the amino acid sequences of the two exemplary heavy chain Human Engineered™ sequences (SEQ ID NOs: 41 and 43), designated "low risk" and "low+ moderate risk" as well as corresponding nucleic acid sequences (SEQ ID NOs: 40 and 42).

FIG. 20A shows (a) the risk line for the murine RX1 light chain (H=high risk, M=moderate risk, L=low risk), (b) the RX1 light chain amino acid sequence (SEQ ID NO: 5), (c) the amino acid sequence of the closest human consensus sequence, Kabat Vk3 consensus, aligned to RX1 (SEQ ED NO: 49) and (d) changes that were made to produce two exemplary Human Engineered™ sequences (SEQ ID NOs: 45 and 47). FIG. 20B shows the amino acid sequences of the two exemplary light chain Human Engineered™ sequences (SEQ ID NOs: 45 and 47), designated "low risk" and "low+ moderate risk" as well as corresponding nucleic acid sequences (SEQ ID NOs: 44 and 46).

FIG. 21A shows (a) the risk line for the murine RX1 light chain (H=high risk, M=moderate risk, L=low risk), (b) the RX1 light chain amino acid sequence (SEQ ID NO: 5), (c) the amino acid sequence of the closest human consensus sequence, Kabat Vk3 consensus, aligned to RX1 (SEQ ID NO: 49) and (d) an alternate exemplary amino acid sequence in which positions 54-56 were not changed (i.e. remained the murine sequence) (SEQ ID NO: 48). FIG. 21B shows the amino acid sequences of two exemplary alternate light chain Human Engineered™ sequences (SEQ ID NOs: 48, 136), as well as corresponding nucleic acid sequences (SEQ ID NOs: 137 and 135).

FIG. 22A shows (a) the risk line for the murine RX1 light chain (H=high risk, M=moderate risk, L=low risk), (b) the RX1 light chain amino acid sequence (SEQ ID NO: 5), (c) the amino acid sequence of the closest human consensus germline sequence, Vk6 Subgroup 2-1-(1) A14, aligned to RX1 (SEQ ID NO: 50) and (d) changes that were made to produce two exemplary Human Engineered™ sequences (SEQ ID NOs: 51 and 53). FIG. 22B shows the amino acid sequences of the two exemplary light chain Human Engineered™ sequences (SEQ ID NOs: 51 and 53), designated "low risk" and "low+moderate risk" as well as the corresponding nucleic acid sequence (SEQ ID NO: 52).

FIGS. 23A and 23B show the alignment of murine RX1 light chain amino acid sequence (SEQ ID NO: 54) with various human consensus and human germline consensus sequences using the Kabat numbering system (amino acid numbering indicated in line designated "POS") (SEQ ID NOs: 55-82).

FIGS. 24A and 24B show the alignment of murine RX1 heavy chain amino acid sequence (SEQ ID NO: 83) with various human consensus and human germline consensus sequences using the Kabat numbering system (amino acid numbering indicated in line designated "POS") (SEQ ID NOs: 84-112). FIGS. 24C-24E show how the amino acid residues of antibodies 5H4, MC1 and MC3 correspond to the Kabat numbering system (SEQ ID NOs: 10 and 11; SEQ ID NOs: 12 and 13; SEQ ID NOs: 14 and 15, respectively).

FIG. 29A shows the amino acid (SEQ ID NO: 114) and nucleotide sequence (SEQ ID NO: 113) for heRX1-1.IgG1 with low risk amino acid changes. FIG. 29B shows the amino acid (SEQ ID NO: 116) and nucleotide sequence (SEQ ID NO: 115) for heRX1-1.IgG1 with low+moderate risk amino acid changes.

FIG. 30 shows the amino acid (SEQ ID NO: 119) and nucleotide sequence (cDNA (SEQ ID NO: 118) and genomic DNA (SEQ ID NO: 117)) for heRX1-1.IgG4 with low risk amino acid changes.

FIG. 31 shows the effect on osteoclastogenesis of 5H4.

DETAILED DESCRIPTION

Figure 1:
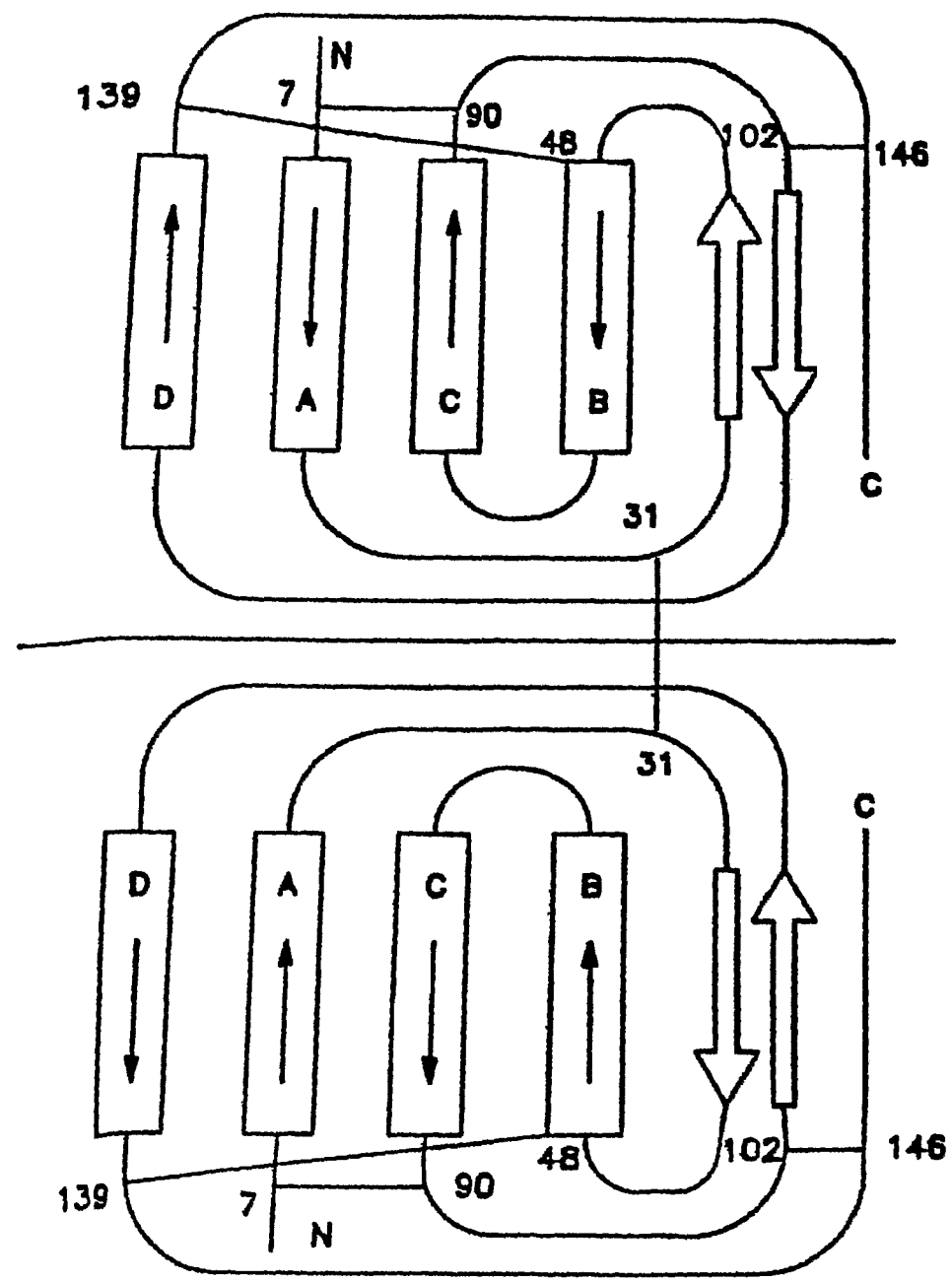
FIG. 1 is a topology diagram showing the disulfide bonds in truncated dimeric M-CSF.
Figure 2:
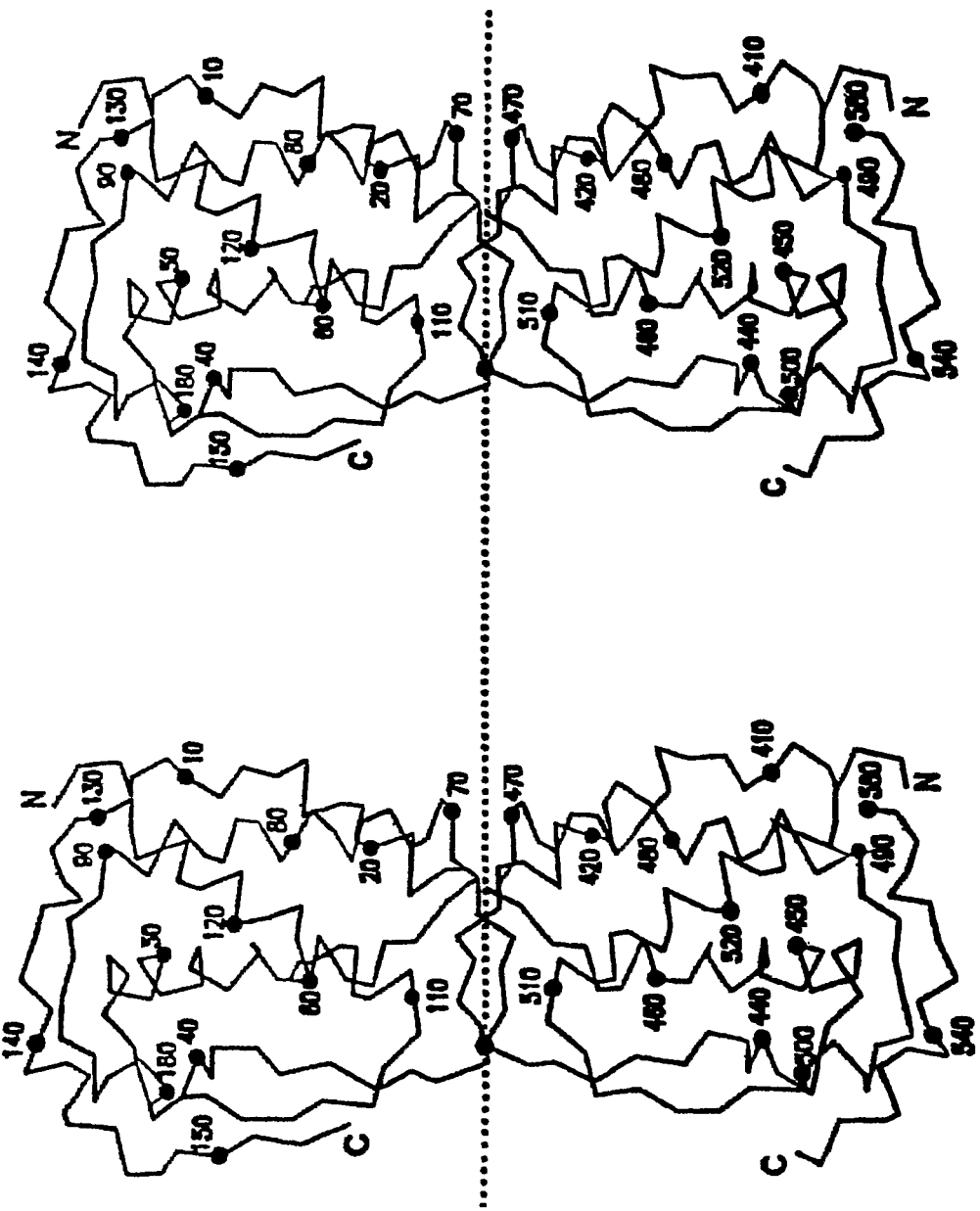
FIG. 2 is a stereodiagram of the C-alpha backbone of M-CSF with every tenth residue labeled and with the non-crystallographic symmetry axis indicated by a dotted line.

The ability to metastasize is a defining characteristic of a cancer. Metastasis refers to the spread of cancer cells to other parts of the body or to the condition produced by this spread. Metastasis is a complex multi-step process that includes changes in the genetic material of a cell, uncontrolled proliferation of the altered cell to form a primary tumor, development of a new blood supply for the primary tumor, invasion of the circulatory system by cells from the primary tumor, dispersal of small clumps of primary tumor cells to other parts of the body, and the growth of secondary tumors in those sites.

Bone is one of the most common sites of metastasis in human breast, lung, prostate and thyroid cancers, as well as other cancers, and in autopsies as many as 60% of cancer patients are found to have bone metastasis. Osteolytic bone metastasis shows a unique step of osteoclastic bone resorption that is not seen in metastasis to other organs. Bone loss associated with cancer metastasis is mediated by osteoclasts (multinucleated giant cells with the capacity to resorb mineralized tissues), which seem to be activated by tumor products. Activation of osteoclasts is associated with some cancers.

Colony stimulating factor (CSF-1), also known as macrophage colony stimulating factor (M-CSF), has been found crucial for osteoclast formation. In addition, M-CSF has been shown to modulate the osteoclastic functions of mature osteoclasts, their migration and their survival in cooperation with other soluble factors and cell to cell interactions provided by osteoblasts and fibroblasts (Fixe and Praloran, Cytokine 10: 3-7, 1998; Martin et al., Critical Rev. in Eukaryotic Gene Expression 8: 107-23 (1998)).

The full-length human M-CSF mRNA encodes a precursor protein of 554 amino acids. Through alternative mRNA splicing and differential post-translational proteolytic processing, M-CSF can either be secreted into the circulation as a glycoprotein or chondroitin sulfate containing proteoglycan or be expressed as a membrane spanning glycoprotein on the surface of M-CSF producing cells. The three-dimensional structure of the bacterially expressed amino terminal 150 amino acids of human M-CSF, the minimal sequence required for full in vitro biological activity, indicates that this protein is a disulfide linked dimer with each monomer consisting of four alpha helical bundles and an anti-parallel beta sheet (Pandit et al., Science 258: 1358-62 (1992)). Three distinct M-CSF species are produced through alternative mRNA splicing. The three polypeptide precursors are M-CFSα of 256 amino acids, M-CSFβ of 554 amino acids, and M-CSFγ of 438 amino acids. M-CSFβ is a secreted protein that does not occur in a membrane-bound form. M-CSFα is expressed as an integral membrane protein that is slowly released by proteolytic cleavage. M-CSFα is cleaved at amino acids 191-197 of the sequence set out in FIG. 10. The membrane-bound form of M-CSF can interact with receptors on nearby cells and therefore mediates specific cell-to-cell contacts. The term "M-CSF" may also include amino acids 36-438 of FIG. 12.

Various forms of M-CSF function by binding to its receptor M-CSFR (also known as CSF-1R) on target cells. M-CSFR is a membrane spanning molecule with five extracellular immunoglobulin-like domains, a transmembrane domain and an intracellular interrupted Src related tyrosine kinase domain. M-CSFR is encoded by the c-fms proto-oncogene. Binding of M-CSF to the extracellular domain of M-CSFR leads to dimerization of the receptor, which activates the cytoplasmic kinase domain, leading to autophosphorylation and phosphorylation of other cellular proteins (Hamilton J. A., J Leukoc Biol., 62(2):145-55 (1997); Hamilton J, A., Immuno Today., 18(7): 313-7 (1997).

Phosphorylated cellular proteins induce a cascade of biochemical events leading to cellular responses: mitosis, secretion of cytokines, membrane ruffling, and regulation of transcription of its own receptor (Fixe and Praloran, Cytokine 10: 32-37 (1998)).

M-CSF is expressed in stromal cells, osteoblasts, and other cells. It is also expressed in breast, uterine, and ovarian tumor cells. The extent of expression in these tumors correlates with high grade and poor prognosis (Kacinski Ann. Med. 27: 79-85 (1995); Smith et al., Clin. Cancer Res. 1: 313-25 (1995)). In breast carcinomas, M-CSF expression is prevalent in invasive tumor cells as opposed to the intraductal (pre-invasive) cancer (Scholl et al., J. Natl. Cancer Inst. 86: 120-6 (1994)). In addition, M-CSF is shown to promote progression of mammary tumors to malignancy (Lin et al., J. Exp. Med. 93: 727-39 (2001)). For breast and ovarian cancer, the production of M-CSF seems to be responsible for the recruitment of macrophages to the tumor. Cancers arising in the prostate induce osteoblastic lesions in which new bone is formed as opposed to resorbed. In addition, prostate metastases are often mixed, consisting of both osteolytic and osteoblastic lesions. Clinically, in some patients, there is an osteolytic phase that often precedes the osteoblastic phase. The osteolytic phase often results in the release of osteoblast growth factors which may help to "prime" the osteoblastic process. Recently, several studies have shown that bisphosphonates, most commonly known to prevent/treat osteoporosis and other bone lytic diseases, can effectively prevent or inhibit growth of osteoblastic metastases. In one embodiment of the present inventition, anti-M-CSF antibodies are used to treat either mixed-disease or osteoblastic disease. Thus, the present invention provides compositions and methods for treating or preventing cancer, cancer metastasis and bone remodeling associated with cancer metastasis.

A preferred anti-M-CSF antibody murine RX1 was modified to be less immunogenic in humans based on the Human Engineering™ method of Studnicka et al. In a preferred embodiment, 8 to 12 surface exposed amino acid residues of the heavy chain variable region and 16 to 19 surface exposed residues in the light chain region were modified to human residues in positions determined to be unlikely to adversely effect either antigen binding or protein folding, while reducing its immunogenicity with respect to a human environment.

Synthetic genes containing modified heavy and/or light chain variable regions were constructed and linked to human γ heavy chain and/or kappa light chain constant regions. Any human heavy chain and light chain constant regions may be used in combination with the Human Engineered™ antibody variable regions. The human heavy and light chain genes were introduced into mammalian cells and the resultant recombinant immunoglobulin products were obtained and characterized. Other exemplary anti-M-CSF antibodies such as 5H4, MC1, or MC3 are similarly Human Engineered™.

The term "RX 1-derived antibody" includes any one of the following:

1) an amino acid variant of murine antibody RX1 having the amino acid sequence set out in FIG. 4, including variants comprising a variable heavy chain amino acid sequence which is at least 60, 65, 70, 75, 80, 85, 90, 91, 92, 93, 94, 95, 96, 97, 98, or 99% homologous to the amino acid sequence as set forth in FIG. 4, and/or comprising a variable light chain amino acid sequence which is at least 60, 65, 70, 75, 80, 85, 90, 91, 92, 93, 94, 95, 96, 97, 98, or 99% homologous to the amino acid sequence as set forth in FIG. 4, taking into account similar amino acids for the homology determination;

2) M-CSF-binding polypeptides (excluding murine antibody RX 1) comprising one or more complementary determining regions (CDRs) of murine antibody RX 1 having the amino acid sequence set out in FIG. 4, preferably comprising at least CDR3 of the RX 1 heavy chain, and preferably comprising two or more, or three or more, or four or more, or five or more, or all six CDRs;

3) Human Engineered™ antibodies having the heavy and light chain amino acid sequences set out in FIGS. 19B through 22B or variants thereof comprising a heavy or light chain having at least 60% amino acid sequence identity with the original Human Engineered™ heavy or the light chain of FIGS. 19B through 22B, more preferably at least 80%, more preferably at least 85%, more preferably at least 90%, and most preferably at least 95%, including for example, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, and 100% identical;

4) M-CSF-binding polypeptides (excluding murine antibody RX1) comprising the high risk residues of one or more CDRs of the Human Engineered™ antibodies of FIGS. 19B through 22B, and preferably comprising high risk residues of two or more, or three or more, or four or more, or five or more, or all six CDRs; exemplary CDRs of Human Engineered™ RX1 antibodies include SEQ ID NOs: 18, 21, 24, 32, 36 and QASQSIGTSIH (SEQ ID NO: 138);

5) Human Engineered™ antibodies or variants retaining the high risk amino acid residues set out in FIG. 4B, and comprising one or more changes at the low or moderate risk residues set out in FIG. 4B;

for example, comprising one or more changes at a low risk residue and conservative substitutions at a moderate risk residue set out in FIG. 4B, or for example, retaining the moderate and high risk amino acid residues set out in FIG. 4B and comprising one or more changes at a low risk residue, where changes include insertions, deletions or substitutions and may be conservative substitutions or may cause the engineered antibody to be closer in sequence to a human light chain or heavy chain sequence, a human germline light chain or heavy chain sequence, a consensus human light chain or heavy chain sequence, or a consensus human germline light chain or heavy chain sequence; that retain ability to bind M-CSF. Such antibodies preferably bind to M-CSF with an affinity of at least $10^{-7}$, $10^{-8}$ or $10^{-9}$ or higher and preferably neutralize the desired biological activity of M-CSF, e.g. osteoclastogenesis-inducing activity of M-CSF.

Similarly, the term "MC3-derived antibody" includes any one of the following:

1) an amino acid variant of murine antibody MC3 having the amino acid sequence set out in FIG. 15, including variants comprising a variable heavy chain amino acid sequence which is at least 60, 65, 70, 75, 80, 85, 90, 91, 92, 93, 94, 95, 96, 97, 98, or 99% homologous to the amino acid sequence as set forth in FIG. 15, and/or comprising a variable light chain amino acid sequence which is at least 60, 65, 70, 75, 80, 85, 90, 91, 92, 93, 94, 95, 96, 97, 98, or 99% homologous to the amino acid sequence as set forth in FIG. 15, taking into account similar amino acids for the homology determination;

2) M-CSF-binding polypeptides (optionally including or excluding murine antibody MC3) comprising one or more complementary determining regions (CDRs) of murine antibody MC3 having the amino acid sequence set out in FIG. 15, preferably comprising at least CDR3 of the MC3 heavy chain, and preferably comprising two or more, or three or more, or four or more, or five or more, or all six CDRs;

3) Human Engineered™ antibodies generated by altering the murine sequence according to the methods set forth in Studnicka et al., U.S. Pat. No. 5,766,886 and Example 5 herein, using the Rabat numbering set forth in FIGS. 24C-24E to identify low, moderate and high risk residues; such antibodies comprising at least one of the following heavy chains and at least one of the following light chains: (a) a heavy chain in which all of the low risk residues have been modified, if necessary, to be the same residues as a human reference immunoglobulin sequence or (b) a heavy chain in which all of the low and moderate risk residues have been modified, if necessary, to be the same residues as a human reference immunoglobulin sequence, (c) a light chain in which all of the low risk residues have been modified, if necessary, to be the same residues as a human reference immunoglobulin sequence or (b) a light chain in which all of the low and moderate risk residues have been modified, if necessary, to be the same residues as a human reference immunoglobulin sequence;

4) variants of the aforementioned antibodies in preceding paragraph (3) comprising a heavy or light chain having at least 60% amino acid sequence identity with the original Human Engineered™ heavy or the light chain, more preferably at least 80%, more preferably at least 85%, more preferably at least 90%, and most preferably at least 95%, including for example, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, and 100% identical;

5) M-CSF-binding polypeptides (optionally including or excluding murine antibody MC3) comprising the high risk residues of one or more CDRs of the murine MC3 antibody of FIG. 15, and preferably comprising high risk residues of two or more, or three or more, or four or more, or five or more, or all six CDRs;

6) Human Engineered™ antibodies or variants retaining the high risk amino acid residues of murine MC3 antibody, and comprising one or more changes at the low or moderate risk residues;

for example, comprising one or more changes at a low risk residue and conservative substitutions at a moderate risk residue, or for example, retaining the moderate and high risk amino acid residues and comprising one or more changes at a low risk residue, where changes include insertions, deletions or substitutions and may be conservative substitutions or may cause the engineered antibody to be closer in sequence to a human light chain or heavy chain sequence, a human germline light chain or heavy chain sequence, a consensus human light chain or heavy chain sequence, or a consensus human germline light chain or heavy chain sequence; that retain ability to bind M-CSF. Such antibodies preferably bind to M-CSF with an affinity of at least $10^{-7}$, $10^{-8}$ or $10^{-9}$ or higher and preferably neutralize the desired biological activity of M-CSF, e.g. osteoclastogenesis-inducing activity of M-CSF.

The term "5H4-derived antibody" or "MC1-derived antibody" is similarly defined according to the above description.

As described in detail herein, anti-M-CSF antibodies such as RX1, 5H4, MC1 or MC3-derived antibodies, including Human Engineered™ antibodies or variants, may be of different isotypes, such as IgG, IgA, IgM or IgE. Antibodies of the IgG class may include a different constant region, e.g. an IgG2 antibody may be modified to display an IgG1 or IgG4 constant region. In preferred embodiments, the invention provides Human Engineered™ antibodies or variants comprising a modified or unmodified IgG1 or IgG4 constant region. In the case of IgG1, modifications to the constant region, particularly the hinge or CH2 region, may increase or decrease effector function, including ADCC and/or CDC activity. In other embodiments, an IgG2 constant region is modified to decrease antibody-antigen aggregate formation. In the case of IgG4, modifications to the constant region, particularly the hinge region, may reduce the formation of half-antibodies. In specific exemplary embodiments, mutating the IgG4 hinge sequence Cys-Pro-Ser-Cys to the IgG1 hinge sequence Cys-Pro-Pro-Cys is provided.

Human Engineered™ antibodies containing IgG1 or IgG4 constant regions are shown herein to have improved properties compared to Human Engineered™ antibodies containing IgG2 constant regions. Choice of the IgG1 or IgG4 Fc region improved binding affinity, MCSF neutralization activity, and anti-osteoclast activity. In addition, choice of the IgG1 or IgG4 Fc region provided antigen-antibody complexes that more closely resembled those formed by the parent murine antibody.

The mobility at the hinge region thus appears to markedly affect binding of antibody to the dimeric antigen MCSF as well as neutralization activity of the antibody. The invention contemplates generally that preparation of antibodies containing a heavy chain comprising a modified or unmodified IgG1 or IgG4 constant region, particularly the hinge and CH2 domains, or preferably at least the hinge domains, improves binding affinity and/or slows dissociation of antibody from dimeric antigens.

The term "RX1-competing antibody" includes 1) a non-murine or non-rodent monoclonal antibody that binds to the same epitope of M-CSF as murine RX1 having the complete light and heavy chain sequences set out in FIG. 4;

2) a non-murine or non-rodent monoclonal antibody that binds to at least 4 contiguous amino acids of amino acids 98-105 of the M-CSF of FIG. 12; and 3) a non-murine or non-rodent monoclonal antibody that competes with murine antibody RX1 having the complete sequence set out in FIG. 4 for binding to M-CSF, by more than 75%, more than 80%, or more than 81%, 82%, 83%, 84%, 85%, 86%, 87%, 88%, 89%, 90%, 91%, 92%, 93%, 94% or 95%. Such antibodies preferably bind to M-CSF with an affinity of at least $10^{-7}$, $10^{-8}$ or $10^{-9}$ or higher and preferably neutralize the desired biological activity of M-CSF, e.g. osteoclastogenesis-inducing activity of M-CSF.

The term "MC1-competing antibody" or "MC3-competing antibody" or "5H4-competing antibody" is similarly defined with reference to the murine 5H4, MC1 or MC3 antibodies having the complete light and heavy chain sequences set out in FIG. 13, 14 or 15, respectively, and with reference to the epitope of M-CSF bound by the antibody, e.g. amino acids 65-73 or 138-144 of FIG. 12 (corresponding to M-CSF epitopes recognized by 5H4 or MC3).

Optionally, any chimeric, human or humanized M-CSF antibody publicly disclosed before the filing date hereof, or disclosed in an application filed before the filing date hereof, is excluded from the scope of the invention.

"Non-rodent" monoclonal antibody is any antibody, as broadly defined herein, that is not a complete intact rodent monoclonal antibody generated by a rodent hybridoma. Thus, non-rodent antibodies specifically include, but are not limited to, variants of rodent antibodies, rodent antibody fragments, linear antibodies, chimeric antibodies, humanized antibodies, Human Engineered™ antibodies and human antibodies, including human antibodies produced from transgenic animals or via phage display technology. Similarly, non-murine antibodies include but are not limited to variants of murine antibodies, murine antibody fragments, linear antibodies, chimeric, humanized, Human Engineered™ and human antibodies.

"Tumor", as used herein, refers to all neoplastic cell growth and proliferation, whether malignant or benign, and all precancerous and cancerous cells and tissues.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colorectal cancer, endometrial carcinoma, salivary gland carcinoma, kidney cancer, liver cancer, vulval cancer, thyroid cancer, hepatic carcinoma and various types of head and neck cancer.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. Treatment of patients suffering from clinical, biochemical, radiological or subjective symptoms of the disease, such as osteoblastic lesions or osteolysis, may include alleviating some or all of such symptoms or reducing the predisposition to the disease. The "pathology" of cancer includes all phenomena that compromise the well being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, etc. Thus, improvement after treatment may be manifested as decreased tumor size, decline in tumor growth rate, destruction of existing tumor cells or metastatic cells, and/or a reduction in the size or number of metastases.

"Mammal" for purposes of treatment refers to any animal classified as a mammal, including humans, domestic and farm animals, and zoo, sports, or pet animals, such as dogs, horses, cats, cows, etc. Preferably, the mammal is human.

As used herein, the phrase "metastatic cancer" is defined as cancers that have potential to spread to other areas of the body, particularly bone. A variety of cancers can metastasize to the bone, but the most common metastasizing cancers are breast, lung, renal, multiple myeloma, thyroid and prostate. By way of example, other cancers that have the potential to metastasize to bone include but are not limited to adenocarcinoma, blood cell malignancies, including leukemia and lymphoma; head and neck cancers; gastrointestinal cancers, including esophageal cancer, stomach cancer, colon cancer, intestinal cancer, colorectal cancer, rectal cancer, pancreatic cancer, liver cancer, cancer of the bile duct or gall bladder; malignancies of the female genital tract, including ovarian carcinoma, uterine endometrial cancers, vaginal cancer, and cervical cancer; bladder cancer; brain cancer, including neuroblastoma; sarcoma, osteosarcoma; and skin cancer, including malignant melanoma and squamous cell cancer. The present invention especially contemplates prevention and treatment of tumor-induced osteolytic lesions or mixed osteoblastic/osteolytic lesions in bone.

As used herein, the phrase "therapeutically effective amount" is meant to refer to an amount of therapeutic or prophylactic M-CSF antibody that would be appropriate for an embodiment of the present invention, that will elicit the desired therapeutic or prophylactic effect or response, including alleviating some or all of such symptoms of disease or reducing the predisposition to the disease, when administered in accordance with the desired treatment regimen.

Human "M-CSF" as used herein refers to a human polypeptide having substantially the same amino acid sequence as the mature human M-CSFα, M-CSFβ, or M-CSFγ polypeptides described in Kawasaki et al., Science 230:291 (1985), Cerretti et al., Molecular Immunology, 25:761 (1988), or Ladner et al., EMBO Journal 6:2693 (1987), each of which are incorporated herein by reference. Such terminology reflects the understanding that the three mature M-CSFs have different amino acid sequences, as described above, and that the active form of M-CSF is a disulfide bonded dimer; thus, when the term "M-CSF" refers to the biologically active form, the dimeric form is intended. "M-CSF dimer" refers to two M-CSF polypeptide monomers that have dimerized and includes both homodimers (consisting of two of the same type of M-CSF monomer) and heterodimers (consisting of two different monomers). M-CSF monomers may be converted to M-CSF dimers in vitro as described in U.S. Pat. No. 4,929,700, which is incorporated herein by reference.

Anti-MCSF Antibodies

The present invention provides a M-CSF-specific antibody, such as RX1, 5H4, MC1, and/or MC3, pharmaceutical formulations including a M-CSF-specific antibody, such as RX1, 5H4, MC1, and/or MC3, methods of preparing the pharmaceutical formulations, and methods of treating patients with the pharmaceutical formulations and compounds. The term "antibody" is used in the broadest sense and includes fully assembled antibodies, monoclonal antibodies, polyclonal antibodies, multispecific antibodies (e.g., bispecific antibodies), antibody fragments that can bind antigen (e.g., Fab', F'(ab)2, Fv, single chain antibodies, diabodies), and recombinant peptides comprising the forgoing as long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that are typically include different antibodies directed against different determinants (epitopes), each monoclonal antibody is directed against a single determinant on the antigen. In addition to their specificity, the monoclonal antibodies are advantageous in that they are synthesized by the homogeneous culture, uncontaminated by other immunoglobulins with different specificities and characteristics.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 [1975], or may be made by recombinant DNA methods (see, e.g., U.S. Pat. No. 4,816,567). The "monoclonal antibodies" may also be isolated from phage antibody libraries using the techniques described in Clackson et al., Nature, 352:624628[1991] end Marks et al., J. Mol. Biol., 222:581-597 (1991), for example.

Depending on the amino acid sequence of the constant domain of their heavy chains, immunoglobulins can be assigned to different classes. There are five major classes, IgA, IgD, IgE, IgG and IgM, and several of these may be further divided into subclasses or isotypes, e.g. IgG1, IgG2, IgG3, IgG4, IgA1 and IgA2. The heavy-chain constant domains that correspond to the different classes of immunoglobulins are called alpha, delta, epsilon, gamma and mu respectively. The subunit structures and three-dimensional configurations of different classes of immunoglobulins are well known. Different isotypes have different effector functions; for example, IgG1 and IgG3 isotypes have ADCC activity.

"Antibody fragments" comprise a portion of an intact full length antibody, preferably the antigen binding or variable region of the intact antibody. Examples of antibody fragments include Fab, Fab', F(ab')2, and Fv fragments; diabodies; linear antibodies (Zapata et al., Protein Eng., 8(10):1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize 35 readily. Pepsin treatment yields an F(ab')2 fragment that has two "Single-chain Fv" or "sFv" antibody fragments comprise the VH and VL domains of antibody, wherein these domains are present in a single polypeptide chain. Preferably, the Fv polypeptide further comprises a polypeptide linker between the VH and VL domains that enables the Fv to form the desired structure for antigen binding. For a review of sFv see Pluckthun in The Pharmacology of Monoclonal Antibodies, vol. 113, Rosenburg and Moore eds., Springer-Verlag, New York, pp. 269-315 (1994).

The term "hypervariable" region refers to the amino acid residues of an antibody which are responsible for antigen-binding. The hypervariable region comprises amino acid residues from a complementarity determining region or CDR [i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5$^{th}$ Ed. Public Health Service, National Institutes of Health, Bethesda, Md. (1991)] and/or those residues from a hypervariable loop (i.e., residues 26-32 (L1), 50-52 (L2) and 91-96 (L3) in the light chain variable domain and 26-32 (H1), 53-55 (H2) and 96-101 (H3) in the heavy chain variable domain as described by [Chothia et al., *J. Mol. Biol.* 196: 901-917 (1987)].

"Framework" or FR residues are those variable domain residues other than the hypervariable region residues.

The term "diabodies" refers to small antibody fragments with two antigen-binding sites, which fragments comprise a heavy-chain variable domain (VH) connected to a light-chain variable domain (VL) in the same polypeptide chain (VH VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and 30 Hollinger et al., Proc. Natl. Acad. Sci. USA, 90:6444-6448 (1993).

In some embodiments, it may be desirable to generate multispecific (e.g. bispecific) monoclonal antibody including monoclonal, human, humanized, Human Engineered™ or variant anti-M-CSF antibodies having binding specificities for at least two different epitopes. Exemplary bispecific antibodies may bind to two different epitopes of M-CSF. Alternatively, an anti-M-CSF arm may be combined with an arm which binds to a triggering molecule on a leukocyte such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the M-CSF-expressing cell. Bispecific antibodies may also be used to localize second therapeutic agents, e.g., cytotoxic agents to cells which express M-CSF. These antibodies possess an M-CSF-binding arm and an arm which binds the cytotoxic agent (e.g., saporin, anti-interferon-60, vinca alkaloid, ricin A chain, methotrexate or radioactive isotope hapten). Bispecific antibodies can be prepared as full length antibodies or antibody fragments (e.g., F(ab').sub.2 bispecific antibodies).

According to another approach for making bispecific antibodies, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO96/27011 published Sep. 6, 1996.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. In yet a further embodiment, Fab'-SH fragments directly recovered from *E. coli* can be chemically coupled in vitro to form bispecific antibodies. (Shalaby et al., J. Exp. Med. 175:217-225 (1992)).

Shalaby et al., J. Exp. Med. 175:217-225 (1992) describe the production of a fully humanized bispecific antibody F(ab')$_2$ molecule. Each Fab' fragment was separately secreted from *E. coli* and subjected to directed chemical coupling in vitro to form the bispecfic antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. (Kostelny et al., J. Immunol. 148(5):1547-1553 (1992)) The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments.

The fragments comprise a heavy chain variable region ($V_H$) connected to a light-chain variable region ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol. 152: 5368 (1994).

Alternatively, the bispecific antibody may be a "linear antibody" produced as described in Zapata et al. Protein Eng. 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

Antibodies with more than two valencies are also contemplated. For example, trispecific antibodies can be prepared. (Tutt et al., J. Immunol. 147:60 (1991)).

In certain embodiments, the monoclonal, human, humanized, Human Engineered™ or variant anti-M-CSF antibody is an antibody fragment, such as an RX1, 5H4, MC1, or MC3 antibody fragment. Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science 229:81 (1985)). However, these fragments can now be produced directly by recombinant host cells. Better et al., Science 240: 1041-1043 (1988) disclose secretion of functional antibody fragments from bacteria (see, e.g., Better et al., Skerra et al. Science 240: 1038-1041 (1988)). For example, Fab'-SH fragments can be directly recovered from E. coli and chemically coupled to form F(ab')$_2$ fragments (Carter et al., Bio/Technology 10:163-167 (1992)). In another embodiment, the F(ab')$_2$ is formed using the leucine zipper GCN4 to promote assembly of the F(ab')$_2$ molecule. According to another approach, Fv, Fab or F(ab')$_2$ fragments can be isolated directly from recombinant host cell culture. Other techniques for the production of antibody fragments will be apparent to the skilled practitioner.

An "isolated" antibody is one that has been identified and separated and recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

For a detailed description of the structure and generation of antibodies, see Roth, D. B., and Craig, N. L., Cell, 94:411-414 (1998), and U.S. Pat. No. 6,255,458, herein incorporated by reference in its entirety. Briefly, the process for generating DNA encoding the heavy and light chain immunoglobulin genes occurs primarily in developing B-cells. Prior to the rearranging and joining of various immunoglobulin gene segments, the V, D, J and constant (C) gene segments are found generally in relatively close proximity on a single chromosome. During B-cell-differentiation, one of each of the appropriate family members of the V, D, J (or only V and J in the case of light chain genes) gene segments are recombined to form functionally rearranged heavy and light immunoglobulin genes. This gene segment rearrangement process appears to be sequential. First, heavy chain D-to-J joints are made, followed by heavy chain V-to-DJ joints and light chain V-to-J joints.

The recombination of variable region gene segments to form functional heavy and light chain variable regions is mediated by recombination signal sequences (RSS's) that flank recombinationally competent V, D and J segments. RSS's necessary and sufficient to direct recombination, comprise a dyad-symmetric heptamer, an AT-rich nonamer and an intervening spacer region of either 12 or 23 base pairs. These signals are conserved among the different loci and species that carry out D-J (or V-J) recombination and are functionally interchangeable. See Oettinger, et al. (1990), Science, 248, 1517-1523 and references cited therein. The heptamer comprises the sequence CACAGTG or its analogue followed by a spacer of unconserved sequence and then a nonamer having the sequence ACAAAAACC or its analogue. These sequences are found on the J, or downstream side, of each V and D gene segment. Immediately preceding the germline D and J segments are again two recombination signal sequences, first the nonamer and then the heptamer again separated by an unconserved sequence. The heptameric and nonameric sequences following a $V_L$, $V_H$ or D segment are complementary to those preceding the $J_L$, D or $J_H$ segments with which they recombine. The spacers between the heptameric and nonameric sequences are either 12 base pairs long or between 22 and 24 base pairs long.

In addition to the rearrangement of V, D and J segments, further diversity is generated in the primary repertoire of immunoglobulin heavy and light chain by way of variable recombination at the locations where the V and J segments in the light chain are joined and where the D and J segments of the heavy chain are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity.

The net effect of such rearrangements in the variable region gene segments and the variable recombination which may occur during such joining is the production of a primary antibody repertoire.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH VI dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them.

By "neutralizing antibody" is meant an antibody molecule that is able to eliminate or significantly reduce an effecter function of a target antigen to which is binds. Accordingly, a "neutralizing" anti-target antibody is capable of eliminating or significantly reducing an effecter function, such as enzyme activity, ligand binding, or intracellular signaling.

As provided herein, the compositions for and methods of treating osteolytic diseases (i.e. diseases associated with increased osteoclastic activity), or cancer metastasis and/or bone remodeling associated with cancer metastasis may utilize one or more antibody used singularly or in combination with other therapeutics to achieve the desired effects. Antibodies according to the present invention may be isolated from an animal producing the antibody as a result of either direct contact with an environmental antigen or immunization with the antigen. Alternatively, antibodies may be produced by recombinant DNA methodology using one of the antibody expression systems well known in the art (See, e.g., Harlow and Lane, Antibodies: A Laboratory Manual, Cold Spring Harbor Laboratory (1988)). Such antibodies may include recombinant IgGs, chimeric fusion proteins having immunoglobulin derived sequences or "Human Engineered™" antibodies that may all be used for the treatment of cancer metastasis and/or bone remodeling associated with cancer metastasis according to the present invention. In addition to intact, full-length molecules, the term "antibody" also refers to fragments thereof (such as, e.g., scFv, Fv, Fd, Fab, Fab' and F(ab)'2 fragments) or multimers or aggregates of intact molecules and/or fragments that bind to M-CSF (or M-CSFR). These antibody fragments bind antigen and may be derivatized to exhibit structural features that facilitate clearance and uptake, e.g., by incorporation of galactose residues.

In one embodiment of the present invention, M-CSF monoclonal antibodies may be prepared essentially as described in Halenbeck et al. U.S. Pat. No. 5,491,065 (1997), incorporated herein by reference. Exemplary M-CSF monoclonal antibodies include those that bind to an apparent conformational epitope associated with recombinant or native dimeric M-CSF with concomitant neutralization of biological activity. These antibodies are substantially unreactive with biologically inactive forms of M-CSF including monomeric and chemically derivatized dimeric M-CSF.

In other embodiments of the present invention, Human Engineered™ anti-M-CSF monoclonal antibodies are provided. The phrase "Human Engineered™ antibody" refers to an antibody derived from a non-human antibody, typically a mouse monoclonal antibody. Alternatively, a Human Engineered™ antibody may be derived from a chimeric antibody that retains or substantially retains the antigen binding properties of the parental, non-human, antibody but which exhibits diminished immunogenicity as compared to the parental antibody when administered to humans. The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

The phrase "complementarity determining region" or the term "CDR" refers to amino acid sequences which together define the binding affinity and specificity of the natural Fv region of a native immunoglobulin binding site (See, e.g., Chothia et al., J. Mol. Biol. 196:901 917 (1987); Kabat et al., U.S. Dept. of Health and Human Services NIH Publication No. 91 3242 (1991)). The phrase "constant region" refers to the portion of the antibody molecule that confers effector functions. In the present invention, mouse constant regions are preferably substituted by human constant regions. The constant regions of the subject antibodies are derived from human immunoglobulins. The heavy chain constant region can be selected from any of the five isotypes: alpha, delta, epsilon, gamma or mu.

The antibodies of the present invention are said to be immunospecific or specifically binding if they bind to antigen with a $K_a$ of greater than or equal to about $10^6 M^{-1}$ preferably greater than or equal to about $10^7 M^{-1}$, more preferably greater than or equal to about $10^8 M^{-1}$, and most preferably greater than or equal to about $10^9 M^{-1}$, $10^{10} M^{-1}$, or $10^{12} M^{-1}$. The anti-M-CSF antibodies may bind to different naturally occurring forms of M-CSF, including those expressed by the host's/subject's tissues as well as that expressed by the tumor. The monoclonal antibodies disclosed herein, such as RX1, 5H4, MC1, or MC3 antibody, have affinity for M-CSF and are characterized by a dissociation equilibrium constant (Kd) of at least $10^{-4}$ M, preferably at least about $10^{-7}$ M to about $10^{-8}$ M, more preferably at least about $10^{-8}$ M, $10^{-10}$ M, $10^{-11}$ M or $10^{-12}$ M. Such affinities may be readily determined using conventional techniques, such as by equilibrium dialysis; by using the BIAcore 2000 instrument, using general procedures outlined by the manufacturer; by radioimmunoassay using $^{125}$I labeled M-CSF; or by another method known to the skilled artisan. The affinity data may be analyzed, for example, by the method of Scatchard et al., Ann N.Y. Acad. Sci., 51:660 (1949). Thus, it will be apparent that preferred M-CSF antibodies will exhibit a high degree of specificity for M-CSF and will bind with substantially lower affinity to other molecules. Preferred antibodies bind M-CSF with a similar affinity as murine RX1 of FIG. 4 binds to M-CSF, exhibit low immunogenicity, and exhibit the desired biological activity when tested in appropriate animal models of disease. Other exemplary antibodies bind M-CSF with a similar affinity as murine 5H4, MC1 or MC3 of FIG. 13, 14 or 15, respectively, binds to M-CSF.

The antigen to be used for production of antibodies may be, e.g., intact M-CSF or a fragment of M-CSF that retains the desired epitope, optionally fused to another polypeptide that allows the epitope to be displayed in its native conformation. Alternatively, cells expressing M-CSF at their cell surface can be used to generate antibodies. Such cells can be transformed to express M-CSF or may be other naturally occurring cells that express M-CSF. Other forms of M-CSF useful for generating antibodies will be apparent to those skilled in the art.

Polyclonal Antibodies

Polyclonal antibodies are preferably raised in animals by multiple subcutaneous (sc) or intraperitoneal (ip) injections of the relevant antigen and an adjuvant. An improved antibody response may be obtained by conjugating the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride or other agents known in the art.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to {fraction (1/10)} the original amount of peptide or conjugate in Freund's complete adjuvant by subcutaneous injection at multiple sites. At 7-14 days post-booster injection, the animals are bled and the serum is assayed for antibody titer: Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Monoclonal antibodies may be made using the hybridoma method first described by Kohler et al., Nature, 256:495 (1975), or may be made by recombinant DNA methods.

In the hybridoma method, a mouse or other appropriate host animal, such as a hamster or macaque monkey, is immunized as herein described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (Kozbor, J. Immunol., 133: 3001 (1984);Brodeur et al., Monoclonal Antibody Production Techniques and Applications, pp. 51-63 (Marcel Dekker, Inc., New York, 1987)). Exemplary murine myeloma lines include those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by Scatchard analysis (Munson et al., Anal. Biochem., 107:220 (1980)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Recombinant Production of Antibodies

DNA encoding the monoclonal antibodies may be isolated and sequenced from the hybridoma cells using conventional procedures (e.g., by using oligonucleotide probes that are capable of binding specifically to genes encoding the heavy and light chains of the monoclonal antibodies). Sequence determination will generally require isolation of at least a portion of the gene or cDNA of interest. Usually this requires cloning the DNA or, preferably, mRNA (i.e., cDNA) encoding the monoclonal antibodies. Cloning is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+ mRNA, preferably membrane-associated mRNA, and the library screened using probes specific for human immunoglobulin polypeptide gene sequences. In a preferred embodiment, however, the polymerase chain reaction (PCR) is used to amplify cDNAs (or portions of full-length cDNAs) encoding an immunoglobulin gene segment of interest (e.g., a light chain variable segment). The amplified sequences can be readily cloned into any suitable vector, e.g., expression vectors, minigene vectors, or phage display vectors. It will be appreciated that the particular method of cloning used not critical, so long as it is possible to determine the sequence of some portion of the immunoglobulin polypeptide of interest. As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined, is considered isolated. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

One source for RNA used for cloning and sequencing is a hybridoma produced by obtaining a B cell from the transgenic mouse and fusing the B cell to an immortal cell. An advantage of using hybridomas is that they can be easily screened, and a hybridoma that produces a human monoclonal antibody of interest selected. Alternatively, RNA can be isolated from B cells (or whole spleen) of the immunized animal. When sources other than hybridomas are used, it may be desirable to screen for sequences encoding immunoglobulins or immunoglobulin polypeptides with specific binding characteristics. One method for such screening is the use of phage display technology. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference. In one embodiment using phage display technology, cDNA from an immunized transgenic mouse (e.g., total spleen cDNA) is isolated, the polymerase chain reaction is used to amplify a cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics, are identified by standard techniques such as panning.

The sequence of the amplified or cloned nucleic acid is then determined. Typically the sequence encoding an entire variable region of the immunoglobulin polypeptide is determined, however, it will sometimes by adequate to sequence only a portion of a variable region, for example, the CDR-encoding portion. Typically the portion sequenced will be at least 30 bases in length, more often based coding for at least about one-third or at least about one-half of the length of the variable region will be sequenced.

Sequencing can be carried out on clones isolated from a cDNA library, or, when PCR is used, after subcloning the amplified sequence or by direct PCR sequencing of the amplified segment. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Once isolated, the DNA may be placed into expression vectors, which are then transfected into host cells such as *E. coli* cells, simian COS cells, human embryonic kidney 293 cells (e.g., 293E cells), Chinese hamster ovary (CHO) cells, or myeloma cells that do not otherwise produce immunoglobulin protein, to obtain the synthesis of monoclonal antibodies in the recombinant host cells. Recombinant production of antibodies is well known in the art.

Expression control sequences refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

In an alternative embodiment, the amino acid sequence of an immunoglobulin of interest may be determined by direct protein sequencing. Suitable encoding nucleotide sequences can be designed according to a universal codon table.

Amino acid sequence variants of the desired antibody may be prepared by introducing appropriate nucleotide changes into the encoding DNA, or by peptide synthesis. Such variants include, for example, deletions from, and/or insertions into and/or substitutions of, residues within the amino acid sequences of the antibodies. Any combination of deletion, insertion, and substitution is made to arrive at the final construct, provided that the final construct possesses the desired characteristics. The amino acid changes also may alter posttranslational processes of the monoclonal, human, humanized, Human Engineered™ or variant antibody, such as changing the number or position of glycosylation sites.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

The invention also provides isolated nucleic acid encoding antibodies of the invention, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium.

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more selective marker genes, an enhancer element, a promoter, and a transcription termination sequence.

(1) Signal Sequence Component

The antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The signal sequence selected preferably is one that is recognized and processed (i.e., cleaved by a signal peptidase) by the host cell. If prokaryotic host cells do not recognize and process the native antibody signal sequence, the signal sequence may be substituted by a signal sequence selected, for example, from the group of the pectate lyase (e.g., pelB) alkaline phosphatase, penicillinase, 1 pp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO90/13646. In mammalian cell expression, mammalian signal sequences as welt as viral secretory leaders, for example, the herpes simplex gD signal, are available.

The DNA for such precursor region is ligated in reading frame to DNA encoding the antibody.

(2) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins are useful for cloning vectors in mammalian cells. Generally, the origin of replication component is not needed for mammalian expression vectors (the SV40 origin may typically be used only because it contains the early promoter).

(3) Selective Marker Component

Expression and cloning vectors may contain a selective gene, also termed a selectable marker. Typical selection genes encode proteins that (a) confer resistance to antibiotics or other toxins, e.g., ampicillin, neomycin, methotrexate, tetracycline, G418, geneticin, histidinol, or mycophenolic acid (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs methotrexate, neomycin, histidinol, puromycin, mycophenolic acid and hygromycin.

Another example of suitable selectable markers for mammalian cells are those that enable the identification of cells competent to take up the antibody-encoding nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding antibody of the invention, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282: 39 (1979)). The trp1 gene provides a selection marker for a mutant strain of yeast lacking the ability to grow in tryptophan, for example, ATCC No. 44076 or PEP4-1. Jones, Genetics, 85: 12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene. Ura3-deficient yeast strains are complemented by plasmids bearing the ura3 gene.

In addition, vectors derived from the 1.6 µm circular plasmid pKD1 can be used for transformation of *Kluyveromyces* yeasts. Alternatively, an expression system for large-scale production of recombinant calf chymosin was reported for *K. lactis*. Van den Berg, Bio/Technology, 8: 135 (1990). Stable multi-copy expression vectors for secretion of mature recombinant human serum albumin by industrial strains of *Kluyveromyces* have also been disclosed. Fleer et al, Bio/Technology, 9: 968-975 (1991).

(4) Promoter Component

Expression and cloning vectors usually contain a promoter that is recognized by the host organism and is operably linked to the antibody-encoding nucleic acid. Promoters suitable for use with prokaryotic hosts include the arabinose (e.g., araB) promoter phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibody of the invention.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as Abelson leukemia virus, polyoma virus, fowlpox virus, adenovirus (such as Adenovirus 2), bovine papilloma virus, avian sarcoma virus, most preferably, cytomegalovirus, a retrovirus, hepatitis-B virus, Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297: 598-601 (1982) on expression of human β-interferon cDNA in mouse cells under the control of a thymidine kinase promoter from herpes simplex virus. Alternatively, the rous sarcoma virus long terminal repeat can be used as the promoter.

(5) Enhancer Element Component

Transcription of a DNA encoding the antibody of this invention by higher eukaryotes is often increased by inserting an enhancer sequence into the vector. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297: 17-18 (1982) on enhancing elements for activation of eukaryotic promoters. The enhancer may be spliced into the vector at a position 5' or 3' to the antibody-encoding sequence, but is preferably located at a site 5' from the promoter.

(6) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein. Another is the mouse immunoglobulin light chain transcription terminator.

(7) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastors* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, tobacco, lemna, and other plant cells can also be utilized as hosts.

However, interest has been greatest in vertebrate cells, and propagation of vertebrate cells in culture (tissue culture) has become routine procedure. Examples of useful mammalian host cell lines are Chinese hamster ovary cells, including CHOK1 cells (ATCC 15, CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, [Graham et al., *J. Gen Virol.* 36: 59 (1977)]; baby hamster kidney cells (BHK, ATCC CCL 10); mouse sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383: 44-68 (1982)); MRC 5 cells; FS4 cells; and a human hepatoma line (Hep G2).

Host cells are transformed or transfected with the above-described expression or cloning vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies that target M-CSF.

(8) Culturing the Host Cells

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. No. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(9) Purification of Antibody

When using recombinant techniques, the antibody can be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration. Better et al. Science 240: 1041-1043 (1988); ICSU Short Reports 10: 105 (1990); and Proc. Natl. Acad. Sci. USA 90: 457-461 (1993) describe a procedure for isolating antibodies which are secreted to the periplasmic space of *E. coli*. (See also, [Carter et al., *Bio/Technology* 10: 163-167 (1992)].

The antibody composition prepared from microbial or mammalian cells can be purified using, for example, hydroxylapatite chromatography cation or avian exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62: 1-13 (1983)). Protein G is recommended for all mouse isotypes and for human γ3 (Guss et al., EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H 3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Chimeric and Humanized Antibodies

Because chimeric or humanized antibodies are less immunogenic in humans than the parental mouse monoclonal antibodies, they can be used for the treatment of humans with far less risk of anaphylaxis. Thus, these antibodies may be preferred in therapeutic applications that involve in vivo administration to a human.

Chimeric monoclonal antibodies, in which the variable Ig domains of a mouse monoclonal antibody are fused to human constant Ig domains, can be generated using standard procedures known in the art (See Morrison, S. L., et al. (1984) Chimeric Human Antibody Molecules; Mouse Antigen Binding Domains with Human Constant Region Domains, Proc. Natl. Acad. Sci. USA 81, 6841-6855; and, Boulianne, G. L., et al, Nature 312, 643-646. (1984)). Although some chimeric monoclonal antibodies have proved less immunogenic in humans, the mouse variable Ig domains can still lead to a significant human anti-mouse response.

Humanized antibodies may be achieved by a variety of methods including, for example: (1) grafting the non-human complementarity determining regions (CDRs) onto a human framework and constant region (a process referred to in the art as humanizing through "CDR grafting"), or, alternatively, (2) transplanting the entire non-human variable domains, but "cloaking" them with a human-like surface by replacement of surface residues (a process referred to in the art as "veneering"). In the present invention, humanized antibodies will include both "humanized" and "veneered" antibodies. These methods are disclosed in, e.g., Jones et al., Nature 321:522 525 (1986); Morrison et al., Proc. Natl. Acad. Sci., U.S.A., 81:6851 6855 (1984); Morrison and Oi, Adv. Immunol., 44:65 92 (1988); Verhoeyer et al., Science 239:1534 1536 (1988); Padlan, Molec. Immun. 28:489 498 (1991); Padlan, Molec. Immunol. 31(3):169 217 (1994); and Kettleborough, C. A. et al., Protein Eng. 4(7):773 83 (1991) each of which is incorporated herein by reference.

In particular, a rodent antibody on repeated in vivo administration in man either alone or as a conjugate will bring about an immune response in the recipient against the rodent antibody; the so-called HAMA response (Human Anti Mouse Antibody). The HAMA response may limit the effectiveness of the pharmaceutical if repeated dosing is required. The immunogenicity of the antibody may be reduced by chemical modification of the antibody with a hydrophilic polymer such as polyethylene glycol or by using the methods of genetic engineering to make the antibody binding structure more human like. For example, the gene sequences for the variable domains of the rodent antibody which bind CEA can be substituted for the variable domains of a human myeloma protein, thus producing a recombinant chimaeric antibody. These procedures are detailed in EP 194276, EP 0120694, EP 0125023, EP 0171496, EP 0173494 and WO 86/01533. Alternatively the gene sequences of the CDRs of the rodent antibody may be isolated or synthesized and substituted for the corresponding sequence regions of a homologous human antibody gene, producing a human antibody with the specificity of the original rodent antibody. These procedures are described in EP 023940, WO 90/07861 and WO91/09967. Alternatively a large number of the surface residues of the variable domain of the rodent antibody may be changed to those residues normally found on a homologous human antibody, producing a rodent antibody which has a surface 'veneer' of residues and which will therefore be recognized as self by the human body. This approach has been demonstrated by Padlan et.al. (1991) Mol. Immunol. 28, 489.

CDR grafting involves introducing one or more of the six CDRs from the mouse heavy and light chain variable Ig domains into the appropriate four framework regions of human variable Ig domains is also called CDR grafting. This technique (Riechmann, L., et al., Nature 332, 323 (1988)), utilizes the conserved framework regions (FR1-FR4) as a scaffold to support the CDR loops which are the primary contacts with antigen. A disadvantage of CDR grafting, however, is that it can result in a humanized antibody that has a substantially lower binding affinity than the original mouse antibody, because amino acids of the framework regions can contribute to antigen binding, and because amino acids of the CDR loops can influence the association of the two variable Ig domains. To maintain the affinity of the humanized monoclonal antibody, the CDR grafting technique can be improved by choosing human framework regions that most closely resemble the framework regions of the original mouse antibody, and by site-directed mutagenesis of single amino acids within the framework or CDRs aided by computer modeling of the antigen binding site (e.g., Co, M. S., et al. (1994), J. Immunol. 152, 2968-2976).

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors (See, e.g., U.S. Pat. Nos. 5,530,101 and 5,585,089 which patents are incorporated herein by reference).

A number of humanizations of mouse monoclonal antibodies by rational design have been reported (See, for example, 20020091240 published Jul. 11, 2002, WO 92/11018 and U.S. Pat. No., 5,693,762, U.S. Pat. No. 5,766,866.

Amino Acid Sequence Variants

A useful method for identification of certain residues or regions of the antibody that are preferred locations for mutagenesis is called "alanine scanning mutagenesis," as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue or the antibody (including antibody fragment) fused to an epitope tag or a salvage receptor epitope. Other insertional variants of the antibody molecule include the fusion to a polypeptide which increases the serum half-life of the antibody, e.g. at the N-terminus or C-terminus.

The term "epitope tagged" refers to the antibody fused to an epitope tag. The epitope tag polypeptide has enough residues to provide an epitope against which an antibody there against can be made, yet is short enough such that it does not interfere with activity of the antibody. The epitope tag preferably is sufficiently unique so that the antibody there against does not substantially cross-react with other epitopes. Suitable tag polypeptides generally have at least 6 amino acid residues and usually between about 8-50 amino acid residues (preferably between about 9-30 residues). Examples include the flu HA tag polypeptide and its antibody 12CA5 [Field et al., *Mol. Cell. Biol.* 8: 2159-2165 (1988)]; the c-myc tag and the 8F9, 3C7, 6E10, G4, B7 and 9E10 antibodies thereto [Evan et al., *Mol. Cell. Biol.* 5(12): 3610-3616 (1985)]; and the Herpes Simplex virus glycoprotein D (gD) tag and its antibody [Paborsky et al., *Protein Engineering* 3(6): 547-553 (1990)]. Other exemplary tags are a poly-histidine sequence, generally around six histidine residues, that pelulits isolation of a compound so labeled using nickel chelation. Other labels and tags, such as the FLAG® tag (Eastman Kodak, Rochester, N.Y.), well known and routinely used in the art, are embraced by the invention.

As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Another type of variant is an amino acid substitution variant. These variants have at least one amino acid residue in the antibody molecule removed and a different residue inserted in its place. Substitutional mutagenesis within any of the hypervariable or CDR regions or framework regions is contemplated. Conservative substitutions are shown in Table 1. The most conservative substitution is found under the heading of "preferred substitutions". If such substitutions result in no change in biological activity, then more substantial changes, denominated "exemplary substitutions" in Table 1, or as further described below in reference to amino acid classes, may be introduced and the products screened.

TABLE 1

| Original | Exemplary | Preferred Residue Substitutions |
|---|---|---|
| Ala (A) | val; leu; ile | val |
| Arg (R) | lys; gln; asn | lys |
| Asn (N) | gln; his; asp, lys; gln | arg |
| Asp (D) | glu; asn | glu |
| Cys (C) | ser; ala | ser |
| Gln (Q) | asn; glu | asn |
| Glu (E) | asp; gln | asp |
| Gly (G) | ala | |
| His (H) | asn; gln; lys; arg | |
| Ile (I) | leu; val; met; ala; phe; | leu norleucine |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | |
| Pro (P) | ala | |
| Ser (S) | thr | |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
    (1) hydrophobic: norleucine, met, ala, val, leu, ile;
    (2) neutral hydrophilic: cys, ser, thr;
    (3) acidic: asp, glu;
    (4) basic: asn, gln, his, lys, arg;
    (5) residues that influence chain orientation: gly, pro; and
    (6) aromatic: trp, tyr, phe.

Conservative substitutions involve replacing an amino acid with another member of its class. Non-conservative substitutions involve replacing a member of one of these classes with a member of another class.

Any cysteine residue not involved in maintaining the proper conformation of the monoclonal, human, humanized, Human Engineered™ or variant antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Affinity maturation involves preparing and screening antibody variants that have substitutions within the CDRs of a parent antibody and selecting variants that have improved biological properties such as binding affinity relative to the parent antibody. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity).

Alanine scanning mutagenesis can be performed to identify hypervariable region residues that contribute significantly to antigen binding. Alternatively, or in addition, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Antibody variants can also be produced that have a modified glycosylation pattern relative to the parent antibody, for example, deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to an antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to an antibody by inserting or substituting one or more serine or threonine residues to the sequence of the original antibody. By way of example, the amino acids of RX1 at positions 41-43 of FIG. 4A (NGS) may be retained. Alternatively, only amino acids 41 and 42 (NG) may be retained.

Ordinarily, amino acid sequence variants of the Human Engineered™ antibody will have an amino acid sequence having at least 60% amino acid sequence identity with the original Human Engineered™ antibody amino acid sequences of either the heavy or the light chain (e.g., as in any of FIGS. 19B through 22B) more preferably at least 80%, more preferably at least 85%, more preferably at least 90%, and most preferably at least 95%, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to this sequence is defined herein as the percentage of amino acid residues in the candidate sequence that are identical with the Human Engineered™ residues, after aligning the sequences and introducing gaps, if necessary, to achieve the maximum percent sequence identity, and not considering any conservative substitutions (as defined in Table 1 above) as part of the sequence identity. None of N-terminal, C-terminal, or internal extensions, deletions, or insertions into the antibody sequence shall be construed as affecting sequence identity or homology. Thus, sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences, or along a pre-determined portion of one or both sequences). The programs provide a default opening penalty and a default gap penalty, and a scoring matrix such as PAM 250 [a standard scoring matrix; see Dayhoff et al., in *Atlas of Protein Sequence and Structure*, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences.

Other modifications of the antibody are contemplated. For example, it may be desirable to modify the antibody of the invention with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148: 2918-2922 (1992). Homodimeric antibodies with enhanced biological activity may also be prepared using heterobifunctional cross-linkers as described in Wolff et al., Cancer Research 53: 2560-2565 (1993). Alternatively, an antibody can be engineered which has dual Fc regions and may thereby have enhanced complement lysis and ADCC capabilities. See Stevenson et al., *Anti-Cancer Drug Design* 3: 219-230 (1989). In addition, it has been shown that sequences within the CDR can cause an antibody to bind to MHC Class II and trigger an unwanted helper T-cell response. A conservative substitution can allow the antibody to retain binding activity yet lose its ability to trigger an unwanted T-cell response. Also see Steplewski et al., Proc Natl Acad Sci USA. 1988; 85(13):4852-6, incorporated herein by reference in its entirety, which described chimeric antibodies wherein a murine variable region was joined with human gamma 1, gamma 2, gamma 3, and gamma 4 constant regions.

In certain embodiments of the invention, it may be desirable to use an antibody fragment, rather than an intact antibody, to increase tissue tumor penetration, for example. In this case, it may be desirable to modify the antibody fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, e.g., WO96/32478).

The salvage receptor binding epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the C.sub.L region or V.sub.L region, or both, of the antibody fragment. See also International applications WO 97/34631 and WO 96/32478 which describe Fc variants and their interaction with the salvage receptor.

Thus, antibodies of the invention may comprise a human Fc portion, a human consensus Fc portion, or a variant thereof that retains the ability to interact with the Fc salvage receptor, including variants in which cysteines involved in disulfide bonding are modified or removed, and/or in which the a met is added at the N-terminus and/or one or more of the N-terminal 20 amino acids are removed, and/or regions that interact with complement, such as the C1q binding site, are removed, and/or the ADCC site is removed [see, e.g., Molec. Immunol. 29 (5): 633-9 (1992)].

Previous studies mapped the binding site on human and murine IgG for FcR primarily to the lower hinge region composed of IgG residues 233-239. Other studies proposed additional broad segments, e.g. Gly316-Lys338 for human Fc receptor I, Lys274-Arg301 and Tyr407-Arg416 for human Fc receptor III, or found a few specific residues outside the lower hinge, e.g. Asn297 and Glu318 for murine IgG2b interacting with murine Fc receptor II. The report of the 3.2-Å crystal structure of the human IgG1 Fc fragment with human Fc receptor IIIA delineated IgG1 residues Leu234-Ser239, Asp265-Glu269, Asn297-Thr299, and Ala327-Ile332 as involved in binding to Fc receptor IIIA. It has been suggested based on crystal structure that in addition to the lower hinge (Leu234-Gly237), residues in IgG CH2 domain loops FG (residues 326-330) and BC (residues 265-271) might play a role in binding to Fc receptor IIA. See Shields et al., J. Biol. Chem., 276(9):6591-6604 (2001), incorporated by reference herein in its entirety. Mutation of residues within Fc receptor binding sites can result in altered effector function, such as altered ADCC or CDC activity, or altered half-life. As described above, potential mutations include insertion, deletion or substitution of one or more residues, including substitution with alanine, a conservative substitution, a non-conservative substitution, or replacement with a corresponding amino acid residue at the same position from a different IgG subclass (e.g. replacing an IgG1 residue with a corresponding IgG2 residue at that position).

Shields et al. reported that IgG1 residues involved in binding to all human Fc receptors are located in the CH2 domain proximal to the hinge and fall into two categories as follows: 1) positions that may interact directly with all FcR include Leu234-Pro238, Ala327, and Pro329 (and possibly Asp265); 2) positions that influence carbohydrate nature or position include Asp265 and Asn297. The additional IgG1 residues that affected binding to Fc receptor II are as follows: (largest effect) Arg255, Thr256, Glu258, Ser267, Asp270, Glu272, Asp280, Arg292, Ser298, and (less effect) His268, Asn276, His285, Asn286, Lys290, Gln295, Arg301, Thr307, Leu309, Asn315, Lys322, Lys326, Pro331, Ser337, Ala339, Ala378, and Lys414. A327Q, A327S, P329A, D265A and D270A reduced binding. In addition to the residues identified above for all FcR, additional IgG1 residues that reduced binding to Fc receptor 111A by 40% or more are as follows: Ser239, Ser267 (Gly only), His268, Glu293, Gln295, Tyr296, Arg301, Val303, Lys338, and Asp376. Variants that improved binding to FcRIIIA include T256A, K290A, S298A, E333A, K334A, and A339T. Lys414 showed a 40% reduction in binding for FcRIIA and FcRIIB, Arg416 a 30% reduction for FcRIIA and FcRIIIA, Gln419 a 30% reduction to FcRIIA and a 40% reduction to FcRIIB, and Lys360 a 23% improvement to FcRIIIA. See also Presta et al., Biochem. Soc. Trans. (2001) 30, 487-490.

For example, U.S. Pat. No. 6,194,551, incorporated herein by reference in its entirety, describes variants with altered effector function containing mutations in the human IgG Fc region, at amino acid position 329, 331 or 322 (using Kabat numbering), some of which display reduced C1q binding or CDC activity. As another example, U.S. Pat. No. 6,737,056, incorporated herein by reference in its entirety, describes variants with altered effector or Fc-gamma-receptor binding containing mutations in the human IgG Fc region, at amino acid position 238, 239, 248, 249, 252, 254, 255, 256, 258, 265, 267, 268, 269, 270, 272, 276, 278, 280, 283, 285, 286, 289, 290, 292, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439 (using Kabat numbering), some of which display receptor binding profiles associated with reduced ADCC or CDC activity. Of these, a mutation at amino acid position 238, 265, 269, 270, 327 or 329 are stated to reduce binding to FcRI, a mutation at amino acid position 238, 265, 269, 270, 292, 294, 295, 298, 303, 324, 327, 329, 333, 335, 338, 373, 376, 414, 416, 419, 435, 438 or 439 are stated to reduce binding to FcRII, and a mutation at amino acid position 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 is stated to reduce binding to FcRIII.

U.S. Pat. No. 5,624,821, incorporated by reference herein in its entirety, reports that C1q binding activity of an murine antibody can be altered by mutating amino acid residue 318, 320 or 322 of the heavy chain and that replacing residue 297 (Asn) results in removal of lytic activity.

United States Application Publication No. 20040132101, incorporated by reference herein in its entirety, describes variants with mutations at amino acid positions 240, 244, 245, 247, 262, 263, 266, 299, 313, 325, 328, or 332 (using Kabat numbering) or positions 234, 235, 239, 240, 241, 243, 244, 245, 247, 262, 263, 264, 265, 266, 267, 269, 296, 297, 298, 299, 313, 325, 327, 328, 329, 330, or 332 (using Kabat numbering), of which mutations at positions 234, 235, 239, 240, 241, 243, 244, 245, 247, 262, 263, 264, 265, 266, 267, 269, 296, 297, 298, 299, 313, 325, 327, 328, 329, 330, or 332 may reduce ADCC activity or reduce binding to an Fc gamma receptor.

Chappel et al., Proc Natl Acad Sci USA. 1991; 88(20): 9036-40, incorporated herein by reference in its entirety, report that cytophilic activity of IgG1 is an intrinsic property of its heavy chain CH2 domain. Single point mutations at any of amino acid residues 234-237 of IgG1 significantly lowered or abolished its activity. Substitution of all of IgG1 residues 234-237 (LLGG) into IgG2 and IgG4 were required to restore full binding activity. An IgG2 antibody containing the entire ELLGGP sequence (residues 233-238) was observed to be more active than wild-type IgG1.

Isaacs et al., J. Immunol. 1998; 161(8):3862-9, incorporated herein by reference in its entirety, report that mutations within a motif critical for Fc gammaR binding (glutamate 233 to proline, leucine/phenylalanine 234 to valine, and leucine 235 to alanine) completely prevented depletion of target cells. The mutation glutamate 318 to alanine eliminated effector function of mouse IgG2b and also reduced the potency of human IgG4.

Armour et al., Mol. Immunol. 2003; 40(9):585-93, incorporated by reference herein in its entirety, identified IgG1 variants which react with the activating receptor, FcgammaRIIa, at least 10-fold less efficiently than wildtype IgG1 but whose binding to the inhibitory receptor, FcgammaRIIb, is only four-fold reduced. Mutations were made in the region of amino acids 233-236 and/or at amino acid positions 327, 330 and 331. See also WO 99/58572, incorporated by reference herein in its entirety.

Xu et al., J Biol Chem. 1994; 269(5):3469-74, incorporated by reference herein in its entirety, report that mutating IgG1 Pro331 to Ser markedly decreased C1q binding and visually eliminated lytic activity. In contrast, the substitution of Pro for Ser331 in IgG4 bestowed partial lytic activity (40%) to the IgG4 Pro331 variant.

Schuurman et al., Mol Immunol. 2001; 38(1):1-8, incorporated by reference herein in its entirety, report that mutating one of the hinge cysteines involved in the inter-heavy chain bond formation, Cys226, to serine resulted in a more stable inter-heavy chain linkage. Mutating the IgG4 hinge sequence Cys-Pro-Ser-Cys to the IgG1 hinge sequence Cys-Pro-Pro-Cys also markedly stabilizes the covalent interaction between the heavy chains.

Angal et al., Mol Immunol. 1993; 30(1):105-8, incorporated by reference herein in its entirety, report that mutating the serine at amino acid position 241 in IgG4 to proline (found at that position in IgG1 and IgG2) led to the production of a homogeneous antibody, as well as extending serum half-life and improving tissue distribution compared to the original chimeric IgG4.

Human and Human Engineered™ Antibodies

Human Engineering™

Human Engineering™ of antibody variable domains has been described by Studnicka [See, e.g., Studnicka et al. U.S. Pat. No. 5,766,886; Studnicka et al. Protein Engineering 7: 805-814 (1994)] as a method for reducing immunogenicity while maintaining binding activity of antibody molecules. According to the method, each variable region amino acid has been assigned a risk of substitution. Amino acid substitutions are distinguished by one of three risk categories: (1) low risk changes are those that have the greatest potential for reducing immunogenicity with the least chance of disrupting antigen binding; (2) moderate risk changes are those that would further reduce immunogenicity, but have a greater chance of affecting antigen binding or protein folding; (3) high risk residues are those that are important for binding or for maintaining antibody structure and carry the highest risk that antigen binding or protein folding will be affected. Due to the three-dimensional structural role of prolines, modifications at prolines are generally considered to be at least moderate risk changes, even if the position is typically a low risk position.

Variable regions of the light and heavy chains of a rodent antibody are Human Engineered™ as follows to substitute human amino acids at positions determined to be unlikely to adversely effect either antigen binding or protein folding, but likely to reduce immunogenicity in a human environment. Amino acid residues that are at "low risk" positions and that are candidates for modification according to the method are identified by aligning the amino acid sequences of the rodent variable regions with a human variable region sequence. Any human variable region can be used, including an individual VH or VL sequence or a human consensus VH or VL sequence or an individual or consensus human germline sequence. The amino acid residues at any number of the low risk positions, or at all of the low risk positions, can be changed. For example, at each low risk position where the aligned murine and human amino acid residues differ, an amino acid modification is introduced that replaces the rodent residue with the human residue. Alternatively, the amino acid residues at all of the low risk positions and at any number of the moderate risk positions can be changed. Ideally, to achieve the least immunogenicity all of the low and moderate risk positions are changed from rodent to human sequence.

Synthetic genes containing modified heavy and/or light chain variable regions are constructed and linked to human γ heavy chain and/or kappa light chain constant regions. Any human heavy chain and light chain constant regions may be used in combination with the Human Engineered™ antibody variable regions, including IgA (of any subclass, such as IgA1 or IgA2), IgD, IgE, IgG (of any subclass, such as IgG1, IgG2, IgG3, or IgG4), or IgM. The human heavy and light chain genes are introduced into host cells, such as mammalian cells, and the resultant recombinant immunoglobulin products are obtained and characterized.

Human Antibodies from Transgenic Animals

Human antibodies to M-CSF can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/741 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions.

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL 6, IL 8, TNFa, human CD4, L selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. patent application no. 20030194404; and U.S. patent application no. 20030031667).

See also Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. No. 5,591,669, U.S. Pat. No. 5,589,369, U.S. Pat. No. 5,545,807; and U.S Patent Application No. 20020199213. U.S. Patent Application No. and 20030092125 describes methods for biasing the immune response of an animal to the desired epitope. Human antibodies may also be generated by in vitro activated B cells (see U.S. Pat. Nos. 5,567,610 and 5,229,275).

Human Antibodies from Phage Display Technology

The development of technologies for making repertoires of recombinant human antibody genes, and the display of the encoded antibody fragments on the surface of filamentous bacteriophage, has provided a means for making human antibodies directly. The antibodies produced by phage technology are produced as antigen binding fragments-usually Fv or Fab fragments-in bacteria and thus lack effector functions. Effector functions can (be introduced by one of two strategies: The fragments can be engineered either into complete antibodies for expression in mammalian cells, or into bispecific antibody fragments with a second binding site capable of triggering an effector function.

Typically, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. By several rounds of antigen binding and re-amplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., J. Mol. Biol., 227:381 (1991); Marks et al., J. Mol. Biol, 222:581-597 (1991); U.S. Pat. Nos. 5,565,332 and 5,573,905; Clackson, T., and Wells, J. A., TIBTECH 12, 173-184 (1994)). In particular, in vitro selection and evolution of antibodies derived from phage display libraries has become a powerful tool (See Burton, D. R., and Barbas III, C. F., Adv. Immunol. 57, 191-280 (1994); and, Winter, G., et al., Annu. Rev. Immunol. 12, 433-455 (1994); U.S. patent application no. 20020004215 and WO92/01047; U.S. patent application no. 20030190317 published Oct. 9, 2003 and U.S. Pat. No. 6,054,287; U.S. Pat. No. 5,877,293.

Watkins, "Screening of Phage-Expressed Antibody Libraries by Capture Lift," Methods in Molecular Biology, Antibody Phage Display: Methods and Protocols 178: 187-193, and U.S. patent application no. 200120030044772 published Mar. 6, 2003 describe methods for screening phage-expressed antibody libraries or other binding molecules by capture lift, a method involving immobilization of the candidate binding molecules on a solid support.

The antibody products may be screened for activity and for suitability in the treatment methods of the invention using assays as described in the section entitled "Screening Methods" herein or using any suitable assays known in the art.

Other Covalent Modifications

Covalent modifications of the antibody are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, .alpha.-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R—N.dbd.C.dbd.N—R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the .alpha.-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulthydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

Removal of any carbohydrate moieties present on the antibody may be accomplished chemically or enzymatically.

Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin, et al. Arch. Biochem. Biophys. 259: 52 (1987) and by Edge et al. Anal. Biochem., 118: 131 (1981). Enzymatic cleavage of carbohydrate moieties on antibodies can be achieved by the use of a variety of endo- and exo-glycosidases as described by Thotakura et al. Meth. Enzymol. 138: 350 (1987).

Another type of covalent modification of the antibody comprises linking the antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315 456.

Gene Therapy

Delivery of a therapeutic antibody to appropriate cells can be effected via gene therapy ex vivo, in situ, or in vivo by use of any suitable approach known in the art, including by use of physical DNA transfer methods (e.g., liposomes or chemical treatments) or by use of viral vectors (e.g., adenovirus, adeno-associated virus, or a retrovirus). For example, for in vivo therapy, a nucleic acid encoding the desired antibody, either alone or in conjunction with a vector, liposome, or precipitate may be injected directly into the subject, and in some embodiments, may be injected at the site where the expression of the antibody compound is desired. For ex vivo treatment, the subject's cells are removed, the nucleic acid is introduced into these cells, and the modified cells are returned to the subject either directly or, for example, encapsulated within porous membranes which are implanted into the patient. See, e.g. U.S. Pat. Nos. 4,892,538 and 5,283,187. There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, and calcium phosphate precipitation. A commonly used vector for ex vivo delivery of a nucleic acid is a retrovirus.

Other in vivo nucleic acid transfer techniques include transfection with viral vectors (such as adenovirus, Herpes simplex I virus, or adeno-associated virus) and lipid-based systems. The nucleic acid and transfection agent are optionally associated with a microparticle. Exemplary transfection agents include calcium phosphate or calcium chloride co-precipitation, DEAE-dextran-mediated transfection, quaternary ammonium amphiphile DOTMA ((dioleoyloxypropyl) trimethylammonium bromide, commercialized as Lipofectin by GIBCO-BRL))(Felgner et al, (1987) Proc. Natl. Acad. Sci. USA 84, 7413-7417; Malone et al. (1989) Proc. Natl. Acad. Sci. USA 86 6077-6081); lipophilic glutamate diesters with pendent trimethylammonium heads (Ito et al. (1990) Biochem. Biophys. Acta 1023, 124-132); the metabolizable parent lipids such as the cationic lipid dioctadecylamido glycylspermine (DOGS, Transfectam, Promega) and dipalmitoylphosphatidyl ethanolamylspermine (DPPES) (J. P. Behr (1986) Tetrahedron Lett. 27, 5861-5864; J. P. Behr et al. (1989) Proc. Natl. Acad. Sci. USA 86, 6982-6986); metabolizable quaternary ammonium salts (DOTB, N-(1-[2,3-dioleoyloxy]propyl)-N,N,N-trimethylammonium methylsulfate (DOTAP)(Boehringer Mannheim), polyethyleneimine (PEI), dioleoyl esters, ChoTB, ChoSC, DOSC) (Leventis et al. (1990) Biochim. Inter. 22, 235-241); 3beta [N—(N', N'-dimethylaminoethane)-carbamoyl] cholesterol (DC-Chol), dioleoylphosphatidyl ethanolamine (DOPE)/3beta[N—(N',N'-dimethylaminoethane)-carbamoyl]cholesterolDC-Chol in one to one mixtures (Gao et al., (1991) Biochim. Biophys. Acta 1065, 8-14), spermine, spermidine, lipopolyamines (Behr et al., Bioconjugate Chem, 1994, 5: 382-389), lipophilic polylysines (LPLL) (Zhou et al., (1991) Biochim. Biophys. Acta 939, 8-18), [[(1,1,3,3-tetramethylbutyl)cre-soxy]ethoxy]ethyl]dimethylbenzylammonium hydroxide (DEBDA hydroxide) with excess phosphatidylcholine/cholesterol (Ballas et al., (1988) Biochim. Biophys. Acta 939, 8-18), cetyltrimethylammonium bromide (CTAB)/DOPE mixtures (Pinnaduwage et al, (1989) Biochim. Biophys. Acta 985, 33-37), lipophilic diester of glutamic acid (TMAG) with DOPE, CTAB, DEBDA, didodecylammonium bromide (DDAB), and stearylamine in admixture with phosphatidylethanolamine (Rose et al., (1991) Biotechnique 10, 520-525), DDAB/DOPE (TransfectACE, GIBCO BRL), and oligogalactose bearing lipids. Exemplary transfection enhancer agents that increase the efficiency of transfer include, for example, DEAE-dextran, polybrene, lysosome-disruptive peptide (Ohmori N I et al, Biochem Biophys Res Commun Jun. 27, 1997; 235(3):726-9), chondroitan-based proteoglycans, sulfated proteoglycans, polyethylenimine, polylysine (Pollard H et al. J Biol Chem, 1998 273 (13):7507-11), integrin-binding peptide CYGGRGDTP, linear dextran nonasaccharide, glycerol, cholesteryl groups tethered at the 3'-terminal internucleoside link of an oligonucleotide (Letsinger, R. L. 1989 Proc Natl Acad Sci USA 86: (17): 6553-6), lysophosphatide, lysophosphatidylcholine, lysophosphatidylethanolamine, and 1-oleoyl lysophosphatidylcholine.

In some situations it may be desirable to deliver the nucleic acid with an agent that directs the nucleic acid-containing vector to target cells. Such "targeting" molecules include antibodies specific for a cell-surface membrane protein on the target cell, or a ligand for a receptor on the target cell. Where liposomes are employed, proteins which bind to a cell-surface membrane protein associated with endocytosis may be used for targeting and/or to facilitate uptake. Examples of such proteins include capsid proteins and fragments thereof tropic for a particular cell type, antibodies for proteins which undergo internalization in cycling, and proteins that target intracellular localization and enhance intracellular half-life. In other embodiments, receptor-mediated endocytosis can be used. Such methods are described, for example, in Wu et al., 1987 or Wagner et al., 1990. For review of the currently known gene marking and gene therapy protocols, see Anderson 1992. See also WO 93/25673 and the references cited therein. For additional reviews of gene therapy technology, see Friedmann, Science, 244: 1275-1281 (1989); Anderson, Nature, supplement to vol. 392, no 6679, pp. 25-30 (1998); Verma, Scientific American: 68-84 (1990); and Miller, Nature, 357: 455-460 (1992).

Screening Methods

Effective therapeutics depend on identifying efficacious agents devoid of significant toxicity. Antibodies may be screened for binding affinity by methods known in the art. For example, gel-shift assays, Western blots, radiolabeled competition assay, co-fractionation by chromatography, co-precipitation, cross linking, ELISA, and the like may be used, which are described in, for example, Current Protocols in Molecular Biology (1999) John Wiley & Sons, NY, which is incorporated herein by reference in its entirety.

To initially screen for antibodies which bind to the desired epitope on M-CSF (e.g., those which block binding of RX1, 5H4, MC1 and/or MC3 to M-CSF), a routine cross-blocking assay such as that described in Antibodies, A Laboratory Manual, Cold Spring Harbor Laboratory, Ed Harlow and David Lane (1988), can be performed. Routine competitive binding assays may also be used, in which the unknown antibody is characterized by its ability to inhibit binding of M-CSF to an M-CSF specific antibody of the invention. Intact M-CSF, fragments thereof, or linear epitopes such as represented by amino acids 98-105 of M-CSF of FIG. 12, or amino acids 65-73 or 138-144 of FIG. 12 (corresponding to M-CSF epitopes recognized by 5H4 or MC3), can be used. Epitope mapping is described in Champe et al., J. Biol. Chem. 270: 1388-1394 (1995).

It is further contemplated that the antibodies are next tested for their effect on osteoclastogenesis, followed by administration to animals. Compounds potentially useful in preventing or treating bone remodeling associated with cancer metastasis may be screened using various assays. For instance, a candidate antagonist may first be characterized in a cultured cell system to determine its ability to neutralize M-CSF in inducing osteoclastogenesis. Such a system may include the co-culture of mouse calvarial osteoblasts and spleen cells (Suda et al., Modulation of osteoclast differentiation. Endocr. Rev. 13: 66 80, 1992; Martin and Udagawa, Trends Endocrinol. Metab. 9: 6-12, 1998), the co-culture of mouse stromal cell lines (e.g., MC3T3-G2/PA6 and ST2) and mouse spleen cells (Udagawa et al., Endocrinology 125: 1805 13, 1989), and the co-culture of ST2 cells and bone marrow cells, peripheral blood mononuclear cells or alveolar macrophages (Udagawa et al., Proc. Natl. Acad. Sci. USA 87: 7260 4, 1990; Sasaki et al., Cancer Res. 58: 462 7, 1998; Mancino et al., J. Surg. Res.100: 18-24, 2001). In the absence of any M-CSF antagonist, multinucleated cells formed in such co-cultures satisfy the major criteria of osteoclasts such as tartrate resistant acid phosphatase (TRAP, a marker enzyme of osteoclasts) activity, calcitonin receptors, p60C-STC, vitronectin receptors, and the ability to form resorption pits on bone and dentine slices. The presence of an effective M-CSF antagonist inhibits the formation of such multinucleated cells.

In addition to the above co-culture systems, the ability of a candidate M-CSF antibody in inhibiting osteoclastogenesis may be assayed in a stromal cell-free or osteoblast-free system. The M-CSF required for osteoclastogenesis may be provided by co-cultured metastatic cancer cells (e.g., MDA 231) or conditioned medium from these cancer cells (Mancino et al., J. Surg. Res. 0: 18-24, 2001) or by addition of purified M-CSF.

Efficacy of a given M-CSF antibody in preventing or treating bone remodeling associated with cancer metastasis may also be tested in any of the animal bone metastasis model systems familiar to those skilled in the art. Such model systems include those involving direct injection of tumor cells into the medullary cavity of bones (Ingall, Proc. Soc. Exp. Biol. Med., 117: 819-22, 1964; Falasko, Clin. Orthop. 169: 20 7, 1982), into the rat abdominal aorta (Powles et al., Br. J. Cancer 28: 316 21, 1973), into the mouse lateral tail vein or into the mouse left ventricle (Auguello et al., Cancer Res. 48: 6876 81, 1988). In the absence of an effective M-CSF antagonist, osteolytic bone metastases fowled from injected tumor cells may be determined by radiographs (areas of osteolytic bone lesions) or histology and immunohistochemistry (bone and soft tissues). Sasaki et al., Cancer Res. 55: 35517, 1995; Yoneda et al., J. Clin. Invest. 99: 2509 17, 1997. Clohisy and Ramnaraine, Orthop Res. 16: 660 6, 1998. Yin et al., J. Clin. Invest. 103: 197 206, 1999. In the presence of an effective M-CSF antibody, osteolytic bone metastases may be prevented, or inhibited to result in fewer and/or smaller metastases.

The M-CSF antibodies of the present invention may also be useful in preventing or treating cancer metastasis. The effectiveness of a candidate M-CSF antibody in preventing or treating cancer metastasis May be screened using a human amnionic basement membrane invasion model as described in Filderman et al., Cancer Res 52: 36616, 1992. In addition, any of the animal model systems for metastasis of various types of cancers may also be used. Such model systems include, but are not limited to, those described in Wenger et al., Clin. Exp. Metastasis 19: 169 73, 2002; Yi et al., Cancer Res. 62: 917 23, 2002; Tsutsumi et al., Cancer Lett 169: 77-85, 2001; Tsingotjidou et al., Anticancer Res. 21: 971 8, 2001; Wakabayashi et al., Oncology 59: 75 80, 2000; Culp and Kogerman, Front Biosci. 3:D672 83, 1998; Runge et al., Invest Radiol. 32: 212 7; Shioda et al., J. Surg. Oncol. 64: 122 6, 1997; Ma et al., Invest Opthalmol Vis Sci. 37: 2293 301, 1996; Kuruppu et al., J Gastroenterol Hepatol. 11: 26 32, 1996. In the presence of an effective M-CSF antibody, cancer metastases may be prevented, or inhibited to result in fewer and/or smaller metastases.

The biological activity of a particular M-CSF antibody, or combination of M-CSF antibodies, may be evaluated in vivo using a suitable animal model. For example, xenogenic lymphoma cancer models wherein human lymphoma cells are introduced into immune compromised animals, such as nude or SCID mice. Efficacy may be predicted using assays which measure inhibition of tumor formation, tumor regression or metastasis, and the like.

In one variation of an in vitro assay, the invention provides a method comprising the steps of (a) contacting an immobilized M-CSF with a candidate antibody and (b) detecting binding of the candidate antibody to the M-CSF. In an alternative embodiment, the candidate antibody is immobilized and binding of M-CSF is detected. Immobilization is accomplished using any of the methods well known in the art, including covalent bonding to a support, a bead, or a chromatographic resin, as well as non-covalent, high affinity interaction such as antibody binding, or use of streptavidin/biotin binding wherein the immobilized compound includes a biotin moiety. Detection of binding can be accomplished (i) using a radioactive label on the compound that is not immobilized, (ii) using a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

Antibodies that modulate (i.e., increase, decrease, or block) the activity or expression of M-CSF may be identified by incubating a putative modulator with a cell expressing a M-CSF and determining the effect of the putative modulator on the activity or expression of the M-CSF. The selectivity of an antibody that modulates the activity of a M-CSF polypeptide or polynucleotide can be evaluated by comparing its effects on the M-CSF polypeptide or polynucleotide to its effect on other related compounds. Selective modulators may include, for example, antibodies and other proteins, peptides, or organic molecules which specifically bind to M-CSF polypeptides or to a nucleic acid encoding a M-CSF polypeptide. Modulators of M-CSF activity will be therapeutically useful in treatment of diseases and physiological conditions in which normal or aberrant activity of M-CSF polypeptide is involved.

The invention also comprehends high throughput screening (HTS) assays to identify antibodies that interact with or inhibit biological activity (i.e., inhibit enzymatic activity, binding activity, etc.) of a M-CSF polypeptide. HTS assays permit screening of large numbers of compounds in an efficient manner. Cell-based HTS systems are contemplated to investigate the interaction between M-CSF polypeptides and their binding partners. HTS assays are designed to identify "hits" or "lead compounds" having the desired property, from which modifications can be designed to improve the desired property. Chemical modification of the "hit" or "lead compound" is often based on an identifiable structure/activity relationship between the "hit" and M-CSF polypeptides.

Another aspect of the present invention is directed to methods of identifying antibodies which modulate (i.e., decrease) activity of a M-CSF comprising contacting a M-CSF with an antibody, and determining whether the antibody modifies activity of the M-CSF. The activity in the presence of the test antibody is compared to the activity in the absence of the test antibody. Where the activity of the sample containing the test antibody is lower than the activity in the sample lacking the test antibody, the antibody will have inhibited activity.

A variety of heterologous systems is available for functional expression of recombinant polypeptides that are well known to those skilled in the art. Such systems include bacteria (Strosberg, et al., Trends in Pharmacological Sciences (1992) 13:95-98), yeast (Pausch, Trends in Biotechnology (1997) 15:487-494), several kinds of insect cells (Vanden Broeck, Int. Rev. Cytology (1996) 164:189-268), amphibian cells (Jayawickreme et al., Current Opinion in Biotechnology (1997) 8: 629-634) and several mammalian cell lines (CHO, HEK293, COS, etc.; see Gerhardt, et al., Eur. J. Pharmacology (1997) 334:1-23). These examples do not preclude the use of other possible cell expression systems, including cell lines obtained from nematodes (PCT application WO 98/37177).

In one embodiment of the invention, methods of screening for antibodies which modulate the activity of M-CSF comprise contacting test antibodies with a M-CSF polypeptide and assaying for the presence of a complex between the antibody and the M-CSF. In such assays, the ligand is typically labeled. After suitable incubation, free ligand is separated from that present in bound form, and the amount of free or uncomplexed label is a measure of the ability of the particular antibody to bind to the M-CSF or M-CSFR polypeptide In another embodiment of the invention, high throughput screening for antibody fragments or CDRs having suitable binding affinity to a M-CSF polypeptide is employed. Briefly, large numbers of different small peptide test compounds are synthesized on a solid substrate. The peptide test antibodies are contacted with a M-CSF polypeptide and washed. Bound M-CSF polypeptides are then detected by methods well known in the art. Purified polypeptides of the invention can also be coated directly onto plates for use in the aforementioned drug screening techniques. In addition, non-neutralizing antibodies can be used to capture the protein and immobilize it on the solid support.

Combination Therapy

Having identified more than one M-CSF antibody that is effective in an animal model, it may be further advantageous to mix two or more such M-CSF antibodies together to provide still improved efficacy against bone loss or against cancer metastasis and/or bone remodeling associated with cancer metastasis. Compositions comprising one or more M-CSF antibody may be administered to persons or mammals suffering from, or predisposed to suffer from, bone loss or cancer metastasis and/or bone remodeling associated with cancer metastasis. Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

Although M-CSF antibody therapy may be useful for all stages of cancers, antibody therapy may be particularly appropriate in advanced or metastatic cancers. Combining the antibody therapy method a chemotherapeutic or radiation regimen may be preferred in patients that have not received chemotherapeutic treatment, whereas treatment with the antibody therapy may be indicated for patients who have received one or more chemotherapies. Additionally, antibody therapy can also enable the use of reduced dosages of concomitant chemotherapy, particularly in patients that do not tolerate the toxicity of the chemotherapeutic agent very well.

The method of the invention contemplate the administration of single anti-M-CSF antibodies, as well as combinations, or "cocktails", of different antibodies. Such antibody cocktails may have certain advantages inasmuch as they contain antibodies which exploit different effector mechanisms or combine directly cytotoxic antibodies with antibodies that rely on immune effector functionality. Such antibodies in combination may exhibit synergistic therapeutic effects.

Combining RX1 or Human Engineered™ derivative of RX1 antibody with other therapeutics can have an effect on a patient experiencing osteoclastic disease and/or tumor growth or metastasis. For example, one could use of RX1 antibody in the manufacture of a medicament for treating a patient having an osteolytic disease wherein said medicament is coordinated with treatment using an anti-RANKL antibody, soluble RANKL receptor, other RANKL inhibitors, or bisphosphonates (e.g., Aredia; Zometa; Clodronate). Alternatively, one could use an anti-RANKL antibody or bisphosphonate in the manufacture of a medicament for treating a for treating a patient having an osteolytic disease wherein said medicament coordinated with treatment using RX1 antibody or human engineered derivative of RX1 antibody. The combination might also have a synergistic effect in a treated patient. The RX1 antibody and other therapeutic need not be administered simultaneously. RX1 or the human engineered variant and the other therapeutic can administered within 1 day, 1 week, 2 weeks, 4 weeks, 2 months, 3 months, 6 months, 1 year or two years of each other.

The invention also contemplates the use of a RX1 antibody or a Human Engineered™ derivative of RX1 antibody in the manufacture of a medicament for treating a patient having an osteolytic disease wherein said medicament is used in a patient that has been pre-treated with an anti-RANKL antibody or bisphosphonates. "Pre-treatment" means that a patient had been treated within 2 years, 1 year, 6 months, 3 months 2 months, 1 month, 2 weeks, 1 week, or at least one day one before treatment with RX1 or Human Engineered™ variant of RX1.

RX1 antibody or Human Engineered™ variants can be used in combination with other cancer therapeutics. For example, one could use RX1 antibody or human engineered variants in the manufacture of a medicament for treating a patient having cancer disease wherein said medicament is coordinated with treatment using other therapeutic agents and/or procedures, including but not limited to various chemotherapeutic agents, androgen-blockers, and immune modulators (e.g., IL-2, GM-CSF, SLC), Bisphosphonate(s) (e.g., Aredia; Zometa; Clodronate), surgery, radiation, cytotoxic chemotherapy, hormone therapy (e.g., Tamoxifen; anti-Androgen therapy), antibody therapy (e.g., antibodies to RANKL/RANK neutralizing; PTHrP neutralizing, anti-Her2, anti-CD20, anti-CD40, CD22, VEGF, IGFR-1, EphA2, HAAH, TMEFF2, CAIX antibodies), therapeutic protein therapy (e.g., soluble RANKL receptor; OPG, and PDGF and MMP inhibitors), small molecule drug therapy (e.g., Src-kinase inhibitor), kinase inhibitors of growth factor receptors, or RANKL inhibitors, oligonucleotides therapy (e.g., RANKL or RANK or PTHrP Anti-sense), gene therapy (e.g., RANKL or RANK inhibitors), peptide therapy (e.g. muteins of RANKL) as well as those proteins, peptides, compounds, and small molecules described herein. Treatment of mixed osteolytic/osteoblastic lesions may include use of RX1 antibody and another therapeutic agent that inhibits osteoblastogenesis, including, for example, a bone morphogenetic protein (BMP) antagonist, such as a BMP-2 antagonist, a transforming growth factor-β1 (TGFβ1) antagonist, a transfoiming growth factor-β2 TGFβ2 antagonist, an insulin-like growth factor 1 (IGF1) antagonist, an insulin-like growth factor 2 (IGF2) antagonist, a fibroblast growth factor (FGF) antagonist, a platelet-derived growth factor (PDGF) antagonist, a WNT antagonist such as DICKKOPF-1 (DKK-1), a β-catenin antagonist, an osterix antagonist, a core binding factor 1 (RUNX2)antagonist, and an endothelin receptor antagonist such as atrasentan.

RX1 and Human Engineered™ variants can be used in the manufacture of a medicament for treating patients that have been pretreated with the above mentioned therapeutics.

A cytotoxic agent refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see, e.g., U.S. Patent Publications 2003/0028071 and 2003/0032995 which are incorporated by reference herein). Such agents may be conjugated, coupled, linked or associated with an antibody according to the invention.

Cancer chemotherapeutic agents include, without limitation, alkylating agents, such as carboplatin and cisplatin; nitrogen mustard alkylating agents; nitrosourea alkylating agents, such as carmustine (BCNU); antimetabolites, such as methotrexate; folinic acid; purine analog antimetabolites, mercaptopurine; pyrimidine analog antimetabolites, such as fluorouracil (5-FU) and gemcitabine (Gemzar®); hormonal antineoplastics, such as goserelin, leuprolide, and tamoxifen; natural antineoplastics, such as aldesleukin, interleukin-2, docetaxel, etoposide (VP-16), interferon alfa, paclitaxel (Taxol®), and tretinoin (ATRA); antibiotic natural antineoplastics, such as bleomycin, dactinomycin, daunorubicin, doxorubicin, daunomycin and mitomycins including mitomycin C; and vinca alkaloid natural antineoplastics, such as vinblastine, vincristine, vindesine; hydroxyurea; aceglatone, adriamycin, Ifosfamide, enocitabine, epitiostanol, aclarubicin, ancitabine, nimustine, procarbazine hydrochloride, carboquone, carboplatin, carmofur, chromomycin A3, antitumor polysaccharides, antitumor platelet factors, cyclophosphamide (Cytoxin®), Schizophyllan, cytarabine (cytosine arabinoside), dacarbazine, thioinosine, thiotepa, tegafur, dolastatins, dolastatin analogs such as auristatin, CPT-11 (irinotecan), mitozantrone, vinorelbine, teniposide, aminopterin, caminomycin, esperamicins (See, e.g., U.S. Pat. No. 4,675,187), neocarzinostatin, OK-432, bleomycin, furtulon, broxuridine, busulfan, honvan, peplomycin, bestatin (Ubenimex®), interferon-β, mepitiostane, mitobronitol, melphalan, laminin peptides, lentinan, *Coriolus versicolor* extract, tegafur/uracil, estramustine (estrogen/mechlorethamine).

Further, additional agents used as therapy for cancer patients include EPO, G-CSF, ganciclovir; antibiotics, leuprolide; meperidine; zidovudine (AZT); interleukins 1 through 18, including mutants and analogues; interferons or cytokines, such as interferons α, β, and γ hormones, such as luteinizing hormone releasing hormone (LHRH) and analogues and, gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α & β (TNF-α & β); invasion inhibiting factor-2 (IIF-2); bone morphogenetic proteins 1-7 (BMP 1-7); somatostatin; thymosin-α-1; γ-globulin; superoxide dismutase (SOD); complement factors; anti-angiogenesis factors; antigenic materials; and prodrugs.

Prodrug refers to a precursor or derivative form of a pharmaceutically active substance that is less cytotoxic or non-cytotoxic to tumor cells compared to the parent drug and is capable of being enzymatically activated or converted into an active or the more active parent form. See, e.g., Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use herein include, but are not limited to, those chemotherapeutic agents described above.

Administration and Preparation

The anti-M-CSF antibodies used in the practice of a method of the invention may be formulated into pharmaceutical compositions comprising a carrier suitable for the desired delivery method. Suitable carriers include any material which, when combined with the anti-M-CSF antibodies, retains the desired activity of the antibody and is nonreactive with the subject's immune systems. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Therapeutic formulations of the antibody are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

The antibody is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. In addition, the antibody is suitably administered by pulse infusion, particularly with declining doses of the antibody. Preferably the dosing is given by injections, most preferably intravenous or subcutaneous injections. Other administration methods are contemplated, including topical, particularly transdermal, transmucosal, rectal, oral or local administration e.g. through a catheter placed close to the desired site.

For nasal administration, the pharmaceutical formulations and medicaments may be a spray or aerosol containing an appropriate solvent(s) and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intennolecular S—S bond formation through thio-disulfide interchange, stabilization may be achieved by modifying sulfhydryl residues, lyophilizing from acidic solutions, controlling moisture content, using appropriate additives, and developing specific polymer matrix compositions. Other strategies known in the art may be used.

The formulations of the invention may be designed to be short-acting, fast-releasing, long-acting, or sustained-releasing as described herein. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Besides those representative dosage forms described above, pharmaceutically acceptable excipients and carries are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

Specific dosages may be adjusted depending on conditions of disease, the age, body weight, general health conditions, genotype, sex, and diet of the subject, dose intervals, administration routes, excretion rate, and combinations of drugs.

Any of the above dosage forms containing effective amounts are well within the bounds of routine experimentation and therefore, well within the scope of the instant invention.

M-CSF antibodies useful as therapeutics for osteolytic diseases, including cancer metastasis to bone and bone remodeling associated with such diseases, will often be prepared substantially free of other naturally occurring immunoglobulins or other biological molecules. Preferred M-CSF antibodies will also exhibit minimal toxicity when administered to a mammal afflicted with, or predisposed to suffer from osteolytic diseases.

The compositions of the invention may be sterilized by conventional, well known sterilization techniques. The resulting solutions may be packaged for use or filtered under aseptic conditions and lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride and stabilizers (e.g., 1 20% maltose, etc.).

The M-CSF antibodies of the present invention may also be administered via liposomes, which are small vesicles composed of various types of lipids and/or phospholipids and/or surfactant which are useful for delivery of a drug (such as the antibodies disclosed herein and, optionally, a chemotherapeutic agent). Liposomes include emulsions, foams, micelles, insoluble monolayers, phospholipid dispersions, lamellar layers and the like, and can serve as vehicles to target the M-CSF antibodies to a particular tissue as well as to increase the half life of the composition. A variety of methods are available for preparing liposomes, as described in, e.g., U.S. Pat. Nos. 4,837,028 and 5,019,369, which patents are incorporated herein by reference.

Liposomes containing the antibody are prepared by methods known in the art, such as described in Epstein et al., Proc. Natl. Acad. Sci. USA 82: 3688 (1985); Hwang et al., Proc. Natl. Acad. Sci. USA 77: 4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257: 286-288 (1982) via a disulfide interchange reaction. A chemotherapeutic agent (such as Doxorubicin) is optionally contained within the liposome [see, e.g., Gabizon et al., J. National Cancer Inst. 81(19): 1484 (1989)].

The concentration of the M-CSF antibody in these compositions can vary widely, i.e., from less than about 10%, usually at least about 25% to as much as 75% or 90% by weight and will be selected primarily by fluid volumes, viscosities, etc., in accordance with the particular mode of administration selected. Actual methods for preparing orally, topically and parenterally administrable compositions will be known or apparent to those skilled in the art and are described in detail in, for example, Remington's Pharmaceutical Science, 19th ed., Mack Publishing Co., Easton, Pa. (1995), which is incorporated herein by reference.

Determination of an effective amount of a composition of the invention to treat disease in a patient can be accomplished through standard empirical methods which are well known in the art. For example, the in vivo neutralizing activity of sera from a subject treated with a given dosage of M-CSF antibody may be evaluated using an assay that determines the ability of the sera to block M-CSF induced proliferation and survival of murine monocytes (CD11b+ cell, a subset of CD11 cells, which expresses high levels of receptor to M-CSF) in vitro as described in Cenci et al., J Clin. Invest. 1055: 1279-87, 2000.

Compositions of the invention are administered to a mammal already suffering from, or predisposed to or at risk of an osteolytic disease, including cancer metastasis to bone and bone remodeling associated with such diseases, in an amount sufficient to prevent or at least partially arrest the development of disease. An amount adequate to accomplish this is defined as a "therapeutically effective dose." Effective amounts of a M-CSF antibody will vary and depend on the severity of the disease and the weight and general state of the patient being treated, but generally range from about 1.0 µg/kg to about 100 mg/kg body weight. Exemplary doses may range from about 10 µg/kg to about 30 mg/kg, or from about 0.1 mg/kg to about 20 mg/kg or from about 1 mg/kg to about 10 mg/kg per application. Antibody may also be dosed by body surface area (e.g. up to 4.5 g/square meter). Other exemplary doses of antibody include up to 8 g total in a single administration (assuming a body weight of 80 kg or body surface area of 1.8 square meters).

Administration may be by any means known in the art. For example, antibody may be administered by one or more separate bolus administrations, or by short or long term infusion over a period of, e.g., 5, 10, 15, 30, 60, 90, 120 minutes or more. Following an initial treatment period, and depending on the patient's response and tolerance of the therapy, maintenance doses may be administered, e.g., weekly, biweekly, every 3 weeks, every 4 weeks, monthly, bimonthly, every 3 months, or every 6 months, as needed to maintain patient response. More frequent dosages may be needed until a desired suppression of disease symptoms occurs, and dosages may be adjusted as necessary. The progress of this therapy is easily monitored by conventional techniques and assays. The therapy may be for a defined period or may be chronic and continue over a period of years until disease progression or death.

Single or multiple administrations of the compositions can be carried out with the dose levels and pattern being selected by the treating physician. For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

In any event, the formulations should provide a quantity of M-CSF antibody over time that is sufficient to effectively prevent or minimize the severity of osteolytic disease, including cancer metastasis to bone and bone remodeling associated with such diseases. The compositions of the present invention may be administered alone or as an adjunct therapy in conjunction with other therapeutics known in the art for the treatment of such diseases.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The therapeutically effective amount of the antibody to be administered will be governed by such considerations, and is the minimum amount necessary to prevent, ameliorate, or treat the M-CSF mediated disease, condition or disorder. Such amount is preferably below the amount that is toxic to the host or renders the host significantly more susceptible to infections.

The antibody need not be, but is optionally formulated with one or more agents currently used to prevent or treat the disorder in question. The effective amount of such other agents depends on the amount of antibody present in the formulation, the type of disease, condition or disorder or treatment, and other factors discussed above. These are generally used in the same dosages and with administration routes as used hereinbefore or about from 1 to 99% of the heretofore employed dosages.

In another embodiment of the invention, there is provided an article of manufacture containing materials useful for the treatment of osteolytic disease, including cancer metastasis to bone and bone remodeling associated with such diseases. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody of the invention. The label on, or associated with, the container indicates that the composition is used for treating the condition of choice. The article of manufacture may further comprise a second container containing a second therapeutic agent (including any of the second therapeutic agents for osteolytic diseases discussed herein or known in the art). The article of manufacture may further comprise another container containing a pharmaceutically-acceptable buffer, such as phosphate-buffered saline, Ringer's solution or dextrose solution for reconstituting a lyophilized antibody formulation. It may further include other materials desirable from a commercial and user standpoint, including other buffers, diluents, filters, needles, syringes, and package inserts with instructions for use.

Immunotherapy

Anti-M-CSF antibodies useful in treating patients having cancers include those which are capable of initiating a potent immune response against the tumor and those which are capable of direct cytotoxicity. In this regard, anti-M-CSF antibodies may elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, anti-M-CSF antibodies that exert a direct biological effect on tumor growth are useful in the practice of the invention. Potential mechanisms by which such directly cytotoxic antibodies may act include inhibition of cell growth, modulation of cellular differentiation, modulation of tumor angiogenesis factor profiles, and the induction of apoptosis. The mechanism by which a particular anti-M-CSF antibody exerts an anti-tumor effect may be evaluated using any number of in vitro assays designed to determine ADCC, ADMMC, complement-mediated cell lysis, and so forth, as is generally known in the art.

In one embodiment, immunotherapy is carried out using antibodies that have a higher affinity for the membrane-bound form of M-CSF (M-CSFα) than for the secreted forms of M-CSF. For example, antibodies may be prepared that specifically bind at or around the cleavage site of M-CSFα or to the portion of M-CSFα adjacent to the membrane. Such antibodies may also beneficially inhibit cleavage and release of the soluble active portion of M-CSFα.

The anti-M-CSF antibodies may be administered in their "naked" or unconjugated form, or may have therapeutic agents conjugated to them. In one embodiment, anti-M-CSF antibodies are used as a radiosensitizer. In such embodiments, the anti-M-CSF antibodies are conjugated to a radiosensitizing agent. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Diseases that are treatable with electromagnetic radiation include neoplastic diseases, benign and malignant tumors, and cancerous cells.

The terms "electromagnetic radiation" and "radiation" as used herein include, but are not limited to, radiation having the wavelength of $10^{-20}$ to 100 meters. Preferred embodiments of the present invention employ the electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1.0 mm), and microwave radiation (1 mm to 30 cm).

Radiosensitizers are known to increase the sensitivity of cancerous cells to the toxic effects of electromagnetic radiation. Many cancer treatment protocols currently employ radiosensitizers activated by the electromagnetic radiation of X-rays. Examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin(r), benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

In another embodiment, the antibody may be conjugated to a receptor (such streptavidin) for utilization in tumor pretargeting wherein the antibody-receptor conjugate is administered to the patient, followed by removal of unbound conjugate from the circulation using a clearing agent and then administration of a ligand (e.g., avidin) which is conjugated to a cytotoxic agent (e.g., a radionuclide).

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are well known in the art; for example, see (Sternberger, L. A. et al., J. Histochem.

Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

"Label" refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable. Alternatively, the label may not be detectable on its own but may be an element that is bound by another agent that is detectable (e.g. an epitope tag or one of a binding partner pair such as biotin-avidin, etc.) Thus, the antibody may comprise a label or tag that facilitates its isolation, and methods of the invention to identify antibodies include a step of isolating the M-CSF/antibody through interaction with the label or tag.

Exemplary therapeutic immunoconjugates comprise the antibody described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fusion proteins are described in further detail below.

Production of immunconjugates is described in U.S. Pat. No. 6,306,393. Immunoconjugates can be prepared by indirectly conjugating a therapeutic agent to an antibody component. General techniques are described in Shih et al., Int. J. Cancer 41:832-839 (1988); Shih et al., Int. J. Cancer 46:1101-1106 (1990); and Shih et al., U.S. Pat. No. 5,057,313. The general method involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer is preferably an aminodextran or polypeptide of at least 50 amino acid residues, although other substantially equivalent polymer carriers can also be used. Preferably, the final immunoconjugate is soluble in an aqueous solution, such as mammalian serum, for ease of administration and effective targeting for use in therapy. Thus, solubilizing functions on the carrier polymer will enhance the serum solubility of the final immunoconjugate. In particular, an aminodextran will be preferred.

The process for preparing an immunoconjugate with an aminodextran carrier typically begins with a dextran polymer, advantageously a dextran of average molecular weight of about 10,000-100,000. The dextran is reacted with an oxidizing agent to affect a controlled oxidation of a portion of its carbohydrate rings to generate aldehyde groups. The oxidation is conveniently effected with glycolytic chemical reagents such as $NaIO_4$, according to conventional procedures.

The oxidized dextran is then reacted with a polyamine, preferably a diamine, and more preferably, a mono- or poly-hydroxy diamine. Suitable amines include ethylene diamine, propylene diamine, or other like polymethylene diamines, diethylene triamine or like polyamines, 1,3-diamino-2-hydroxypropane, or other like hydroxylated diamines or polyamines, and the like. An excess of the amine relative to the aldehyde groups of the dextran is used to ensure substantially complete conversion of the aldehyde functions to Schiff base groups.

A reducing agent, such as $NaBH_4$, $NaBH_3CN$ or the like, is used to effect reductive stabilization of the resultant Schiff base intermediate. The resultant adduct can be purified by passage through a conventional sizing column to remove cross-linked dextrans.

Other conventional methods of derivatizing a dextran to introduce amine functions can also be used, e.g., reaction with cyanogen bromide, followed by reaction with a diamine.

The aminodextran is then reacted with a derivative of the particular drug, toxin, chelator, immunomodulator, boron addend, or other therapeutic agent to be loaded, in an activated form, preferably, a carboxyl-activated derivative, prepared by conventional means, e.g., using dicyclohexylcarbodiimide (DCC) or a water soluble variant thereof, to form an intermediate adduct.

Alternatively, polypeptide toxins such as pokeweed antiviral protein or ricin A-chain, and the like, can be coupled to aminodextran by glutaraldehyde condensation or by reaction of activated carboxyl groups on the protein with amines on the aminodextran.

Chelators for radiometals or magnetic resonance enhancers are well-known in the art. Typical are derivatives of ethylenediaminetetraacetic acid (EDTA) and diethylenetriaminepentaacetic acid (DTPA). These chelators typically have groups on the side chain by which the chelator can be attached to a carrier. Such groups include, e.g., benzylisothiocyanate, by which the DTPA or EDTA can be coupled to the amine group of a carrier. Alternatively, carboxyl groups or amine groups on a chelator can be coupled to a carrier by activation or prior derivatization and then coupling, all by well-known means.

Boron addends, such as carboranes, can be attached to antibody components by conventional methods. For example, carboranes can be prepared with carboxyl functions on pendant side chains, as is well known in the art. Attachment of such carboranes to a carrier, e.g., aminodextran, can be achieved by activation of the carboxyl groups of the carboranes and condensation with amines on the carrier to produce an intermediate conjugate. Such intermediate conjugates are then attached to antibody components to produce therapeutically useful immunoconjugates, as described below.

A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, copolymers thereof, and mixed polymers of these amino acids and others, e.g., serines, to confer desirable solubility properties on the resultant loaded carrier and immunoconjugate.

Conjugation of the intermediate conjugate with the antibody component is effected by oxidizing the carbohydrate portion of the antibody component and reacting the resulting aldehyde (and ketone) carbonyls with amine groups remaining on the carrier after loading with a drug, toxin, chelator, immunomodulator, boron addend, or other therapeutic agent. Alternatively, an intermediate conjugate can be attached to an oxidized antibody component via amine groups that have been introduced in the intermediate conjugate after loading with the therapeutic agent. Oxidation is conveniently effected either chemically, e.g., with $NaIO_4$ or other glycolytic reagent, or enzymatically, e.g., with neuraminidase and galactose oxidase. In the case of an aminodextran carrier, not all of the amines of the aminodextran are typically used for loading a therapeutic agent. The remaining amines of aminodextran condense with the oxidized antibody component to form Schiff base adducts, which are then reductively stabilized, normally with a borohydride reducing agent.

Analogous procedures are used to produce other immunoconjugates according to the invention. Loaded polypeptide carriers preferably have free lysine residues remaining for condensation with the oxidized carbohydrate portion of an antibody component. Carboxyls on the polypeptide carrier can, if necessary, be converted to amines by, e.g., activation with DCC and reaction with an excess of a diamine.

The final immunoconjugate is purified using conventional techniques, such as sizing chromatography on Sephacryl S-300 or affinity chromatography using one or more CD84Hy epitopes.

Alternatively, immunoconjugates can be prepared by directly conjugating an antibody component with a therapeutic agent. The general procedure is analogous to the indirect method of conjugation except that a therapeutic agent is directly attached to an oxidized antibody component. For example, a carbohydrate moiety of an antibody can be attached to polyethyleneglycol to extend half-life.

It will be appreciated that other therapeutic agents can be substituted for the chelators described herein. Those of skill in the art will be able to devise conjugation schemes without undue experimentation.

As a further illustration, a therapeutic agent can be attached at the hinge region of a reduced antibody component via disulfide bond formation. For example, the tetanus toxoid peptides can be constructed with a single cysteine residue that is used to attach the peptide to an antibody component. As an alternative, such peptides can be attached to the antibody component using a heterobifunctional cross-linker, such as N-succinyl 3-(2-pyridyldithio)proprionate (SPDP). Yu et al., Int. J. Cancer 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Enineering and Clinical Application, Ritter et al. (eds.), pages 60-84 (Cambridge University Press 1995).

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaredehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionuclide to the antibody (see, e.g., WO94/11026).

As described above, carbohydrate moieties in the Fc region of an antibody can be used to conjugate a therapeutic agent. However, the Fc region may be absent if an antibody fragment is used as the antibody component of the immunoconjugate. Nevertheless, it is possible to introduce a carbohydrate moiety into the light chain variable region of an antibody or antibody fragment. See, for example, Leung et al., J. Immunol. 154:5919 (1995); Hansen et al., U.S. Pat. No. 5,443,953. The engineered carbohydrate moiety is then used to attach a therapeutic agent.

In addition, those of skill in the art will recognize numerous possible variations of the conjugation methods. For example, the carbohydrate moiety can be used to attach polyethyleneglycol in order to extend the half-life of an intact antibody, or antigen-binding fragment thereof, in blood, lymph, or other extracellular fluids. Moreover, it is possible to construct a "divalent immunoconjugate" by attaching therapeutic agents to a carbohydrate moiety and to a free sulfhydryl group. Such a free sulfhydryl group may be located in the hinge region of the antibody component.

Anti-M-CSF Antibody Fusion Proteins

The present invention contemplates the use of fusion proteins comprising one or more anti-M-CSF antibody moieties and another polypeptide, such as an immunomodulator or toxin moiety. Methods of making antibody fusion proteins are well known in the art. See, e.g., U.S. Pat. No. 6,306,393. Antibody fusion proteins comprising an interleukin-2 moiety are described by Boleti et al., Ann. Oncol. 6:945 (1995), Nicolet et al., Cancer Gene Ther. 2:161 (1995), Becker et al., Proc. Nat'l Acad. Sci. USA 93:7826 (1996), Hank et al., Clin. Cancer Res. 2:1951 (1996), and Hu et al., Cancer Res. 56:4998 (1996). In addition, Yang et al., Hum. Antibodies Hybridomas 6:129 (1995), describe a fusion protein that includes an F(ab')$_2$ fragment and a tumor necrosis factor alpha moiety.

Methods of making antibody-toxin fusion proteins in which a recombinant molecule comprises one or more antibody components and a toxin or chemotherapeutic agent also are known to those of skill in the art. For example, antibody-Pseudomonas exotoxin A fusion proteins have been described by Chaudhary et al., Nature 339:394 (1989), Brinkmann et al., Proc. Nat'l Acad. Sci. USA 88:8616 (1991), Batra et al., Proc. Nat'l Acad. Sci. USA 89:5867 (1992), Friedman et al., J. Immunol. 150:3054 (1993), Wels et al., Int. J. Can. 60:137 (1995), Fominaya et al., J. Biol. Chem. 271:10560 (1996), Kuan et al., Biochemistry 35:2872 (1996), and Schmidt et al., Int. J. Can. 65:538 (1996). Antibody-toxin fusion proteins containing a diphtheria toxin moiety have been described by Kreitman et al., Leukemia 7:553 (1993), Nicholls et al., J. Biol. Chem. 268:5302 (1993), Thompson et al., J. Biol. Chem. 270:28037 (1995), and Vallera et al., Blood 88:2342 (1996). Deonarain et al., Tumor Targeting 1:177 (1995), have described an antibody-toxin fusion protein having an RNase moiety, while Linardou et al., Cell Biophys. 24-25:243 (1994), produced an antibody-toxin fusion protein comprising a DNase I component. Gelonin was used as the toxin moiety in the antibody-toxin fusion protein of Wang et al., Abstracts of the 209th ACS National Meeting, Anaheim, Calif., Apr. 2-6, 1995, Part 1, BIOT005. As a further example, Dohlsten et al., Proc. Nat'l Acad. Sci. USA 91:8945 (1994), reported an antibody-toxin fusion protein comprising Staphylococcal enterotoxin-A.

Illustrative of toxins which are suitably employed in the preparation of such conjugates are ricin, abrin, ribonuclease, DNase I, Staphylococcal enterotoxin-A, pokeweed antiviral protein, gelonin, diphtherin toxin, *Pseudomonas* exotoxin, and *Pseudomonas* endotoxin. See, for example, Pastan et al., Cell 47:641 (1986), and Goldenberg, C A—A Cancer Journal for Clinicians 44:43 (1994). Other suitable toxins are known to those of skill in the art.

Antibodies of the present invention may also be used in ADEPT by conjugating the antibody to a prodrug-activating enzyme which converts a prodrug (e.g., a peptidyl chemotherapeutic agent, See WO81/01145) to an active anti-cancer drug. See, for example, WO88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as abzymes, can be used to convert the prodrugs of the invention into free active drugs (See, e.g., Massey, Nature 328: 457-458 (1987)). Antibody-abzyme conjugates can be prepared as described herein for delivery of the abzyme to a tumor cell population.

The enzymes of this invention can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (See, e.g., Neuberger et al., Nature 312: 604-608. (1984))

Non-Therapeutic Uses

The antibodies of the invention may be used as affinity purification agents for M-CSF or in diagnostic assays for M-CSF protein, e.g., detecting its expression in specific cells, tissues, or serum. The antibodies may also be used for in vivo diagnostic assays. Generally, for these purposes the antibody is labeled with a radionuclide (such as $^{111}$In, $^{99}$Tc, $^{14}$C, $^{131}$I, $^{125}$I, $^{3}$H, $^{32}$P or $^{35}$S) so that the tumor can be localized using immunoscintiography.

The antibodies of the present invention may be employed in any known assay method, such as competitive binding assays, direct and indirect sandwich assays, such as ELISAs, and immunoprecipitation assays. Zola, Monoclonal Antibodies: A Manual of Techniques, pp. 147-158 (CRC Press, Inc. 1987). The antibodies may also be used for immunohistochemistry, to label tumor samples using methods known in the art.

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

The invention is illustrated by the following examples, which are not intended to be limiting in any way.

EXAMPLES

Example 1

This example shows that M-CSF antibodies RX1 and 5A1 are species specific and that antibodies RX1, MC1, and MC3 neutralize human M-CSF activity. RX1 is a commercially sold antibody that was available more than a year prior to the filing date of this application. Exemplary commercial sources include, but are not limited to, mouse anti-human M-CSF monoclonal antibody clones 116, 692, and 21 (Anogen); anti-human M-CSF antibody clones 21113.131, 26730, and 26786 (R & D Systems, Inc.); and anti-human M-CSF antibody clone M16 (Antigenix America, Inc.).

To test the neutralizing activity of RX1 and 5A1, a proliferation assay of M-NFS-60 cell line was used (American Type Culture Collection Accession No. CRL-1838, available from ATCC in Rockville, Md., USA, derived from a myelogenous leukemia induced with the Cas-Br-MuLV wild mouse ecotropic retrovirous, responsive to both interleukin 3 and M-CSF and which contain a truncated c-myb proto-oncogene caused by the integration of a retrovirus). Proliferation of M-NFS-60 requires active M-CSF in a dose-dependent fashion. In the assay, M-NFS-60 cells were washed and plated in RPMI 1640 medium with 10% FBS and 3000 U/ml of M-CSF and 1% Pen/Strep. Recombinant human M-CSF (at 10 ng/ml final concentration), human or murine-specific, was incubated with various concentrations of antibodies for 1 hour at 37° C. in 5% $CO_2$ in an incubator. Following the incubation, the mixture was added to the M-NFS-60 culture in 96 well microtiter plates. The total assay volume per well was 100 µl, with 10 ng/ml M-CSF, and the antibody concentration indicated in FIG. 5. Cells were incubated at 37° C. under 5% $CO_2$ for 72 hours before cell numbers were quantified by CellTiter Glo assay (Promega). The aforementioned assay was repeated for antibodies MC3 and MC1.

Figure 5A:
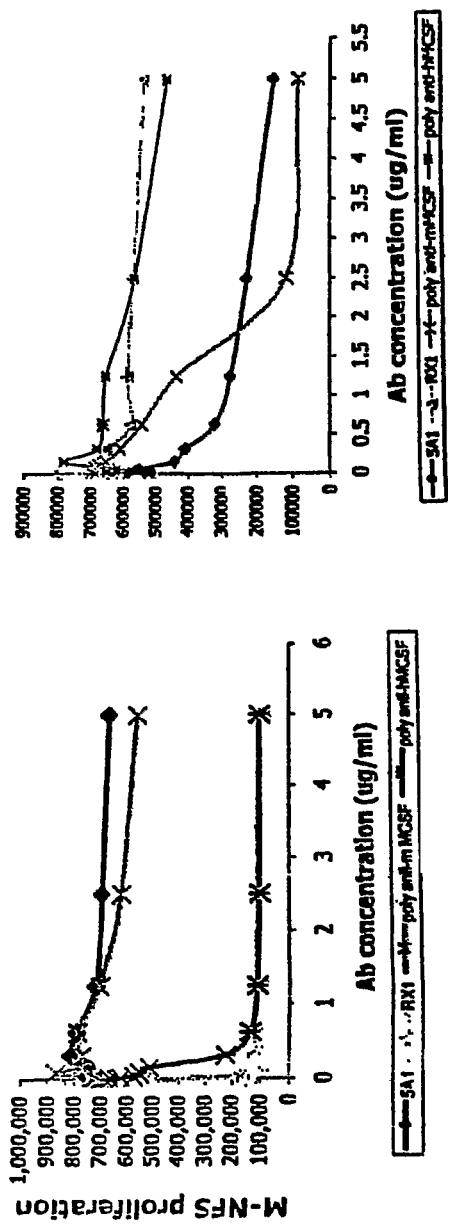
FIG. 5A shows that M-CSF antibodies RX1 and 5A1 are species specific.

As shown in FIG. 5, M-CSF antibodies RX1 and 5A1 are species specific. Cell proliferation is presented as the fluorescent reading from CellTiter Glo assay, which is linear with cell number. Species specific neutralizing activity of RX1 and 5A1 is shown by its ability to inhibit M-NFS-60 in the presence of either human or murine M-CSF. Finally, as shown in FIG. 5B, antibodies MC3 and MC1 are also effective inhibitors of human M-CSF activity.

Example 2

Figure 6:
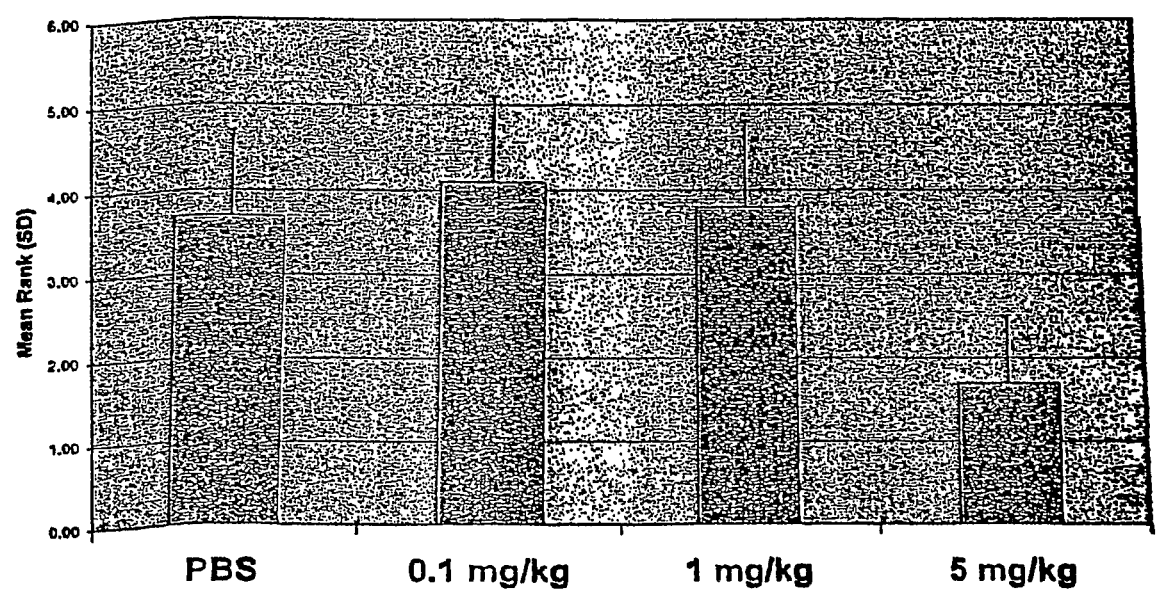
FIG. 6 shows that antibody RX1 effectively inhibits osteolysis in a human xenograft model at a concentration 5 mg/kg.

This example shows that antibody RX1 effectively inhibits osteolysis in a human xenograft model at a dose of 5 mg/kg. Female nude mice at the age of 4-7 weeks old, average weight ~20 g were used in this study. Tumor cells (MDA-MB-231, 3×10$^5$) suspended in 10 µl of saline was be injected into the right tibia bone marrow cavity. Radiograms of the hind legs were taken one day after tumor inoculation for getting baseline image and checking for bone fracture caused by injection. Mice were randomized into treatment groups at 10 mice per group including PBS and RX1 at 5 mg/kg, injected i.p. once a week for 6 weeks. At the end of study, radiograms of the hind legs were taken again and compared against baseline for bone damage. The degree of bone damage caused by tumor was defined as shown in FIG. 6. The group with RX1 5 mg/kg treatment showed statistically significant protection of the bone from tumor-cased damage.

Example 3

This example shows that the number of metastases is reduced when antibody RX1 is administered to human breast cancer MDA-MB-231 bearing nude mice at a concentration of 5 mg/kg.

Female nude mice at the age of 4-7 weeks old, average weight ~20 g were used for this study. Tumor cells (MDA-MB-231, $3 \times 10^5$) suspended in 10 μl of saline was injected into the right tibia bone marrow cavity. Radiograms of the hind legs were taken one day after tumor inoculation for getting baseline image and checking for bone fracture caused by injection. Mice were randomly grouped into the treatment groups including PBS and RX1 at 5 mg/kg injected i.p. once a week for 6 weeks. At the end of study, lungs of each treatment group were collected and fixed in Bouin's solution for metastatic lung nodule counting.

Figure 7:
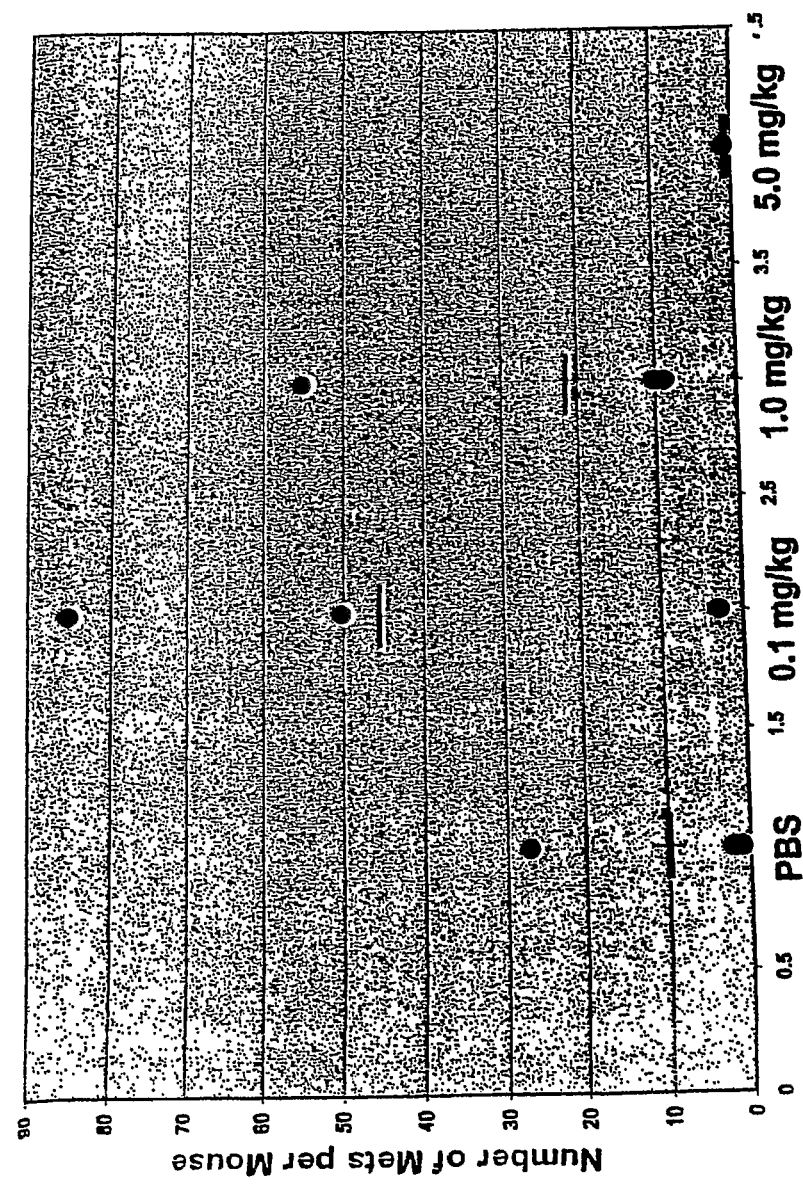
FIG. 7 shows that the number of metastases is reduced when antibody RX1 is administered to human breast cancer MDA-MB-231 bearing nude mice at a concentration of 5 mg/kg.

As shown in FIG. 7, that the number of metastases is reduced when antibody RX1 is administered to human breast cancer MDA-MB-231 bearing nude mice at a dose of 5 mg/kg.

Example 4

This example sets out a procedure for humanization of the RX1 antibody. 5H4, MC1 and MC3 are humanized using similar procedures.

Design of Genes for Humanized RX1 Light and Heavy Chains

The nucleotide and amino acid sequence for murine RX1 are set forth in FIG. 4B. The sequence of a human antibody identified using the National Biomedical Foundation Protein Identification Resource or similar database is used to provide the framework of the humanized antibody. To select the sequence of the humanized heavy chain, the murine RX1 heavy chain sequence is aligned with the sequence of the human antibody heavy chain. At each position, the human antibody amino acid is selected for the humanized sequence, unless that position falls in any one of four categories defined below, in which case the murine RX1 amino acid is selected:

(1) The position falls within a complementarity determining region (CDR), as defined by Kabat, J. Immunol., 125, 961-969 (1980);

(2) The human antibody amino acid is rare for human heavy chains at that position, whereas the murine RX1 amino acid is common for human heavy chains at that position;

(3) The position is immediately adjacent to a CDR in the amino acid sequence of the murine RX1 heavy chain; or (4) 3-dimensional modeling of the murine RX1 antibody suggests that the amino acid is physically close to the antigen binding region.

To select the sequence of the humanized light chain, the murine RX1 light chain sequence is aligned with the sequence of the human antibody light chain. The human antibody amino acid is selected at each position for the humanized sequence, unless the position again falls into one of the categories described above and repeated below:

(1) CDR's;

(2) murine RX1 amino acid more typical than human antibody;

(3) Adjacent to CDR's; or (4) Possible 3-dimensional proximity to binding region.

The actual nucleotide sequence of the heavy and light chain genes is selected as follows:

(1) The nucleotide sequences code for the amino acid sequences chosen as described above;

(2) 5' of these coding sequences, the nucleotide sequences code for a leader (signal) sequence. These leader sequences were chosen as typical of antibodies;

(3) 3' of the coding sequences, the nucleotide sequences are the sequences that follow the mouse light chain J5 segment and the mouse heavy chain J2 segment, which are part of the murine RX1 sequence. These sequences are included because they contain splice donor signals; and (4) At each end of the sequence is an Xba I site to allow cutting at the Xba I sites and cloning into the Xba I site of a vector.

Construction of Humanized Light and Heavy Chain Genes

To synthesize the heavy chain, four oligonucleotides are synthesized using an Applied Biosystems 380B DNA synthesizer. Two of the oligonucleotides are part of each strand of the heavy chain, and each oligonucleotide overlaps the next one by about 20 nucleotides to allow annealing. Together, the oligonucleotides cover the entire humanized heavy chain variable region with a few extra nucleotides at each end to allow cutting at the Xba I sites. The oligonucleotides are purified from polyacrylamide gels.

Each oligonucleotide is phosphorylated using ATP and T4 polynucleotide kinase by standard procedures (Maniatis et al., Molecular Cloning: A Laboratory Manual, 2nd ed., Cold Spring Harbor Laboratory, Cold Spring Harbor, N.Y. (1989)). To anneal the phosphorylated oligonucleotides, they are suspended together in 40 ul of TA (33 mM Tris acetate, pH 7.9, 66 mM potassium acetate, 10 mM magnesium acetate) at a concentration of about 3.75 uM each, heated to 95° C. for 4 min. and cooled slowly to 4° C. To synthesize the complete gene from the oligonucleotides by synthesizing the opposite strand of each oligonucleotide, the following components are added in a final volume of 100 ul:

| | |
|---|---|
| 10 ul | annealed oligonucleotides |
| 0.16 mM | each deoxyribonucleotide |
| 0.5 mM | ATP |
| 0.5 mM | DTT |
| 100 ug/ml | BSA |
| 3.5 ug/ml | T4 g43 protein (DNA polymerase) |
| 25 ug/ml | T4 g44/62 protein (polymerase accessory protein) |
| 25 ug/ml | 45 protein (polymerase accessory protein) |

The mixture is incubated at 37° C. for 30 mM. Then 10 u of T4 DNA ligase is added and incubation at 37° C. is resumed for 30 min. The polymerase and ligase are inactivated by incubation of the reaction at 70° C. for 15 min. To digest the gene with Xba I, 50 ul of 2×TA containing BSA at 200 ug/ml and DTT at 1 mM, 43 ul of water, and 50 u of Xba I in 5 ul is added to the reaction. The reaction is incubated for 3 hr at 37° C., and then purified on a gel. The Xba I fragment is purified from a gel and cloned into the Xba I site of the plasmid pUC19 by standard methods. Plasmids are purified using standard techniques and sequenced using the dideoxy method.

Construction of plasmids to express humanized light and heavy chains is accomplished by isolating the light and heavy chain Xba I fragments from the pUC19 plasmid in which it had been inserted and then inserting it into the Xba I site of an appropriate expression vector which will express high levels of a complete heavy chain when transfected into an appropriate host cell.

Synthesis and Affinity of Humanized Antibody

The expression vectors are transfected into mouse Sp2/0 cells, and cells that integrate the plasmids are selected on the basis of the selectable marker(s) conferred by the expression vectors by standard methods. To verify that these cells secreted antibody that binds to M-CSF, supernatant from the cells are incubated with cells that are known to express M-CSF. After washing, the cells are incubated with fluorescein-conjugated goat anti-human antibody, washed, and analyzed for fluorescence on a FACSCAN cytofluorometer.

For the next experiments, cells producing the humanized antibody are injected into mice, and the resultant ascites is collected. Humanized antibody is purified to substantial homogeneity from the ascites by passage through an affinity column of goat anti-human immunoglobulin antibody, prepared on an Affigel-10 support (Bio-Rad Laboratories, Inc., Richmond, Calif.) according to standard techniques. To determine the affinity of the humanized antibody relative to the original murine RX1 antibody, a competitive binding experiment is performed according to techniques known in the art.

Example 5

This example describes cloning and expression of Human Engineered™ RX1 antibodies, as well as purification of such antibodies and testing for binding activity. Human Engineered™ 5H4, MC1, and MC3 antibodies are prepared using similar procedures.

Design of Human Engineered™ Sequences

Human Engineering™ of antibody variable domains has been described by Studnicka [See, e.g., Studnicka et al. U.S. Pat. No. 5,766,886; Studnicka et al. Protein Engineering 7: 805-814 (1994)] as a method for reducing immunogenicity while maintaining binding activity of antibody molecules. According to the method, each variable region amino acid has been assigned a risk of substitution. Amino acid substitutions are distinguished by one of three risk categories: (1) low risk changes are those that have the greatest potential for reducing immunogenicity with the least chance of disrupting antigen binding; (2) moderate risk changes are those that would further reduce immunogenicity, but have a greater chance of affecting antigen binding or protein folding; (3) high risk residues are those that are important for binding or for maintaining antibody structure and carry the highest risk that antigen binding or protein folding will be affected. Due to the three-dimensional structural role of prolines, modifications at prolines are generally considered to be at least moderate risk changes, even if the position is typically a low risk position. Subtitutional changes are preferred but insertions and deletions are also possible. FIGS. 4B and 4C show the risk assignment for each amino acid residue of murine RX1 light and heavy chains, respectively, categorized as a high, moderate or low risk change.

Variable regions of the light and heavy chains of the murine RX1 antibody were Human Engineered™ using this method. Amino acid residues that are candidates for modification according to the method at low risk positions were identified by aligning the amino acid sequences of the murine variable regions with a human variable region sequence. Any human variable region can be used, including an individual VH or VL sequence or a human consensus VH or VL sequence. The amino acid residues at any number of the low risk positions, or at all of the low risk positions, can be changed. For the Human Engineered™ "low risk" heavy chain sequence in FIGS. 19A-B, human consensus Vh2 (based on Kabat) was used as the template, and for each position where the murine and human amino acid residues differed at low risk positions, an amino acid modification was introduced that replaced the murine residue with the human residue. For the Human Engineered™ "low risk" light chain sequence in FIGS. 20A-B, human consensus kappa 3 (based on Kabat) was used as the template, and for each position where the murine and human amino acid residues differed at low risk positions, an amino acid modification was introduced that replaced the murine residue with the human residue. A total of 16 amino acid low risk modifications were made to the light chain and 8 low risk modifications were made to the heavy chain.

Similarly, amino acid residues that are candidates for modification according to the method at all of the low and moderate risk positions were identified by aligning the amino acid sequences of the murine variable regions with a human variable region sequence. The amino acid residues at any number of the low or moderate risk positions, or at all of the low and moderate risk positions, can be changed. For the Human Engineered™ heavy chain sequence, in FIGS. 19A-B, human consensus Vh2 (based on Kabat) was used as the template, and for each position where the murine and human amino acid residues differed at low or moderate risk positions, an amino acid modification was introduced that replaced the murine residue with the human residue. For the Human Engineered™ light chain sequence in FIGS. 20A-B, human consensus kappa 3 (based on Kabat) was used as the template, and for each position where the murine and human amino acid residues differed at low or moderate risk positions, an amino acid modification was introduced that replaced the murine residue with the human residue. A total of 19 low and moderate risk amino acid modifications were made to the light chain and 12 low and moderate modifications were made to the heavy chain.

An "alternative low risk" light chain sequence was also prepared as shown in FIGS. 21A-B, in which the modification at position 54 was reversed back to murine. An "alternative low+moderate risk" light chain sequence was also prepared as shown in FIGS. 21A-B, in which the modifications at positions 54-56 were reversed back to murine.

Finally, a Human Engineered™ "low+moderate risk" light chain V region sequence also was produced using human germline VK6 subgroup 2-1-(1) A14 as the template, as shown in FIGS. 22A-B.

Also contemplated by the present invention is retaining amino acids 41-43 (NGS) of FIG. 4A which represent the glycosylation site. Alternatively, only one or two of amino acids 41-43 (e.g., NG) may be retained.

Preparation of Expression Vectors for Permanent Cell Line Development

DNA fragments encoding each of the above-described heavy and light chain V region sequences along with antibody-derived signal sequences were constructed using synthetic nucleotide synthesis. DNA encoding each of the light chain V region amino acid sequences described above were inserted into vector pMXP10 containing the human Kappa light chain constant region. DNA encoding each of the heavy chain V region amino acid sequences described above were inserted into vector pMXP6 containing the human Gamma-2 heavy chain constant region. Additional vectors were constructed containing the heavy chain V region amino acid sequences fused to the human Gamma-1 (cDNA) and Gamma-4 (genomic and cDNA) constant regions having sequences displayed in FIGS. 29A, 29b, and 30. All of these vectors contain a hCMV promoter and a mouse kappa light chain 3' untranslated region as well as selectable marker genes such as neo or or his for selection of G418 or histidinol—resistant transfectants, respectively. The light and heavy chain vectors are described in Tables 2 and 3, respectively.

TABLE 2

Single gene permanent Kappa light chain vectors.

| Plasmid | V Region | Selective Marker |
|---|---|---|
| pMXC5 | Low + Mod Risk (Kabat) | neo |
| pMXC6 | Low Risk (Kabat) | neo |
| pMXC13 | Low Risk (Kabat) - R54 to S | neo |
| pMXC14 | Low + Mod Risk (Kabat)-RAT54, 55, 56 to SIS | neo |
| pMXC22 | Low + Mod Risk (Germline) | neo |

TABLE 3

Single gene permanent heavy chain vectors.

| Plasmid | V Region | C Region | Selective Marker |
|---|---|---|---|
| pMXC7 | Low + Mod Risk (Kabat) | Gamma 2 | neo |
| pMXC8 | Low Risk (Kabat) | Gamma 2 | neo |
| pMXC40 | Low Risk (Kabat) | Gamma 1 | neo |
| pMXC41 | Low + Mod Risk (Kabat) | Gamma 1 | neo |
| pMXC45 | Low + Mod Risk (Kabat) | Gamma 4 (genomic) | neo |
| pMXC46 | Low + Mod Risk (Kabat) | Gamma 4 (cDNA) | neo |

Vectors comprising the desired Human Engineered™ light plus heavy chain genes (Gamma-1, Gamma-2 and Gamma-4) were then constructed. These "2-Gene" vectors contain genes encoding each antibody chain, heavy and light, under control of the hCMV promoter, CMV splice donor, SV40 16S splice acceptor and the mouse kappa light chain 3' untranslated DNA including the polyA site. They also contain a selectable marker gene such as neo or his and the ampicillin resistance gene. Vectors containing both heavy and light chain genes are described in Table 4. Vectors comprising two copies of each light and heavy chain genes (four gene vectors) also can be constructed.

TABLE 4

Two-gene permanent expression vectors

| Plasmid | Kappa Light Chain | Heavy Chain V region | Heavy Chain C region | Selective Marker |
|---|---|---|---|---|
| pMXC12 | Low Risk (Kabat) | Low Risk (Kabat) | Gamma 2 | neo |
| pMXC37 | Low Risk (Kabat) | Low Risk (Kabat) | Gamma 2 | his |
| pMXC9 | Low + Mod Risk (Kabat) | Low + Mod Risk (Kabat) | Gamma 2 | neo |
| pMXC16 | Low Risk (Kabat) | Low + Mod Risk (Kabat) | Gamma 2 | neo |
| pMXC17 | Low + Mod Risk (Kabat) | Low Risk (Kabat) | Gamma 2 | neo |
| pMXC18 | Low Risk (Kabat) R54 to S | Low + Mod Risk (Kabat) | Gamma 2 | neo |
| pMXC19 | Low + Mod Risk (Kabat)-RAT54, 55, 56 to SIS | Low + Mod Risk (Kabat) | Gamma 2 | neo |
| pMXC20 | Low Risk (Kabat) - R54 to S | Low Risk (Kabat) | Gamma 2 | neo |
| pMXC21 | Low + Mod Risk (Kabat)-RAT54, 55, 56 to SIS | Low Risk (Kabat) | Gamma 2 | neo |
| pMXC25 | Low + Mod Risk (Germline) | Low + Mod Risk (Kabat) | Gamma 2 | neo |
| pMXC47 | Low + Mod Risk (Germline) | Low + Mod Risk (Kabat) | Gamma 2 | his |
| pMXC26 | Low + Mod Risk (Germline) | Low Risk (Kabat) | Gamma 2 | neo |
| pMXC42 | Low + Mod Risk (Germline) | Low Risk (Kabat) | Gamma 1 | neo |
| pMXC43 | Low + Mod Risk (Germline) | Low + Mod Risk (Kabat) | Gamma 1 | neo |
| pMXC50 | Low + Mod Risk (Germline) | Low + Mod Risk (Kabat) | Gamma 1 | his |
| pMXC48 | Low + Mod Risk (Germline) | Low + Mod Risk (Kabat) | Gamma 4 (cDNA) | Neo |
| pMXC49 | Low + Mod Risk (Germline) | Low + Mod Risk (Kabat) | Gamma 4 (genomic) | neo |

Preparation of Expression Vectors for Transient Expression

Vectors containing either the light or heavy chain genes described above also were constructed for transient transfection. These vectors are similar to those described above for permanent transfections except that instead of the neo or his genes, they contain the Epstein-Barr virus oriP for replication in HEK293 cells that express the Epstein-Barr virus nuclear antigen. The vectors for transient transfection are described in Tables 5 and 6.

TABLE 5

Transient Kappa light chain vectors.

| Plasmid | V Region |
| --- | --- |
| pMXC1 | Low + Mod Risk (Kabat) |
| pMXC2 | Low Risk (Kabat) |
| pMXC10 | Low + Mod Risk (Kabat)-RAT54, 55, 56 to SIS |
| pMXC11 | Low Risk (Kabat) - R54 to S |
| pMXC15 | Low + Mod Risk (Germline) |

TABLE 6

Transient heavy chain vectors.

| Plasmid | V Region | C Region |
| --- | --- | --- |
| pMXC3 | Low + Mod Risk (Kabat) | Gamma 2 |
| pMXC4 | Low Risk (Kabat) | Gamma 2 |
| pMXC29 | Low Risk (Kabat) | Gamma 1 |
| pMXC38 | Low Risk (Kabat) | Gamma 4 (genomic) |
| pMXC39 | Low + Mod Risk (Kabat) | Gamma 1 |

Transient Expression of Human-Engineered RX1 in HEK293E Cells

Separate vectors each containing oriP from the Epstein-Barr Virus and the light chain or heavy chain genes described above were transfected transiently into HEK293E cells. Transiently transfected cells were allowed to incubate for up to 10 days after which the supernatant was recovered and antibody purified using Protein A chromatography. The proteins produced by transient transfection of 293E cells are described in Table 7 below.

Development of Permanently Transfected CHO-K1 Cells

The vectors described above (Table 4) containing one copy each of the light and heavy genes together are transfected into Ex-Cell 302-adapted CHO-K1 cells. CHO-K1 cells adapted to suspension growth in Ex-Cell 302 medium are typically electroporated with 40 ug of linearized vector. Alternatively, linearized DNA can be complexed with linear polyethyleneimine (PEI) and used for transfection. The cells are plated in 96 well plates containing Ex-Cell 302 medium supplemented with 1% FBS and G418. Clones are screened in 96 well plates and the top ~10% of clones from each transfection are transferred to 24 well plates containing Ex-Cell 302 medium.

A productivity test is performed in 24 well plates in Ex-Cell 302 medium for cultures grown for 7 and 14 days at which time culture supernatants are tested for levels of secreted antibody by an immunoglobulin ELISA assay for IgG.

The top clones are transferred to shake flasks containing Ex-Cell 302 medium. As soon as the cells are adapted to suspension growth, a shake flask test is performed with these clones in Ex-Cell 302 medium. The cells are grown for up to 10 days in 125 ml Erlenmeyer flasks containing 25 ml media. The flasks are opened at least every other day of the incubation period to allow for gas exchange and the levels of immunoglobulin polypeptide in the culture medium are determined by IgG ELISA at the end of the incubation period. Multiple sequential transfections of the same cell line with two or three multi-unit transcription vectors results in clones and cell lines that exhibit further increases in levels of immunoglobulin production, preferably to 300 µg/ml or more.

Purification

A process for the purification of immunoglobulin polypeptides from vectors and all lines according to the invention may be designed. According to methods well known in the art, cells are removed by filtration after termination. The filtrate is loaded onto a Protein A column (in multiple passes, if needed). The column is washed and then the expressed and secreted immunoglobulin polypeptides are eluted from the column. For preparation of antibody product, the Protein A pool is held at a low pH (pH 3 for a minimum of 30 minutes and a maximum of one hour) as a viral inactivation step. An adsorptive cation exchange step is next used to further purify the product. The eluate from the adsorptive separation column is passed through a virus retaining filter to provide further clearance of potential viral particles. The filtrate is fur-

TABLE 7

Human-engineered RX1 antibodies prepared.

| | Light Chain | | Heavy Chain | |
| --- | --- | --- | --- | --- |
| Antibody | Plasmid | Protein | Plasmid | Protein |
| heRX1-1.G2 | pMXC2 | Low Risk (Kabat) | pMXC4 | Low Risk (Kabat) |
| heRX1-2.G2 | pMXC2 | Low Risk (Kabat) | pMXC3 | Low + Mod Risk (Kabat) |
| heRX1-3.G2 | pMXC1 | Low + Mod Risk (Kabat) | pMXC4 | Low Risk (Kabat) |
| heRX1-4.G2 | pMXC1 | Low + Mod Risk (Kabat) | pMXC3 | Low + Mod Risk (Kabat) |
| heRX1-5.G2 | pMXC11 | Low Risk (Kabat) - R54 to S | pMXC4 | Low Risk (Kabat) |
| heRX1-6.G2 | pMXC11 | Low Risk (Kabat) - R54 to S | pMXC4 | Low Risk (Kabat) |
| heRX1-7.G2 | pMXC10 | Low + Mod Risk (Kabat)-RAT54, 55, 56 to SIS | pMXC4 | Low Risk (Kabat) |
| heRX1-8.G2 | pMXC10 | Low + Mod Risk (Kabat)-RAT 54, 55, 56 to SIS | pMXC3 | Low + Mod Risk (Kabat) |
| heRX1-9.G2 | pMXC15 | Low + Mod Risk (Germline) | pMXC4 | Low Risk (Kabat) |
| heRX1-10.G2 | pMXC15 | Low + Mod Risk (Germline) | pMXC3 | Low + Mod Risk (Kabat) |
| heRX1-1.G1 | pMXC2 | Low Risk (Germline) | pMXC29 | Low Risk (Kabat) |
| heRX1-10.G1 | pMXC15 | Low + Mod Risk (Germline) | pMXC39 | Low + Mod Risk (Kabat) |
| heRX1-9.G4 | pMXC15 | Low + Mod Risk (Germline) | pMXC38 | Low Risk (Kabat) | ther purified by passing through an anion exchange column in which the product does not bind. Finally, the purification process is concluded by transferring the product into the formulation buffer through diafiltration. The retentate is adjusted to a protein concentration of at least 1 mg/mL and a stabilizer is added.

Binding Activity

The MCSF binding activity of the recombinant Human Engineered™ antibodies is evaluated. Protein is purified from shake flask culture supernatants by passage over a protein A column followed by concentration determination by $A_{280}$. Binding assays are performed as described in Example 1 above or 13 below. Immulon II plates are precoated with the sM-CSF antigen pre-diluted in a PBS coating solution to immobilize it to the microplate. Various test concentrations of M-CSF ranging from 0.25 to 20 ug/ml are added at 50 ul/well and incubated at 4° C. overnight. The plates are then washed 3 times with PBS-0.05% Tween. Blocking is performed by adding in PBS-0.05% Tween 1% BSA followed by a 30 minute incubation at 37° C. Dilutions of immunoglobulin polypeptides are prepared in PBS-0.05% Tween 1% BSA solution. 2- or 3-fold serial dilutions are prepared and added (100 ul/well) in duplicate or triplicate. After a 90 minute incubation at 37° C., the microplate is washed 3 times with PBS-0.05% Tween. For signal development, goat anti-human IgG (gamma- or Fc-specific) secondary antibody conjugated to peroxidase is added to each well and incubated for 60 minutes at 37° C. followed by addition of OPD at 0.4 mg/ml in citrate buffer plus 0.012% $H_2O_2$. After 5-10 minutes at room temperature the assay is stopped by the addition of 100 ul 1M $H_2SO_4$ and the plates are read at 490 nm. Both goat anti-human IgG (gamma-specific) and goat anti-human IgG (Fc-specific) antibodies have been employed.

Example 6

The following example sets out a procedure for the treatment of humans using M-CSF-specific antibody, such as an RX1-derived or RX1-competing antibody, including an RX1 Human Engineered™ antibody with a modified or unmodified IgG1 or IgG4 constant region. The procedure can also be followed for an MC1- or MC3-derived or MC1- or MC3-competing antibody. The expected efficacious dosing range is 2 ug/kg to 10 mg/kg. This estimation is based on following rationale substantiated by experimental data:

The measured M-CSF level in human plasma (both healthy and breast cancer patients) is about 1 ng/ml. M-CSF neutralizing antibody RX1 has a measured $EC_{50}$ of 2 ng/ml against 1 ng/ml human M-CSF. Accordingly, the effective antibody concentration in human plasma is expected to be 10 to 50,000 fold over its $EC_{50}$, i.e. 20 ng/ml to 100 ug/ml antibody in human plasma. Based on PK studies, in order to effectuate this concentration in human patients, a dosing of 2 μg/kg to 10 mg/kg is required to reach 20 ng/ml to 100 ug/ml antibody concentration in plasma.

Example 7

This example sets out a procedure for the evaluation of the anti-cancer activity of anti-M-CSF monoclonal antibody in a subcutaneous model. Example 2 above showed that anti-M-CSF monoclonal antibody treatment significantly inhibited the bone loss induced by tumor growth in bone marrow. The purpose of this study is to evaluate whether the antibody can also inhibit the tumor growth in soft tissue.

Female mice at the age of 10 weeks old, average weight ~20 g will be used for this study. Mice will undergo an acclimation period of at least 7 days prior to study start. On day 0, the right flank of nude mice will be injected with Lewis lung carcinoma or CT26 cancer cells subcutaneously at $5 \times 10^6$ cells per mouse per 100 μl. When tumor volume reaches 100-200 mm$^3$ (usually 1 week after tumor inoculation), mice will be randomized into 5 groups at 10 mice per group as follows:
1) PBS
2) RX1
3) 5A1
4) mIgG1+rIgG1 isotype Ab control
5) 5A1+RX1

Mice will be treated intraperitoneally with the designated antibodies at 10 mpk once a week for 4 weeks. When tumor volume reaches 2000 mm$^3$, the study will be terminated. Alternatively, animals will also be euthanized when any of the following situations are met: tumor surface ulceration is bigger than 30% of total tumor surface area, significant body weight loss (>20%), dehydration, and moribund. Whole blood will be collected from all of the mice and monocyte population will be analyzed as a potential surrogate marker. Measurements of tumor width and length will be used to calculate tumor volume. It is expected that tumor growth will be inhibted as a result of the foregoing experiment.

Example 8

The following example sets out a procedure for the evaluation of combination therapy for the treatment and prevention of severe osteolytic disease associated with cancer metastasis.

Experimental Design. The study described in Example 2 or 3 above is repeated essentially as described with the following exceptions. In addition to the antibody or antibody combination set out in the treatment groups below, the animals will receive one of the following additional treatments:

1. Bisphosphonate (e.g., Aredia; Zometa; Clodronate).
2. Surgery
3. Radiation
4. Chemotherapy
5. Hormone therapy (e.g., Tamoxifen; anti-Androgen therapy)
6. Antibody therapy (e.g., RANKL/RANK neutralizing antibodies; PTHrP neutralizing antibody)
7. Therapeutic protein therapy (e.g., soluble RANKL receptor; OPG, and PDGF and MMP inhibitors)
8. Small molecule drug therapy (e.g., Src-kinase inhibitor)
9. Oligonucleotides therapy (e.g., RANKL or RANK or PTHrP Anti-sense)
10. Gene therapy (e.g., RANKL or RANK inhibitors)
11. Peptide therapy (e.g. muteins of RANKL)

The treatment groups are as follows. The above additional treatments are indicated below as "plus therapy X":
1. PBS only
2. treatment with therapy X only
3. rat IgG1 isotype control
4. murine IG1 isotype control
5. RX1 anti-human MCSF only
6. 5A1 rat IgG1 anti-mouse MCSF only
7. rat IgG1 and murine IgG1 isotype control combination
8. RX1 an 5A1 combination
9. rat IgG1 isotype control plus therapy X
10. murine IG1 isotype control plus therapy X
11. RX1 anti-human MCSF plus therapy X
12. 5A1 rat IgG1 anti-mouse MCSF plus therapy X
13. rat IgG1 and murine IgG1 isotype control combination plus therapy X
14. RX1 and 5A1 combination plus therapy X Dosing: 0.1-30 mg/kg each antibody is used for administration to each animal. Preferred dosing is 10 mg/kg. The administration route can be IV, IP, SC. The preferred route is IP. Treatment will begin the day following injection of tumor cells, as described in Example 6, above.

Measurements. To assess the severity of osteolysis among the various treatment groups, each mouse receives a baseline Faxitron image taken the day following injection of tumor cells. A Faxitron image is also taken at the end of the study (8 weeks). Tumor growth is simultaneously measured using the Xenogen system since the tumor cells stably express luciferase. It is expected that combination therapy for the treatment and prevention severe osteolytic disease associated with cancer metastasis will be improved with relative to antibody therapy alone.

Example 9

The following example provides a protocol for evaluating the ability of M-CSF-specific antibody to bind to, for example, breast cancer cells (cell line MDA231) or multiple myeloma cancer cells (cell line ARH77) using a fluorescence-activated cell sorter.

The cells were first washed twice with PBS (no $Ca^{2+}$, $Mg^{2+}$). For each 10-cm plate, 2 ml of 3 mM EDTA was added, and the paltes were incubated at 37° C. for 2-3 minutes, until the cells were rounded and began to detach from the dish. Next, 10 ml of buffer A (PBS+5% FBS) was added and mixed. At that time, the cells were pelleted and resuspended at about $5 \times 10^6$ cells/ml in PBS+5% FBS, and the cells were placed into tubules at 100 μL/sample.

At this point, 0.1-10 ug/ml of the primary antibody (used at indicated concentration of M-CSF antibody or control antibody) was added. Dilution, if necessary, was made in 5% FBS/PBS. The mixture was then incubated for 30 min at 4° C. Following the incubation period, the cells were washed 3 times by centrifugation at 400 g for 5 min., and the cells were resuspended in PBS.

The FITC or PE-labeld anti-IgG antibody (0.25 ug/sample) was diluted in 1% BSA/PBS at the optimal dilution, and the cells were resuspended in this solution and incubated for 30 min at 4° C. Next, the cells were washed 3 times as described above. Following th cell washes, the cells were resuspended with 0.5 ml/sample PI-PBS (if necessary to distinguish dead cells from live ones). The cells can also be fixed for later analysis (the cells can last about 3 days if they are fixed with 0.1% formaldehyde). The cells were next analyzed in a fluorescence-active FACS using standard procedures.

Figure 8A:
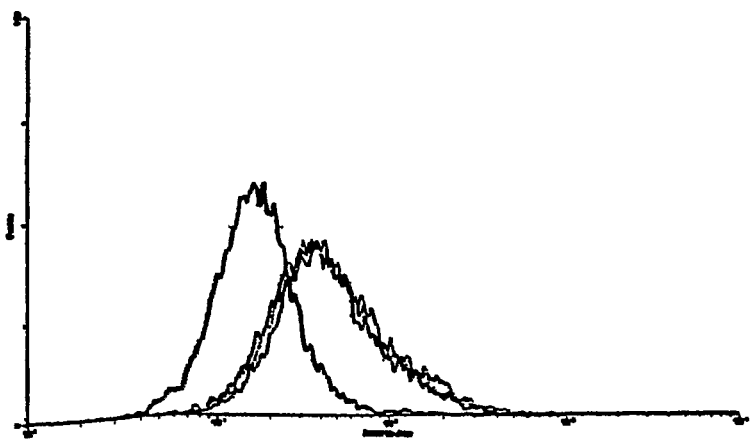
FIGS. 8A and 8B shows that an M-CSF-specific antibody bound to breast cancer cell line MDA-MB-231 or to multiple myeloma cancer cell line ARH77.
Figure 8B:
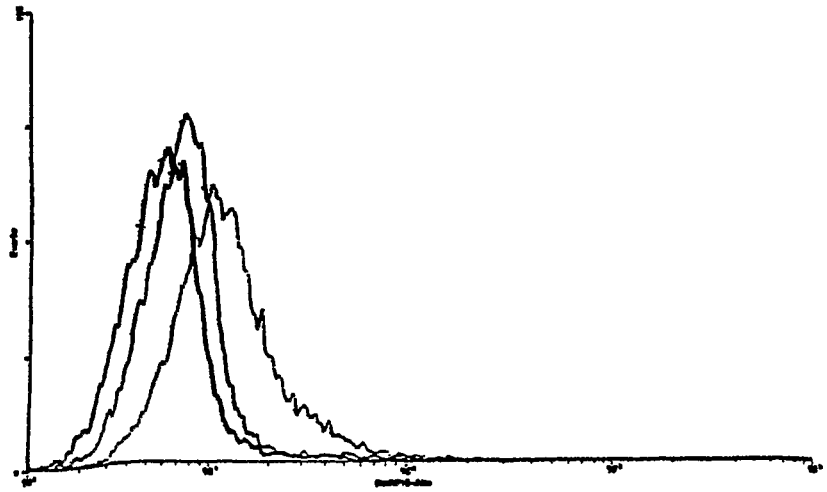

As shown in FIGS. 8A and 8B, an MCSF-specific antibody RX1 bound to breast cancer cell line MDA231 or to multiple myeloma cancer cell line ARH77 at a variety of antibody concentrations as indicated.

Example 10

The following example shows M-CSF is prevalent on a number of cancer cell surfaces Immunohistochemical staining of M-CSF was carried out using a M-CSF-specific antibody RX1 as follows.

At the outset, slides were heated in anoven at 55-60° C. for 1 hour and allowed to cool for 2-3 minutes. The following de-waxing and re-hydration parameters were used:

| | |
|---|---|
| a. Xylene | 3 × 5 minutes |
| b. 100% Reagent Alcohol | 2 × 5 minutes |
| c. 95% Reagent Alcohol | 2 × 4 minutes |
| d. 75% Reagent Alcohol | 2 × 3 minutes |
| e. 50% Reagent Alcohol | 1 × 3 minutes |
| g. dI H2O | 2-3 quick rinses |

Prior to the peroxide blocking step, antigen retrieval was prepared using 1× Biogenex Citra Plus. The solution was initially microwaved at full power to boil. Once the solution boiled, the microwave was quickly set for another 13 min at power-level 2, and allowed to cool before proceeding. The peroxide blocking step was performed as follows. The slides were immersed slides in 3% $H_2O_2$ (25 ml 30% to 250 ml dI $H_2O$) and placed at room temperature for 10 minutes. The slides were next rinsed 2× with dI $H_2O$, and washed with 1×PBS 2×2 minutes.

The avidin/biotin blocking procedure was performed as follows. Slides were palced flat on a metal rack. A Blue PAP pen was used (hydrophobic slide marker) around tissue. Next, 2 drops Zymed Avidin (Reagent A)—enough to cover tissue—was added and the slides were incuabated at room temperature for 10 min. Following the incubation, the slides were washed as follows:

2×3 minute washes in 1×PBS.

2 drops Zymed Biotin (Reagent B), room temperature for 10 min. 2×3 minute washes in 1×PBS.

The protein blocking procedure was performed as follows. First, 10% serum [to 2% final concentration] of secondary antibody species was added. The BioGenex Power Block was next diluted to 1× with dI $H_2O$. The rack of slides was immersed in Power Block for 8 min at room temperature, and the slides were rinsed 2× in 1×PBS.

For the addition of the primary antibody (RX1), the slides were placed flat on a metal rack. Antibody was added to cover each section (~350 μl), and the antibody was spread with pipet tip (if necessary) without scraping tissue. The slides were then incubated for 1 hour at room temperature. Following the incubation, the slides were washed 3× with 1×PBS 3-5 minutes each time. At this point, BioGenex Multi-Link was applied to sections & incubated for 10-11 minutes at room temperature. The sections were then washed 3 minutes each time.

Labelling was performed by applying BioGenex HRP Label to sections, which were then incubated at room temperature for 10-11 min and washed with 1×PBS 3×3 minutes. Next, BioGenex $H_2O_2$ substrate was added (1 drop AEC for every 2.5 ml $H_2O_2$) to the sections and incubated at room temperature for 10 min. The sections were then rinsed several times with dI $H_2O$. The counterstaining step was performed as follows. The sections were staine with hematoxylin for 1 minute at room temperature. Next, the sections were rinse with $H_2O$ twice, and then incubated in 1×PBS for 1 minute. Sections were then rinsed well with $H_2O$ to remove PBS. Sections were mounted by applying a drop of BioGenex Super Mount to the section section and then air drying over night at room temperature.

As shown in FIG. 9, M-CSF is prevalent on a number of cancer cell surfaces. Sections for the indicated cancer cell types were scored as follows:

0 No staining
1 Staining was similar to background
2 Positive, but weak staining
3 Positive and significant staining
4 Positive and strong staining Example 11

The following example shows the procedure for producing antibodies MC1 and MC3. MC1 and MC3 are two monoclonal murine antibodies that neutralize human M-CSF antibody and bind to human M-CSF. The amino acid sequences of these antibodies are shown in FIGS. 14 and 15, respectively. They were identified by a series of steps including a) immunization of Balb C mice with recombinant human M-CSF; b) screening for positive clones that produce antibodies which bind to human M-CSF in an ELISA format; c) subcloning of positive clones to generate stable hybridoma clones; d) scale-up of cell culture to produce large quantity of antibodies; e) purification and characterization of antibodies in affinity analysis, cell binding, and neutralizing activity assay as described in previous examples.

FIGS. 16A and 16B show the alignment of the CDRs of the heavy and light chains, respectively, of antibodies RX1, 5H4, MC1 and MC3.

Humanized and Human Engineered™ versions are generated as described in the examples above.

Example 12

This example shows that M-CSF antibodies RX1 and 5H4, as well as Fab fragments thereof, have different neutralizing activities. The fallowing example also shows that antibodies RX1, 5H4, and MC3 have varying affinities for M-CSF. This example further demonstrates that the affinities of the aforementioned intact antibodies are higher relative to Fab fragments of the aforementioned antibodies.

Figure 17:
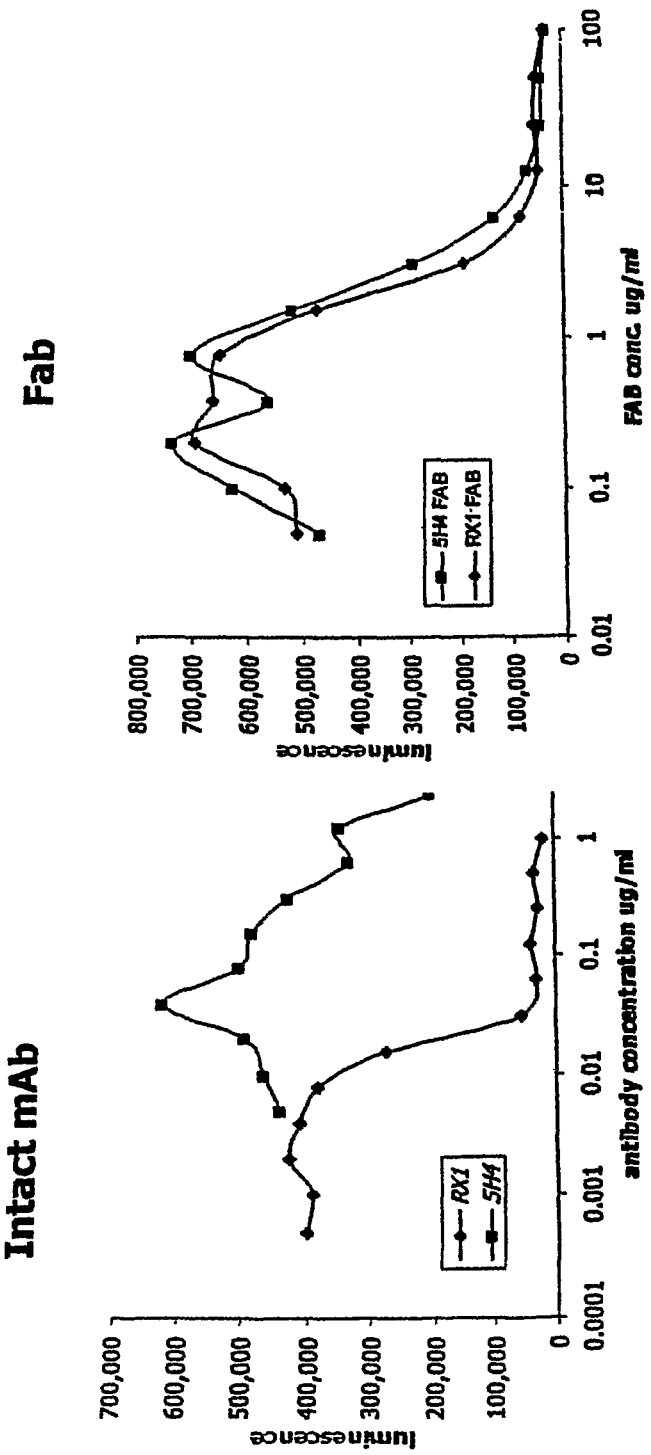
FIG. 17 shows the neutralization activities of intact versus Fab fragments for RX1 versus 5H4.

Neutralization activities of intact RX1 and 5H4 versus Fab fragments of RX1 and 5H4 were determined by measuring M-CSF-dependent cell proliferation in the presence of various concentrations of antibody. The cell proliferation was determined by chemiluminescent dye. As shown in FIG. 17, intact RX1 has the highest potency, while the Fab fragment of RX1 loses its potency and behaves like 5H4 and the 5H4Fab fragment.

Binding properties of the aforementioned antibodies were analyzed using Biacore analyses. In order to determine the relative affinities of RX1, 5H4, and MC3 to M-CSF, rabbit anti-mouse Fc was immobilized onto a CM5 biosensor chip via amine coupling. The aforementioned antibodies were then captured on the anti-mouse Fc/CM5 biosensor chip at 1.5 μg/ml for 3 mM at 2 μl/min. MCSF was flowed over the modified biosensor surface at varying concentrations (Rmax ~15). Test antibodies and antigen were diluted in 0.01 M HEPES pH 7.4, 0.15 M NaCL, 3 mM EDTA, 0.005% Surfactant P20 (HBS-EP). All experiments were performed at 25° C. Kinetic and affinity constants were determined using Biaevaluation software (Biacore) with a 1:1 interaction model/global fit. As shown below in Table 8, RX1 binds to M-CSF with the highest affinity relative to 5H4 and MC3.

TABLE 8

|  | Ka (M−1 Sec−1) | Kd (sec−1) | KD (nM) |
| --- | --- | --- | --- |
| RX1 | 1.64e6 | 2.7e−4 | 0.16 |
| 5H4 | 5.94e5 | 1.77e−3 | 3.0 |
| MC3 | 7.04e5 | 1.93e−4 | 0.27 |

To determine the relative differences in the binding affinity of intact Mab and Fab fragments of RX1, 5H4, and MC3, an alternate configuration was used in the Biacore analysis. Specifically, M-CSF was immobilized onto CM5 biosensor chip via amine coupling. 0.05 μg/ml M-CSF in 10 mM Na Acetate pH 4.0 was injected at 1 μl/min for 5 minutes to achieve RL=6-12 RU. Test antibody (or Fab fragment) were flowed over the modified biosensor surface at varying concentrations. Test antibodies were diluted in 0.01 M HEPES pH 7.4, 0.15 M NaCL, 3 mM EDTA, 0.005% Surfactant P20 (HBS-EP) and all experiments were done at 25° C. Kinetic and affinity constants were determined using Biaevaluation software (Biacore) with a 1:1 interaction model/global fit. As shown below in Table 9, RX1 binds M-CSF with the highest affinity relative to the other antibodies tested. The Fab fragment of RX1 binds M-SCF with a significantly lower affinity relative to the RX1 holoprotein.

TABLE 9

|  | Ka (M−1 Sec−1) | Kd (sec−1) | KD (nM) |
| --- | --- | --- | --- |
| rRX1(mouse) | 2.34e5 | 2.35e−4 | 1.0 |
| rRX1 Fab (mouse) | 2.81e5 | 3.03e−3 | 10.8 |
| 5H4 | 1.27e5 | 1.26e−3 | 9.9 |
| 5H4 Fab | 2.04e5 | 2.85e−3 | 14.0 |

The binding, affinity and neutralization data indicate that the neutralization activity of RX1 is due primarily to its remarkably high affinity for M-CSF, and that this high affinity may be due at least in part to the ability of both amus of the antibody to bind the M-CSF dimer simultaneously.

Example 13

The following example reveals the linear epitope (i.e., amino acid sequence) on M-CSF recognized by antibodies RX1, 5H4, and MC3.

Initially, the epitope mapping strategy was designed to determine whether antibodies RX1, 5H4, and MC3 recognized linear epitopes or conformational epitopes within M-CSF. Accordingly, the anti-M-CSF antibodies were tested against 0.1 μg M-CSF under reducing as well as non-reducing conditions. Only the non-reduced form of M-CSF was recognized by each of the antibodies, suggesting the epitopes recognized are discontinuous in nature.

Figure 18:
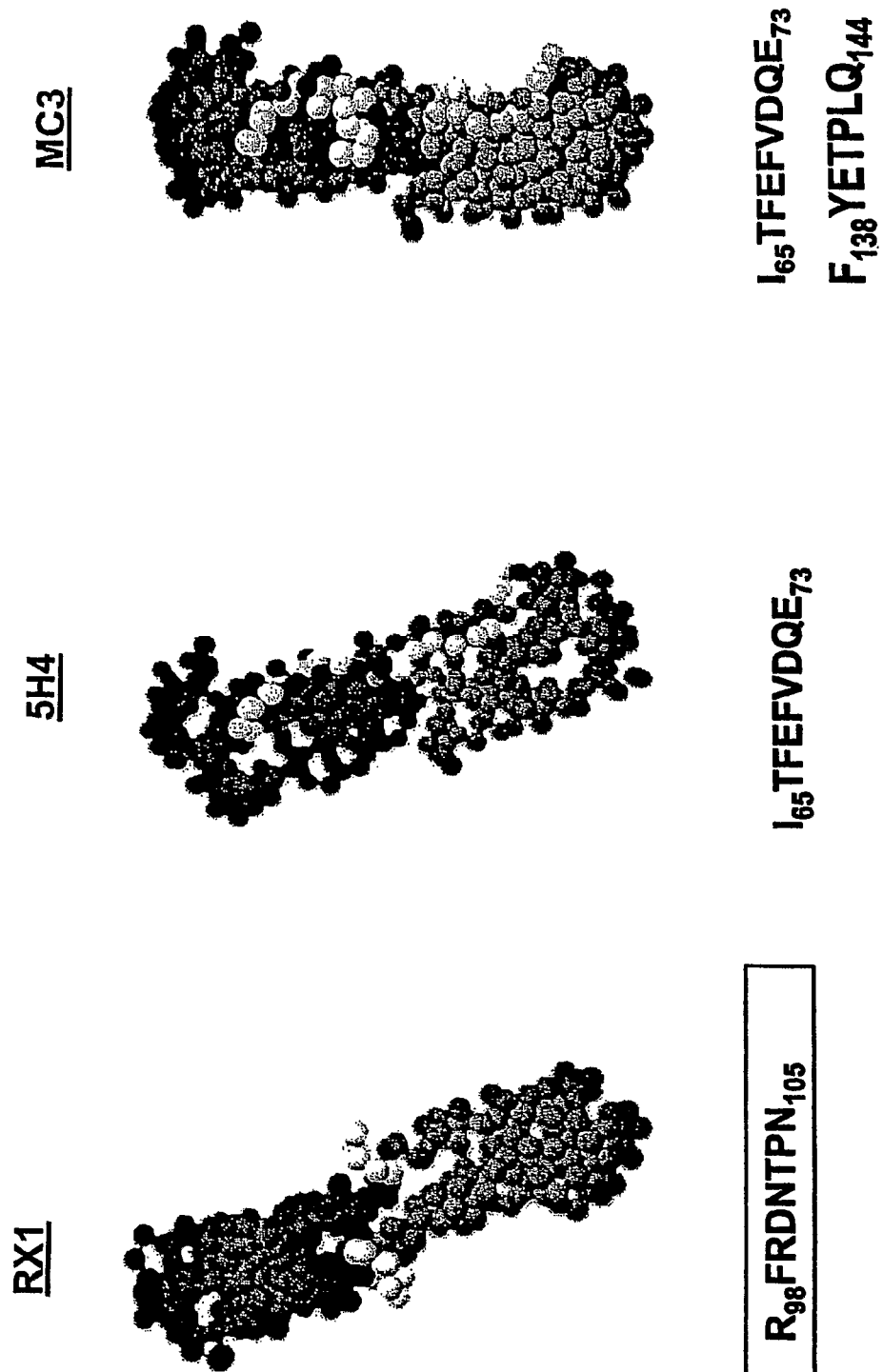
FIG. 18 shows the structure of M-CSF with RX1, 5H4, and MC3 epitopes highlighted (SEQ ID NOs: 120, 122, and 123).

Next, the linear epitope of M-CSF was determined for each antibody. Specifically, SPOTs membranes (Sigma Genosys) were prepared where the M-CSF fragment sequence of interest, overlapping 10mer peptides synthesized with one amino acid offset, were loaded onto the cellulose membrane support. These membranes were then probed with the aforementioned antibodies and reactive SPOTs were identified. The peptide sequence was then identified by its corresponding location on the membrane, and overlapping amino acids within the positive reacting peptides were identified as the epitope. As shown in FIG. 18, RX1 binds to a different linear epitope than 5H4 and MC3, which map to a different location on M-CSF. RX1 binds to a linear epitope represented by RFRDNTPN (SEQ ID NO: 120) or RFRDNTAN (SEQ ID NO: 121), amino acids 98-105 of M-CSF of FIG. 12. 5H4 binds to a linear epitope represented by ITFEFVDQE (SEQ ID NO: 122), amino acids 65-73 of M-CSF of FIG. 12. MC3 binds to two linear epitopes represented by (1) ITFEFVDQE (SEQ ID NO: 122), amino acids 65-73 of M-CSF of FIGS. 12 and (2) FYETPLQ (SEQ ID NO: 123), amino acids 138-144 of M-CSF of FIG. 12.

Example 14

The binding affinity of the Human Engineered™ versions of RX1 antibodies prepared as described above in Example 5 was determined. This example shows that Human Engineered™ RX1 antibodies with different IgG subclass constant regions bind M-CSF with different affinities in vitro. To determine the relative differences in the binding affinity of intact antibodies by Biacore analysis, M-CSF was immobilized onto CM5 biosensor chip via amine coupling. 0.05 μg/ml M-CSF in 10 mM Na-Acetate pH 4.0 was injected at 1 μl/min for 5 minutes to achieve RL=6-12 RU. Test antibody or Fab fragments were flowed over the modified biosensor surface at varying concentrations ranging from 100 nM to 1.5 nM in 2-fold dilutions. Test antibodies were diluted in 0.01 M HEPES pH 7.4, 0.15 M NaCL, 3 mM EDTA, 0.005% Surfactant P20 (HBS-EP) and all experiments were done at 25° C. Each concentration point and buffer blanks were run in triplicate, and data was collected over 3 minutes of association and 8 minutes of dissociation. Kinetic and affinity constants were determined using Biaevaluation software with a 1:1 interaction model/global fit. As shown in Table 10 below, heRX1-1.G1 and heRX1-1.G4 binds M-CSF with affinities that most closely resemble the murine RX1M-CSF binding affinity.

TABLE 10

| Antibody | ka (M−1 sec−1) | kd (sec−1) | KD (nM) |
| --- | --- | --- | --- |
| Murine RX1 n = 21 | $(2.23 \pm 0.35) \times 10^5$ | $(1.56 \pm 0.67) \times 10^{-4}$ | $0.7 \pm 0.27$ |
| heRX1-1.G2 n = 5 | $(2.36 \pm 0.18) \times 10^5$ | $(1.37 \pm 0.24) \times 10^{-3}$ | $5.9 \pm 1.4$ |
| heRX1-10.G2 n = 2 | $(1.73 \pm 0.29) \times 10^5$ | $(1.1 \pm 0.11) \times 10^{-3}$ | $6.3 \pm 1.7$ |
| heRX1-1.G1 | $2.50 \times 10^5$ | $2.38 \times 10^{-4}$ | 0.95 |
| heRX1-1.G4 | $2.07 \times 10^5$ | $2.93 \times 10^{-4}$ | 1.42 |

In contrast, as shown in Table 11 below, although there was some variation in binding affinity, all of the Gamma-2 constructs displayed at least a 7-fold decrease in binding affinity compared to the parent murine antibody.

TABLE 11

| Antibody | ka (M−1 sec−1) | kd (sec−1) | KD (nM) |
| --- | --- | --- | --- |
| Murine RX1 n = 21 | $(2.23 \pm 0.35) \times 10^5$ | $(1.56 \pm 0.67) \times 10^{-4}$ | $0.7 \pm 0.27$ |
| heRX1-1.G2 n = 5 | $(2.36 \pm 0.18) \times 10^5$ | $(1.37 \pm 0.24) \times 10^{-3}$ | $5.9 \pm 1.4$ |
| heRX1-2.G2 | $2.18 \times 10^5$ | $1.65 \times 10^{-3}$ | 7.6 |
| heRX1-3.G2 | $2.01 \times 10^5$ | $1.18 \times 10^{-3}$ | 5.9 |
| heRX1-4.G2 | $2.38 \times 10^5$ | $1.08 \times 10^{-3}$ | 4.6 |
| heRX1-5.G2 | $1.75 \times 10^5$ | $1.29 \times 10^{-3}$ | 7.4 |
| heRX1-6.G2 | $1.88 \times 10^5$ | $1.49 \times 10^{-3}$ | 7.9 |
| heRX1-7.G2 | $1.57 \times 10^5$ | $1.49 \times 10^{-3}$ | 9.5 |
| heRX1-8.G2 | $1.52 \times 10^5$ | $1.48 \times 10^{-3}$ | 9.8 |
| heRX1-9.G2 | $2 \times 10^5$ | $1.44 \times 10^{-3}$ | 7.2 |
| heRX1-10.G2 n = 2 | $(1.73 \pm 0.29) \times 10^5$ | $(1.1 + 0.11) \times 10^{-3}$ | $6.3 \pm 1.7$ |

Example 15

This example shows that Human Engineered™ RX1 antibodies with different IgG subclass constant regions possess different neutralization activities in vitro. To test the neutralizing activity of M-CSF antibodies, a proliferation assay of M-NFS-60 cell line was used (American Type Culture Collection, Accession No. CRL-1838, available from ATCC in Rockville, Md., USA, derived from a myologenous leukemia induced with the Cas-Br.MuLV wild mouse ecotropic retrovirus. The cell line responds to both interleukin 3 and M-CSF and contains a truncated c-myb proto-oncogene caused by the integration of a retrovirus). Proliferation of M-NFS-60 requires active M-CSF in a dose-dependent fashion. In the assay, M-NFS-60 cells were washed and plated in RPIM1640 medium with 10% FBS and 1% Pen/Strep. Recombinant human M-CSF (at 10 ng/ml final concentration, which is equivalent to 3000 U/ml of M-CSF activity), was incubated with various concentrations of antibodies ranging from 1 ug/ml to 0.5 ng/ml (in serial 2-fold dilution) for 1 hour at 37° C. in 5% $CO_2$ in an incubator. Following the incubation, the mixture was added to the M-NFS-60 culture in 96 well microtiter plates. The total assay volume per well was 100 ul, with 10 ng/ml M-CSF, and the antibody concentration indicated. Cells were incubated at 37° C. under 5% $CO_2$ for 72 hours before cell numbers were quantified by CellTiter Glo assay (Promega). Each antibody was tested in triplicate, with a repeat on the following day (for a total of six assays per antibody). The IC50 of each antibody was analyzed by curve fit.

Figure 25:
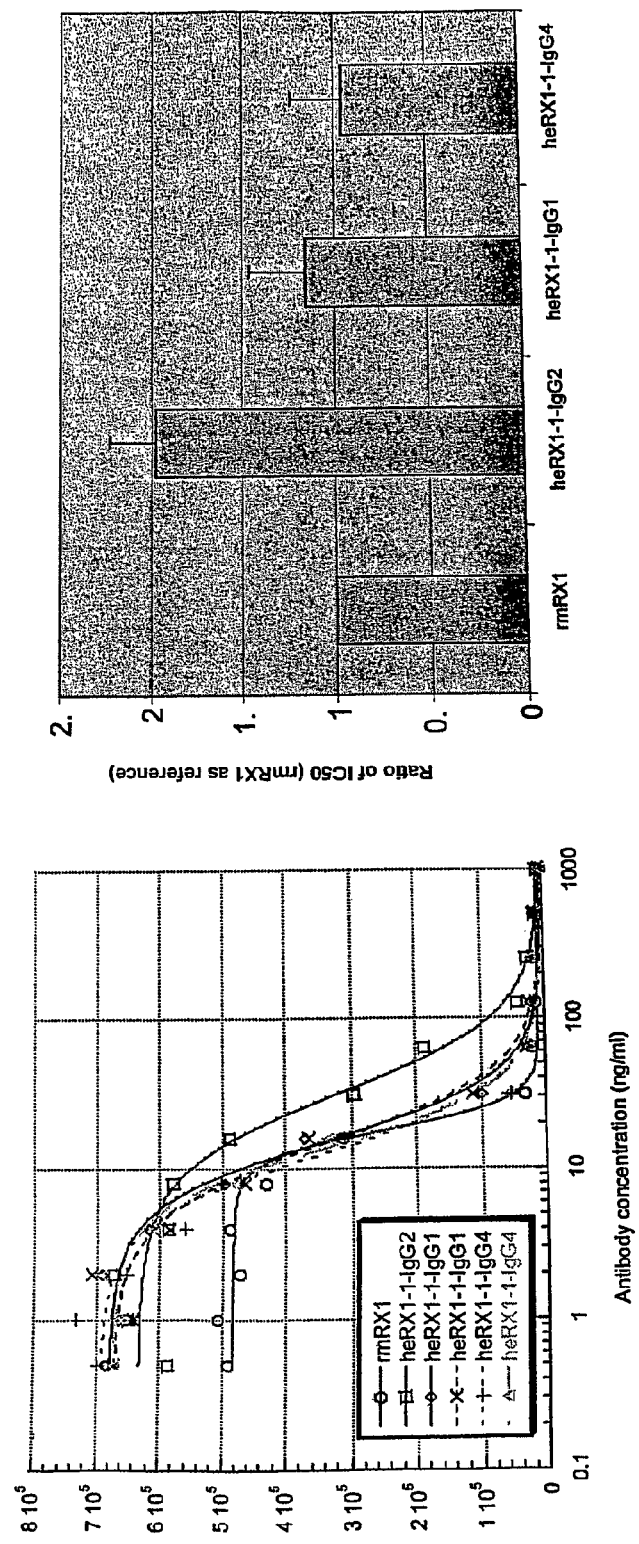
FIG. 25 shows the comparative neutralization of recombinant human M-CSF by recombinant murine RX1 antibody, labeled as rmRX1, and three versions of Human Engineered™ RX1-1 antibody (in which all of the low risk changes have been made) that each have a different constant region (IgG1, IgG2 or IgG4), labeled as heRX1-IG1, heRX1-1.G2, and heRX1-1.G4.
Figure 26:
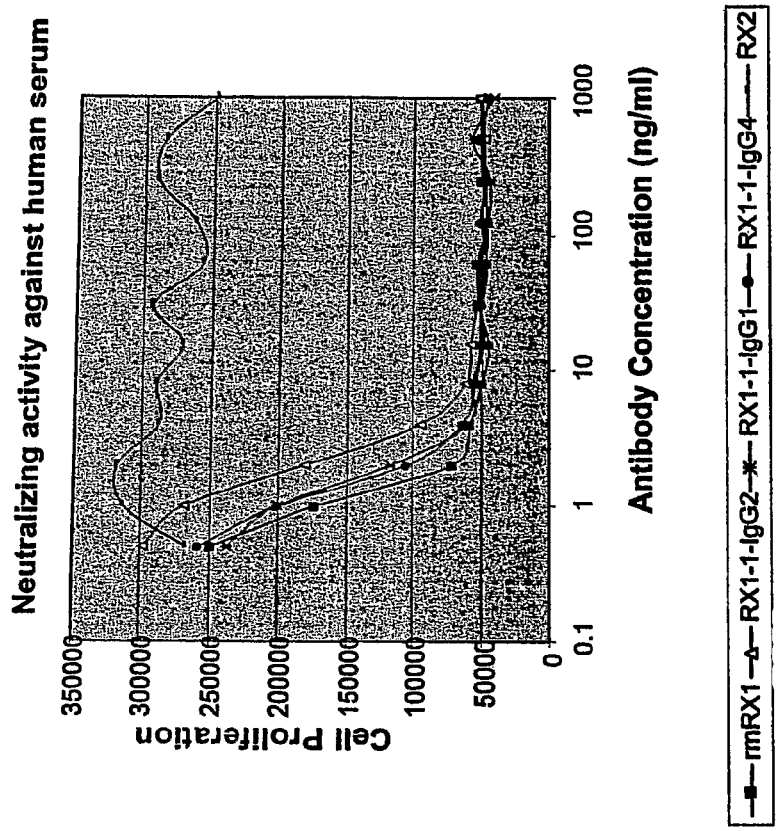
FIG. 26 shows the comparative neutralization of human serum by recombinant murine RX1 antibody, labeled as rmRX1 and several different versions of heRX1-1 (in which all of the low risk changes have been made) that each have a different constant region (IgG1, IgG2 or IgG4), labeled as RX2, RX1-1-IgG2, RX1-1-IgG1, RX1-1-IgG1, RX1-1-IgG4, RX1-a-IgG4.
Figure 27:
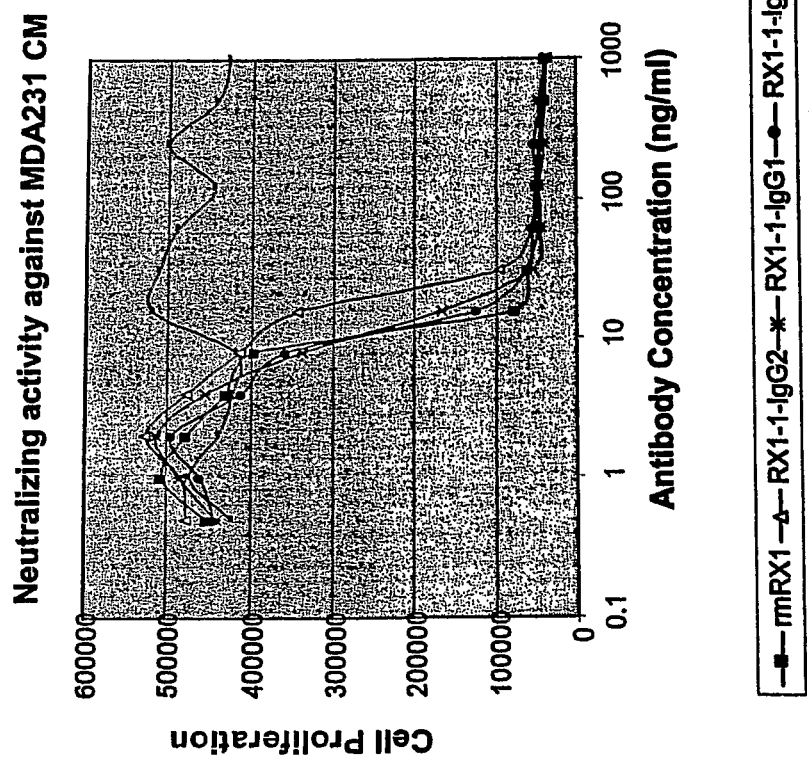
FIG. 27 shows the comparative neutralization of MDA231 (breast cancer cell line) medium by recombinant murine RX1 antibody, rmRX1, and several different versions of heRX1-1 (in which all of the low risk changes have been made) that each have a different constant region (IgG1, IgG2 or IgG4), labeled as RX2, RX1-1-IgG2, RX1-1-IgG1, RX1-1-IgG1, RX1-1-IgG4, RX1-a-IgG4.

The assay was repeated using human MCSF in serum, MDA231 conditioned medium (which contains M-CSF), cynomologous monkey MCSF in serum, and cynomologous monkey recombinant MCSF. The results are presented in FIGS. 25 (recombinant MCSF), 26 (human MCSF in serum) and 27 (MDA231 conditioned medium) as the fluorescent reading from CellTiter Glo assay, which is linear with cell number. Neutralizing activity of the antibodies is shown as an inhibition of the proliferation of M-NFS-60 cells.

The results show that the IC50 of heRX1-1-IgG1 and heRX1-1-IgG4 were about the same as the recombinant murine parent RX1 antibody, while the IC50 of heRX1-1-IgG2 was about 2-fold to 4-fold higher.

Table 12 below shows the relative IC50 (in terms of IC50 fold loss) of the various IgG2 constructs prepared as described above in Example 5. Of these constructs, heRX1-1.G2 and heRX1-10.G2 showed the least reduction in IC50.

TABLE 12

| Antibody | IC50 Fold Loss |
| --- | --- |
| heRX1-1.G2 | 2.8× |
| heRX1-2.G2 | 3.1× |
| heRX1-3.G2 | 5.3× |
| heRX1-4.G2 | 4.6× |
| heRX1-5.G2 | 6.5× |
| heRX1-6.G2 | 5.9× |
| heRX1-7.G2 | 6.1× |
| heRX1-8.G2 | 5.9× |
| heRX1-9.G2 | 3.6× |
| heRX1-10.G2 | 2.2× |
| heRX1-1.G1 | No loss |
| heRX1-1.G4 | No loss |
| heRX1-10.G1 | No loss |
| heRX1-10.G4 | No loss |

Example 16

This example shows that Human Engineered™ RX1 antibodies with different IgG subclass constant regions result in different TRAP activities in an in vitro osteoclastogenesis assay.

The human bone marrow CD34+ cells (Biowhittaker catalog number 2M-101A, $3 \times 10^5$ cells/vial) were induced to differentiate into osteoclasts under the experimental conditions described herein. On Day 1, CD34+ cells were thawed from one frozen vial into 10 ml of media (Alpha MEM with 10% FCS, 1× Pen Strep and 1× fungizone). The cells were washed once and re-suspended in 2 ml of media and placed into a 96 well plate at 100 ul per well. On Day 2, without removing the original media, 50 ul of 4×CSF-1 to 30 ng/ml final concentration and 50 ul of 4×RANKL (sRANKL, Chemicon catalog #GF091, 10 ug/package) to final concentration of 100 ng/ml was added to each well. On Day 7, 50 ul of 5×RANKL to final concentration of 100 ng/ml was added to each well. On Day 17, the cells were stained for TRAP activity (Leukocyte Acid Phosphatase kit for TRAP staining, Sigma catalog#387-A) and examined under the microscope.

Figure 28:
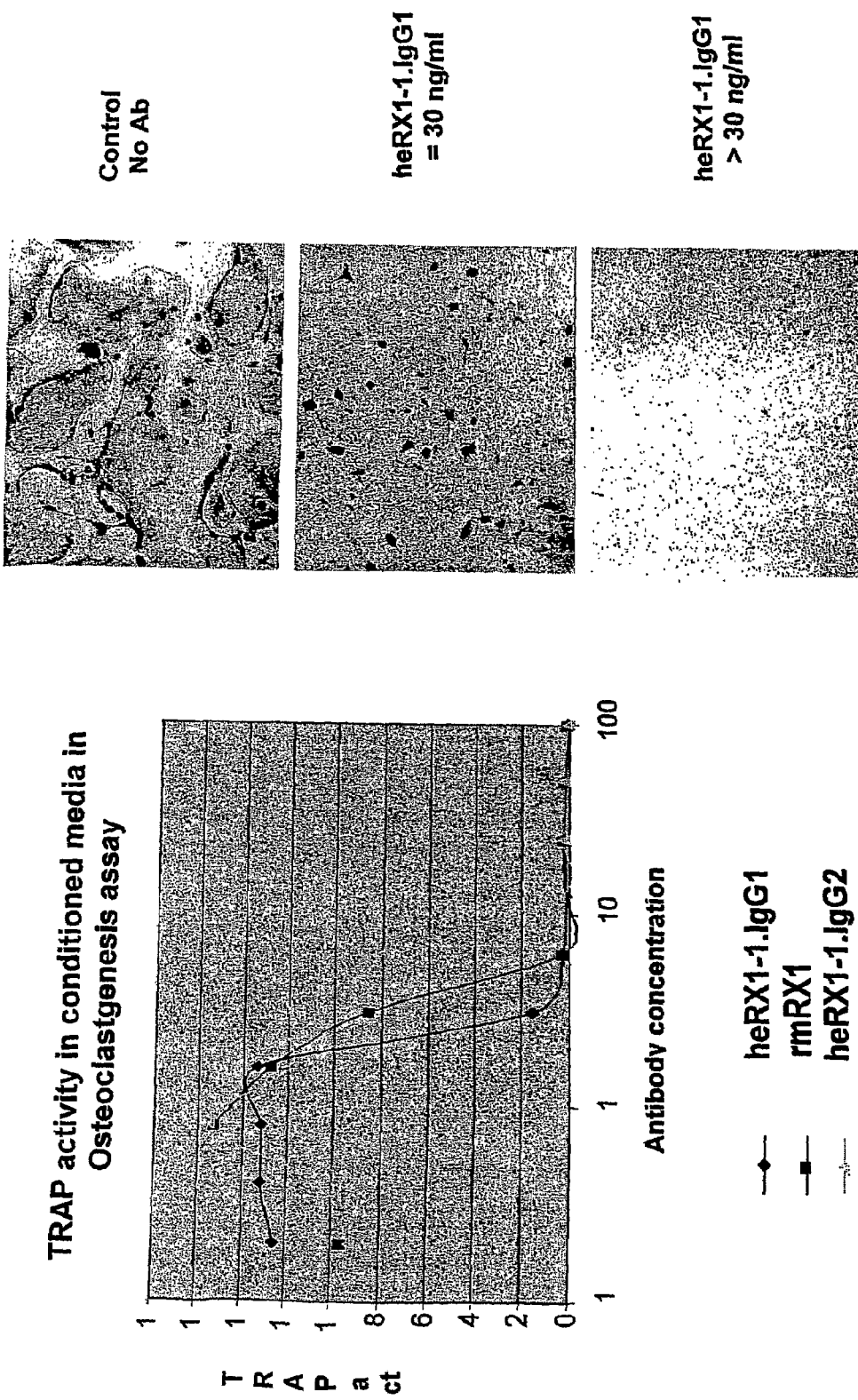
FIG. 28 shows the effect on osteoclastogenesis (as measured by TRAP activity) of recombinant murine RX1 antibody, rmRX1, and two different versions heRX1-1 that each have a different constant region (Ig1 or IgG2), labeled heRX1-1.IgG1 and heRX1-1.IgG2.

M-CSF-neutralizing antibodies are added on Day 2 of the assay. The antibodies inhibit osteoclast differentiation in a dose-dependent manner as shown in FIG. 28. The inhibitory activity of the antibodies in the osteoclast differentiation assay is shown as lack of visible osteoclasts on Day 17 of the assay.

Example 17

The Human Engineered™ RX1 antibodies with different IgG subclass constant regions were further characterized.

The antigen-antibody complexes that the various Human Engineered™ RX1 antibodies formed with MCSF were studied by combining M-CSF and antibody in buffer at equal molar ratios, followed by analysis of the size of the antigen-antibody complex using size exclusion chromatography or light scattering. The results showed that the murine parent RX1 appeared to form 1:1 complexes with MCSF of about 200 kDa. The heRX1-9.G2 or 1-10.G2 antibodies appeared to form 2:1 or 2:2 complexes with MCSF of about 400 kDa. The heRX1-1.G2 appeared to form large lattice aggregates with MCSF of greater than $2 \times 10^6$ Da. The IgG1 and IgG4 constructs formed small complexes similar to that of murine parent RX1.

Denaturing reducing and non-reducing SDS-PAGE of heRX1-1.G4 showed that the IgG4 version appeared to form half-antibodies, as expected.

Example 18

This example shows the effect of Human Engineered™ RX1 antibody or other anti-M-CSF antibodies on osteoclastogenesis in vitro. Primary human Osteoclast Precursors (Cambrex Bio Science Walkersville, Inc. Cat#2T-110) are seeded at 10,000 cells per well at 0.2 ml/well in the cell culture media containing 30 ng/ml human M-CSF and 100 ng/ml RANKL. Test anti-M-CSF antibodies are added to the wells at indicated concentrations on the same day of cell plating. The cells are incubated at 37° C., in a humidified atmosphere of 5% $CO_2$. On day 7, osteoclasts can be identified by phase microscopy as unusually large multinucleate cells. The culture can be continued for an additional week, with feeding, during which time the osteoclasts will continue to increase in size. At the end of the culture, cells are Stained for tartrate-resistant acid phosphatase, the positive staining of which indicates the presence of osteoclasts. The number of osteoclasts in each well is identified and counted under the light microscope and can be shown in a graph as an average of osteoclasts under the viewing field of the microscope.

Results of testing murine anti-MCSF antibody 5H4 are shown in FIG. 31.

Example 19

The following example sets forth an intratibial model to assess the ability of anti-M-CSF antibodies to reduce the effects of mixed osteoblastic/osteoclastic bone lesions.

Male SCID mice, aged 4-5 weeks, average weight 15-18 g are used. Mice are chipped for identification, and undergo a 7 day acclimation period prior to the study start date. Mice will receive s.c. injection of flunixin (2.5 mpk) 30 minutes before cell implantation. Mice are next anesthetized via isoflurane inhalation; their right hind leg cleaned with 70% ethanol and tumor cells ($2.5 \times 10^5$/10 ul saline) injected into the right tibia bone marrow cavity using a 50 or 100 ml micro-syringe. A total of 20 mice are inoculated.

One day following tumor cell injection, the mice are imaged by a Faxitron machine to establish baseline measurements and to ensure that the injections did not damage the bone. Treatment groups (treatment will begin day 2) are as follows:

Murine/Human IgG isotype control: 10 mpk each, i.p. once a week for 5 weeks

Anti-MCSF (rat anti-mouse IgG1 5A1 and mouse anti-human IgG1 5H4): 10 mpk each, i.p. once a week for 5 weeks Bone damage (assessed by Faxitron analysis once/week from week 1 until bone damage in the first mouse of the control group reaches stage 3, at which time Faxitron analysis is performed twice a week) is monitored and body weight is taken on a weekly basis. Mice are observed for clinical signs of distress daily until termination of study. Mice that develop severe clinical signs (>15% weight loss, hunched posture, inability to put weight on right leg, immobility, cold to the touch, leg swelling) or reaching stage 4 disease will be euthanized. At the completion of the study, final imaging, blood collection (heparanized) by cardiac puncture. from all 20 animals in the study, and tibia collection (3 right tibias from each group for histology, with 3 normal-left side tibias) is performed.

Example 20

This example sets out an in vivo procedure for assessing periprosthetic bone loss in the presence of anti-M-CSF antibodies. The generation and biological effects of wear debris, especially polyethylene particles, are a major concern to surgeons, due to effects on the longevity of total joint replacements. Particulate debris induce a number of factors that interfere with normal homeostatic mechanisms of bone by promoting osteoclast differentiation and maturation, and inhibiting osteoblast function. The net effect is bone loss, undermining the periprosthetic bone bed (Goodman et al., J. Biomed. Mater. Res., 65A: 454-461 (2003)). In this procedure, a drug test chamber (DTC) is surgically implanted in the bone within a rabbit's limb and allowed to integrate within the bone. Subsequently, polyethylene particles, with or without drug, are infused into the cavity, and bone tissue is periodically removed to assess bone formation.

The drug test chamber (DTC)

The DTC is a titanium device that is implanted at the level of the cortex in the proximal medial tibial metaphysis of rabbits, similar to the bone harvest chamber. The removable core of the DTC is provided with a 10-μL cavity acting as a fluid reservoir linked to the 1×1×5-mm ingrowth canal via a 1-mm long 0.25-mm diameter diffusion capillary. For continuous infusion, two tubes are connected to the reservoir. One tube is connected to a subcutaneous osmotic minipump (Alza Corp, Palo Alto, Calif.). The other tube is open to the subcutis, thereby functioning as a drain for the reservoir. This allows a slow continuous flow of the solution through the reservoir, creating a concentration gradient along the diffusion capillary. The percolation of the solvent through the diffusion capillary to the bone is minimal due to the reservoir being drained to the subcutaneous tissue. Thus, the ingrowing tissue can be locally treated with a solution without disturbance of solvent flow. After each treatment, through a small 1-cm incision, the chamber is exposed and disassembled, leaving the outer osseointegrated cylinder intact within bone. The inner core is temporarily removed, exposing the tissue in the chamber, which is harvested for subsequent analysis. The chamber parts are then reassembled for the next treatment. At the same time, through another small incision, the minipump and tubing (containing the new solution to be infused) are replaced.

Surgical Procedure

DTCs are first implanted in mature, male, New Zealand white rabbits, preferably aged 6-12 months and weighing 3.5-4.5 kg under general endotracheal anesthesia, as has been previously described. One dose of cephalosporin antibiotic is given as prophylaxis for infection. After a 6-week period for osseointegration, the contents of the chamber are harvested and discarded. The DTC is then connected, via polyvinyl tubing, to an Alzet osmotic diffusion pump (Model #2004, Alza, Palo Alto, Calif.). The diffusion pump contains 200 µL of fluid, and has a delivery rate of 0.25 µL/h. Carrier solution alone (i.e., the formulation solution without M-CSF antibodies, diluent, heparin sulphate, BSA, and the like) is infused for 3 weeks, followed by a harvest.

All rabbits are given M-CSF antibody treatments sequentially (see Table I). Anti-M-CSF antibody is first infused at dosages of 0, 0.5, 5, 50, or 500 ng/day for 3-week periods in the absence of polyethylene particles. The contents of the chamber are harvested after each treatment, and the diffusion pump and tubing are exchanged for another one with the appropriate solution. Ultra high molecular weight polyethylene particles at either a low dose ($5.8 \times 10^{11}$ particles/mL) or high dose ($1.7 \times 10^{12}$ particles/mL) are then placed in the DTC, with and without infusion of 50 ng/day of anti-M-CSF antibody for 3 weeks. The contents of the chamber are harvested after each treatment and a new diffusion pump, and tubing with the appropriate solution, are placed in the rabbit.

Tissue Processing and Immunohistochemistry.

Harvested specimens are placed in optimal cutting medium (OCT), snap frozen in liquid nitrogen, and stored at $-70°$ C. until processed. Serial 6 µm sections are cut using a cryostat (Cambridge Instruments, Buffalo, N.Y.) and mounted on microscope slides. Five or more sections from the center of the specimen are stained with hematoxylin and eosin for general morphological characterization. Sequential sections on both sides of the central sections above are used for immunoperoxidase staining using monoclonal antibodies to identify cells expressing the vitronectin receptor (osteoclast-like cells).

Frozen sections are fixed in absolute acetone at $4°$ C. The slides are fixed in the acetone for 10 min, air dried, and treated with the acetone for an additional 10 min. The slides are then dried for 45 min, placed in an airtight container, and stored at $-70°$ C. until processed. After thawing, the sections are incubated at room temperature with monoclonal antibodies to identify osteoclast-like cells exhibiting the vitronectin receptor (CD51, mouse antihuman monoclonal antibody to integrin $\alpha V \beta 3$, Chemicon, Temecula, Calif.). The use of this monoclonal antibody (although not specific for osteoclasts) has been used previously to identify osteoclast-like cells, and correlates, strongly with tartrate resistant acid phosphatase staining. Furthermore, CD51-positive cells demonstrate more concentrated staining and are easier to count than cells stained with tartrate resistant acid phosphatase. The sections are then incubated with biotinylated rabbit antimouse immunoglobulins and ABC solution (Vector, Burlingame, Calif.). The sections are washed in phosphate-buffered saline after each antibody step. Positively stained cells are visualized with diaminobenzidine, 0.01% $H_2O_2$, 0.3% sodium azide in 0.05 M Tris buffer pH 7.6. The slides are counterstained with toluidine blue, dehydrated, and mounted.

Assessment and Statistical Analysis

Histomorphologic analysis is performed of multiple (minimum=5) serial, longitudinal sections stained with hematoxylin and eosin, which enables the entire length of the specimen to be visualized on one slide. These sections are examined qualitatively using magnifications ranging from 40-400× for the cellular and stromal components and the type of bone present. A computerized, interactive image analysis system utilizing NIH Image interfaced with a MacIntosh Quadra computer (Apple, Cupertino, Calif.) and a real-time video light microscope system is used to perform the morphometric analysis. One entire section from the center of the specimen stained with hematoxylin and eosin is used for the morphometric analysis for bone ingrowth using 100× magnification. The areas for measurement on the entire section are outlined manually using a mouse pad, which was connected to the computer and a television screen containing the histological image. CD51-positive and negative cells are counted using 400× magnification using the appropriate sections processed by immunohistochemistry. All measurements are performed blindly, without knowledge of the treatment.

Histomorphometric analyses are performed to determine total tissue area, total bone area, ratio of bone area divided by total area and expressed as a percentage, and the total number of vitronectin-receptor positive cells abutting the bone and away from the bone in the entire section.

Statistical analysis is accomplished using the StatView software program (Abacus Concepts, Berkeley, Calif.). Parametric statistics are used for assessment of percentage of bone ingrowth, including an analysis of variance to compare sequential 3-week treatments. Post hoc tests may utilize the paired t-test, which compares different treatments performed in the same animals. Cell counting data is analyzed using the Kruskal-Wallis test and signed-rank test. A significance level of 0.05 is used.

Using the aforementioned procedure, the effects of anti-M-CSF antibodies on bone formation may be readily analyzed. It is expected that adition of anti-M-CSF antibodies will increase net bone formation and thus provide a means to enhance osseointegration of, for example, cementless implants.

All of the above U.S. patents, U.S. patent application publications, U.S. patent applications, foreign patents, foreign patent applications and non patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

What is claimed is:

1. A method of treating a subject suffering from a disease associated with periprosthetic bone loss or increased osteoclastic activity and increased osteoblastic activity comprising administering to the subject a non-murine antibody that competes with monoclonal antibody RX1 for binding to M-CSF by more than 75%, wherein said monoclonal antibody RX1 comprises the heavy chain and light chain amino acid sequences set forth in SEQ ID NOs: 2 and 4, respectively; and wherein the non-murine antibody comprises SEQ ID NOs: 18, 21, 24, 32, 36 and QASQSIGTSIH (SEQ ID NO: 138).

2. The method of claim 1 wherein the non-murine antibody specifically binds to the same epitope of M-CSF as said monoclonal antibody RX1, said epitope comprising at least 4 contiguous residues of SEQ ID NO: 120 or 121.

3. The method of claim 1 wherein the non-murine antibody is a monoclonal antibody.

4. The method of claim 1 wherein the non-murine antibody is a chimeric antibody, a humanized antibody, a human engineered antibody, a human antibody, or a single chain antibody.

5. The method of claim 1 wherein the non-murine antibody retains an affinity Kd with respect to M-CSF of SEQ ID NO: 9 of at least 10-8 M or higher.

6. The method of claim 1 wherein the non-murine antibody comprises a constant region of a human antibody sequence and one or more heavy and light chain variable framework regions of a human antibody sequence.

7. The method of claim 6 wherein the human antibody sequence is an individual human sequence, a human consensus sequence, an individual human germline sequence, or a human consensus germline sequence.

8. The method of claim 1 wherein the non-murine antibody comprises a fragment of an IgG1 constant region.

9. The method of claim 8 wherein the non-murine antibody comprises a mutation in the IgG1 constant region that reduces antibody-dependent cellular cytotoxicity or complement dependent cytotoxicity activity.

10. The method of claim 1 wherein the non-murine antibody comprises a fragment of an IgG4 constant region.

11. The method of claim 10 wherein the non-murine antibody comprises a mutation in the IgG4 constant region that reduces formation of half-antibodies.

12. The method of claim 1 further comprising administering a second therapeutic agent.

13. The method of claim 1 wherein the antibody is administered at a dose between about 0.1 mg/kg to 30 mg/kg body weight.

* * * * *

UNITED STATES PATENT AND TRADEMARK OFFICE
CERTIFICATE OF CORRECTION

PATENT NO. : 8,652,469 B2  
APPLICATION NO. : 11/996905  
DATED : February 18, 2014  
INVENTOR(S) : William Michael Kavanaugh et al.

Page 1 of 1

It is certified that error appears in the above-identified patent and that said Letters Patent is hereby corrected as shown below:

On the Title Page:

Item (75), line 2, "Aukerman," should be -- Auckerman, --.

In the Claims:

At Column 219, line 46, "10-8" should be -- $10^{-8}$ --.

Signed and Sealed this
Twenty-ninth Day of December, 2015

Michelle K. Lee
*Director of the United States Patent and Trademark Office*

SEQUENCE LISTING

<160> NUMBER OF SEQ ID NOS: 138

<210> SEQ ID NO 1
<211> LENGTH: 1401
<212> TYPE: DNA
<213> ORGANISM: Mus musculus

```
<400> SEQUENCE: 1
atgggttggt cctgtatcat cctattcctg gtggccactg ccacaggtgt gcactccgac      60
gtgcagcttc aggagtcagg acctggcctc gtgaaacctt ctcagagtct gtccctcacc     120
tgtactgtca ctgactactc catcaccagt gattacgcct ggaactggat acggcaattc     180
ccagggaata aacttgagtg gatggggtac ataagctaca gtggtagcac ttcctacaat     240
ccatctctca aaagtcggat ctccatcact gagacacatc caagaaccag gttcttcctg     300
cagctgaact ctgtgactac tgaggacaca gccacatatt actgtgcatc cttcgactat     360
gcccacgcca tggattactg gggccaaggg acttcggtca ctgtctcttc cgccaaaaca     420
acagccccat cggtctatcc actggcccct gtgtgtggag atacaactgg ctcctcggtg     480
actctaggat gcctggtcaa gggttatttc cctgagccag tgaccttgac ctggaactct     540
ggatccctgt ccagtggtgt gcacaccttc ccagctgtcc tgcagtctga cctctacacc     600
ctcagcagct cagtgactgt aacctcgagc acctggccca gccagtccat cacctgcaat     660
gtggcccacc cggcaagcag caccaaggtg gacaagaaaa ttgagcccag agggcccaca     720
atcaagccct gtcctccatg caaatgccca gcacctaacc tcttgggtgg accatccgtc     780
ttcatcttcc ctccaaagat caaggatgta ctcatgatct ccctgagccc catagtcaca     840
tgtgtggtgg tggatgtgag cgaggatgac ccagatgtcc agatcagctg gtttgtgaac     900
aacgtggaag tacacacagc tcagacacaa acccatagag aggattacaa cagtactctc     960
cgggtggtca gtgccctccc catccagcac caggactgga tgagtggcaa ggagttcaaa    1020
tgcaaggtca acaacaaaga cctcccagcg cccatcgaga gaaccatctc aaaacccaaa    1080
gggtcagtaa gagctccaca ggtatatgtc ttgcctccac cagaagaaga gatgactaag    1140
aaacaggtca ctctgacctg catggtcaca gacttcatgc ctgaagacat ttacgtggag    1200
tggaccaaca cgggaaaac agagctaaac tacaagaaca ctgaaccagt cctggactct    1260
gatggttctt acttcatgta cagcaagctg agagtggaaa agaagaactg ggtggaaaga    1320
aatagctact cctgttcagt ggtccacgag ggtctgcaca tcaccacac gactaagagc    1380 ttctcccgga ctccgggtaa a                                              1401

<210> SEQ ID NO 2
<211> LENGTH: 447
<212> TYPE: PRT
<213> ORGANISM: Mus musculus

<400> SEQUENCE: 2

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Ser Phe Asp Tyr Ala His Ala Met Asp Tyr Trp Gly Gln Gly Thr
            100                 105                 110

Ser Val Thr Val Ser Ser Ala Lys Thr Thr Ala Pro Ser Val Tyr Pro
```

```
            115                 120                 125
Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly
        435                 440                 445

<210> SEQ ID NO 3
<211> LENGTH: 702
<212> TYPE: DNA
<213> ORGANISM: Mus musculus

<400> SEQUENCE: 3
atggtatcca cacctcagtt ccttgtattt tgcttttct ggattccagc ctccagaggt        60
gacatcttgc tgactcagtc tccagccatc ctgtctgtga gtccaggaga aagagtcagt       120
ttctcctgca gggccagtca gagcattggc acaagcatac actggtatca gcaaagaaca       180
aatggttctc caaggcttct cataaagtat gcttctgagt ctatctctgg gatcccttcc       240
aggtttagtg gcagtggatc aggacagat tttactctta gcatcaacag tgtggagtct       300
```

```
gaagatattg cagattatta ctgtcaacaa attaatagct ggccaaccac gttcggcggg    360
gggacaaagt tggaaataaa acgggctgat gctgcaccaa ctgtatccat cttcccacca    420
tccagtgagc agttaacatc tggaggtgcc tcagtcgtgt gcttcttgaa caacttctac    480
cccaaagaca tcaatgtcaa gtggaagatt gatggcagtg aacgacaaaa tggcgtcctg    540
aacagttgga ctgatcagga cagcaaagac agcacctaca gcatgagcag caccctcacg    600
ttgaccaagg acgagtatga acgacataac agctatacct gtgaggccac tcacaagaca    660
tcaacttcac ccattgtcaa gagcttcaac aggaatgagt gt                      702
```

<210> SEQ ID NO 4
<211> LENGTH: 214
<212> TYPE: PRT
<213> ORGANISM: Mus musculus

<400> SEQUENCE: 4

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ile Asn Ser Trp Pro Thr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 5
<211> LENGTH: 109
<212> TYPE: PRT
<213> ORGANISM: Mus musculus

<400> SEQUENCE: 5

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
                20                  25                  30

Ile His Trp Tyr Gln Gln Arg Thr Asn Gly Ser Pro Arg Leu Leu Ile
            35                  40                  45

```
Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ile Asn Ser Trp Pro Thr
                85                  90                  95

Thr Phe Gly Gly Gly Thr Lys Leu Glu Ile Lys Arg Ala
            100                 105
```

<210> SEQ ID NO 6
<211> LENGTH: 118
<212> TYPE: PRT
<213> ORGANISM: Mus musculus

<400> SEQUENCE: 6

```
Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Ile Thr Ser Asp
                20                  25                  30

Tyr Ala Trp Asn Trp Ile Arg Gln Phe Pro Gly Asn Lys Leu Glu Trp
            35                  40                  45

Met Gly Tyr Ile Ser Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Ser Phe Asp Tyr Ala His Ala Met Asp Tyr Trp Gly Gln Gly Thr
            100                 105                 110

Ser Val Thr Val Ser Ser
        115
```

<210> SEQ ID NO 7
<211> LENGTH: 256
<212> TYPE: PRT
<213> ORGANISM: Mus musculus

<400> SEQUENCE: 7

```
Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
                20                  25                  30

Glu Glu Val Ser Glu Tyr Cys Ser His Met Ile Gly Ser Gly His Leu
            35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140
```

```
Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Gly His Glu Arg Gln Ser Glu Gly Ser Ser Ser
            180                 185                 190

Pro Gln Leu Gln Glu Ser Val Phe His Leu Leu Val Pro Ser Val Ile
        195                 200                 205

Leu Val Leu Leu Ala Val Gly Gly Leu Leu Phe Tyr Arg Trp Arg Arg
210                 215                 220

Arg Ser His Gln Glu Pro Gln Arg Ala Asp Ser Pro Leu Glu Gln Pro
225                 230                 235                 240

Glu Gly Ser Pro Leu Thr Gln Asp Asp Arg Gln Val Glu Leu Pro Val
                245                 250                 255
```

<210> SEQ ID NO 8
<211> LENGTH: 554
<212> TYPE: PRT
<213> ORGANISM: Mus musculus

<400> SEQUENCE: 8

```
Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
                20                  25                  30

Glu Glu Val Ser Glu Tyr Cys Ser His Met Ile Gly Ser Gly His Leu
            35                  40                  45

Gln Ser Leu Gln Arg Leu Ile Asp Ser Gln Met Glu Thr Ser Cys Gln
        50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
                100                 105                 110

Gln Glu Leu Ser Leu Arg Leu Lys Ser Cys Phe Thr Lys Asp Tyr Glu
            115                 120                 125

Glu His Asp Lys Ala Cys Val Arg Thr Phe Tyr Glu Thr Pro Leu Gln
        130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
                260                 265                 270
```

Thr Ile Gly Gly Ser Pro Gln Pro Arg Pro Ser Val Gly Ala Phe Asn
    275                 280                 285

Pro Gly Met Glu Asp Ile Leu Asp Ser Ala Met Gly Thr Asn Trp Val
290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
            340                 345                 350

Ser Ala Lys Gly Gln Gln Pro Ala Asp Val Thr Gly Thr Ala Leu Pro
        355                 360                 365

Arg Val Gly Pro Val Arg Pro Thr Gly Gln Asp Trp Asn His Thr Pro
    370                 375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
                405                 410                 415

Ser Thr Leu Ser Ala Gln Pro Gln Leu Ser Arg Ser His Ser Ser Gly
            420                 425                 430

Ser Val Leu Pro Leu Gly Glu Leu Glu Gly Arg Arg Ser Thr Arg Asp
        435                 440                 445

Arg Arg Ser Pro Ala Glu Pro Glu Gly Gly Pro Ala Ser Glu Gly Ala
    450                 455                 460

Ala Arg Pro Leu Pro Arg Phe Asn Ser Val Pro Leu Thr Asp Thr Gly
465                 470                 475                 480

His Glu Arg Gln Ser Glu Gly Ser Ser Ser Pro Gln Leu Gln Glu Ser
                485                 490                 495

Val Phe His Leu Leu Val Pro Ser Val Ile Leu Val Leu Leu Ala Val
            500                 505                 510

Gly Gly Leu Leu Phe Tyr Arg Trp Arg Arg Arg Ser His Gln Glu Pro
        515                 520                 525

Gln Arg Ala Asp Ser Pro Leu Glu Gln Pro Glu Gly Ser Pro Leu Thr
    530                 535                 540

Gln Asp Asp Arg Gln Val Glu Leu Pro Val
545                 550

<210> SEQ ID NO 9
<211> LENGTH: 438
<212> TYPE: PRT
<213> ORGANISM: Mus musculus

<400> SEQUENCE: 9

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

```
Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Ser Phe Ala
                165                 170                 175

Glu Cys Ser Ser Gln Asp Val Val Thr Lys Pro Asp Cys Asn Cys Leu
    180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
        260                 265                 270

Thr Ile Gly Gly Ser Pro Gln Pro Arg Pro Ser Val Gly Ala Phe Asn
        275                 280                 285

Pro Gly Met Glu Asp Ile Leu Asp Ser Ala Met Gly Thr Asn Trp Val
    290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
            325                 330                 335

Pro Ala Arg Pro Ser Asn Phe Leu Ser Ala Ser Ser Pro Leu Pro Ala
        340                 345                 350

Ser Ala Lys Gly Gln Gln Pro Ala Asp Val Thr Gly His Glu Arg Gln
        355                 360                 365

Ser Glu Gly Ser Ser Ser Pro Gln Leu Gln Glu Ser Val Phe His Leu
    370                 375                 380

Leu Val Pro Ser Val Ile Leu Val Leu Leu Ala Val Gly Gly Leu Leu
385                 390                 395                 400

Phe Tyr Arg Trp Arg Arg Arg Ser His Gln Glu Pro Gln Arg Ala Asp
                405                 410                 415

Ser Pro Leu Glu Gln Pro Glu Gly Ser Pro Leu Thr Gln Asp Asp Arg
        420                 425                 430

Gln Val Glu Leu Pro Val
            435

<210> SEQ ID NO 10
<211> LENGTH: 441
<212> TYPE: PRT
<213> ORGANISM: Mus musculus

<400> SEQUENCE: 10

Glu Ile Gln Leu Gln Gln Ser Gly Pro Glu Leu Val Lys Thr Gly Thr
1               5                   10                  15

Ser Val Lys Ile Ser Cys Lys Ala Ser Gly Tyr Ser Phe Thr Gly Tyr
            20                  25                  30
```

```
Phe Met His Trp Val Lys Gln Ser His Gly Lys Ser Leu Glu Trp Ile
         35                  40                  45
Gly Tyr Ile Ser Cys Tyr Asn Gly Asp Thr Asn Tyr Asn Gln Asn Phe
 50                  55                  60
Lys Gly Lys Ala Thr Phe Thr Val Asp Thr Ser Ser Ser Thr Ala Tyr
 65                  70                  75                  80
Met Gln Phe Asn Ser Leu Thr Ser Glu Asp Ser Ala Val Tyr Tyr Cys
                 85                  90                  95
Ala Arg Glu Gly Gly Asn Tyr Pro Ala Tyr Trp Gly Gln Gly Thr Leu
            100                 105                 110
Val Thr Val Ser Ala Ala Lys Thr Thr Pro Pro Ser Val Tyr Pro Leu
        115                 120                 125
Ala Pro Gly Ser Ala Ala Gln Thr Asn Ser Met Val Thr Leu Gly Cys
130                 135                 140
Leu Val Lys Gly Tyr Phe Pro Glu Pro Val Thr Val Thr Trp Asn Ser
145                 150                 155                 160
Gly Ser Leu Ser Ser Gly Val His Thr Phe Pro Ala Val Leu Gln Ser
                165                 170                 175
Asp Leu Tyr Thr Leu Ser Ser Ser Val Thr Val Pro Ser Ser Thr Trp
            180                 185                 190
Pro Ser Glu Thr Val Thr Cys Asn Val Ala His Pro Ala Ser Ser Thr
        195                 200                 205
Lys Val Asp Lys Lys Ile Val Pro Arg Asp Cys Gly Cys Lys Pro Cys
210                 215                 220
Ile Cys Thr Val Pro Glu Val Ser Ser Val Phe Ile Phe Pro Pro Lys
225                 230                 235                 240
Pro Lys Asp Val Leu Thr Ile Thr Leu Thr Pro Lys Val Thr Cys Val
                245                 250                 255
Val Val Asp Ile Ser Lys Asp Asp Pro Glu Val Gln Phe Ser Trp Phe
            260                 265                 270
Val Asp Asp Val Glu Val His Thr Ala Gln Thr Gln Pro Arg Glu Glu
        275                 280                 285
Gln Phe Asn Ser Thr Phe Arg Ser Val Ser Glu Leu Pro Ile Met His
290                 295                 300
Gln Asp Trp Leu Asn Gly Lys Glu Phe Lys Cys Arg Val Asn Ser Ala
305                 310                 315                 320
Ala Phe Pro Ala Pro Ile Glu Lys Thr Ile Ser Lys Thr Lys Gly Arg
                325                 330                 335
Pro Lys Ala Pro Gln Val Tyr Thr Ile Pro Pro Pro Lys Glu Gln Met
            340                 345                 350
Ala Lys Asp Lys Val Ser Leu Thr Cys Met Ile Thr Asp Phe Phe Pro
        355                 360                 365
Glu Asp Ile Thr Val Glu Trp Gln Trp Asn Gly Gln Pro Ala Glu Asn
370                 375                 380
Tyr Lys Asn Thr Gln Pro Ile Met Asp Thr Asp Gly Ser Tyr Phe Val
385                 390                 395                 400
Tyr Ser Lys Leu Asn Val Gln Lys Ser Asn Trp Glu Ala Gly Asn Thr
                405                 410                 415
Phe Thr Cys Ser Val Leu His Glu Gly Leu His Asn His His Thr Glu
            420                 425                 430
Lys Ser Leu Ser His Ser Pro Gly Lys
        435                 440

<210> SEQ ID NO 11
```

```
<211> LENGTH: 214
<212> TYPE: PRT
<213> ORGANISM: Mus musculus

<400> SEQUENCE: 11

Asp Ile Val Met Thr Gln Ser His Lys Phe Met Ser Thr Ser Val Gly
1               5                   10                  15

Asp Arg Val Thr Ile Thr Cys Lys Ala Ser Gln Asn Val Gly Thr Ala
            20                  25                  30

Val Thr Trp Tyr Gln Gln Lys Pro Gly Gln Ser Pro Lys Leu Leu Ile
        35                  40                  45

Tyr Trp Thr Ser Thr Arg His Ala Gly Val Pro Asp Arg Phe Thr Gly
    50                  55                  60

Ser Gly Ser Gly Thr Asp Phe Thr Leu Thr Ile Ser Asp Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Pro Ile Val Lys Ser
        195                 200                 205

Phe Asn Arg Asn Glu Cys
    210

<210> SEQ ID NO 12
<211> LENGTH: 449
<212> TYPE: PRT
<213> ORGANISM: Mus musculus

<400> SEQUENCE: 12

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Gln Gly Ser Tyr Gly Tyr Pro Phe Ala Tyr Trp Gly Gln Gly
            100                 105                 110

Thr Leu Val Thr Val Ser Ala Ala Lys Thr Thr Ala Pro Ser Val Tyr
        115                 120                 125
```

-continued

Pro Leu Ala Pro Val Cys Gly Asp Thr Thr Gly Ser Ser Val Thr Leu
130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
            165                 170                 175

Gln Ser Asp Leu Tyr Thr Leu Ser Ser Val Thr Val Thr Ser Ser
        180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
            245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
            325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
            405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
        435                 440                 445

Lys

<210> SEQ ID NO 13
<211> LENGTH: 214
<212> TYPE: PRT
<213> ORGANISM: Mus musculus

<400> SEQUENCE: 13

Ala Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly

```
                50                   55                   60
Ser Gly Ser Gly Thr Asp Tyr Ser Leu Thr Ile Ser Asn Leu Glu Pro
 65                   70                   75                   80

Glu Asp Ile Ala Thr Tyr Tyr Cys Gln Gln Tyr Ser Lys Leu Pro Trp
                 85                   90                   95

Thr Phe Gly Gly Gly Thr Lys Leu Glu Ile Lys Arg Ala Asp Ala Ala
                100                  105                  110

Pro Thr Val Ser Ile Phe Pro Pro Ser Ser Glu Gln Leu Thr Ser Gly
                115                  120                  125

Gly Ala Ser Val Val Cys Phe Leu Asn Asn Phe Tyr Pro Lys Asp Ile
            130                  135                  140

Asn Val Lys Trp Lys Ile Asp Gly Ser Glu Arg Gln Asn Gly Val Leu
145                  150                  155                  160

Asn Ser Trp Thr Asp Gln Asp Ser Lys Asp Ser Thr Tyr Ser Met Ser
                165                  170                  175

Ser Thr Leu Thr Leu Thr Lys Asp Glu Tyr Glu Arg His Asn Ser Tyr
            180                  185                  190

Thr Cys Glu Ala Thr His Lys Thr Ser Thr Ser Pro Ile Val Lys Ser
        195                  200                  205

Phe Asn Arg Asn Glu Cys
210

<210> SEQ ID NO 14
<211> LENGTH: 522
<212> TYPE: PRT
<213> ORGANISM: Mus musculus

<400> SEQUENCE: 14

Asp Val Gln Leu Gln Glu Ser Gly Pro Gly Leu Val Lys Pro Ser Gln
  1               5                   10                  15

Ser Leu Ser Leu Thr Cys Thr Val Thr Gly Tyr Ser Ile Thr Ser Asp
                 20                  25                  30

Tyr Ala Trp Asn Trp Ile Arg Gln Phe Pro Gly Asn Lys Leu Glu Trp
             35                  40                  45

Met Gly Tyr Ile Ser Tyr Ser Gly Ser Thr Ser Tyr Asn Pro Ser Leu
 50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Ala Arg Leu Glu Thr Trp Leu Phe Asp Tyr Trp Gly Gln Gly Thr Thr
                100                  105                  110

Leu Thr Val Ser Ser Ala Lys Thr Thr Pro Pro Ser Val Tyr Pro Leu
            115                  120                  125

Ala Pro Gly Cys Gly Asp Thr Thr Gly Ser Ser Val Thr Leu Gly Cys
        130                  135                  140

Leu Val Lys Gly Tyr Phe Pro Glu Ser Val Thr Val Thr Trp Asn Ser
145                  150                  155                  160

Gly Ser Leu Ser Ser Ser Val His Thr Phe Pro Ala Leu Leu Gln Ser
                165                  170                  175

Gly Leu Tyr Thr Met Ser Ser Ser Val Thr Val Pro Ser Ser Thr Trp
            180                  185                  190

Pro Ser Gln Thr Val Thr Cys Ser Val Ala His Pro Ala Ser Ser Thr
        195                  200                  205

Thr Val Asp Lys Lys Leu Glu Pro Ser Gly Pro Ile Ser Thr Ile Asn
```

```
                210                 215                 220
Pro Cys Pro Pro Cys Lys Glu Cys His Lys Cys Pro Ala Pro Asn Leu
225                 230                 235                 240

Glu Gly Gly Pro Ser Val Phe Ile Phe Pro Asn Ile Lys Asp Val
                245                 250                 255

Leu Met Ile Ser Leu Thr Pro Lys Val Thr Cys Val Val Asp Val
                260                 265                 270

Ser Glu Asp Asp Pro Asp Val Gln Ile Ser Trp Phe Val Asn Asn Val
                275                 280                 285

Glu Val His Thr Ala Gln Thr Gln Thr His Arg Glu Asp Tyr Asn Ser
                290                 295                 300

Thr Ile Arg Val Val Ser Thr Leu Pro Ile Gln His Gln Asp Trp Met
305                 310                 315                 320

Ser Gly Lys Glu Phe Lys Cys Lys Val Asn Asn Lys Asp Leu Pro Ser
                325                 330                 335

Pro Ile Glu Arg Thr Ile Ser Lys Ile Lys Gly Leu Val Arg Ala Pro
                340                 345                 350

Gln Val Tyr Ile Leu Pro Pro Pro Ala Glu Gln Leu Ser Arg Lys Asp
                355                 360                 365

Val Ser Leu Thr Cys Leu Val Val Gly Phe Asn Pro Gly Asp Ile Ser
                370                 375                 380

Val Glu Trp Thr Ser Asn Gly His Thr Glu Glu Asn Tyr Lys Asp Thr
385                 390                 395                 400

Ala Pro Val Leu Asp Ser Asp Gly Ser Tyr Phe Ile Tyr Ser Lys Leu
                405                 410                 415

Asn Met Lys Thr Ser Lys Trp Glu Lys Thr Asp Ser Phe Ser Cys Asn
                420                 425                 430

Val Arg His Glu Gly Leu Lys Asn Tyr Tyr Leu Lys Lys Thr Ile Ser
                435                 440                 445

Arg Ser Pro Gly Leu Asp Leu Asp Asp Ile Cys Ala Glu Ala Lys Asp
                450                 455                 460

Gly Glu Leu Asp Gly Leu Trp Thr Thr Ile Thr Ile Phe Ile Ser Leu
465                 470                 475                 480

Phe Leu Leu Ser Val Cys Tyr Ser Ala Ser Val Thr Leu Phe Lys Val
                485                 490                 495

Lys Trp Ile Phe Ser Ser Val Val Glu Leu Lys Gln Lys Ile Ser Pro
                500                 505                 510

Asp Tyr Arg Asn Met Ile Gly Gln Gly Ala
                515                 520

<210> SEQ ID NO 15
<211> LENGTH: 214
<212> TYPE: PRT
<213> ORGANISM: Mus musculus

<400> SEQUENCE: 15

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
                20                  25                  30

Ile His Trp Tyr Gln Gln Arg Thr Asn Gly Ser Pro Arg Leu Leu Ile
                35                  40                  45

Lys Tyr Ala Ser Glu Ser Ile Ser Gly Ile Pro Ser Arg Phe Ser Gly
                50                  55                  60

Ser Gly Ser Gly Thr Asp Phe Thr Leu Ser Ile Asn Ser Val Glu Ser
```

-continued

```
                65                  70                  75                  80
Glu Asp Ile Ala Asp Tyr Tyr Cys Gln Gln Ser Asn Ser Trp Pro Thr
                    85                  90                  95

Thr Phe Gly Gly Gly Thr Lys Leu Glu Ile Lys Trp Ala Asp Ala Ala
                100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 16
<211> LENGTH: 5
<212> TYPE: PRT
<213> ORGANISM: Homo sapiens

<400> SEQUENCE: 16

Gly Tyr Phe Met His
1               5

<210> SEQ ID NO 17
<211> LENGTH: 5
<212> TYPE: PRT
<213> ORGANISM: Homo sapiens

<400> SEQUENCE: 17

Asp Tyr Tyr Met Tyr
1               5

<210> SEQ ID NO 18
<211> LENGTH: 6
<212> TYPE: PRT
<213> ORGANISM: Homo sapiens

<400> SEQUENCE: 18

Ser Asp Tyr Ala Trp Asn
1               5

<210> SEQ ID NO 19
<211> LENGTH: 17
<212> TYPE: PRT
<213> ORGANISM: Homo sapiens

<400> SEQUENCE: 19

Tyr Ile Ser Cys Tyr Asn Gly Asp Thr Asn Tyr Asn Gln Asn Phe Lys
1               5                   10                  15

Gly

<210> SEQ ID NO 20
<211> LENGTH: 17
<212> TYPE: PRT
<213> ORGANISM: Homo sapiens
```

```
<400> SEQUENCE: 20

Tyr Ile Ser Asn Gly Gly Gly Ser Thr Tyr Tyr Pro Asp Thr Val Lys
1               5                   10                  15

Gly

<210> SEQ ID NO 21
<211> LENGTH: 16
<212> TYPE: PRT
<213> ORGANISM: Homo sapiens

<400> SEQUENCE: 21

Tyr Ile Ser Tyr Ser Gly Ser Thr Ser Tyr Asn Pro Ser Leu Lys Ser
1               5                   10                  15

<210> SEQ ID NO 22
<211> LENGTH: 8
<212> TYPE: PRT
<213> ORGANISM: Homo sapiens

<400> SEQUENCE: 22

Glu Gly Gly Asn Tyr Pro Ala Tyr
1               5

<210> SEQ ID NO 23
<211> LENGTH: 10
<212> TYPE: PRT
<213> ORGANISM: Homo sapiens

<400> SEQUENCE: 23

Gln Gly Ser Tyr Gly Tyr Pro Phe Ala Tyr
1               5                   10

<210> SEQ ID NO 24
<211> LENGTH: 9
<212> TYPE: PRT
<213> ORGANISM: Homo sapiens

<400> SEQUENCE: 24

Phe Asp Tyr Ala His Ala Met Asp Tyr
1               5

<210> SEQ ID NO 25
<211> LENGTH: 8
<212> TYPE: PRT
<213> ORGANISM: Homo sapiens

<400> SEQUENCE: 25

Leu Glu Thr Trp Leu Phe Asp Tyr
1               5

<210> SEQ ID NO 26
<211> LENGTH: 7
<212> TYPE: PRT
<213> ORGANISM: Homo sapiens

<400> SEQUENCE: 26

Asp Tyr Gly Trp Phe Asp Tyr
1               5

<210> SEQ ID NO 27
<211> LENGTH: 11
<212> TYPE: PRT
<213> ORGANISM: Homo sapiens
```

```
<400> SEQUENCE: 27

Lys Ala Ser Gln Asn Val Gly Thr Ala Val Thr
1               5                   10

<210> SEQ ID NO 28
<211> LENGTH: 11
<212> TYPE: PRT
<213> ORGANISM: Homo sapiens

<400> SEQUENCE: 28

Ser Ala Ser Gln Gly Ile Ser Asn Tyr Leu Asn
1               5                   10

<210> SEQ ID NO 29
<211> LENGTH: 11
<212> TYPE: PRT
<213> ORGANISM: Homo sapiens

<400> SEQUENCE: 29

Arg Ala Ser Gln Ser Ile Gly Thr Ser Ile His
1               5                   10

<210> SEQ ID NO 30
<211> LENGTH: 7
<212> TYPE: PRT
<213> ORGANISM: Homo sapiens

<400> SEQUENCE: 30

Trp Thr Ser Thr Arg His Ala
1               5

<210> SEQ ID NO 31
<211> LENGTH: 7
<212> TYPE: PRT
<213> ORGANISM: Homo sapiens

<400> SEQUENCE: 31

Tyr Thr Ser Ser Leu His Ser
1               5

<210> SEQ ID NO 32
<211> LENGTH: 7
<212> TYPE: PRT
<213> ORGANISM: Homo sapiens

<400> SEQUENCE: 32

Tyr Ala Ser Glu Ser Ile Ser
1               5

<210> SEQ ID NO 33
<211> LENGTH: 7
<212> TYPE: PRT
<213> ORGANISM: Homo sapiens

<400> SEQUENCE: 33

Tyr Thr Ser Glu Ser Ile Ser
1               5

<210> SEQ ID NO 34
<211> LENGTH: 9
<212> TYPE: PRT
<213> ORGANISM: Homo sapiens

<400> SEQUENCE: 34

Gln Gln Tyr Ser Ser Tyr Pro Leu Thr
```

<210> SEQ ID NO 35
<211> LENGTH: 9
<212> TYPE: PRT
<213> ORGANISM: Homo sapiens

<400> SEQUENCE: 35

Gln Gln Tyr Ser Lys Leu Pro Trp Thr
1               5

<210> SEQ ID NO 36
<211> LENGTH: 9
<212> TYPE: PRT
<213> ORGANISM: Homo sapiens

<400> SEQUENCE: 36

Gln Gln Ile Asn Ser Trp Pro Thr Thr
1               5

<210> SEQ ID NO 37
<211> LENGTH: 9
<212> TYPE: PRT
<213> ORGANISM: Homo sapiens

<400> SEQUENCE: 37

Gln Gln Ser Asn Ser Trp Pro Thr Thr
1               5

<210> SEQ ID NO 38
<211> LENGTH: 9
<212> TYPE: PRT
<213> ORGANISM: Homo sapiens

<400> SEQUENCE: 38

Gln Gln Tyr Ser Ser Trp Pro Thr Thr
1               5

<210> SEQ ID NO 39
<211> LENGTH: 130
<212> TYPE: PRT
<213> ORGANISM: Homo sapiens
<220> FEATURE:
<221> NAME/KEY: misc_feature
<222> LOCATION: (23)..(23)
<223> OTHER INFORMATION: Xaa= any amino acid
<220> FEATURE:
<221> NAME/KEY: misc_feature
<222> LOCATION: (27)..(27)
<223> OTHER INFORMATION: Xaa= any amino acid
<220> FEATURE:
<221> NAME/KEY: misc_feature
<222> LOCATION: (29)..(29)
<223> OTHER INFORMATION: Xaa= any amino acid
<220> FEATURE:
<221> NAME/KEY: misc_feature
<222> LOCATION: (31)..(36)
<223> OTHER INFORMATION: Xaa= any amino acid
<220> FEATURE:
<221> NAME/KEY: misc_feature
<222> LOCATION: (51)..(51)
<223> OTHER INFORMATION: Xaa= any amino acid
<220> FEATURE:
<221> NAME/KEY: misc_feature
<222> LOCATION: (56)..(57)
<223> OTHER INFORMATION: Xaa= any amino acid
<220> FEATURE:
<221> NAME/KEY: misc_feature
<222> LOCATION: (59)..(59)
<223> OTHER INFORMATION: Xaa= any amino acid
<220> FEATURE:

```
<221> NAME/KEY: misc_feature
<222> LOCATION: (61)..(61)
<223> OTHER INFORMATION: Xaa= any amino acid
<220> FEATURE:
<221> NAME/KEY: misc_feature
<222> LOCATION: (84)..(84)
<223> OTHER INFORMATION: Xaa= any amino acid
<220> FEATURE:
<221> NAME/KEY: misc_feature
<222> LOCATION: (86)..(86)
<223> OTHER INFORMATION: Xaa= any amino acid
<220> FEATURE:
<221> NAME/KEY: misc_feature
<222> LOCATION: (101)..(116)
<223> OTHER INFORMATION: Xaa= any amino acid
<220> FEATURE:
<221> NAME/KEY: misc_feature
<222> LOCATION: (119)..(119)
<223> OTHER INFORMATION: Xaa= any amino acid
<220> FEATURE:
<221> NAME/KEY: misc_feature
<222> LOCATION: (125)..(125)
<223> OTHER INFORMATION: Xaa= any amino acid

<400> SEQUENCE: 39

Asp Val Gln Leu Gln Glu Ser Gly Pro Gly Leu Val Lys Pro Ser Gln
1               5                   10                  15

Thr Leu Ser Leu Thr Cys Xaa Val Ser Gly Xaa Ser Xaa Ser Xaa Xaa
            20                  25                  30

Xaa Xaa Xaa Xaa Trp Ile Arg Gln Pro Pro Gly Lys Gly Leu Glu Trp
        35                  40                  45

Ile Gly Xaa Tyr Tyr Arg Ala Xaa Xaa Gly Xaa Thr Xaa Tyr Asn Pro
    50                  55                  60

Ser Leu Lys Ser Arg Val Thr Ile Ser Val Asp Thr Ser Lys Asn Gln
65                  70                  75                  80

Phe Ser Leu Xaa Leu Xaa Ser Val Thr Ala Ala Asp Thr Ala Val Tyr
                85                  90                  95

Tyr Cys Ala Arg Xaa Xaa Xaa Xaa Xaa Xaa Xaa Xaa Xaa Xaa Xaa Xaa
            100                 105                 110

Xaa Xaa Xaa Xaa Phe Asp Xaa Trp Gly Gln Gly Thr Xaa Val Thr Val
        115                 120                 125

Ser Ser
    130

<210> SEQ ID NO 40
<211> LENGTH: 354
<212> TYPE: DNA
<213> ORGANISM: Homo sapiens

<400> SEQUENCE: 40
gacgtacaac ttcaagaatc tggcccaggt ctcgtcaaac cttctcaaac tctctcactc     60
acctgcactg ttactgacta ctctattaca tccgactacg cttggaactg gatccgacaa    120
tttcctggta aaaaactcga atggatgggt tatatttctt actctggctc cacctcctac    180
aatccttctc tgaaatcacg catcacaatt tcccgcgata cctctaaaaa tcaattttca    240
ctccaactca attctgttac cgccgccgat actgccacct actactgtgc ctcttttgac    300
tacgctcacg ccatggatta ttggggacag ggtactaccg ttaccgtaag ctca          354

<210> SEQ ID NO 41
<211> LENGTH: 118
<212> TYPE: PRT
<213> ORGANISM: Homo sapiens

<400> SEQUENCE: 41
```

Asp Val Gln Leu Gln Glu Ser Gly Pro Gly Leu Val Lys Pro Ser Gln
1               5                   10                  15

Thr Leu Ser Leu Thr Cys Thr Val Thr Asp Tyr Ser Ile Thr Ser Asp
                20                  25                  30

Tyr Ala Trp Asn Trp Ile Arg Gln Phe Pro Gly Lys Lys Leu Glu Trp
            35                  40                  45

Met Gly Tyr Ile Ser Tyr Ser Gly Ser Thr Ser Tyr Asn Pro Ser Leu
50                      55                  60

Lys Ser Arg Ile Thr Ile Ser Arg Asp Thr Ser Lys Asn Gln Phe Ser
65                  70                  75                  80

Leu Gln Leu Asn Ser Val Thr Ala Ala Asp Thr Ala Thr Tyr Tyr Cys
                85                  90                  95

Ala Ser Phe Asp Tyr Ala His Ala Met Asp Tyr Trp Gly Gln Gly Thr
                100                 105                 110

Thr Val Thr Val Ser Ser
            115

<210> SEQ ID NO 42
<211> LENGTH: 354
<212> TYPE: DNA
<213> ORGANISM: Homo sapiens

<400> SEQUENCE: 42
caagttcaac ttcaagaatc aggccccgga ctcgttaaac cctctcaaac tctctctctt      60
acttgcactg tatccgatta ctctattact tcagactacg cttggaactg gatcagacaa     120
tttcccggaa aaggactcga atggatggga tatatctctt actctggctc aacctcttac     180
aaccccctctc tcaaatctcg aataacaatc tcacgcgata cttctaaaaa tcaattctca     240
cttcaactta actccgttac tgccgccgac actgccgttt actactgtgc ttccttcgat     300
tacgcccacg ctatggatta ttggggacaa ggaactaccg tcactgtcag ctca            354

<210> SEQ ID NO 43
<211> LENGTH: 118
<212> TYPE: PRT
<213> ORGANISM: Homo sapiens

<400> SEQUENCE: 43

Gln Val Gln Leu Gln Glu Ser Gly Pro Gly Leu Val Lys Pro Ser Gln
1               5                   10                  15

Thr Leu Ser Leu Thr Cys Thr Val Ser Asp Tyr Ser Ile Thr Ser Asp
                20                  25                  30

Tyr Ala Trp Asn Trp Ile Arg Gln Phe Pro Gly Lys Gly Leu Glu Trp
            35                  40                  45

Met Gly Tyr Ile Ser Tyr Ser Gly Ser Thr Ser Tyr Asn Pro Ser Leu
50                      55                  60

Lys Ser Arg Ile Thr Ile Ser Arg Asp Thr Ser Lys Asn Gln Phe Ser
65                  70                  75                  80

Leu Gln Leu Asn Ser Val Thr Ala Ala Asp Thr Ala Val Tyr Tyr Cys
                85                  90                  95

Ala Ser Phe Asp Tyr Ala His Ala Met Asp Tyr Trp Gly Gln Gly Thr
                100                 105                 110

Thr Val Thr Val Ser Ser
            115

<210> SEQ ID NO 44
<211> LENGTH: 327

```
<212> TYPE: DNA
<213> ORGANISM: Homo sapiens

<400> SEQUENCE: 44
gaaatagttc ttactcaatc ccccggtaca ctctcagttt ccccaggcga acgcgtcact    60
ttttcttgca gagcatcaca atcaatcggc acttcaattc attggtatca acaaaaaaca   120
ggacaggccc cacgacttct tattaaatat gcatcagaac gagccacagg catcccagac   180
agattttcag gttcaggatc aggcaccgat ttcacactta caatatccag agtcgaatca   240
gaagattttg cagattacta ttgtcaacaa ataaacagct ggcccactac attcggacaa   300
ggcacaaaac tcgaaattaa acgtacg                                       327

<210> SEQ ID NO 45
<211> LENGTH: 109
<212> TYPE: PRT
<213> ORGANISM: Homo sapiens

<400> SEQUENCE: 45

Glu Ile Val Leu Thr Gln Ser Pro Gly Thr Leu Ser Val Ser Pro Gly
1               5                   10                  15

Glu Arg Val Thr Phe Ser Cys Arg Ala Ser Gln Ser Ile Gly Thr Ser
            20                  25                  30

Ile His Trp Tyr Gln Gln Lys Thr Gly Gln Ser Pro Arg Leu Leu Ile
        35                  40                  45

Lys Tyr Ala Ser Glu Arg Ile Ser Gly Ile Pro Asp Arg Phe Ser Gly
    50                  55                  60

Ser Gly Ser Gly Thr Asp Phe Thr Leu Thr Ile Ser Arg Val Glu Ser
65                  70                  75                  80

Glu Asp Phe Ala Asp Tyr Tyr Cys Gln Gln Ile Asn Ser Trp Pro Thr
                85                  90                  95

Thr Phe Gly Gln Gly Thr Lys Leu Glu Ile Lys Arg Thr
            100                 105

<210> SEQ ID NO 46
<211> LENGTH: 327
<212> TYPE: DNA
<213> ORGANISM: Homo sapiens

<400> SEQUENCE: 46
gaaatagttc ttactcaatc ccccggtaca ctctcagttt ccccaggcga acgcgtcact    60
ttttcttgca gagcatcaca atcaatcggc acttcaattc attggtatca acaaaaaaca   120
ggacaggccc cacgacttct tattaaatat gcatcagaac gagccacagg catcccagac   180
agattttcag gttcaggatc aggcaccgat ttcacactta caatatccag agtcgaatca   240
gaagattttg cagattacta ttgtcaacaa ataaacagct ggcccactac attcggacaa   300
ggcacaaaac tcgaaattaa acgtacg                                       327

<210> SEQ ID NO 47
<211> LENGTH: 109
<212> TYPE: PRT
<213> ORGANISM: Homo sapiens

<400> SEQUENCE: 47

Glu Ile Val Leu Thr Gln Ser Pro Gly Thr Leu Ser Val Ser Pro Gly
1               5                   10                  15

Glu Arg Val Thr Phe Ser Cys Arg Ala Ser Gln Ser Ile Gly Thr Ser
            20                  25                  30
```

-continued

Ile His Trp Tyr Gln Gln Lys Thr Gly Gln Ala Pro Arg Leu Leu Ile
        35                  40                  45

Lys Tyr Ala Ser Glu Arg Ala Thr Gly Ile Pro Asp Arg Phe Ser Gly
 50                  55                  60

Ser Gly Ser Gly Thr Asp Phe Thr Leu Thr Ile Ser Arg Val Glu Ser
 65                  70                  75                  80

Glu Asp Phe Ala Asp Tyr Tyr Cys Gln Gln Ile Asn Ser Trp Pro Thr
                 85                  90                  95

Thr Phe Gly Gln Gly Thr Lys Leu Glu Ile Lys Arg Thr
                100                 105

<210> SEQ ID NO 48
<211> LENGTH: 109
<212> TYPE: PRT
<213> ORGANISM: Homo sapiens

<400> SEQUENCE: 48

Asp Ile Leu Leu Thr Gln Ser Pro Ala Ile Leu Ser Val Ser Pro Gly
 1               5                  10                  15

Glu Arg Val Ser Phe Ser Cys Arg Ala Ser Gln Ser Ile Gly Thr Ser
                 20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Asp Arg Phe Ser Gly
 50                  55                  60

Ser Gly Ser Gly Thr Asp Phe Thr Leu Thr Ile Ser Arg Val Glu Ser
 65                  70                  75                  80

Glu Asp Phe Ala Asp Tyr Tyr Cys Gln Gln Ile Asn Ser Trp Pro Thr
                 85                  90                  95

Thr Phe Gly Gln Gly Thr Lys Leu Glu Ile Lys Arg Thr
                100                 105

<210> SEQ ID NO 49
<211> LENGTH: 111
<212> TYPE: PRT
<213> ORGANISM: Homo sapiens
<220> FEATURE:
<221> NAME/KEY: misc_feature
<222> LOCATION: (98)..(98)
<223> OTHER INFORMATION: Xaa= any amino acid

<400> SEQUENCE: 49

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Xaa Thr Phe Gly Gln Gly Thr Lys Val Glu Ile Lys Arg Thr
                100                 105                 110

<210> SEQ ID NO 50
<211> LENGTH: 108

<212> TYPE: PRT
<213> ORGANISM: Homo sapiens

<400> SEQUENCE: 50

```
Asp Val Val Met Thr Gln Ser Pro Ala Phe Leu Ser Val Thr Pro Gly
1               5                   10                  15

Glu Lys Val Thr Ile Thr Cys Gln Ala Ser Glu Gly Ile Gly Asn Tyr
            20                  25                  30

Leu Tyr Trp Tyr Gln Gln Lys Pro Asp Gln Ala Lys Leu Leu Ile Lys
        35                  40                  45

Tyr Ala Ser Gln Ser Ile Ser Gly Val Pro Ser Arg Phe Ser Gly Ser
50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Gly Asn Lys His Pro Leu Thr
                85                  90                  95

Phe Gly Gly Gly Thr Lys Val Glu Ile Lys Arg Thr
            100                 105
```

<210> SEQ ID NO 51
<211> LENGTH: 109
<212> TYPE: PRT
<213> ORGANISM: Artificial sequence
<220> FEATURE:
<223> OTHER INFORMATION: Low Risk Light Chain vs. VK6 Subgroup 2-1-(1) A14:

<400> SEQUENCE: 51

```
Asp Ile Val Leu Thr Gln Ser Pro Ala Phe Leu Ser Val Thr Pro Gly
1               5                   10                  15

Glu Lys Val Thr Phe Thr Cys Gln Ala Ser Gln Ser Ile Gly Thr Ser
            20                  25                  30

Ile His Trp Tyr Gln Gln Lys Thr Asp Gln Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Val Glu Ala
65                  70                  75                  80

Glu Asp Ala Ala Asp Tyr Tyr Cys Gln Gln Ile Asn Ser Trp Pro Thr
                85                  90                  95

Thr Phe Gly Gly Gly Thr Lys Leu Glu Ile Lys Arg Thr
            100                 105
```

<210> SEQ ID NO 52
<211> LENGTH: 327
<212> TYPE: DNA
<213> ORGANISM: Homo sapiens

<400> SEQUENCE: 52

```
gacatagttc tcacacaatc accagcattc ctctcagtta cacccggcga aaaagtaacc      60
tttacctgtc aggcttctca atctatcggc acttctattc actggtatca acaaaaaacc    120
gatcaagctc ctaaactcct cataaaatac gcatccgaat ccatctccgg tatcccctcc    180
agattttcag gctccggctc cggcacagat ttcaccctta ccattagctc agttgaagcc    240
gaagacgcag ctgattacta ctgtcaacaa ataaactcat ggcccactac tttcggcggc    300
ggcactaaac tcgaaataaa acgtacg                                        327
```

<210> SEQ ID NO 53

```
<211> LENGTH: 109
<212> TYPE: PRT
<213> ORGANISM: Homo sapiens

<400> SEQUENCE: 53

Asp Ile Val Leu Thr Gln Ser Pro Ala Phe Leu Ser Val Thr Pro Gly
1               5                   10                  15

Glu Lys Val Thr Phe Thr Cys Gln Ala Ser Gln Ser Ile Gly Thr Ser
            20                  25                  30

Ile His Trp Tyr Gln Gln Lys Thr Asp Gln Ala Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Val Glu Ala
65                  70                  75                  80

Glu Asp Ala Ala Asp Tyr Tyr Cys Gln Gln Ile Asn Ser Trp Pro Thr
                85                  90                  95

Thr Phe Gly Gly Gly Thr Lys Leu Glu Ile Lys Arg Thr
            100                 105

<210> SEQ ID NO 54
<211> LENGTH: 99
<212> TYPE: PRT
<213> ORGANISM: Homo sapiens

<400> SEQUENCE: 54

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ile Asn Ser Trp Pro Thr
                85                  90                  95

Thr Phe Gly

<210> SEQ ID NO 55
<211> LENGTH: 95
<212> TYPE: PRT
<213> ORGANISM: Homo sapiens

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95
```

-continued

<210> SEQ ID NO 56
<211> LENGTH: 101
<212> TYPE: PRT
<213> ORGANISM: Homo sapiens

<400> SEQUENCE: 56

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro
            100

<210> SEQ ID NO 57
<211> LENGTH: 96
<212> TYPE: PRT
<213> ORGANISM: Homo sapiens

<400> SEQUENCE: 57

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 58
<211> LENGTH: 101
<212> TYPE: PRT
<213> ORGANISM: Homo sapiens

<400> SEQUENCE: 58

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln

```
                    85                  90                  95

Tyr Tyr Ser Thr Pro
                100

<210> SEQ ID NO 59
<211> LENGTH: 95
<212> TYPE: PRT
<213> ORGANISM: Homo sapiens

<400> SEQUENCE: 59

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro
                85                  90                  95

<210> SEQ ID NO 60
<211> LENGTH: 95
<212> TYPE: PRT
<213> ORGANISM: Homo sapiens

<400> SEQUENCE: 60

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 61
<211> LENGTH: 52
<212> TYPE: PRT
<213> ORGANISM: Mus musculus

<400> SEQUENCE: 61

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser
    50

<210> SEQ ID NO 62
<211> LENGTH: 57
```

```
<212> TYPE: PRT
<213> ORGANISM: Homo sapiens
<220> FEATURE:
<221> NAME/KEY: misc_feature
<222> LOCATION: (31)..(33)
<223> OTHER INFORMATION: Xaa= any amino acid
<220> FEATURE:
<221> NAME/KEY: misc_feature
<222> LOCATION: (36)..(37)
<223> OTHER INFORMATION: Xaa= any amino acid
<220> FEATURE:
<221> NAME/KEY: misc_feature
<222> LOCATION: (39)..(39)
<223> OTHER INFORMATION: Xaa= any amino acid
<220> FEATURE:
<221> NAME/KEY: misc_feature
<222> LOCATION: (55)..(55)
<223> OTHER INFORMATION: Xaa= any amino acid

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Leu Val Xaa Xaa
            20                  25                  30

Xaa Ile Ser Xaa Xaa Leu Xaa Trp Tyr Gln Gln Lys Pro Gly Lys Ala
        35                  40                  45

Pro Lys Leu Leu Ile Tyr Xaa Ala Ser
    50                  55

<210> SEQ ID NO 63
<211> LENGTH: 58
<212> TYPE: PRT
<213> ORGANISM: Homo sapiens
<220> FEATURE:
<221> NAME/KEY: misc_feature
<222> LOCATION: (33)..(33)
<223> OTHER INFORMATION: Xaa= any amino acid
<220> FEATURE:
<221> NAME/KEY: misc_feature
<222> LOCATION: (36)..(37)
<223> OTHER INFORMATION: Xaa= any amino acid
<220> FEATURE:
<221> NAME/KEY: misc_feature
<222> LOCATION: (56)..(57)
<223> OTHER INFORMATION: Xaa= any amino acid

<400> SEQUENCE: 63

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Xaa Asp Gly Xaa Xaa Tyr Leu Asn Trp Tyr Leu Gln Lys Pro Gly Gln
        35                  40                  45

Ser Pro Gln Leu Leu Ile Tyr Xaa Xaa Ser
    50                  55

<210> SEQ ID NO 64
<211> LENGTH: 53
<212> TYPE: PRT
<213> ORGANISM: Homo sapiens

<400> SEQUENCE: 64

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
```

```
                35                  40                  45

Ile Tyr Gly Ala Ser
    50
```

<210> SEQ ID NO 65
<211> LENGTH: 58
<212> TYPE: PRT
<213> ORGANISM: Homo sapiens

<400> SEQUENCE: 65

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser
    50                  55
```

<210> SEQ ID NO 66
<211> LENGTH: 52
<212> TYPE: PRT
<213> ORGANISM: Homo sapiens

<400> SEQUENCE: 66

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser
    50
```

<210> SEQ ID NO 67
<211> LENGTH: 58
<212> TYPE: PRT
<213> ORGANISM: Homo sapiens

<400> SEQUENCE: 67

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser
    50                  55
```

<210> SEQ ID NO 68
<211> LENGTH: 53
<212> TYPE: PRT
<213> ORGANISM: Homo sapiens

<400> SEQUENCE: 68

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
```

```
                35                  40                  45

Ile Tyr Gly Ala Ser
    50

<210> SEQ ID NO 69
<211> LENGTH: 58
<212> TYPE: PRT
<213> ORGANISM: Homo sapiens

<400> SEQUENCE: 69

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser
    50                  55

<210> SEQ ID NO 70
<211> LENGTH: 52
<212> TYPE: PRT
<213> ORGANISM: Homo sapiens

<400> SEQUENCE: 70

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr
    50

<210> SEQ ID NO 71
<211> LENGTH: 52
<212> TYPE: PRT
<213> ORGANISM: Homo sapiens

<400> SEQUENCE: 71

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser
    50

<210> SEQ ID NO 72
<211> LENGTH: 57
<212> TYPE: PRT
<213> ORGANISM: Mus musculus

<400> SEQUENCE: 72

Glu Ser Ile Ser Gly Ile Pro Ser Arg Phe Ser Gly Ser Gly Ser Gly
1               5                   10                  15

Thr Asp Phe Thr Leu Ser Ile Asn Ser Val Glu Ser Glu Asp Ile Ala
            20                  25                  30

Asp Tyr Tyr Cys Gln Gln Ile Asn Ser Trp Pro Thr Thr Phe Gly Gly
```

```
                35                  40                  45
Gly Thr Lys Leu Glu Ile Lys Arg Ala
    50                  55
```

<210> SEQ ID NO 73
<211> LENGTH: 58
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa= any amino acid
<220> FEATURE:
<221> NAME/KEY: misc_feature
<222> LOCATION: (3)..(3)
<223> OTHER INFORMATION: Xaa= any amino acid
<220> FEATURE:
<221> NAME/KEY: misc_feature
<222> LOCATION: (39)..(42)
<223> OTHER INFORMATION: Xaa= any amino acid
<220> FEATURE:
<221> NAME/KEY: misc_feature
<222> LOCATION: (45)..(45)
<223> OTHER INFORMATION: Xaa= any amino acid

<400> SEQUENCE: 73

```
Xaa Leu Xaa Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys Gln Gln Xaa Xaa Xaa Xaa Pro Glu Xaa Thr Phe Gly
        35                  40                  45

Gln Gly Thr Lys Val Glu Ile Lys Arg Thr
    50                  55
```

<210> SEQ ID NO 74
<211> LENGTH: 58
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa= any amino acid
<220> FEATURE:
<221> NAME/KEY: misc_feature
<222> LOCATION: (40)..(40)
<223> OTHER INFORMATION: Xaa= any amino acid
<220> FEATURE:
<221> NAME/KEY: misc_feature
<222> LOCATION: (42)..(42)
<223> OTHER INFORMATION: Xaa= any amino acid
<220> FEATURE:
<221> NAME/KEY: misc_feature
<222> LOCATION: (45)..(45)
<223> OTHER INFORMATION: Xaa= any amino acid

<400> SEQUENCE: 74

```
Asn Arg Xaa Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys Met Gln Ala Xaa Gln Xaa Pro Arg Xaa Thr Phe Gly
        35                  40                  45

Gln Gly Thr Lys Val Glu Ile Lys Arg Thr
    50                  55
```

<210> SEQ ID NO 75
<211> LENGTH: 58

```
<212> TYPE: PRT
<213> ORGANISM: Homo sapiens
<220> FEATURE:
<221> NAME/KEY: misc_feature
<222> LOCATION: (45)..(45)
<223> OTHER INFORMATION: Xaa= any amino acid

<400> SEQUENCE: 75

Ser Arg Ala Thr Gly Ile Pro Asp Arg Phe Ser Gly Ser Gly Ser Gly
1               5                   10                  15

Thr Asp Phe Thr Leu Thr Ile Ser Arg Leu Glu Pro Glu Asp Phe Ala
            20                  25                  30

Val Tyr Tyr Cys Gln Gln Tyr Gly Ser Ser Pro Xaa Thr Phe Gly
        35                  40                  45

Gln Gly Thr Lys Val Glu Ile Lys Arg Thr
    50                  55

<210> SEQ ID NO 76
<211> LENGTH: 57
<212> TYPE: PRT
<213> ORGANISM: Homo sapiens
<220> FEATURE:
<221> NAME/KEY: misc_feature
<222> LOCATION: (44)..(44)
<223> OTHER INFORMATION: Xaa= any amino acid

<400> SEQUENCE: 76

Thr Arg Glu Ser Gly Val Pro Asp Arg Phe Ser Gly Ser Gly Ser Gly
1               5                   10                  15

Thr Asp Phe Thr Leu Thr Ile Ser Ser Leu Gln Ala Glu Asp Val Ala
            20                  25                  30

Val Tyr Tyr Cys Gln Gln Tyr Tyr Ser Thr Pro Xaa Thr Phe Gly Gln
        35                  40                  45

Gly Thr Lys Val Glu Ile Lys Arg Thr
    50                  55

<210> SEQ ID NO 77
<211> LENGTH: 57
<212> TYPE: PRT
<213> ORGANISM: Homo sapiens

<400> SEQUENCE: 77

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys Gln Gln Ser Tyr Ser Thr Pro Leu Thr Phe Gly Gly
        35                  40                  45

Gly Thr Lys Val Glu Ile Lys Arg Thr
    50                  55

<210> SEQ ID NO 78
<211> LENGTH: 57
<212> TYPE: PRT
<213> ORGANISM: Homo sapiens

<400> SEQUENCE: 78

Tyr Arg Ala Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys Met Gln Arg Ile Glu Phe Pro Leu Thr Phe Gly Gly
```

```
                35                  40                  45

Gly Thr Lys Val Glu Ile Lys Arg Thr
     50                  55

<210> SEQ ID NO 79
<211> LENGTH: 57
<212> TYPE: PRT
<213> ORGANISM: Homo sapiens

<400> SEQUENCE: 79

Ser Arg Ala Thr Gly Ile Pro Asp Arg Phe Ser Gly Ser Gly Ser Gly
1               5                   10                  15

Thr Asp Phe Thr Leu Thr Ile Ser Arg Leu Glu Pro Glu Asp Phe Ala
            20                  25                  30

Val Tyr Tyr Cys Gln Gln Tyr Gly Ser Ser Pro Leu Thr Phe Gly Gly
        35                  40                  45

Gly Thr Lys Val Glu Ile Lys Arg Thr
     50                  55

<210> SEQ ID NO 80
<211> LENGTH: 57
<212> TYPE: PRT
<213> ORGANISM: Homo sapiens

<400> SEQUENCE: 80

Thr Arg Glu Ser Gly Val Pro Asp Arg Phe Ser Gly Ser Gly Ser Gly
1               5                   10                  15

Thr Asp Phe Thr Leu Thr Ile Ser Ser Leu Gln Ala Glu Asp Val Ala
            20                  25                  30

Val Tyr Tyr Cys Gln Gln Tyr Tyr Ser Thr Pro Leu Thr Phe Gly Gly
        35                  40                  45

Gly Thr Lys Val Glu Ile Lys Arg Thr
     50                  55

<210> SEQ ID NO 81
<211> LENGTH: 57
<212> TYPE: PRT
<213> ORGANISM: Homo sapiens

<400> SEQUENCE: 81

Thr Leu Val Pro Gly Ile Pro Pro Arg Phe Ser Gly Ser Gly Tyr Gly
1               5                   10                  15

Thr Asp Phe Thr Leu Thr Ile Asn Asn Ile Glu Ser Glu Asp Ala Ala
            20                  25                  30

Tyr Tyr Phe Cys Leu Gln His Asp Asn Phe Pro Leu Thr Phe Gly Gly
        35                  40                  45

Gly Thr Lys Val Glu Ile Lys Arg Thr
     50                  55

<210> SEQ ID NO 82
<211> LENGTH: 57
<212> TYPE: PRT
<213> ORGANISM: Homo sapiens

<400> SEQUENCE: 82

Gln Ser Phe Ser Gly Val Pro Ser Arg Phe Ser Gly Ser Gly Ser Gly
1               5                   10                  15

Thr Asp Phe Thr Leu Thr Ile Asn Ser Leu Glu Ala Glu Asp Ala Ala
            20                  25                  30

Thr Tyr Tyr Cys His Gln Ser Ser Ser Leu Pro Leu Thr Phe Gly Gly
```

```
                35                  40                  45
Gly Thr Lys Val Glu Ile Lys Arg Thr
         50                  55
```

```
<210> SEQ ID NO 83
<211> LENGTH: 101
<212> TYPE: PRT
<213> ORGANISM: Homo sapiens

<400> SEQUENCE: 83

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Ser Phe Asp Tyr
            100
```

```
<210> SEQ ID NO 84
<211> LENGTH: 98
<212> TYPE: PRT
<213> ORGANISM: Homo sapiens

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg
```

```
<210> SEQ ID NO 85
<211> LENGTH: 100
<212> TYPE: PRT
<213> ORGANISM: Homo sapiens

<400> SEQUENCE: 85

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
```

-continued

```
                50                  55                  60
Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Arg
            100

<210> SEQ ID NO 86
<211> LENGTH: 98
<212> TYPE: PRT
<213> ORGANISM: Homo sapiens

<400> SEQUENCE: 86

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
             35                  40                  45

Ala Asn Ile Lys Gln Asp Gly Ser Glu Lys Tyr Tyr Val Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 87
<211> LENGTH: 98
<212> TYPE: PRT
<213> ORGANISM: Homo sapiens

<400> SEQUENCE: 87

Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
             35                  40                  45

Ile Gly Glu Ile Tyr His Ser Gly Ser Thr Asn Tyr Asn Pro Ser Leu
         50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg

<210> SEQ ID NO 88
<211> LENGTH: 98
<212> TYPE: PRT
<213> ORGANISM: Homo sapiens

<400> SEQUENCE: 88

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                20                  25                  30
```

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg

<210> SEQ ID NO 89
<211> LENGTH: 101
<212> TYPE: PRT
<213> ORGANISM: Homo sapiens

<400> SEQUENCE: 89

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
 50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg
            100

<210> SEQ ID NO 90
<211> LENGTH: 98
<212> TYPE: PRT
<213> ORGANISM: Homo sapiens

<400> SEQUENCE: 90

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
 50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
            85                  90                  95

Ala Arg

<210> SEQ ID NO 91
<211> LENGTH: 58
<212> TYPE: PRT
<213> ORGANISM: Mus musculus

<400> SEQUENCE: 91

```
Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Ile Thr Ser Asp
                20                  25                  30

Tyr Ala Trp Asn Trp Ile Arg Gln Phe Pro Gly Asn Lys Leu Glu Trp
            35                  40                  45

Met Gly Tyr Ile Ser Tyr Ser Gly Ser Thr
            50                  55
```

<210> SEQ ID NO 92
<211> LENGTH: 59
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa= any amino acid
<220> FEATURE:
<221> NAME/KEY: misc_feature
<222> LOCATION: (16)..(16)
<223> OTHER INFORMATION: Xaa= any amino acid
<220> FEATURE:
<221> NAME/KEY: misc_feature
<222> LOCATION: (30)..(30)
<223> OTHER INFORMATION: Xaa= any amino acid
<220> FEATURE:
<221> NAME/KEY: misc_feature
<222> LOCATION: (33)..(33)
<223> OTHER INFORMATION: Xaa= any amino acid
<220> FEATURE:
<221> NAME/KEY: misc_feature
<222> LOCATION: (35)..(35)
<223> OTHER INFORMATION: Xaa= any amino acid
<220> FEATURE:
<221> NAME/KEY: misc_feature
<222> LOCATION: (50)..(50)
<223> OTHER INFORMATION: Xaa= any amino acid
<220> FEATURE:
<221> NAME/KEY: misc_feature
<222> LOCATION: (52)..(52)
<223> OTHER INFORMATION: Xaa= any amino acid
<220> FEATURE:
<221> NAME/KEY: misc_feature
<222> LOCATION: (55)..(56)
<223> OTHER INFORMATION: Xaa= any amino acid
<220> FEATURE:
<221> NAME/KEY: misc_feature
<222> LOCATION: (58)..(58)
<223> OTHER INFORMATION: Xaa= any amino acid

<400> SEQUENCE: 92

```
Xaa Val Gln Leu Val Gln Ser Gly Ala Glu Val Lys Lys Pro Gly Xaa
1               5                   10                  15

Ser Val Lys Val Ser Cys Lys Ala Ser Gly Tyr Thr Phe Xaa Ser Tyr
                20                  25                  30

Xaa Ile Xaa Trp Val Arg Gln Ala Pro Gly Gln Gly Leu Glu Trp Met
            35                  40                  45

Gly Xaa Ile Xaa Pro Tyr Xaa Xaa Gly Xaa Thr
            50                  55
```

<210> SEQ ID NO 93
<211> LENGTH: 62
<212> TYPE: PRT
<213> ORGANISM: Homo sapiens
<220> FEATURE:
<221> NAME/KEY: misc_feature
<222> LOCATION: (23)..(23)
<223> OTHER INFORMATION: Xaa= any amino acid
<220> FEATURE:
<221> NAME/KEY: misc_feature
<222> LOCATION: (27)..(27)

```
<223> OTHER INFORMATION: Xaa= any amino acid
<220> FEATURE:
<221> NAME/KEY: misc_feature
<222> LOCATION: (29)..(29)
<223> OTHER INFORMATION: Xaa= any amino acid
<220> FEATURE:
<221> NAME/KEY: misc_feature
<222> LOCATION: (32)..(37)
<223> OTHER INFORMATION: Xaa= any amino acid
<220> FEATURE:
<221> NAME/KEY: misc_feature
<222> LOCATION: (52)..(52)
<223> OTHER INFORMATION: Xaa= any amino acid
<220> FEATURE:
<221> NAME/KEY: misc_feature
<222> LOCATION: (58)..(59)
<223> OTHER INFORMATION: Xaa= any amino acid
<220> FEATURE:
<221> NAME/KEY: misc_feature
<222> LOCATION: (61)..(61)
<223> OTHER INFORMATION: Xaa= any amino acid

<400> SEQUENCE: 93

Gln Val Gln Leu Gln Glu Ser Gly Pro Gly Leu Val Lys Pro Ser Gln
1               5                   10                  15

Thr Leu Ser Leu Thr Cys Xaa Val Ser Gly Xaa Ser Xaa Ser Ser Xaa
            20                  25                  30

Xaa Xaa Xaa Xaa Xaa Trp Ile Arg Gln Pro Pro Gly Lys Gly Leu Glu
        35                  40                  45

Trp Ile Gly Xaa Ile Tyr Tyr Arg Ala Xaa Gly Xaa Thr
50                  55                  60

<210> SEQ ID NO 94
<211> LENGTH: 60
<212> TYPE: PRT
<213> ORGANISM: Homo sapiens
<220> FEATURE:
<221> NAME/KEY: misc_feature
<222> LOCATION: (31)..(31)
<223> OTHER INFORMATION: Xaa= any amino acid
<220> FEATURE:
<221> NAME/KEY: misc_feature
<222> LOCATION: (33)..(33)
<223> OTHER INFORMATION: Xaa= any amino acid
<220> FEATURE:
<221> NAME/KEY: misc_feature
<222> LOCATION: (35)..(35)
<223> OTHER INFORMATION: Xaa= any amino acid
<220> FEATURE:
<221> NAME/KEY: misc_feature
<222> LOCATION: (49)..(50)
<223> OTHER INFORMATION: Xaa= any amino acid
<220> FEATURE:
<221> NAME/KEY: misc_feature
<222> LOCATION: (52)..(53)
<223> OTHER INFORMATION: Xaa= any amino acid
<220> FEATURE:
<221> NAME/KEY: misc_feature
<222> LOCATION: (55)..(56)
<223> OTHER INFORMATION: Xaa= any amino acid
<220> FEATURE:
<221> NAME/KEY: misc_feature
<222> LOCATION: (58)..(59)
<223> OTHER INFORMATION: Xaa= any amino acid

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Tyr
            20                  25                  30

Xaa Met Xaa Trp Val Arg Gln Ala Pro Gly Lys Gly Leu Glu Trp Val
        35                  40                  45
```

```
Xaa Xaa Ile Xaa Xaa Lys Xaa Xaa Gly Xaa Xaa Thr
        50                  55                  60

<210> SEQ ID NO 95
<211> LENGTH: 58
<212> TYPE: PRT
<213> ORGANISM: Homo sapiens

<400> SEQUENCE: 95

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr
    50                  55

<210> SEQ ID NO 96
<211> LENGTH: 59
<212> TYPE: PRT
<213> ORGANISM: Homo sapiens

<400> SEQUENCE: 96

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys
    50                  55

<210> SEQ ID NO 97
<211> LENGTH: 58
<212> TYPE: PRT
<213> ORGANISM: Homo sapiens

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys
    50                  55

<210> SEQ ID NO 98
<211> LENGTH: 58
<212> TYPE: PRT
<213> ORGANISM: Homo sapiens

<400> SEQUENCE: 98

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45
```

Ile Gly Glu Ile Tyr His Ser Gly Ser Thr
    50                  55

<210> SEQ ID NO 99
<211> LENGTH: 58
<212> TYPE: PRT
<213> ORGANISM: Homo sapiens

<400> SEQUENCE: 99

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr
    50                  55

<210> SEQ ID NO 100
<211> LENGTH: 61
<212> TYPE: PRT
<213> ORGANISM: Homo sapiens

<400> SEQUENCE: 100

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn
    50                  55                  60

<210> SEQ ID NO 101
<211> LENGTH: 58
<212> TYPE: PRT
<213> ORGANISM: Homo sapiens

<400> SEQUENCE: 101

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro
    50                  55

<210> SEQ ID NO 102
<211> LENGTH: 60
<212> TYPE: PRT
<213> ORGANISM: Mus musculus

<400> SEQUENCE: 102

Ser Tyr Asn Pro Ser Leu Lys Ser Arg Ile Ser Ile Thr Arg Asp Thr
1               5                   10                  15

Ser Lys Asn Gln Phe Phe Leu Gln Leu Asn Ser Val Thr Thr Glu Asp
            20                  25                  30

Thr Ala Thr Tyr Tyr Cys Ala Ser Phe Asp Tyr Ala His Ala Met Asp
        35                  40                  45

```
Tyr Trp Gly Gln Gly Thr Ser Val Thr Val Ser Ser
     50                  55                  60

<210> SEQ ID NO 103
<211> LENGTH: 70
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa= any amino acid
<220> FEATURE:
<221> NAME/KEY: misc_feature
<222> LOCATION: (16)..(16)
<223> OTHER INFORMATION: Xaa= any amino acid
<220> FEATURE:
<221> NAME/KEY: misc_feature
<222> LOCATION: (31)..(31)
<223> OTHER INFORMATION: Xaa= any amino acid
<220> FEATURE:
<221> NAME/KEY: misc_feature
<222> LOCATION: (41)..(53)
<223> OTHER INFORMATION: Xaa= any amino acid
<220> FEATURE:
<221> NAME/KEY: misc_feature
<222> LOCATION: (55)..(56)
<223> OTHER INFORMATION: Xaa= any amino acid
<220> FEATURE:
<221> NAME/KEY: misc_feature
<222> LOCATION: (59)..(59)
<223> OTHER INFORMATION: Xaa= any amino acid

<400> SEQUENCE: 103

Asn Tyr Ala Gln Lys Phe Gln Gly Arg Val Thr Ile Thr Xaa Asp Xaa
1               5                   10                  15

Ser Thr Ser Thr Ala Tyr Met Glu Leu Ser Ser Leu Arg Ser Xaa Asp
            20                  25                  30

Thr Ala Val Tyr Tyr Cys Ala Arg Xaa Xaa Xaa Xaa Xaa Xaa Xaa Xaa
        35                  40                  45

Xaa Xaa Xaa Xaa Xaa Asp Xaa Xaa Phe Asp Xaa Trp Gly Gln Gly Thr
    50                  55                  60

Leu Val Thr Val Ser Ser
65                  70

<210> SEQ ID NO 104
<211> LENGTH: 70
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa= any amino acid
<220> FEATURE:
<221> NAME/KEY: misc_feature
<222> LOCATION: (24)..(24)
<223> OTHER INFORMATION: Xaa= any amino acid
<220> FEATURE:
<221> NAME/KEY: misc_feature
<222> LOCATION: (26)..(26)
<223> OTHER INFORMATION: Xaa= any amino acid
<220> FEATURE:
<221> NAME/KEY: misc_feature
<222> LOCATION: (41)..(56)
<223> OTHER INFORMATION: Xaa= any amino acid
<220> FEATURE:
<221> NAME/KEY: misc_feature
<222> LOCATION: (59)..(59)
<223> OTHER INFORMATION: Xaa= any amino acid
<220> FEATURE:
<221> NAME/KEY: misc_feature
<222> LOCATION: (65)..(65)
<223> OTHER INFORMATION: Xaa= any amino acid
```

<400> SEQUENCE: 104

Xaa Tyr Asn Pro Ser Leu Lys Ser Arg Val Thr Ile Ser Val Asp Thr
1               5                   10                  15

Ser Lys Asn Gln Phe Ser Leu Xaa Leu Xaa Ser Val Thr Ala Ala Asp
            20                  25                  30

Thr Ala Val Tyr Tyr Cys Ala Arg Xaa Xaa Xaa Xaa Xaa Xaa Xaa Xaa
        35                  40                  45

Xaa Xaa Xaa Xaa Xaa Xaa Xaa Phe Asp Xaa Trp Gly Gln Gly Thr
    50                  55                  60

Xaa Val Thr Val Ser Ser
65                  70

<210> SEQ ID NO 105
<211> LENGTH: 70
<212> TYPE: PRT
<213> ORGANISM: Homo sapiens
<220> FEATURE:
<221> NAME/KEY: misc_feature
<222> LOCATION: (40)..(52)
<223> OTHER INFORMATION: Xaa= any amino acid
<220> FEATURE:
<221> NAME/KEY: misc_feature
<222> LOCATION: (55)..(56)
<223> OTHER INFORMATION: Xaa= any amino acid
<220> FEATURE:
<221> NAME/KEY: misc_feature
<222> LOCATION: (59)..(59)
<223> OTHER INFORMATION: Xaa= any amino acid

<400> SEQUENCE: 105

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys Ala Xaa Xaa Xaa Xaa Xaa Xaa Xaa Xaa Xaa
        35                  40                  45

Xaa Xaa Xaa Xaa Tyr Tyr Xaa Xaa Phe Asp Xaa Trp Gly Gln Gly Thr
    50                  55                  60

Leu Val Thr Val Ser Ser
65                  70

<210> SEQ ID NO 106
<211> LENGTH: 70
<212> TYPE: PRT
<213> ORGANISM: Homo sapiens
<220> FEATURE:
<221> NAME/KEY: misc_feature
<222> LOCATION: (41)..(55)
<223> OTHER INFORMATION: Xaa= any amino acid

<400> SEQUENCE: 106

Asn Tyr Ala Gln Lys Phe Gln Gly Arg Val Thr Met Thr Arg Asp Thr
1               5                   10                  15

Ser Ile Ser Thr Ala Tyr Met Glu Leu Ser Arg Leu Arg Ser Asp Asp
            20                  25                  30

Thr Ala Val Tyr Tyr Cys Ala Arg Xaa Xaa Xaa Xaa Xaa Xaa Xaa Xaa
        35                  40                  45

Xaa Xaa Xaa Xaa Xaa Xaa Xaa Tyr Phe Asp Tyr Trp Gly Gln Gly Thr
    50                  55                  60

Leu Val Thr Val Ser Ser
65                  70

```
<210> SEQ ID NO 107
<211> LENGTH: 70
<212> TYPE: PRT
<213> ORGANISM: Homo sapiens
<220> FEATURE:
<221> NAME/KEY: misc_feature
<222> LOCATION: (42)..(55)
<223> OTHER INFORMATION: Xaa= any amino acid

<400> SEQUENCE: 107

Arg Tyr Ser Pro Ser Leu Lys Ser Arg Leu Thr Ile Thr Lys Asp Thr
1               5                   10                  15

Ser Lys Asn Gln Val Val Leu Thr Met Thr Asn Met Asp Pro Val Asp
            20                  25                  30

Thr Ala Thr Tyr Tyr Cys Ala His Arg Xaa Xaa Xaa Xaa Xaa Xaa Xaa
        35                  40                  45

Xaa Xaa Xaa Xaa Xaa Xaa Xaa Tyr Phe Asp Tyr Trp Gly Gln Gly Thr
    50                  55                  60

Leu Val Thr Val Ser Ser
65                  70

<210> SEQ ID NO 108
<211> LENGTH: 70
<212> TYPE: PRT
<213> ORGANISM: Homo sapiens
<220> FEATURE:
<221> NAME/KEY: misc_feature
<222> LOCATION: (41)..(55)
<223> OTHER INFORMATION: Xaa= any amino acid

<400> SEQUENCE: 108

Tyr Tyr Val Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys Ala Arg Xaa Xaa Xaa Xaa Xaa Xaa Xaa Xaa
        35                  40                  45

Xaa Xaa Xaa Xaa Xaa Xaa Xaa Tyr Phe Asp Tyr Trp Gly Gln Gly Thr
    50                  55                  60

Leu Val Thr Val Ser Ser
65                  70

<210> SEQ ID NO 109
<211> LENGTH: 70
<212> TYPE: PRT
<213> ORGANISM: Homo sapiens
<220> FEATURE:
<221> NAME/KEY: misc_feature
<222> LOCATION: (41)..(55)
<223> OTHER INFORMATION: Xaa= any amino acid

<400> SEQUENCE: 109

Asn Tyr Asn Pro Ser Leu Lys Ser Arg Val Thr Ile Ser Val Asp Lys
1               5                   10                  15

Ser Lys Asn Gln Phe Ser Leu Lys Leu Ser Ser Val Thr Ala Ala Asp
            20                  25                  30

Thr Ala Val Tyr Tyr Cys Ala Arg Xaa Xaa Xaa Xaa Xaa Xaa Xaa Xaa
        35                  40                  45

Xaa Xaa Xaa Xaa Xaa Xaa Xaa Tyr Phe Asp Tyr Trp Gly Gln Gly Thr
    50                  55                  60

Leu Val Thr Val Ser Ser
65                  70
```

```
<210> SEQ ID NO 110
<211> LENGTH: 70
<212> TYPE: PRT
<213> ORGANISM: Homo sapiens
<220> FEATURE:
<221> NAME/KEY: misc_feature
<222> LOCATION: (41)..(55)
<223> OTHER INFORMATION: Xaa= any amino acid

<400> SEQUENCE: 110

Arg Tyr Ser Pro Ser Phe Gln Gly Gln Val Thr Ile Ser Ala Asp Lys
1               5                   10                  15

Ser Ile Ser Thr Ala Tyr Leu Gln Trp Ser Ser Leu Lys Ala Ser Asp
            20                  25                  30

Thr Ala Met Tyr Tyr Cys Ala Arg Xaa Xaa Xaa Xaa Xaa Xaa Xaa Xaa
        35                  40                  45

Xaa Xaa Xaa Xaa Xaa Xaa Xaa Tyr Phe Asp Tyr Trp Gly Gln Gly Thr
    50                  55                  60

Leu Val Thr Val Ser Ser
65                  70

<210> SEQ ID NO 111
<211> LENGTH: 70
<212> TYPE: PRT
<213> ORGANISM: Homo sapiens
<220> FEATURE:
<221> NAME/KEY: misc_feature
<222> LOCATION: (41)..(55)
<223> OTHER INFORMATION: Xaa= any amino acid

<400> SEQUENCE: 111

Asp Tyr Ala Val Ser Val Lys Ser Arg Ile Thr Ile Asn Pro Asp Thr
1               5                   10                  15

Ser Lys Asn Gln Phe Ser Leu Gln Leu Asn Ser Val Thr Pro Glu Asp
            20                  25                  30

Thr Ala Val Tyr Tyr Cys Ala Arg Xaa Xaa Xaa Xaa Xaa Xaa Xaa Xaa
        35                  40                  45

Xaa Xaa Xaa Xaa Xaa Xaa Xaa Tyr Phe Asp Tyr Trp Gly Gln Gly Thr
    50                  55                  60

Leu Val Thr Val Ser Ser
65                  70

<210> SEQ ID NO 112
<211> LENGTH: 70
<212> TYPE: PRT
<213> ORGANISM: Homo sapiens
<220> FEATURE:
<221> NAME/KEY: misc_feature
<222> LOCATION: (41)..(55)
<223> OTHER INFORMATION: Xaa= any amino acid

<400> SEQUENCE: 112

Thr Tyr Ala Gln Gly Phe Thr Gly Arg Phe Val Phe Ser Leu Asp Thr
1               5                   10                  15

Ser Val Ser Thr Ala Tyr Leu Gln Ile Cys Ser Leu Lys Ala Glu Asp
            20                  25                  30

Thr Ala Val Tyr Tyr Cys Ala Arg Xaa Xaa Xaa Xaa Xaa Xaa Xaa Xaa
        35                  40                  45

Xaa Xaa Xaa Xaa Xaa Xaa Xaa Tyr Phe Asp Tyr Trp Gly Gln Gly Thr
    50                  55                  60

Leu Val Thr Val Ser Ser
```

<210> SEQ ID NO 113
<211> LENGTH: 1404
<212> TYPE: DNA
<213> ORGANISM: Homo sapiens

<400> SEQUENCE: 113

| | |
|---|---|
| atgggatgga gttgcattat acttttcctc gttgccaccg ccactggagt tcactctgac | 60 |
| gtacaacttc aagaatctgg cccaggtctc gtcaaacctt ctcaaactct ctcactcacc | 120 |
| tgcactgtta ctgactactc tattacatcc gactacgctt ggaactggat ccgacaattt | 180 |
| cctggtaaaa aactcgaatg gatgggttat atttcttact ctggctccac ctcctacaat | 240 |
| ccttctctga atcacgcat cacaatttcc cgcgataccct ctaaaaatca attttcactc | 300 |
| caactcaatt ctgttaccgc cgccgatact gccacctact actgtgcctc ttttgactac | 360 |
| gctcacgcca tggattattg ggacaggggt actaccgtta ccgtaagctc agccagcaca | 420 |
| aagggcccat cggtcttccc cctggcaccc tcctccaaga gcacctctgg gggcacagcg | 480 |
| gccctgggct gcctggtcaa ggactacttc cccgaaccgg tgacggtgtc gtggaactca | 540 |
| ggcgccctga ccagcggcgt gcacaccttc ccggctgtcc tacagtcctc aggactctac | 600 |
| tccctcagca gcgtggtgac cgtgccctcc agcagcttgg gcacccagac ctacatctgc | 660 |
| aacgtgaatc acaagcccag caacaccaag gtggacaaga gagttgagcc caaatcttgt | 720 |
| gacaaaactc acacatgtcc accgtgccca gcacctgaac tcctgggggg accgtcagtc | 780 |
| ttcctcttcc ccccaaaacc caaggacacc ctcatgatct cccggacccc tgaggtcaca | 840 |
| tgcgtggtgg tggacgtgag ccacgaagac cctgaggtca agttcaactg gtacgtggac | 900 |
| ggcgtggagg tgcataatgc caagacaaag ccgcgggagg agcagtacaa cagcacgtac | 960 |
| cgtgtggtca gcgtcctcac cgtcctgcac caggactggc tgaatggcaa ggagtacaag | 1020 |
| tgcaaggtct ccaacaaagc cctcccagcc cccatcgaga aaaccatctc caaagccaaa | 1080 |
| gggcagcccc gagaaccaca ggtgtacacc ctgcccccat cccgggagga tgaccaag | 1140 |
| aaccaggtca gcctgacctg cctggtcaaa ggcttctatc ccagcgacat cgccgtggag | 1200 |
| tgggagagca atgggcagcc ggagaacaac tacaagacca cgcctcccgt gctggactcc | 1260 |
| gacggctcct tcttcctcta tagcaagctc accgtggaca agagcaggtg gcagcagggg | 1320 |
| aacgtcttct catgctccgt gatgcatgag gctctgcaca accactacac gcagaagagc | 1380 |
| ctctccctgt ccccgggtaa atga | 1404 |

<210> SEQ ID NO 114
<211> LENGTH: 467
<212> TYPE: PRT
<213> ORGANISM: Homo sapiens

<400> SEQUENCE: 114

Met Gly Trp Ser Cys Ile Ile Leu Phe Leu Val Ala Thr Ala Thr Gly
1               5                   10                  15

Val His Ser Asp Val Gln Leu Gln Glu Ser Gly Pro Gly Leu Val Lys
            20                  25                  30

Pro Ser Gln Thr Leu Ser Leu Thr Cys Thr Val Thr Asp Tyr Ser Ile
        35                  40                  45

Thr Ser Asp Tyr Ala Trp Asn Trp Ile Arg Gln Phe Pro Gly Lys Lys
    50                  55                  60

Leu Glu Trp Met Gly Tyr Ile Ser Tyr Ser Gly Ser Thr Ser Tyr Asn
65                  70                  75                  80

Pro Ser Leu Lys Ser Arg Ile Thr Ile Ser Arg Asp Thr Ser Lys Asn
            85                  90                  95

Gln Phe Ser Leu Gln Leu Asn Ser Val Thr Ala Ala Asp Thr Ala Thr
            100                 105                 110

Tyr Tyr Cys Ala Ser Phe Asp Tyr Ala His Ala Met Asp Tyr Trp Gly
            115                 120                 125

Gln Gly Thr Thr Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
            210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465

<210> SEQ ID NO 115
<211> LENGTH: 1404
<212> TYPE: DNA

<213> ORGANISM: Homo sapiens

<400> SEQUENCE: 115

```
atgggttggt cttgcatcat tctctttctc gtcgctaccg caactggtgt acactcccaa      60
gttcaacttc aagaatcagg ccccggactc gttaaaccct ctcaaactct ctctcttact     120
tgcactgtat ccgattactc tattacttca gactacgctt ggaactggat cagacaattt     180
cccgaaaag gactcgaatg gatgggatat atctcttact ctggctcaac tcttacaac      240
ccctctctca aatctcgaat aacaatctca cgcgatactt ctaaaaatca attctcactt     300
caacttaact ccgttactgc cgccgacact gccgtttact actgtgcttc cttcgattac     360
gcccacgcta tggattattg gggacaagga actaccgtca ctgtcagctc agccagcaca     420
aagggcccat cggtcttccc cctggcaccc tcctccaaga gcacctctgg ggcacagcg     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga gagttgagcc caaatcttgt     720
gacaaaactc acacatgtcc accgtgccca gcacctgaac tcctgggggg accgtcagtc     780
ttcctcttcc cccaaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcgggagg agcagtacaa cagcacgtac     960
cgtgtggtca gcgtcctcac cgtcctgcac caggactggc tgaatggcaa ggagtacaag    1020
tgcaaggtct ccaacaaagc cctcccagcc cccatcgaga aaaccatctc aaagccaaa     1080
gggcagcccc gagaaccaca ggtgtacacc ctgcccccat cccgggagga gatgaccaag    1140
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta tagcaagctc accgtggaca agagcaggtg gcagcagggg    1320
aacgtcttct catgctccgt gatgcatgag gctctgcaca accactacac gcagaagagc    1380
ctctccctgt ccccgggtaa atga                                          1404
```

<210> SEQ ID NO 116
<211> LENGTH: 467
<212> TYPE: PRT
<213> ORGANISM: Homo sapiens

<400> SEQUENCE: 116

```
Met Gly Trp Ser Cys Ile Ile Leu Phe Leu Val Ala Thr Ala Thr Gly
 1               5                  10                  15

Val His Ser Gln Val Gln Leu Gln Glu Ser Gly Pro Gly Leu Val Lys
             20                  25                  30

Pro Ser Gln Thr Leu Ser Leu Thr Cys Thr Val Ser Asp Tyr Ser Ile
         35                  40                  45

Thr Ser Asp Tyr Ala Trp Asn Trp Ile Arg Gln Phe Pro Gly Lys Gly
     50                  55                  60

Leu Glu Trp Met Gly Tyr Ile Ser Tyr Ser Gly Ser Thr Ser Tyr Asn
 65                  70                  75                  80

Pro Ser Leu Lys Ser Arg Ile Thr Ile Ser Arg Asp Thr Ser Lys Asn
                 85                  90                  95

Gln Phe Ser Leu Gln Leu Asn Ser Val Thr Ala Ala Asp Thr Ala Val
            100                 105                 110
```

```
Tyr Tyr Cys Ala Ser Phe Asp Tyr Ala His Ala Met Asp Tyr Trp Gly
        115                 120                 125

Gln Gly Thr Thr Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 117
<211> LENGTH: 2002
<212> TYPE: DNA
<213> ORGANISM: Homo sapiens

<400> SEQUENCE: 117
atgggatgga gttgcattat acttttcctc gttgccaccg ccactggagt tcactctgac      60
```

```
gtacaacttc aagaatctgg cccaggtctc gtcaaacctt ctcaaactct ctcactcacc      120
tgcactgtta ctgactactc tattacatcc gactacgctt ggaactggat ccgacaattt      180
cctggtaaaa aactcgaatg gatgggttat atttcttact ctggctccac ctcctacaat      240
ccttctctga aatcacgcat cacaatttcc cgcgatacct ctaaaaatca attttcactc      300
caactcaatt ctgttaccgc cgccgatact gccacctact actgtgcctc ttttgactac      360
gctcacgcca tggattattg gggacagggt actaccgtta ccgtaagctc agccagcaca      420
aagggcccat ccgtcttccc cctggcgccc tgctccagga gcacctccga gagcacagcc      480
gccctgggct gcctggtcaa ggactacttc cccgaaccgg tgacggtgtc gtggaactca      540
ggcgccctga ccagcggcgt gcacaccttc ccggctgtcc tacagtcctc aggactctac      600
tccctcagca gcgtggtgac cgtgccctcc agcagcttgg gcacgaagac ctacacctgc      660
aacgtagatc acaagcccag caacaccaag gtggacaaga gagttggtga gaggccagca      720
caggagggga gggtgtctgc tggaagccag gctcagccct cctgcctgga cgcacccccgg      780 ctgtgcagcc ccagcccagg gcagcaaggc atgcccatc tgtctcctca cccggaggcc       840
tctgaccacc ccactcatgc tcaggagag ggtcttctgg attttccac caggctccgg       900 gcagccacag gctggatgcc cctaccccag gccctgcgca tacaggggca ggtgctgcgc      960
tcagacctgc caagagccat atccgggagg accctgcccc tgacctaagc ccaccccaaa     1020
ggccaaactc tccactccct cagctcagac accttctctc ctcccagatc tgagtaactc     1080
ccaatcttct ctctgcagag tccaaatatg gtccccatg cccatcatgc ccaggtaagc      1140
caacccaggc ctcgccctcc agctcaaggc gggacaggtg ccctagagta gcctgcatcc     1200
agggacaggc cccagccggg tgctgacgca tccacctcca tctcttcctc agcacctgag     1260
ttcctggggg gaccatcagt cttcctgttc cccccaaaac ccaaggacac tctcatgatc     1320
tcccggaccc ctgaggtcac gtgcgtggtg gtggacgtga gccaggaaga ccccgaggtc     1380
cagttcaact ggtacgtgga tggcgtggag gtgcataatg ccaagacaaa gccgcgggag     1440
gagcagttca acagcacgta ccgtgtggtc agcgtcctca ccgtcctgca ccaggactgg     1500
ctgaacggca aggagtacaa gtgcaaggtc tccaacaaag gcctcccgtc ctccatcgag     1560
aaaaccatct ccaaagccaa aggtgggacc cacggggtgc gagggccaca tggacagagg     1620
tcagctcggc ccaccctctg ccctgggagt gaccgctgtg ccaacctctg tccctacagg     1680
gcagccccga gagccacagg tgtacaccct gcccccatcc caggaggaga tgaccaagaa     1740
ccaggtcagc ctgacctgcc tggtcaaagg cttctacccc agcgacatcg ccgtggagtg     1800
ggagagcaat gggcagccgg agaacaacta caagaccacg cctcccgtgc tggactccga     1860
cggctccttc ttcctctaca gcaggctaac cgtggacaag agcaggtggc aggaggggaa     1920
tgtcttctca tgctccgtga tgcatgaggc tctgcacaac cactacacac agaagagcct     1980
ctccctgtct ctgggtaaat ga                                              2002
```

<210> SEQ ID NO 118
<211> LENGTH: 1395
<212> TYPE: DNA
<213> ORGANISM: Homo sapiens

<400> SEQUENCE: 118

```
atgggatgga gttgcattat actttctc gttgccaccg ccactggagt tcactctgac       60
gtacaacttc aagaatctgg cccaggtctc gtcaaacctt ctcaaactct ctcactcacc     120
tgcactgtta ctgactactc tattacatcc gactacgctt ggaactggat ccgacaattt     180
```

```
cctggtaaaa aactcgaatg gatgggttat atttcttact ctggctccac ctcctacaat      240
ccttctctga aatcacgcat cacaatttcc cgcgatacct ctaaaaatca attttcactc      300
caactcaatt ctgttaccgc cgccgatact gccacctact actgtgcctc ttttgactac      360
gctcacgcca tggattattg gggacagggt actaccgtta ccgtaagctc agccagcaca      420
aagggcccat ccgtcttccc cctggcgccc tgctccagga gcacctccga gagcacagcc      480
gccctgggct gcctggtcaa ggactacttc cccgaaccgg tgacggtgtc gtggaactca      540
ggcgccctga ccagcggcgt gcacaccttc ccggctgtcc tacagtcctc aggactctac      600
tccctcagca gcgtggtgac cgtgccctcc agcagcttgg gcacgaagac ctacacctgc      660
aacgtagatc acaagcccag caacaccaag gtggacaaga gagttgagtc caaatatggt      720
cccccatgcc catcatgccc agcacctgag ttcctggggg gaccatcagt cttcctgttc      780 ccccaaaac ccaaggacac tctcatgatc tcccggaccc ctgaggtcac gtgcgtggtg      840
gtggacgtga gccaggaaga ccccgaggtc cagttcaact ggtacgtgga tggcgtggag      900
gtgcataatg ccaagacaaa gccgcgggag gagcagttca acagcacgta ccgtgtggtc      960
agcgtcctca ccgtcctgca ccaggactgg ctgaacggca aggagtacaa gtgcaaggtc     1020
tccaacaaag gcctcccgtc ctccatcgag aaaaccatct ccaaagccaa agggcagccc     1080
cgagagccac aggtgtacac cctgccccca tcccaggagg agatgaccaa gaaccaggtc     1140
agcctgacct gcctggtcaa aggcttctac cccagcgaca tcgccgtgga gtgggagagc     1200
aatgggcagc cggagaacaa ctacaagacc acgcctcccg tgctggactc cgacggctcc     1260
ttcttcctct acagcaggct aaccgtggac aagagcaggt ggcaggaggg gaatgtcttc     1320
tcatgctccg tgatgcatga ggctctgcac aaccactaca cacagaagag cctctccctg     1380
tctctgggta aatga                                                      1395
```

<210> SEQ ID NO 119
<211> LENGTH: 464
<212> TYPE: PRT
<213> ORGANISM: Homo sapiens

<400> SEQUENCE: 119

```
Met Gly Trp Ser Cys Ile Ile Leu Phe Leu Val Ala Thr Ala Thr Gly
1               5                   10                  15

Val His Ser Asp Val Gln Leu Gln Glu Ser Gly Pro Gly Leu Val Lys
            20                  25                  30

Pro Ser Gln Thr Leu Ser Leu Thr Cys Thr Val Thr Asp Tyr Ser Ile
        35                  40                  45

Thr Ser Asp Tyr Ala Trp Asn Trp Ile Arg Gln Phe Pro Gly Lys Lys
    50                  55                  60

Leu Glu Trp Met Gly Tyr Ile Ser Tyr Ser Gly Ser Thr Ser Tyr Asn
65                  70                  75                  80

Pro Ser Leu Lys Ser Arg Ile Thr Ile Ser Arg Asp Thr Ser Lys Asn
                85                  90                  95

Gln Phe Ser Leu Gln Leu Asn Ser Val Thr Ala Ala Asp Thr Ala Thr
            100                 105                 110

Tyr Tyr Cys Ala Ser Phe Asp Tyr Ala His Ala Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160
```

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
        180                 185                 190

Val Leu Gln Ser Ser Gly Leu Tyr Ser Leu Ser Ser Val Val Thr Val
            195                 200                 205

Pro Ser Ser Ser Leu Gly Thr Lys Thr Tyr Thr Cys Asn Val Asp His
210                 215                 220

Lys Pro Ser Asn Thr Lys Val Asp Lys Arg Val Glu Ser Lys Tyr Gly
225                 230                 235                 240

Pro Pro Cys Pro Ser Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly Lys
450                 455                 460

<210> SEQ ID NO 120
<211> LENGTH: 8
<212> TYPE: PRT
<213> ORGANISM: Homo sapiens

<400> SEQUENCE: 120

Arg Phe Arg Asp Asn Thr Pro Asn
1               5

<210> SEQ ID NO 121
<211> LENGTH: 8
<212> TYPE: PRT
<213> ORGANISM: Homo sapiens

<400> SEQUENCE: 121

Arg Phe Arg Asp Asn Thr Ala Asn
1               5

```
<210> SEQ ID NO 122
<211> LENGTH: 9
<212> TYPE: PRT
<213> ORGANISM: Homo sapiens

<400> SEQUENCE: 122

Ile Thr Phe Glu Phe Val Asp Gln Glu
1               5

<210> SEQ ID NO 123
<211> LENGTH: 7
<212> TYPE: PRT
<213> ORGANISM: Homo sapiens

<400> SEQUENCE: 123

Phe Tyr Glu Thr Pro Leu Gln
1               5

<210> SEQ ID NO 124
<211> LENGTH: 118
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa= any amino acid
<220> FEATURE:
<221> NAME/KEY: misc_feature
<222> LOCATION: (3)..(3)
<223> OTHER INFORMATION: Xaa= any amino acid
<220> FEATURE:
<221> NAME/KEY: misc_feature
<222> LOCATION: (5)..(5)
<223> OTHER INFORMATION: Xaa= any amino acid
<220> FEATURE:
<221> NAME/KEY: misc_feature
<222> LOCATION: (7)..(7)
<223> OTHER INFORMATION: Xaa= any amino acid
<220> FEATURE:
<221> NAME/KEY: misc_feature
<222> LOCATION: (9)..(17)
<223> OTHER INFORMATION: Xaa= any amino acid
<220> FEATURE:
<221> NAME/KEY: misc_feature
<222> LOCATION: (19)..(19)
<223> OTHER INFORMATION: Xaa= any amino acid
<220> FEATURE:
<221> NAME/KEY: misc_feature
<222> LOCATION: (21)..(21)
<223> OTHER INFORMATION: Xaa= any amino acid
<220> FEATURE:
<221> NAME/KEY: misc_feature
<222> LOCATION: (23)..(23)
<223> OTHER INFORMATION: Xaa= any amino acid
<220> FEATURE:
<221> NAME/KEY: misc_feature
<222> LOCATION: (25)..(25)
<223> OTHER INFORMATION: Xaa= any amino acid
<220> FEATURE:
<221> NAME/KEY: misc_feature
<222> LOCATION: (39)..(39)
<223> OTHER INFORMATION: Xaa= any amino acid
<220> FEATURE:
<221> NAME/KEY: misc_feature
<222> LOCATION: (41)..(45)
<223> OTHER INFORMATION: Xaa= any amino acid
<220> FEATURE:
<221> NAME/KEY: misc_feature
<222> LOCATION: (47)..(47)
<223> OTHER INFORMATION: Xaa= any amino acid
<220> FEATURE:
<221> NAME/KEY: misc_feature
<222> LOCATION: (60)..(60)
<223> OTHER INFORMATION: Xaa= any amino acid
<220> FEATURE:
<221> NAME/KEY: misc_feature
```

```
<222> LOCATION: (62)..(63)
<223> OTHER INFORMATION: Xaa= any amino acid
<220> FEATURE:
<221> NAME/KEY: misc_feature
<222> LOCATION: (65)..(67)
<223> OTHER INFORMATION: Xaa= any amino acid
<220> FEATURE:
<221> NAME/KEY: misc_feature
<222> LOCATION: (69)..(69)
<223> OTHER INFORMATION: Xaa= any amino acid
<220> FEATURE:
<221> NAME/KEY: misc_feature
<222> LOCATION: (71)..(71)
<223> OTHER INFORMATION: Xaa= any amino acid
<220> FEATURE:
<221> NAME/KEY: misc_feature
<222> LOCATION: (73)..(78)
<223> OTHER INFORMATION: Xaa= any amino acid
<220> FEATURE:
<221> NAME/KEY: misc_feature
<222> LOCATION: (80)..(80)
<223> OTHER INFORMATION: Xaa= any amino acid
<220> FEATURE:
<221> NAME/KEY: misc_feature
<222> LOCATION: (82)..(82)
<223> OTHER INFORMATION: Xaa= any amino acid
<220> FEATURE:
<221> NAME/KEY: misc_feature
<222> LOCATION: (84)..(85)
<223> OTHER INFORMATION: Xaa= any amino acid
<220> FEATURE:
<221> NAME/KEY: misc_feature
<222> LOCATION: (87)..(89)
<223> OTHER INFORMATION: Xaa= any amino acid
<220> FEATURE:
<221> NAME/KEY: misc_feature
<222> LOCATION: (91)..(91)
<223> OTHER INFORMATION: Xaa= any amino acid
<220> FEATURE:
<221> NAME/KEY: misc_feature
<222> LOCATION: (93)..(93)
<223> OTHER INFORMATION: Xaa= any amino acid
<220> FEATURE:
<221> NAME/KEY: misc_feature
<222> LOCATION: (110)..(110)
<223> OTHER INFORMATION: Xaa= any amino acid
<220> FEATURE:
<221> NAME/KEY: misc_feature
<222> LOCATION: (113)..(113)
<223> OTHER INFORMATION: Xaa= any amino acid
<220> FEATURE:
<221> NAME/KEY: misc_feature
<222> LOCATION: (115)..(115)
<223> OTHER INFORMATION: Xaa= any amino acid
<220> FEATURE:
<221> NAME/KEY: misc_feature
<222> LOCATION: (117)..(118)
<223> OTHER INFORMATION: Xaa= any amino acid

<400> SEQUENCE: 124

Xaa Val Xaa Leu Xaa Glu Xaa Gly Xaa Xaa Xaa Xaa Xaa Xaa Xaa
 1               5                  10                  15

Xaa Leu Xaa Leu Xaa Cys Xaa Val Xaa Asp Tyr Ser Ile Thr Ser Asp
             20                  25                  30

Tyr Ala Trp Asn Trp Ile Xaa Gln Xaa Xaa Xaa Xaa Xaa Leu Xaa Trp
         35                  40                  45

Met Gly Tyr Ile Ser Tyr Ser Gly Ser Thr Ser Xaa Asn Xaa Xaa Leu
     50                  55                  60

Xaa Xaa Xaa Ile Xaa Ile Xaa Arg Xaa Xaa Xaa Xaa Xaa Xaa Phe Xaa
 65                  70                  75                  80

Leu Xaa Leu Xaa Xaa Val Xaa Xaa Xaa Asp Xaa Ala Xaa Tyr Tyr Cys
             85                  90                  95

Ala Ser Phe Asp Tyr Ala His Ala Met Asp Tyr Trp Gly Xaa Gly Thr
```

```
                       100                 105                 110

Xaa Val Xaa Val Xaa Xaa
        115

<210> SEQ ID NO 125
<211> LENGTH: 118
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa= any amino acid
<220> FEATURE:
<221> NAME/KEY: misc_feature
<222> LOCATION: (5)..(5)
<223> OTHER INFORMATION: Xaa= any amino acid
<220> FEATURE:
<221> NAME/KEY: misc_feature
<222> LOCATION: (7)..(7)
<223> OTHER INFORMATION: Xaa= any amino acid
<220> FEATURE:
<221> NAME/KEY: misc_feature
<222> LOCATION: (10)..(11)
<223> OTHER INFORMATION: Xaa= any amino acid
<220> FEATURE:
<221> NAME/KEY: misc_feature
<222> LOCATION: (13)..(13)
<223> OTHER INFORMATION: Xaa= any amino acid
<220> FEATURE:
<221> NAME/KEY: misc_feature
<222> LOCATION: (15)..(17)
<223> OTHER INFORMATION: Xaa= any amino acid
<220> FEATURE:
<221> NAME/KEY: misc_feature
<222> LOCATION: (19)..(19)
<223> OTHER INFORMATION: Xaa= any amino acid
<220> FEATURE:
<221> NAME/KEY: misc_feature
<222> LOCATION: (21)..(21)
<223> OTHER INFORMATION: Xaa= any amino acid
<220> FEATURE:
<221> NAME/KEY: misc_feature
<222> LOCATION: (23)..(23)
<223> OTHER INFORMATION: Xaa= any amino acid
<220> FEATURE:
<221> NAME/KEY: misc_feature
<222> LOCATION: (41)..(41)
<223> OTHER INFORMATION: Xaa= any amino acid
<220> FEATURE:
<221> NAME/KEY: misc_feature
<222> LOCATION: (43)..(44)
<223> OTHER INFORMATION: Xaa= any amino acid
<220> FEATURE:
<221> NAME/KEY: misc_feature
<222> LOCATION: (66)..(66)
<223> OTHER INFORMATION: Xaa= any amino acid
<220> FEATURE:
<221> NAME/KEY: misc_feature
<222> LOCATION: (69)..(69)
<223> OTHER INFORMATION: Xaa= any amino acid
<220> FEATURE:
<221> NAME/KEY: misc_feature
<222> LOCATION: (71)..(71)
<223> OTHER INFORMATION: Xaa= any amino acid
<220> FEATURE:
<221> NAME/KEY: misc_feature
<222> LOCATION: (73)..(73)
<223> OTHER INFORMATION: Xaa= any amino acid
<220> FEATURE:
<221> NAME/KEY: misc_feature
<222> LOCATION: (75)..(76)
<223> OTHER INFORMATION: Xaa= any amino acid
<220> FEATURE:
<221> NAME/KEY: misc_feature
<222> LOCATION: (78)..(78)
<223> OTHER INFORMATION: Xaa= any amino acid
<220> FEATURE:
<221> NAME/KEY: misc_feature
```

<222> LOCATION: (80)..(80)
<223> OTHER INFORMATION: Xaa= any amino acid
<220> FEATURE:
<221> NAME/KEY: misc_feature
<222> LOCATION: (82)..(82)
<223> OTHER INFORMATION: Xaa= any amino acid
<220> FEATURE:
<221> NAME/KEY: misc_feature
<222> LOCATION: (84)..(85)
<223> OTHER INFORMATION: Xaa= any amino acid
<220> FEATURE:
<221> NAME/KEY: misc_feature
<222> LOCATION: (87)..(89)
<223> OTHER INFORMATION: Xaa= any amino acid
<220> FEATURE:
<221> NAME/KEY: misc_feature
<222> LOCATION: (91)..(91)
<223> OTHER INFORMATION: Xaa= any amino acid
<220> FEATURE:
<221> NAME/KEY: misc_feature
<222> LOCATION: (110)..(110)
<223> OTHER INFORMATION: Xaa= any amino acid
<220> FEATURE:
<221> NAME/KEY: misc_feature
<222> LOCATION: (113)..(113)
<223> OTHER INFORMATION: Xaa= any amino acid
<220> FEATURE:
<221> NAME/KEY: misc_feature
<222> LOCATION: (115)..(115)
<223> OTHER INFORMATION: Xaa= any amino acid
<220> FEATURE:
<221> NAME/KEY: misc_feature
<222> LOCATION: (117)..(118)
<223> OTHER INFORMATION: Xaa= any amino acid

<400> SEQUENCE: 125

Asp Val Xaa Leu Xaa Glu Xaa Gly Pro Xaa Xaa Val Xaa Pro Xaa Xaa
1               5                   10                  15

Xaa Leu Xaa Leu Xaa Cys Xaa Val Thr Asp Tyr Ser Ile Thr Ser Asp
                20                  25                  30

Tyr Ala Trp Asn Trp Ile Arg Gln Xaa Pro Xaa Xaa Lys Leu Glu Trp
            35                  40                  45

Met Gly Tyr Ile Ser Tyr Ser Gly Ser Thr Ser Tyr Asn Pro Ser Leu
        50                  55                  60

Lys Xaa Arg Ile Xaa Ile Xaa Arg Xaa Thr Xaa Xaa Asn Xaa Phe Xaa
65                  70                  75                  80

Leu Xaa Leu Xaa Xaa Val Xaa Xaa Xaa Asp Xaa Ala Thr Tyr Tyr Cys
                85                  90                  95

Ala Ser Phe Asp Tyr Ala His Ala Met Asp Tyr Trp Gly Xaa Gly Thr
            100                 105                 110

Xaa Val Xaa Val Xaa Xaa
        115

<210> SEQ ID NO 126
<211> LENGTH: 118
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa= any amino acid
<220> FEATURE:
<221> NAME/KEY: misc_feature
<222> LOCATION: (17)..(17)
<223> OTHER INFORMATION: Xaa= any amino acid
<220> FEATURE:
<221> NAME/KEY: misc_feature
<222> LOCATION: (25)..(25)
<223> OTHER INFORMATION: Xaa= any amino acid
<220> FEATURE:
<221> NAME/KEY: misc_feature

```
<222> LOCATION: (44)..(45)
<223> OTHER INFORMATION: Xaa= any amino acid
<220> FEATURE:
<221> NAME/KEY: misc_feature
<222> LOCATION: (69)..(69)
<223> OTHER INFORMATION: Xaa= any amino acid
<220> FEATURE:
<221> NAME/KEY: misc_feature
<222> LOCATION: (71)..(71)
<223> OTHER INFORMATION: Xaa= any amino acid
<220> FEATURE:
<221> NAME/KEY: misc_feature
<222> LOCATION: (80)..(80)
<223> OTHER INFORMATION: Xaa= any amino acid
<220> FEATURE:
<221> NAME/KEY: misc_feature
<222> LOCATION: (88)..(89)
<223> OTHER INFORMATION: Xaa= any amino acid
<220> FEATURE:
<221> NAME/KEY: misc_feature
<222> LOCATION: (93)..(93)
<223> OTHER INFORMATION: Xaa= any amino acid
<220> FEATURE:
<221> NAME/KEY: misc_feature
<222> LOCATION: (113)..(113)
<223> OTHER INFORMATION: Xaa= any amino acid

<400> SEQUENCE: 126

Xaa Val Gln Leu Gln Glu Ser Gly Pro Gly Leu Val Lys Pro Ser Gln
1               5                   10                  15

Xaa Leu Ser Leu Thr Cys Thr Val Xaa Asp Tyr Ser Ile Thr Ser Asp
            20                  25                  30

Tyr Ala Trp Asn Trp Ile Arg Gln Phe Pro Gly Xaa Xaa Leu Glu Trp
        35                  40                  45

Met Gly Tyr Ile Ser Tyr Ser Gly Ser Thr Tyr Asn Pro Ser Leu
    50                  55                  60

Lys Ser Arg Ile Xaa Ile Xaa Arg Asp Thr Ser Lys Asn Gln Phe Xaa
65                  70                  75                  80

Leu Gln Leu Asn Ser Val Thr Xaa Xaa Asp Thr Ala Xaa Tyr Tyr Cys
                85                  90                  95

Ala Ser Phe Asp Tyr Ala His Ala Met Asp Tyr Trp Gly Gln Gly Thr
            100                 105                 110

Xaa Val Thr Val Ser Ser
        115

<210> SEQ ID NO 127
<211> LENGTH: 118
<212> TYPE: PRT
<213> ORGANISM: Homo sapiens
<220> FEATURE:
<221> NAME/KEY: misc_feature
<222> LOCATION: (17)..(17)
<223> OTHER INFORMATION: Xaa= any amino acid
<220> FEATURE:
<221> NAME/KEY: misc_feature
<222> LOCATION: (44)..(44)
<223> OTHER INFORMATION: Xaa= any amino acid
<220> FEATURE:
<221> NAME/KEY: misc_feature
<222> LOCATION: (69)..(69)
<223> OTHER INFORMATION: Xaa= any amino acid
<220> FEATURE:
<221> NAME/KEY: misc_feature
<222> LOCATION: (71)..(71)
<223> OTHER INFORMATION: Xaa= any amino acid
<220> FEATURE:
<221> NAME/KEY: misc_feature
<222> LOCATION: (80)..(80)
<223> OTHER INFORMATION: Xaa= any amino acid
<220> FEATURE:
<221> NAME/KEY: misc_feature
```

```
<222> LOCATION: (88)..(89)
<223> OTHER INFORMATION: Xaa= any amino acid
<220> FEATURE:
<221> NAME/KEY: misc_feature
<222> LOCATION: (113)..(113)
<223> OTHER INFORMATION: Xaa= any amino acid

<400> SEQUENCE: 127
```

Asp Val Gln Leu Gln Glu Ser Gly Pro Gly Leu Val Lys Pro Ser Gln
1               5                   10                  15

Xaa Leu Ser Leu Thr Cys Thr Val Thr Asp Tyr Ser Ile Thr Ser Asp
            20                  25                  30

Tyr Ala Trp Asn Trp Ile Arg Gln Phe Pro Gly Xaa Lys Leu Glu Trp
        35                  40                  45

Met Gly Tyr Ile Ser Tyr Ser Gly Ser Thr Ser Tyr Asn Pro Ser Leu
    50                  55                  60

Lys Ser Arg Ile Xaa Ile Xaa Arg Asp Thr Ser Lys Asn Gln Phe Xaa
65                  70                  75                  80

Leu Gln Leu Asn Ser Val Thr Xaa Xaa Asp Thr Ala Thr Tyr Tyr Cys
                85                  90                  95

Ala Ser Phe Asp Tyr Ala His Ala Met Asp Tyr Trp Gly Gln Gly Thr
            100                 105                 110

Xaa Val Thr Val Ser Ser
        115

```
<210> SEQ ID NO 128
<211> LENGTH: 109
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa= any amino acid
<220> FEATURE:
<221> NAME/KEY: misc_feature
<222> LOCATION: (3)..(3)
<223> OTHER INFORMATION: Xaa= any amino acid
<220> FEATURE:
<221> NAME/KEY: misc_feature
<222> LOCATION: (5)..(5)
<223> OTHER INFORMATION: Xaa= any amino acid
<220> FEATURE:
<221> NAME/KEY: misc_feature
<222> LOCATION: (7)..(12)
<223> OTHER INFORMATION: Xaa= any amino acid
<220> FEATURE:
<221> NAME/KEY: misc_feature
<222> LOCATION: (14)..(18)
<223> OTHER INFORMATION: Xaa= any amino acid
<220> FEATURE:
<221> NAME/KEY: misc_feature
<222> LOCATION: (20)..(20)
<223> OTHER INFORMATION: Xaa= any amino acid
<220> FEATURE:
<221> NAME/KEY: misc_feature
<222> LOCATION: (22)..(22)
<223> OTHER INFORMATION: Xaa= any amino acid
<220> FEATURE:
<221> NAME/KEY: misc_feature
<222> LOCATION: (24)..(24)
<223> OTHER INFORMATION: Xaa= any amino acid
<220> FEATURE:
<221> NAME/KEY: misc_feature
<222> LOCATION: (26)..(26)
<223> OTHER INFORMATION: Xaa= any amino acid
<220> FEATURE:
<221> NAME/KEY: misc_feature
<222> LOCATION: (37)..(37)
<223> OTHER INFORMATION: Xaa= any amino acid
<220> FEATURE:
<221> NAME/KEY: misc_feature
```

```
<222> LOCATION: (39)..(43)
<223> OTHER INFORMATION: Xaa= any amino acid
<220> FEATURE:
<221> NAME/KEY: misc_feature
<222> LOCATION: (45)..(45)
<223> OTHER INFORMATION: Xaa= any amino acid
<220> FEATURE:
<221> NAME/KEY: misc_feature
<222> LOCATION: (54)..(57)
<223> OTHER INFORMATION: Xaa= any amino acid
<220> FEATURE:
<221> NAME/KEY: misc_feature
<222> LOCATION: (59)..(61)
<223> OTHER INFORMATION: Xaa= any amino acid
<220> FEATURE:
<221> NAME/KEY: misc_feature
<222> LOCATION: (63)..(63)
<223> OTHER INFORMATION: Xaa= any amino acid
<220> FEATURE:
<221> NAME/KEY: misc_feature
<222> LOCATION: (65)..(65)
<223> OTHER INFORMATION: Xaa= any amino acid
<220> FEATURE:
<221> NAME/KEY: misc_feature
<222> LOCATION: (67)..(67)
<223> OTHER INFORMATION: Xaa= any amino acid
<220> FEATURE:
<221> NAME/KEY: misc_feature
<222> LOCATION: (69)..(70)
<223> OTHER INFORMATION: Xaa= any amino acid
<220> FEATURE:
<221> NAME/KEY: misc_feature
<222> LOCATION: (72)..(72)
<223> OTHER INFORMATION: Xaa= any amino acid
<220> FEATURE:
<221> NAME/KEY: misc_feature
<222> LOCATION: (74)..(74)
<223> OTHER INFORMATION: Xaa= any amino acid
<220> FEATURE:
<221> NAME/KEY: misc_feature
<222> LOCATION: (76)..(77)
<223> OTHER INFORMATION: Xaa= any amino acid
<220> FEATURE:
<221> NAME/KEY: misc_feature
<222> LOCATION: (79)..(81)
<223> OTHER INFORMATION: Xaa= any amino acid
<220> FEATURE:
<221> NAME/KEY: misc_feature
<222> LOCATION: (83)..(83)
<223> OTHER INFORMATION: Xaa= any amino acid
<220> FEATURE:
<221> NAME/KEY: misc_feature
<222> LOCATION: (100)..(100)
<223> OTHER INFORMATION: Xaa= any amino acid
<220> FEATURE:
<221> NAME/KEY: misc_feature
<222> LOCATION: (103)..(103)
<223> OTHER INFORMATION: Xaa= any amino acid
<220> FEATURE:
<221> NAME/KEY: misc_feature
<222> LOCATION: (105)..(109)
<223> OTHER INFORMATION: Xaa= any amino acid

<400> SEQUENCE: 128

Xaa Ile Xaa Leu Xaa Gln Xaa Xaa Xaa Xaa Xaa Val Xaa Xaa Xaa
 1               5                  10                  15

Xaa Xaa Val Xaa Phe Xaa Cys Xaa Ala Xaa Gln Ser Ile Gly Thr Ser
             20                  25                  30

Ile His Trp Tyr Xaa Gln Xaa Xaa Xaa Xaa Pro Xaa Leu Leu Ile
         35                  40                  45

Lys Tyr Ala Ser Glu Xaa Xaa Xaa Ile Xaa Xaa Xaa Phe Xaa Gly
     50                  55                  60

Xaa Gly Xaa Gly Xaa Xaa Phe Xaa Leu Xaa Ile Xaa Xaa Val Xaa Xaa
65                  70                  75                  80
```

```
Xaa Asp Xaa Ala Asp Tyr Tyr Cys Gln Gln Ile Asn Ser Trp Pro Thr
            85                  90                  95

Thr Phe Gly Xaa Gly Thr Xaa Leu Xaa Xaa Xaa Xaa Xaa
            100                 105

<210> SEQ ID NO 129
<211> LENGTH: 109
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa= any amino acid
<220> FEATURE:
<221> NAME/KEY: misc_feature
<222> LOCATION: (3)..(3)
<223> OTHER INFORMATION: Xaa= any amino acid
<220> FEATURE:
<221> NAME/KEY: misc_feature
<222> LOCATION: (5)..(5)
<223> OTHER INFORMATION: Xaa= any amino acid
<220> FEATURE:
<221> NAME/KEY: misc_feature
<222> LOCATION: (7)..(7)
<223> OTHER INFORMATION: Xaa= any amino acid
<220> FEATURE:
<221> NAME/KEY: misc_feature
<222> LOCATION: (9)..(10)
<223> OTHER INFORMATION: Xaa= any amino acid
<220> FEATURE:
<221> NAME/KEY: misc_feature
<222> LOCATION: (12)..(12)
<223> OTHER INFORMATION: Xaa= any amino acid
<220> FEATURE:
<221> NAME/KEY: misc_feature
<222> LOCATION: (14)..(14)
<223> OTHER INFORMATION: Xaa= any amino acid
<220> FEATURE:
<221> NAME/KEY: misc_feature
<222> LOCATION: (16)..(18)
<223> OTHER INFORMATION: Xaa= any amino acid
<220> FEATURE:
<221> NAME/KEY: misc_feature
<222> LOCATION: (20)..(20)
<223> OTHER INFORMATION: Xaa= any amino acid
<220> FEATURE:
<221> NAME/KEY: misc_feature
<222> LOCATION: (22)..(22)
<223> OTHER INFORMATION: Xaa= any amino acid
<220> FEATURE:
<221> NAME/KEY: misc_feature
<222> LOCATION: (24)..(24)
<223> OTHER INFORMATION: Xaa= any amino acid
<220> FEATURE:
<221> NAME/KEY: misc_feature
<222> LOCATION: (39)..(39)
<223> OTHER INFORMATION: Xaa= any amino acid
<220> FEATURE:
<221> NAME/KEY: misc_feature
<222> LOCATION: (41)..(42)
<223> OTHER INFORMATION: Xaa= any amino acid
<220> FEATURE:
<221> NAME/KEY: misc_feature
<222> LOCATION: (54)..(54)
<223> OTHER INFORMATION: Xaa= any amino acid
<220> FEATURE:
<221> NAME/KEY: misc_feature
<222> LOCATION: (57)..(57)
<223> OTHER INFORMATION: Xaa= any amino acid
<220> FEATURE:
<221> NAME/KEY: misc_feature
<222> LOCATION: (60)..(60)
<223> OTHER INFORMATION: Xaa= any amino acid
<220> FEATURE:
<221> NAME/KEY: misc_feature
<222> LOCATION: (63)..(63)
<223> OTHER INFORMATION: Xaa= any amino acid
<220> FEATURE:
```

<221> NAME/KEY: misc_feature
<222> LOCATION: (65)..(65)
<223> OTHER INFORMATION: Xaa= any amino acid
<220> FEATURE:
<221> NAME/KEY: misc_feature
<222> LOCATION: (67)..(67)
<223> OTHER INFORMATION: Xaa= any amino acid
<220> FEATURE:
<221> NAME/KEY: misc_feature
<222> LOCATION: (69)..(70)
<223> OTHER INFORMATION: Xaa= any amino acid
<220> FEATURE:
<221> NAME/KEY: misc_feature
<222> LOCATION: (72)..(72)
<223> OTHER INFORMATION: Xaa= any amino acid
<220> FEATURE:
<221> NAME/KEY: misc_feature
<222> LOCATION: (74)..(74)
<223> OTHER INFORMATION: Xaa= any amino acid
<220> FEATURE:
<221> NAME/KEY: misc_feature
<222> LOCATION: (76)..(77)
<223> OTHER INFORMATION: Xaa= any amino acid
<220> FEATURE:
<221> NAME/KEY: misc_feature
<222> LOCATION: (79)..(81)
<223> OTHER INFORMATION: Xaa= any amino acid
<220> FEATURE:
<221> NAME/KEY: misc_feature
<222> LOCATION: (83)..(83)
<223> OTHER INFORMATION: Xaa= any amino acid
<220> FEATURE:
<221> NAME/KEY: misc_feature
<222> LOCATION: (100)..(100)
<223> OTHER INFORMATION: Xaa= any amino acid
<220> FEATURE:
<221> NAME/KEY: misc_feature
<222> LOCATION: (103)..(103)
<223> OTHER INFORMATION: Xaa= any amino acid
<220> FEATURE:
<221> NAME/KEY: misc_feature
<222> LOCATION: (105)..(109)
<223> OTHER INFORMATION: Xaa= any amino acid

<400> SEQUENCE: 129

Xaa Ile Xaa Leu Xaa Gln Xaa Pro Xaa Xaa Leu Xaa Val Xaa Pro Xaa
1               5                   10                  15

Xaa Xaa Val Xaa Phe Xaa Cys Xaa Ala Ser Gln Ser Ile Gly Thr Ser
            20                  25                  30

Ile His Trp Tyr Gln Gln Xaa Thr Xaa Xaa Ser Pro Arg Leu Leu Ile
        35                  40                  45

Lys Tyr Ala Ser Glu Xaa Ile Ser Xaa Ile Pro Xaa Arg Phe Xaa Gly
    50                  55                  60

Xaa Gly Xaa Gly Xaa Xaa Phe Xaa Leu Xaa Ile Xaa Xaa Val Xaa Xaa
65                  70                  75                  80

Xaa Asp Xaa Ala Asp Tyr Tyr Cys Gln Gln Ile Asn Ser Trp Pro Thr
                85                  90                  95

Thr Phe Gly Xaa Gly Thr Xaa Leu Xaa Xaa Xaa Xaa Xaa
                100                 105

<210> SEQ ID NO 130
<211> LENGTH: 109
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa= any amino acid
<220> FEATURE:
<221> NAME/KEY: misc_feature
<222> LOCATION: (3)..(3)
<223> OTHER INFORMATION: Xaa= any amino acid

```
<220> FEATURE:
<221> NAME/KEY: misc_feature
<222> LOCATION: (9)..(10)
<223> OTHER INFORMATION: Xaa= any amino acid
<220> FEATURE:
<221> NAME/KEY: misc_feature
<222> LOCATION: (20)..(20)
<223> OTHER INFORMATION: Xaa= any amino acid
<220> FEATURE:
<221> NAME/KEY: misc_feature
<222> LOCATION: (39)..(39)
<223> OTHER INFORMATION: Xaa= any amino acid
<220> FEATURE:
<221> NAME/KEY: misc_feature
<222> LOCATION: (41)..(43)
<223> OTHER INFORMATION: Xaa= any amino acid
<220> FEATURE:
<221> NAME/KEY: misc_feature
<222> LOCATION: (54)..(56)
<223> OTHER INFORMATION: Xaa= any amino acid
<220> FEATURE:
<221> NAME/KEY: misc_feature
<222> LOCATION: (60)..(60)
<223> OTHER INFORMATION: Xaa= any amino acid
<220> FEATURE:
<221> NAME/KEY: misc_feature
<222> LOCATION: (74)..(74)
<223> OTHER INFORMATION: Xaa= any amino acid
<220> FEATURE:
<221> NAME/KEY: misc_feature
<222> LOCATION: (76)..(77)
<223> OTHER INFORMATION: Xaa= any amino acid
<220> FEATURE:
<221> NAME/KEY: misc_feature
<222> LOCATION: (83)..(83)
<223> OTHER INFORMATION: Xaa= any amino acid
<220> FEATURE:
<221> NAME/KEY: misc_feature
<222> LOCATION: (100)..(100)
<223> OTHER INFORMATION: Xaa= any amino acid
<220> FEATURE:
<221> NAME/KEY: misc_feature
<222> LOCATION: (109)..(109)
<223> OTHER INFORMATION: Xaa= any amino acid

<400> SEQUENCE: 130

Xaa Ile Xaa Leu Thr Gln Ser Pro Xaa Xaa Leu Ser Val Ser Pro Gly
 1               5                  10                  15

Glu Arg Val Xaa Phe Ser Cys Arg Ala Ser Gln Ser Ile Gly Thr Ser
                20                  25                  30

Ile His Trp Tyr Gln Gln Xaa Thr Xaa Xaa Xaa Pro Arg Leu Leu Ile
            35                  40                  45

Lys Tyr Ala Ser Glu Xaa Xaa Xaa Gly Ile Pro Xaa Arg Phe Ser Gly
 50                  55                  60

Ser Gly Ser Gly Thr Asp Phe Thr Leu Xaa Ile Xaa Xaa Val Glu Ser
 65                  70                  75                  80

Glu Asp Xaa Ala Asp Tyr Tyr Cys Gln Gln Ile Asn Ser Trp Pro Thr
                85                  90                  95

Thr Phe Gly Xaa Gly Thr Lys Leu Glu Ile Lys Arg Xaa
                100                 105

<210> SEQ ID NO 131
<211> LENGTH: 109
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa= any amino acid
<220> FEATURE:
<221> NAME/KEY: misc_feature
<222> LOCATION: (3)..(3)
```

<220> FEATURE:
<221> NAME/KEY: misc_feature
<222> LOCATION: (9)..(10)
<223> OTHER INFORMATION: Xaa= any amino acid
<220> FEATURE:
<221> NAME/KEY: misc_feature
<222> LOCATION: (20)..(20)
<223> OTHER INFORMATION: Xaa= any amino acid
<220> FEATURE:
<221> NAME/KEY: misc_feature
<222> LOCATION: (39)..(39)
<223> OTHER INFORMATION: Xaa= any amino acid
<220> FEATURE:
<221> NAME/KEY: misc_feature
<222> LOCATION: (41)..(42)
<223> OTHER INFORMATION: Xaa= any amino acid
<220> FEATURE:
<221> NAME/KEY: misc_feature
<222> LOCATION: (54)..(54)
<223> OTHER INFORMATION: Xaa= any amino acid
<220> FEATURE:
<221> NAME/KEY: misc_feature
<222> LOCATION: (60)..(60)
<223> OTHER INFORMATION: Xaa= any amino acid
<220> FEATURE:
<221> NAME/KEY: misc_feature
<222> LOCATION: (74)..(74)
<223> OTHER INFORMATION: Xaa= any amino acid
<220> FEATURE:
<221> NAME/KEY: misc_feature
<222> LOCATION: (76)..(77)
<223> OTHER INFORMATION: Xaa= any amino acid
<220> FEATURE:
<221> NAME/KEY: misc_feature
<222> LOCATION: (83)..(83)
<223> OTHER INFORMATION: Xaa= any amino acid
<220> FEATURE:
<221> NAME/KEY: misc_feature
<222> LOCATION: (100)..(100)
<223> OTHER INFORMATION: Xaa= any amino acid
<220> FEATURE:
<221> NAME/KEY: misc_feature
<222> LOCATION: (109)..(109)
<223> OTHER INFORMATION: Xaa= any amino acid

<400> SEQUENCE: 131

Xaa Ile Xaa Leu Thr Gln Ser Pro Xaa Xaa Leu Ser Val Ser Pro Gly
1               5                   10                  15

Glu Arg Val Xaa Phe Ser Cys Arg Ala Ser Gln Ser Ile Gly Thr Ser
            20                  25                  30

Ile His Trp Tyr Gln Gln Xaa Thr Xaa Xaa Ser Pro Arg Leu Leu Ile
        35                  40                  45

Lys Tyr Ala Ser Glu Xaa Ile Ser Gly Ile Pro Xaa Arg Phe Ser Gly
    50                  55                  60

Ser Gly Ser Gly Thr Asp Phe Thr Leu Xaa Ile Xaa Xaa Val Glu Ser
65                  70                  75                  80

Glu Asp Xaa Ala Asp Tyr Tyr Cys Gln Gln Ile Asn Ser Trp Pro Thr
            85                  90                  95

Thr Phe Gly Xaa Gly Thr Lys Leu Glu Ile Lys Arg Xaa
            100                 105

<210> SEQ ID NO 132
<211> LENGTH: 109
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa= any amino acid
<220> FEATURE:
<221> NAME/KEY: misc_feature
<222> LOCATION: (3)..(3)
<223> OTHER INFORMATION: Xaa= any amino acid
<220> FEATURE:
<221> NAME/KEY: misc_feature
<222> LOCATION: (9)..(10)
<223> OTHER INFORMATION: Xaa= any amino acid
<220> FEATURE:
<221> NAME/KEY: misc_feature
<222> LOCATION: (20)..(20)
<223> OTHER INFORMATION: Xaa= any amino acid
<220> FEATURE:
<221> NAME/KEY: misc_feature
<222> LOCATION: (39)..(39)
<223> OTHER INFORMATION: Xaa= any amino acid
<220> FEATURE:
<221> NAME/KEY: misc_feature
<222> LOCATION: (41)..(43)
<223> OTHER INFORMATION: Xaa= any amino acid
<220> FEATURE:
<221> NAME/KEY: misc_feature
<222> LOCATION: (60)..(60)
<223> OTHER INFORMATION: Xaa= any amino acid
<220> FEATURE:
<221> NAME/KEY: misc_feature
<222> LOCATION: (74)..(74)
<223> OTHER INFORMATION: Xaa= any amino acid
<220> FEATURE:
<221> NAME/KEY: misc_feature
<222> LOCATION: (76)..(77)
<223> OTHER INFORMATION: Xaa= any amino acid
<220> FEATURE:
<221> NAME/KEY: misc_feature
<222> LOCATION: (83)..(83)
<223> OTHER INFORMATION: Xaa= any amino acid
<220> FEATURE:
<221> NAME/KEY: misc_feature
<222> LOCATION: (100)..(100)
<223> OTHER INFORMATION: Xaa= any amino acid
<220> FEATURE:
<221> NAME/KEY: misc_feature
<222> LOCATION: (109)..(109)
<223> OTHER INFORMATION: Xaa= any amino acid

<400> SEQUENCE: 132

Xaa Ile Xaa Leu Thr Gln Ser Pro Xaa Xaa Leu Ser Val Ser Pro Gly
1               5                   10                  15

Glu Arg Val Xaa Phe Ser Cys Arg Ala Ser Gln Ser Ile Gly Thr Ser
            20                  25                  30

Ile His Trp Tyr Gln Gln Xaa Thr Xaa Xaa Xaa Pro Arg Leu Leu Ile
        35                  40                  45

Lys Tyr Ala Ser Glu Ser Ile Ser Gly Ile Pro Xaa Arg Phe Ser Gly
    50                  55                  60

Ser Gly Ser Gly Thr Asp Phe Thr Leu Xaa Ile Xaa Xaa Val Glu Ser
65                  70                  75                  80

Glu Asp Xaa Ala Asp Tyr Tyr Cys Gln Gln Ile Asn Ser Trp Pro Thr
                85                  90                  95

Thr Phe Gly Xaa Gly Thr Lys Leu Glu Ile Lys Arg Xaa
            100                 105

<210> SEQ ID NO 133
<211> LENGTH: 118
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa= any amino acid
<220> FEATURE:
<221> NAME/KEY: misc_feature
<222> LOCATION: (3)..(3)
<223> OTHER INFORMATION: Xaa= any amino acid
<220> FEATURE:

```
<221> NAME/KEY: misc_feature
<222> LOCATION: (5)..(5)
<223> OTHER INFORMATION: Xaa= any amino acid
<220> FEATURE:
<221> NAME/KEY: misc_feature
<222> LOCATION: (7)..(7)
<223> OTHER INFORMATION: Xaa= any amino acid
<220> FEATURE:
<221> NAME/KEY: misc_feature
<222> LOCATION: (9)..(17)
<223> OTHER INFORMATION: Xaa= any amino acid
<220> FEATURE:
<221> NAME/KEY: misc_feature
<222> LOCATION: (19)..(19)
<223> OTHER INFORMATION: Xaa= any amino acid
<220> FEATURE:
<221> NAME/KEY: misc_feature
<222> LOCATION: (21)..(21)
<223> OTHER INFORMATION: Xaa= any amino acid
<220> FEATURE:
<221> NAME/KEY: misc_feature
<222> LOCATION: (23)..(23)
<223> OTHER INFORMATION: Xaa= any amino acid
<220> FEATURE:
<221> NAME/KEY: misc_feature
<222> LOCATION: (25)..(25)
<223> OTHER INFORMATION: Xaa= any amino acid
<220> FEATURE:
<221> NAME/KEY: misc_feature
<222> LOCATION: (39)..(39)
<223> OTHER INFORMATION: Xaa= any amino acid
<220> FEATURE:
<221> NAME/KEY: misc_feature
<222> LOCATION: (41)..(45)
<223> OTHER INFORMATION: Xaa= any amino acid
<220> FEATURE:
<221> NAME/KEY: misc_feature
<222> LOCATION: (47)..(47)
<223> OTHER INFORMATION: Xaa= any amino acid
<220> FEATURE:
<221> NAME/KEY: misc_feature
<222> LOCATION: (60)..(60)
<223> OTHER INFORMATION: Xaa= any amino acid
<220> FEATURE:
<221> NAME/KEY: misc_feature
<222> LOCATION: (62)..(63)
<223> OTHER INFORMATION: Xaa= any amino acid
<220> FEATURE:
<221> NAME/KEY: misc_feature
<222> LOCATION: (65)..(67)
<223> OTHER INFORMATION: Xaa= any amino acid
<220> FEATURE:
<221> NAME/KEY: misc_feature
<222> LOCATION: (69)..(69)
<223> OTHER INFORMATION: Xaa= any amino acid
<220> FEATURE:
<221> NAME/KEY: misc_feature
<222> LOCATION: (71)..(71)
<223> OTHER INFORMATION: Xaa= any amino acid
<220> FEATURE:
<221> NAME/KEY: misc_feature
<222> LOCATION: (73)..(78)
<223> OTHER INFORMATION: Xaa= any amino acid
<220> FEATURE:
<221> NAME/KEY: misc_feature
<222> LOCATION: (80)..(80)
<223> OTHER INFORMATION: Xaa= any amino acid
<220> FEATURE:
<221> NAME/KEY: misc_feature
<222> LOCATION: (82)..(82)
<223> OTHER INFORMATION: Xaa= any amino acid
<220> FEATURE:
<221> NAME/KEY: misc_feature
<222> LOCATION: (84)..(85)
<223> OTHER INFORMATION: Xaa= any amino acid
<220> FEATURE:
<221> NAME/KEY: misc_feature
<222> LOCATION: (87)..(89)
<223> OTHER INFORMATION: Xaa= any amino acid
<220> FEATURE:
```

<220> FEATURE:
<221> NAME/KEY: misc_feature
<222> LOCATION: (91)..(91)
<223> OTHER INFORMATION: Xaa= any amino acid
<220> FEATURE:
<221> NAME/KEY: misc_feature
<222> LOCATION: (93)..(93)
<223> OTHER INFORMATION: Xaa= any amino acid
<220> FEATURE:
<221> NAME/KEY: misc_feature
<222> LOCATION: (110)..(110)
<223> OTHER INFORMATION: Xaa= any amino acid
<220> FEATURE:
<221> NAME/KEY: misc_feature
<222> LOCATION: (113)..(113)
<223> OTHER INFORMATION: Xaa= any amino acid
<220> FEATURE:
<221> NAME/KEY: misc_feature
<222> LOCATION: (115)..(115)
<223> OTHER INFORMATION: Xaa= any amino acid
<220> FEATURE:
<221> NAME/KEY: misc_feature
<222> LOCATION: (117)..(118)
<223> OTHER INFORMATION: Xaa= any amino acid

<400> SEQUENCE: 133

Xaa Val Xaa Leu Xaa Glu Xaa Gly Xaa Xaa Xaa Xaa Xaa Xaa Xaa
1               5                   10                  15

Xaa Leu Xaa Leu Xaa Cys Xaa Val Xaa Asp Tyr Ser Ile Thr Ser Asp
            20                  25                  30

Tyr Ala Trp Asn Trp Ile Xaa Gln Xaa Xaa Xaa Xaa Leu Xaa Trp
        35                  40                  45

Met Gly Tyr Ile Ser Tyr Ser Gly Ser Thr Ser Xaa Asn Xaa Xaa Leu
    50                  55                  60

Xaa Xaa Xaa Ile Xaa Ile Xaa Arg Xaa Xaa Xaa Xaa Xaa Phe Xaa
65                  70                  75                  80

Leu Xaa Leu Xaa Xaa Val Xaa Xaa Xaa Asp Xaa Ala Xaa Tyr Tyr Cys
            85                  90                  95

Ala Ser Phe Asp Tyr Ala His Ala Met Asp Tyr Trp Gly Xaa Gly Thr
            100                 105                 110

Xaa Val Xaa Val Xaa Xaa
        115

<210> SEQ ID NO 134
<211> LENGTH: 109
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa= any amino acid
<220> FEATURE:
<221> NAME/KEY: misc_feature
<222> LOCATION: (3)..(3)
<223> OTHER INFORMATION: Xaa= any amino acid
<220> FEATURE:
<221> NAME/KEY: misc_feature
<222> LOCATION: (5)..(5)
<223> OTHER INFORMATION: Xaa= any amino acid
<220> FEATURE:
<221> NAME/KEY: misc_feature
<222> LOCATION: (7)..(12)
<223> OTHER INFORMATION: Xaa= any amino acid
<220> FEATURE:
<221> NAME/KEY: misc_feature
<222> LOCATION: (14)..(18)
<223> OTHER INFORMATION: Xaa= any amino acid
<220> FEATURE:
<221> NAME/KEY: misc_feature
<222> LOCATION: (20)..(20)
<223> OTHER INFORMATION: Xaa= any amino acid
<220> FEATURE:

```
<221> NAME/KEY: misc_feature
<222> LOCATION: (22)..(22)
<223> OTHER INFORMATION: Xaa= any amino acid
<220> FEATURE:
<221> NAME/KEY: misc_feature
<222> LOCATION: (24)..(24)
<223> OTHER INFORMATION: Xaa= any amino acid
<220> FEATURE:
<221> NAME/KEY: misc_feature
<222> LOCATION: (26)..(26)
<223> OTHER INFORMATION: Xaa= any amino acid
<220> FEATURE:
<221> NAME/KEY: misc_feature
<222> LOCATION: (37)..(37)
<223> OTHER INFORMATION: Xaa= any amino acid
<220> FEATURE:
<221> NAME/KEY: misc_feature
<222> LOCATION: (39)..(43)
<223> OTHER INFORMATION: Xaa= any amino acid
<220> FEATURE:
<221> NAME/KEY: misc_feature
<222> LOCATION: (45)..(45)
<223> OTHER INFORMATION: Xaa= any amino acid
<220> FEATURE:
<221> NAME/KEY: misc_feature
<222> LOCATION: (54)..(57)
<223> OTHER INFORMATION: Xaa= any amino acid
<220> FEATURE:
<221> NAME/KEY: misc_feature
<222> LOCATION: (59)..(61)
<223> OTHER INFORMATION: Xaa= any amino acid
<220> FEATURE:
<221> NAME/KEY: misc_feature
<222> LOCATION: (63)..(63)
<223> OTHER INFORMATION: Xaa= any amino acid
<220> FEATURE:
<221> NAME/KEY: misc_feature
<222> LOCATION: (65)..(65)
<223> OTHER INFORMATION: Xaa= any amino acid
<220> FEATURE:
<221> NAME/KEY: misc_feature
<222> LOCATION: (67)..(67)
<223> OTHER INFORMATION: Xaa= any amino acid
<220> FEATURE:
<221> NAME/KEY: misc_feature
<222> LOCATION: (69)..(70)
<223> OTHER INFORMATION: Xaa= any amino acid
<220> FEATURE:
<221> NAME/KEY: misc_feature
<222> LOCATION: (72)..(72)
<223> OTHER INFORMATION: Xaa= any amino acid
<220> FEATURE:
<221> NAME/KEY: misc_feature
<222> LOCATION: (74)..(74)
<223> OTHER INFORMATION: Xaa= any amino acid
<220> FEATURE:
<221> NAME/KEY: misc_feature
<222> LOCATION: (76)..(77)
<223> OTHER INFORMATION: Xaa= any amino acid
<220> FEATURE:
<221> NAME/KEY: misc_feature
<222> LOCATION: (79)..(81)
<223> OTHER INFORMATION: Xaa= any amino acid
<220> FEATURE:
<221> NAME/KEY: misc_feature
<222> LOCATION: (83)..(83)
<223> OTHER INFORMATION: Xaa= any amino acid
<220> FEATURE:
<221> NAME/KEY: misc_feature
<222> LOCATION: (100)..(100)
<223> OTHER INFORMATION: Xaa= any amino acid
<220> FEATURE:
<221> NAME/KEY: misc_feature
<222> LOCATION: (103)..(103)
<223> OTHER INFORMATION: Xaa= any amino acid
<220> FEATURE:
<221> NAME/KEY: misc_feature
<222> LOCATION: (105)..(109)
<223> OTHER INFORMATION: Xaa= any amino acid
```

-continued

<400> SEQUENCE: 134

Xaa Ile Xaa Leu Xaa Gln Xaa Xaa Xaa Xaa Xaa Val Xaa Xaa Xaa
1               5                   10                  15

Xaa Xaa Val Xaa Phe Xaa Cys Xaa Ala Xaa Gln Ser Ile Gly Thr Ser
            20                  25                  30

Ile His Trp Tyr Xaa Gln Xaa Xaa Xaa Xaa Pro Xaa Leu Leu Ile
        35                  40                  45

Lys Tyr Ala Ser Glu Xaa Xaa Xaa Ile Xaa Xaa Xaa Phe Xaa Gly
50                  55                  60

Xaa Gly Xaa Gly Xaa Xaa Phe Xaa Leu Xaa Ile Xaa Xaa Val Xaa Xaa
65              70                  75                  80

Xaa Asp Xaa Ala Asp Tyr Tyr Cys Gln Gln Ile Asn Ser Trp Pro Thr
                85                  90                  95

Thr Phe Gly Xaa Gly Thr Xaa Leu Xaa Xaa Xaa Xaa Xaa
            100                 105

<210> SEQ ID NO 135
<211> LENGTH: 327
<212> TYPE: DNA
<213> ORGANISM: Homo sapiens

<400> SEQUENCE: 135
gaaatagtcc ttacccaatc tcccggaacc ctctcagtat ctcccggcga acgagtaacc      60
ttttcatgta gagcatccca atccatcggc acttcaattc actggtatca gcagaaaaca     120
ggtcaatccc cacggcttct tataaaatat gcatcgaatc aatttctgg catcccagac      180
agattttcag gttcaggatc aggcaccgat ttcacactta caatatccag agtcgaatca     240
gaagattttg cagattacta ttgtcaacaa ataaacagct ggcccactac attcggacaa     300
ggcacaaaac tcgaaattaa acgtacg                                         327

<210> SEQ ID NO 136
<211> LENGTH: 109
<212> TYPE: PRT
<213> ORGANISM: Homo sapiens

<400> SEQUENCE: 136

Glu Ile Val Leu Thr Gln Ser Pro Gly Thr Leu Ser Val Ser Pro Gly
1               5                   10                  15

Glu Arg Val Thr Phe Ser Cys Arg Ala Ser Gln Ser Ile Gly Thr Ser
            20                  25                  30

Ile His Trp Tyr Gln Gln Lys Thr Gly Gln Ser Pro Arg Leu Leu Ile
        35                  40                  45

Lys Tyr Ala Ser Glu Ser Ile Ser Gly Ile Pro Asp Arg Phe Ser Gly
50                  55                  60

Ser Gly Ser Gly Thr Asp Phe Thr Leu Thr Ile Ser Arg Val Glu Ser
65              70                  75                  80

Glu Asp Phe Ala Asp Tyr Tyr Cys Gln Gln Ile Asn Ser Trp Pro Thr
                85                  90                  95

Thr Phe Gly Gln Gly Thr Lys Leu Glu Ile Lys Arg Thr
            100                 105

<210> SEQ ID NO 137
<211> LENGTH: 327
<212> TYPE: DNA
<213> ORGANISM: Homo sapiens

<400> SEQUENCE: 137

-continued

```
gaaatagttc ttactcaatc ccccggtaca ctctcagttt ccccaggcga acgcgtcact      60
ttttcttgca gagcatcaca atcaatcggc acttcaattc attggtatca acaaaaaaca     120
ggacaggccc cacgacttct tattaaatat gcatcagaat caatttctgg catcccagac     180
agattttcag gttcaggatc aggcaccgat ttcacactta caatatccag agtcgaatca     240
gaagattttg cagattacta ttgtcaacaa ataaacagct ggcccactac attcggacaa     300
ggcacaaaac tcgaaattaa acgtacg                                         327

<210> SEQ ID NO 138
<211> LENGTH: 11
<212> TYPE: PRT
<213> ORGANISM: Homo sapiens

<400> SEQUENCE: 138

Gln Ala Ser Gln Ser Ile Gly Thr Ser Ile His
1               5                   10
```